US009364000B2

(12) United States Patent
Takahashi et al.

(10) Patent No.: US 9,364,000 B2
(45) Date of Patent: Jun. 14, 2016

(54) METHOD OF CONTROLLING PESTS WITH FUSED HETEROCYCLIC COMPOUND

(71) Applicant: Sumitomo Chemical Company, Limited, Tokyo (JP)

(72) Inventors: Masaki Takahashi, Takarazuka (JP); Mai Ito, Takarazuka (JP); Yoshihiko Nokura, Takarazuka (JP); Takamasa Tanabe, Takarazuka (JP); Chie Shimizu, Tokyo (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 14/850,243

(22) Filed: Sep. 10, 2015

(65) Prior Publication Data
US 2015/0373982 A1  Dec. 31, 2015

Related U.S. Application Data

(62) Division of application No. 14/403,021, filed as application No. PCT/JP2013/064963 on May 23, 2013, now abandoned.

(30) Foreign Application Priority Data

May 30, 2012 (JP) .................. 2012-123168

(51) Int. Cl.
| | |
|---|---|
| A61K 31/50 | (2006.01) |
| A01N 43/90 | (2006.01) |
| A01N 43/76 | (2006.01) |
| A01N 43/78 | (2006.01) |
| C07D 413/04 | (2006.01) |
| C07D 471/04 | (2006.01) |
| C07D 498/04 | (2006.01) |
| C07D 513/04 | (2006.01) |
| C07D 401/04 | (2006.01) |
| C07D 417/04 | (2006.01) |
| A01N 47/02 | (2006.01) |

(52) U.S. Cl.
CPC .............. *A01N 43/90* (2013.01); *A01N 43/76* (2013.01); *A01N 43/78* (2013.01); *A01N 47/02* (2013.01); *C07D 401/04* (2013.01); *C07D 413/04* (2013.01); *C07D 417/04* (2013.01); *C07D 471/04* (2013.01); *C07D 498/04* (2013.01); *C07D 513/04* (2013.01)

(58) Field of Classification Search
None
See application file for complete search history.

(56) References Cited

U.S. PATENT DOCUMENTS

2003/0036544 A1  2/2003  Steiger et al.
2011/0039843 A1  2/2011  Iwakoshi et al.
2012/0015975 A1  1/2012  Takahashi et al.
2012/0108586 A1  5/2012  Iwakoshi et al.
2012/0178779 A1  7/2012  Takahashi et al.
2012/0196891 A1  8/2012  Iwakoshi
2012/0245167 A1  9/2012  Iwakoshi et al.
2013/0090353 A1  4/2013  Iwakoshi et al.
2013/0252981 A1  9/2013  Takahashi et al.
2014/0018373 A1  1/2014  Takyo et al.
2014/0194290 A1  7/2014  Takahashi et al.
2015/0166573 A1  6/2015  Takahashi et al.

OTHER PUBLICATIONS

Hisano et al, "Synthesis of Benzoaxazoles, Benzothiazoles and Benzimidazoles and Evaluation of Their Antifungal, Insecticidal and Herbicidal Activities," Chem. Pharm. Bull., vol. 30, No. 8, pp. 2996-3004 (1982).
Int'l Search Report issued Jun. 25, 2013 in Int'l Application No. PCT/JP2013/064963.
File Registry, CAS Registry No. 838100-59-7 (No. 1).
File Registry, CAS Registry No. 838101-65-8 (No. 2).
File Registry, CAS Registry No. 838100-62-2 (No. 3).

(Continued)

*Primary Examiner* — Heidi Reese
(74) *Attorney, Agent, or Firm* — Panitch Schwarze Belisario & Nadel LLP

(57) ABSTRACT

Fused heterocyclic compounds of formula (1):

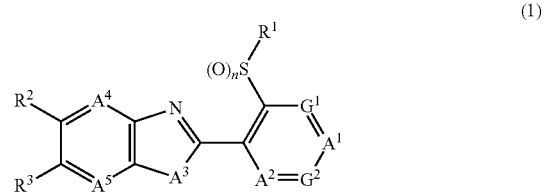

($G^1$ and $G^2$ represent a nitrogen atom or the like, $A^1$ and $A^2$ represent a nitrogen atom or the like, $A^3$ represents —$NR^8$— or the like, $A^4$ and $A^5$ represent a nitrogen atom or the like, $R^1$ represents a C1-C6 chain hydrocarbon group or the like optionally having one or more atoms or groups selected from a group X, $R^2$ and $R^3$ are the same or different and represent a C1-C6 chain hydrocarbon group or the like optionally having one or more atoms or groups selected from the group X, $R^8$ represents a C1-C6 chain hydrocarbon group or the like optionally having one or more atoms or groups selected from a group W, and n represents 0, 1 or 2), or N-oxides thereof are described. The disclosed compounds are very effective for pest control.

3 Claims, No Drawings

(56) References Cited

OTHER PUBLICATIONS

Rose, U., "2-Arylsubstituierte...", Pharmazie, vol. 46, pp. 775-777, (1991).

Rose, U., "2-Arylsubstituierte benzoanellierte...", Chemiker-Zeitung, vol. 115, No. 2, pp. 55-58, (1991).

Office Action issued Jun. 10, 2015 in U.S. Appl. No. 14/403,021 by Takahashi.

CAPLUS 1989: 231657.

METHOD OF CONTROLLING PESTS WITH FUSED HETEROCYCLIC COMPOUND

CROSS-REFERENCE TO RELATED APPLICATION

This application is a divisional of co-pending U.S. patent application Ser. No. 14/403,021, filed Nov. 21, 2014, which was a Section 371 of International Application No. PCT/JP2013/064963, filed May 23, 2013, which was published in the Japanese language on Dec. 5, 2013, under International Publication No. WO 2013/180194 A1, and the disclosures of which are incorporated herein by reference.

TECHNICAL FIELD

The present invention relates to a fused heterocyclic compound and a use thereof for pest control.

BACKGROUND ART

In Pharmazie, 46(11), 775(1991) and Chemiker-Zeitung, 115(2), 55(1991), a certain kind of a fused heterocyclic compound is known.

SUMMARY OF THE INVENTION

The present invention provides a compound having an excellent control effect on pests and a method for controlling pests using the compound.

More specifically, the present invention is as described below.

[1] A fused heterocyclic compound represented by formula (1) or an N-oxide thereof (hereinafter, referred to as the compound of the present invention),

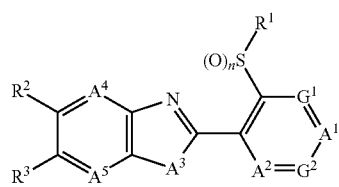

(1)

wherein
$G^1$ represents a nitrogen atom or $=CR^4—$;
$G^2$ represents a nitrogen atom or $=CR^5—$ (wherein at least one of $G^1$ and $G^2$ is a nitrogen atom);
$A^1$ represents a nitrogen atom or $=CR^6—$;
$A^2$ represents a nitrogen atom or $=CR^7—$;
$A^3$ represents $—NR^8—$, an oxygen atom, or a sulfur atom;
$A^4$ represents a nitrogen atom or $=CR^9—$;
$A^5$ represents a nitrogen atom or $=CR^{10}—$;
$R^1$ represents a C1 to C6 chain hydrocarbon group optionally having one or more atoms or groups selected from group X or a C3 to C6 alicyclic hydrocarbon group optionally having one or more atoms or groups selected from group Y;
$R^2$ and $R^3$ are the same or different and represent a C1 to C6 chain hydrocarbon group optionally having one or more atoms or groups selected from group X, a phenyl group optionally having one or more atoms or groups selected from group Z, a 6-membered heterocyclic group optionally having one or more atoms or groups selected from group Z, $—OR^{11}$, $—S(O)_mR^{11}$, $—S(O)_2NR^{11}R^{12}$, $—NR^{11}R^{12}$, $—NR^{11}CO_2R^{12}$, $—NR^{11}C(O)R^{12}$, $—CO_2R^{11}$, $—C(O)R^{11}$, $—C(O)NR^{11}R^{12}$, $—SF_5$, a cyano group, a nitro group, a halogen atom, or a hydrogen atom;
$R^4$, $R^5$, $R^6$ and $R^7$ are the same or different and represent a C1 to C6 chain hydrocarbon group optionally having one or more atoms or groups selected from group X, a phenyl group optionally having one or more atoms or groups selected from group Z, a 5- or 6-membered heterocyclic group optionally having one or more atoms or groups selected from group Z, $—OR^{13}$, $—S(O)_mR^{13}$, $—S(O)_2NR^{13}R^{14}$, $—NR^{13}R^{14}$, $—NR^{13}CO_2R^{14}$, $—NR^{13}C(O)R^{14}$, $—CO_2R^{13}$, $—C(O)R^{13}$, $—C(O)NR^{13}R^{14}$, $—SF_5$, a cyano group, a nitro group, a halogen atom, or a hydrogen atom;
$R^8$ represents a C1 to C6 chain hydrocarbon group optionally having one or more atoms or groups selected from group W, a C1 to C6 chain hydrocarbon group having one phenyl group (wherein the phenyl group optionally has one or more atoms or groups selected from group Z), a C1 to C6 chain hydrocarbon group having one 5- or 6-membered heterocyclic group (wherein the 5- or 6-membered heterocyclic group optionally has one or more atoms or groups selected from group Z), $—CO_2R^{15}$, $—C(O)R^{15}$, a C3 to C6 alicyclic hydrocarbon group optionally having one or more atoms or groups selected from group Y, or a hydrogen atom;
$R^9$ and $R^{10}$ are the same or different and represent a C1 to C6 chain hydrocarbon group optionally having one or more halogen atoms, $—OR^{16}$, $—S(O)_mR^{16}$, $—NR^{16}R^{17}$, $—CO_2R^{16}$, $—C(O) R^{16}$, a cyano group, a nitro group, a halogen atom, or a hydrogen atom;
$R^{11}$, $R^{12}$, $R^{13}$, $R^{14}$, $R^{15}$, $R^{16}$ and $R^{17}$ are the same or different and represent a C1 to C6 chain hydrocarbon group optionally having one or more atoms or groups selected from group X, or a hydrogen atom;
each m independently represents 0, 1, or 2; and
n represents 0, 1, or 2;
wherein $R^2$ and $R^3$ do not simultaneously represent a hydrogen atom or do not simultaneously represent a methyl group;
when m is 1 or 2 in $—S(O)_mR^{11}$, $R^{11}$ does not represent a hydrogen atom;
when m is 1 or 2 in $—S(O)_mR^{13}$, $R^{13}$ does not represent a hydrogen atom; and
when m is 1 or 2 in $—S(O)_mR^{16}$, $R^{16}$ does not represent a hydrogen atom.

Group X: a group consisting of C1 to C6 alkoxy groups optionally having one or more halogen atoms, C2 to C6 alkenyloxy groups optionally having one or more halogen atoms, C2 to C6 alkynyloxy groups optionally having one or more halogen atoms, C1 to C6 alkylsulfanyl groups optionally having one or more halogen atoms, C1 to C6 alkylsulfinyl groups optionally having one or more halogen atoms, C1 to C6 alkylsulfonyl groups optionally having one or more halogen atoms, C2 to C6 alkylcarbonyl groups optionally having one or more halogen atoms, C2 to C6 alkoxycarbonyl groups optionally having one or more halogen atoms, C3 to C6 cycloalkyl groups optionally having one or more halogen atoms or one or more C1 to C3 alkyl groups, cyano groups, hydroxy groups, and halogen atoms.

Group Y: a group consisting of C1 to C6 chain hydrocarbon groups optionally having one or more halogen atoms, C1 to C6 alkoxy groups optionally having one or more halogen atoms, C2 to C6 alkenyloxy groups optionally having one or more halogen atoms, C2 to C6 alkynyloxy groups optionally having one or more halogen atoms, and halogen atoms.

Group Z: a group consisting of C1 to C6 chain hydrocarbon groups optionally having one or more halogen atoms, C1 to C6 alkoxy groups optionally having one or more halogen atoms, C1 to C6 alkylsulfanyl groups optionally having one or more halogen atoms, C1 to C6 alkylsulfinyl groups optionally having one or more halogen atoms, C1 to C6 alkylsulfonyl groups optionally having one or more halogen atoms, C2 to C6 alkylcarbonyl groups optionally having one or more halogen atoms, C2 to C6 alkoxycarbonyl groups optionally having one or more halogen atoms, C1 to C6 alkylamino groups optionally having one or more halogen atoms, C2 to C8 dialkylamino groups optionally having one or more halogen atoms, halogen atoms, cyano groups, nitro groups, and $SF_5$.

Group W: a group consisting of C1 to C6 alkoxy groups optionally having one or more halogen atoms, C2 to C6 alkenyloxy groups optionally having one or more halogen atoms, C2 to C6 alkynyloxy groups optionally having one or more halogen atoms, C1 to C6 alkylsulfanyl groups optionally having one or more halogen atoms, C1 to C6 alkylsulfinyl groups optionally having one or more halogen atoms, C1 to C6 alkylsulfonyl groups optionally having one or more halogen atoms, C2 to C6 alkylcarbonyl groups optionally having one or more halogen atoms, C2 to C6 alkoxycarbonyl groups optionally having one or more halogen atoms, C3 to C6 cycloalkyl groups optionally having one or more halogen atoms, hydroxy groups, halogen atoms, and cyano groups.

[2]

The fused heterocyclic compound according to [1], wherein $A^4$ is =$CR^9$—;

$R^1$ is a C1 to C6 alkyl group optionally having one or more atoms or groups selected from halogen atoms and a cyclopropyl group (wherein the cyclopropyl group optionally has one or more halogen atoms or one or more C1 to C3 alkyl groups), a C2 to C6 alkenyl group optionally having one or more halogen atoms, or a C2 to C6 alkynyl group optionally having one or more halogen atoms;

$R^2$ is a C1 to C6 alkyl group optionally having one or more halogen atoms, —$OR^{11}$ (wherein $R^{11}$ is a C1 to C6 alkyl group optionally having one or more halogen atoms), —$S(O)_mR^{11}$ (wherein $R^{11}$ is a C1 to C6 alkyl group optionally having one or more halogen atoms and m is 0, 1 or 2), $SF_5$, or a halogen atom;

$R^3$ is a hydrogen atom;

$R^4$ and $R^5$ are the same or different and are a halogen atom or a hydrogen atom;

$R^6$ is a C1 to C6 alkyl group optionally having one or more halogen atoms, a C2 to C6 alkenyl group optionally having one or more halogen atoms, a C2 to C6 alkynyl group optionally having one or more halogen atoms, a 5- or 6-membered aromatic heterocyclic group (wherein the 5- or 6-membered aromatic heterocyclic group optionally has one or more atoms or groups selected from a group consisting of halogen atoms, C1 to C3 alkyl groups optionally having a halogen atom and C1 to C3 alkoxy groups optionally having a halogen atom), —$OR^{13}$ (wherein $R^{13}$ is a C1 to C6 alkyl group optionally having one or more halogen atoms), —$S(O)_mR^{13}$ (wherein $R^{13}$ is a C1 to C6 alkyl group optionally having one or more halogen atoms, and m is 0, 1, or 2), a cyano group, a nitro group, a halogen atom or a hydrogen atom;

$R^7$ is a halogen atom or a hydrogen atom;

$R^8$ is a C1 to C6 alkyl group optionally having one or more halogen atoms, a C3 to C6 alkenyl group optionally having one or more halogen atoms, a C3 to C6 alkynyl group optionally having one or more halogen atoms, a C1 to C6 alkyl group optionally having one 5- or 6-membered aromatic heterocyclic group (wherein the 5- or 6-membered aromatic heterocyclic group optionally has one or more atoms or groups selected from a group consisting of halogen atoms, C1 to C3 alkyl groups optionally having a halogen atom and C1 to C3 alkoxy groups optionally having a halogen atom), a C2 to C6 alkoxyalkyl group optionally having one or more halogen atoms, or a hydrogen atom;

$R^9$ is a hydrogen atom; and $R^{10}$ is a C1 to C6 alkyl group optionally having one or more halogen atoms, —$OR^{16}$ (wherein $R^{16}$ is a C1 to C6 alkyl group optionally having one or more halogen atoms), —$S(O)_mR^{16}$ (wherein $R^{16}$ is a C1 to C6 alkyl group optionally having one or more halogen atoms, and m is 0, 1, or 2), a halogen atom, or a hydrogen atom.

[3]

The fused heterocyclic compound according to [1] or [2], wherein $A^4$ is =$CR^9$—;

$R^1$ is an ethyl group or a cyclopropylmethyl group;

$R^2$ is a C1 to C6 haloalkyl group, —$OR^1$ (wherein $R^{11}$ is a C1 to C6 haloalkyl group), —$S(O)_mR^{11}$ (wherein $R^{11}$ is a C1 to C6 haloalkyl group, and m is 0, 1, or 2), $SF_5$, or a halogen atom;

$R^3$ is a hydrogen atom;

$R^4$ and $R^5$ are a hydrogen atom;

$R^6$ is a C1 to C6 alkyl group optionally having one or more halogen atoms, —$OR^{13}$ (wherein $R^{13}$ is a C1 to C6 alkyl group optionally having one or more halogen atoms), —$S(O)_mR^3$ (wherein $R^{13}$ is a C1 to C6 alkyl group optionally having one or more halogen atoms, and m is 0, 1, or 2), a halogen atom, or a hydrogen atom;

$R^7$ is a hydrogen atom;

$R^8$ is a methyl group, a propargyl group, a methoxymethyl group, or an ethoxymethyl group;

$R^9$ is a hydrogen atom; and $R^{10}$ is a hydrogen atom or a halogen atom.

[4]

The fused heterocyclic compound as defined in any of [1] to [3], wherein $A^1$ is =$CR^6$—.

[5]

The fused heterocyclic compound as defined in any of [1] to [3], wherein $A^1$ is =$CR^6$—, $G^1$ is a nitrogen atom, and $G^2$ is =$CR^5$

[6]

The fused heterocyclic compound as defined in any of [1] to [3], wherein $A^1$ is =$CR^6$—, $G^1$ is a nitrogen atom, $G^2$ is =$CR^5$—, and $A^2$ is =$CR^7$—.

[7]

The fused heterocyclic compound as defined in any of [1] to [3], wherein $A^1$ is =$CR^6$—, $G^1$ is =$CR^5$—, and $G^2$ is a nitrogen atom.

[8]

The fused heterocyclic compound as defined in any of [1] to [3], wherein A is =$CR^6$—, and $G^1$ and $G^2$ are a nitrogen atom.

[9]

The fused heterocyclic compound as defined in any of [1] to [3], wherein $A^1$ is a nitrogen atom.

[10]

The fused heterocyclic compound as defined in any of [1] to [3], wherein $A^1$ is a nitrogen atom, and $A^2$ is =$CR^7$—.

[11]
The fused heterocyclic compound as defined in any of [1] to [3], wherein

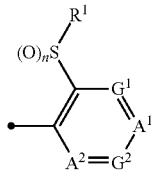

in the formula (1) is J1 to J6 as shown below,

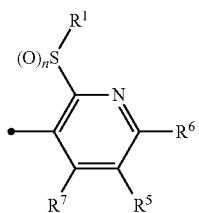
J1

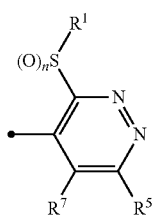
J2

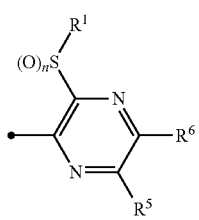
J3

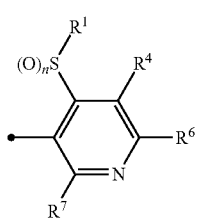
J4

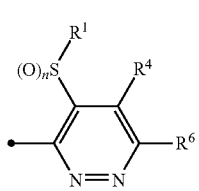
J5

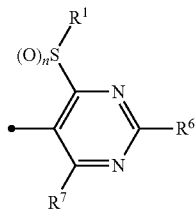
J6

[symbols represent the same meaning as in the formula (1)].

[12]
A pest control composition comprising the fused heterocyclic compound as defined in any of [1] to [11], and an inert carrier.

[13]
A method for controlling pests comprising applying an effective amount of the fused heterocyclic compound as defined in any of [1] to [11] to a pest or a pest-infested area.

MODE FOR CARRYING OUT THE INVENTION

In the compound of the present invention, an N-oxide is a compound in which the nitrogen atom constituting the ring on the heterocyclic group is oxidized. Examples of the heterocyclic group that may form the N-oxide include a pyridine ring, fused rings containing a pyridine ring, and the like.

The groups used in the description of the present specification will be described below with examples.

The notation of "Ca to Cb chain hydrocarbon group" in the present specification represents a straight-chain or branched-chain saturated or unsaturated hydrocarbon group having the number of carbon atoms of a to b.

Examples of the "C1 to C6 chain hydrocarbon group" include C1 to C6 alkyl groups such as a methyl group, an ethyl group, a propyl group, an isopropyl group, a butyl group, an isobutyl group, a sec-butyl group, a tert-butyl group, a pentyl group, a neopentyl group and a hexyl group; C2 to C6 alkenyl groups such as a vinyl group, a 1-propenyl group, a 2-propenyl group, a 1-methylvinyl group, a 2-methyl-1-propenyl group, a 1-butenyl group, a 2-butenyl group, a 3-butenyl group, a 1-pentenyl group and a 1-hexenyl group; and C2 to C6 alkynyl groups such as an ethynyl group, a propargyl group, a 2-butynyl group, a 3-butynyl group, a 1-pentynyl group and a 1-hexynyl group.

The notation of "Ca to Cb alkyl group" in the present specification represents a straight-chain or branched-chain hydrocarbon group having the number of carbon atoms of a to b.

Examples of the "C1 to C6 alkyl group" include a methyl group, an ethyl group, a propyl group, an isopropyl group, a butyl group, an isobutyl group, a sec-butyl group, a tert-butyl group, a pentyl group, a neopentyl group, and a hexyl group.

Examples of the "C2 to C6 alkyl group" include an ethyl group, a propyl group, an isopropyl group, a butyl group, an isobutyl group, a sec-butyl group, a tert-butyl group, a pentyl group, a neopentyl group, and a hexyl group.

Examples of the "C1 to C3 alkyl group" include a methyl group, an ethyl group, a propyl group, and an isopropyl group.

The notation of "Ca to Cb alkenyl group" in the present specification represents a straight-chain or branched-chain unsaturated hydrocarbon group having the number of carbon atoms of a to b, and having one or two or more double bonds in the molecule.

Examples of the "C2 to C6 alkenyl group" include a vinyl group, a 1-propenyl group, a 2-propenyl group, a 1-methylvinyl group, a 2-methyl-1-propenyl group, a 1-butenyl group, a 2-butenyl group, a 3-butenyl group, a 1-pentenyl group, and a 1-hexenyl group.

The notation of "Ca to Cb alkynyl group" in the present specification represents a straight-chain or branched-chain unsaturated hydrocarbon group having the number of carbon atoms of a to b, and having one or two or more triple bonds in the molecule.

Examples of the "C2 to C6 alkynyl group" include an ethynyl group, a propargyl group, a 2-butynyl group, a 3-butynyl group, a 1-pentynyl group, and a 1-hexynyl group.

The notation of "Ca to Cb haloalkyl group" in the present specification represents a straight-chain or branched-chain hydrocarbon group having the number of carbon atoms of a to b, in which one or more hydrogen atoms bound to the carbon atom are substituted by a halogen atom, and at that time, when having two or more halogen atoms, those halogen atoms may be the same or different from each other.

Examples of the "C1 to C6 haloalkyl group" include a fluoromethyl group, a chloromethyl group, a bromomethyl group, an iodomethyl group, a difluoromethyl group, a dichloromethyl group, a trifluoromethyl group, a chlorodifluoromethyl group, a bromodifluoromethyl group, a trichloromethyl group, a 2-fluoroethyl group, a 2-chloroethyl group, a 2-bromoethyl group, a 2,2-difluoroethyl group, a 2,2,2-trifluoroethyl group, a pentafluoroethyl group, a heptafluoropropyl group, and a heptafluoroisopropyl group.

The notation of "Ca to Cb alkoxy group" in the present specification represents a group represented by a straight-chain or branched-chain alkyl —O— having the number of carbon atoms of a to b.

Examples of the "C1 to C6 alkoxy group" include a methoxy group, an ethoxy group, a propoxy group, an isopropoxy group, a butoxy group, an isobutoxy group, a sec-butoxy group, a tert-butoxy group, a pentyloxy group, a neopentyloxy group, and a hexyloxy group.

Examples of the "C1 to C3 alkoxy group" include a methoxy group, an ethoxy group, a propoxy group, and an isopropoxy group.

The notation of "Ca to Cb alkenyloxy group" in the present specification represents a group represented by a straight-chain or branched-chain alkenyl —O— having the number of carbon atoms of a to b, and having one or two or more double bonds in the molecule.

Examples of the "C2 to C6 alkenyloxy group" include a vinyloxy group, a 1-propenyloxy group, a 2-propenyloxy group, a 1-methylvinyloxy group, a 2-methyl-1-propenyloxy group, a 1-butenyloxy group, a 2-butenyloxy group, a 3-butenyloxy group, a 1-pentenyloxy group, and a 1-hexenyloxy group.

The notation of "Ca to Cb alkynyloxy group" in the present specification represents a straight-chain or branched-chain alkynyl —O— having the number of carbon atoms of a to b, and having one or two or more triple bonds in the molecule.

Examples of the "C2 to C6 alkynyloxy group" include an ethynyloxy group, a propargyloxy group, a 2-butynyloxy group, a 3-butynyloxy group, a 1-pentynyloxy group, and a 1-hexynyloxy group.

The notation of "Ca to Cb alkylsulfanyl group" in the present specification represents a straight-chain or branched-chain alkyl —S— having the number of carbon atoms of a to b.

Examples of the "C1 to C6 alkylsulfanyl group" include a methylsulfanyl group, an ethylsulfanyl group, a propylsulfanyl group, an isopropylsulfanyl group, a butylsulfanyl group, a pentylsulfanyl group, and a hexylsulfanyl group.

The notation of "Ca to Cb alkylsulfinyl group" in the present specification represents a straight-chain or branched-chain alkyl —S(O)— having the number of carbon atoms of a to b.

Examples of the "C1 to C6 alkylsulfinyl group" include a methylsulfinyl group, an ethylsulfinyl group, a propylsulfinyl group, an isopropylsulfinyl group, a butylsulfinyl group, a pentylsulfinyl group, and a hexylsulfinyl group.

The notation of "Ca to Cb alkylsulfonyl group" in the present specification represents a straight-chain or branched-chain alkyl —S(O)$_2$— having the number of carbon atoms of a to b.

Examples of the "C1 to C6 alkylsulfonyl group" include a methylsulfonyl group, an ethylsulfonyl group, a propylsulfonyl group, an isopropylsulfonyl group, a butylsulfonyl group, a pentylsulfonyl group, and a hexylsulfonyl group.

The notation of "Ca to Cb alkylcarbonyl group" in the present specification represents a straight-chain or branched-chain alkyl —C(O)— having the number of carbon atoms of a to b.

Examples of the "C2 to C6 alkylcarbonyl group" include an acetyl group, a propionyl group, a butyryl group, a pentanoyl group, and a hexanoyl group.

The notation of "Ca to Cb alkoxycarbonyl group" in the present specification represents a straight-chain or branched-chain alkyl —O—C(O)— having the number of carbon atoms of a to b.

Examples of the "C2 to C6 alkoxycarbonyl group" include a methoxycarbonyl group, an ethoxycarbonyl group, a propoxycarbonyl group, a butoxycarbonyl group, a pentyloxycarbonyl group, and a tert-butoxycarbonyl group.

The notation of "Ca to Cb alicyclic hydrocarbon group" in the present specification represents a cyclic non-aromatic hydrocarbon group having the number of carbon atoms of a to b.

Examples of the "C3 to C6 alicyclic hydrocarbon group" include a cyclopropyl group, a cyclobutyl group, a cyclopentyl group, a cyclohexyl group, a 1-cyclohexenyl group, a 2-cyclohexenyl group, and a 3-cyclohexenyl group.

The notation of "Ca to Cb cycloalkyl group" in the present specification represents a cyclic alkyl group having the number of carbon atoms of a to b.

The "C3 to C6 cycloalkyl group" includes a cyclopropyl group, a cyclobutyl group, a cyclopentyl group, and a cyclohexyl group.

The notation of "Ca to Cb alkylamino group" in the present specification represents a straight-chain or branched-chain alkyl —NH— having the number of carbon atoms of a to b.

Examples of the "C1 to C6 alkylamino group" include a methylamino group, an ethylamino group, a propylamino group, an isopropylamino group, and a butylamino group.

The notation of "Ca to Cb dialkylamino group" in the present specification represents a straight-chain or branched-chain dialkylamino group having a total number of carbon atoms of each alkyl group of a to b, in which the number of carbon atoms of each alkyl group may be the same or different.

Examples of the "C2 to C8 dialkylamino group" include a dimethylamino group, a diethylamino group, and a dipropylamino group.

The notation of "Ca to Cb alkoxyalkyl group" in the present specification represents a straight-chain or branched-chain alkyl —O— alkyl having a total number of carbon atoms of each alkyl group of a to b, in which the number of carbon atoms of each alkyl group may be the same or different.

Examples of the "C2 to C6 alkoxyalkyl group" include a methoxymethyl group, an ethoxymethyl group, a 1-(methoxy)ethyl group, a 2-(methoxy)ethyl group, a 1-(ethoxy)ethyl group, and a 2-(ethoxy)ethyl group.

In the notation of "optionally having one or more atoms or groups selected from group X" in the present specification, when having two or more atoms or groups selected from group X, the atoms or groups selected from the group X may be the same or different from each other.

In the notation of "optionally having one or more atoms or groups selected from group Y" in the present specification, when having two or more atoms or groups selected from group Y, the atoms or groups selected from group Y may be the same or different from each other.

In the notation of "optionally having one or more atoms or groups selected from group Z" in the present specification, when having two or more atoms or groups selected from group Z, the atoms or groups selected from group Z may be the same or different from each other.

In the notation of "optionally having one or more atoms or groups selected from group W" in the present specification, when having two or more atoms or groups selected from group W, the atoms or groups selected from group W may be the same or different from each other.

In the notation of "optionally having one or more halogen atoms" in the present specification, when having two or more halogen atoms, those halogen atoms may be the same or different from each other.

The notation of "heterocyclic group" in the present specification represents a heterocyclic compound residue containing one or more atoms selected from the group consisting of a nitrogen atom, an oxygen atom and a sulfur atom, other than a carbon atom, in the cyclic structure, and examples include a 5-membered heterocyclic group and a 6-membered heterocyclic group.

The "5-membered heterocyclic group" represents a 5-membered heterocyclic compound residue containing one or more atoms selected from the group consisting of a nitrogen atom, an oxygen atom and a sulfur atom, other than a carbon atom, in the cyclic structure, and examples include a 5-membered aromatic heterocyclic group and a 5-membered nonaromatic heterocyclic group.

Examples of the "5-membered aromatic heterocyclic group" include a pyrrolyl group, a furyl group, a pyrazolyl group, a thienyl group, an imidazolyl group, a triazolyl group, a tetrazolyl group, and an isoxazolyl group.

Examples of the "5-membered nonaromatic heterocyclic group" include a pyrrolidinyl group, a pyrazolidinyl group, and a tetrahydrofuryl group.

The "6-membered heterocyclic group" represents a 6-membered heterocyclic compound residue containing one or more atoms selected from the group consisting of a nitrogen atom, an oxygen atom and a sulfur atom, other than a carbon atom, in the cyclic structure, and examples include a 6-membered aromatic heterocyclic group and a 6-membered nonaromatic heterocyclic group.

Examples of the "6-membered aromatic heterocyclic group" include a pyrazinyl group, a pyrimidinyl group, and a pyridyl group.

Examples of the "6-membered nonaromatic heterocyclic group" include a piperidyl group, a morpholinyl group, a piperazinyl group, and a thiomorpholinyl group.

The "halogen atom" in the compound of the present invention refers to a fluorine atom, a chlorine atom, a bromine atom, and an iodine atom.

The notation of the "C1 to C6 chain hydrocarbon group optionally having one or more atoms or groups selected from group X" in the compound of the present invention represents a straight-chain or branched-chain hydrocarbon group comprising a carbon atom number of 1 to 6, in which a hydrogen atom bound to the carbon atom is optionally substituted by an atom or group selected from group X, and at that time, when having two or more atoms or groups selected from group X, the atoms or groups selected from group X may be the same or different from each other.

Examples of the "C1 to C6 chain hydrocarbon group optionally having one or more atoms or groups selected from group X" include C1 to C6 alkyl groups optionally having one or more atoms or groups selected from group X such as a methyl group, an ethyl group, a propyl group, an isopropyl group, a butyl group, an isobutyl group, a sec-butyl group, a tert-butyl group, a pentyl group, a neopentyl group, a hexyl group, a methoxymethyl group, an ethoxymethyl group, a propoxymethyl group, an isopropoxymethyl group, a butoxymethyl group, a sec-butoxymethyl group, a tert-butoxymethyl group, a 2-methoxyethyl group, a 2-ethoxyethyl group, a 2-propoxyethyl group, a 2-isopropoxyethyl group, a 2-butoxyethyl group, a 2-sec-butoxyethyl group, a 2-tert-butoxyethyl group, a trifluoromethyl group, a trichloromethyl group, a 2-fluoroethyl group, a 2,2-difluoroethyl group, a 2,2,2,-trifluoroethyl group, a pentafluoroethyl group, a methylsulfanylethyl group, an ethylsulfanylethyl group, a methylsulfinylethyl group, a methylsulfonylethyl group, a 2-hydroxyethyl group, a cyclopropylmethyl group, a 1-methylcyclopropylmethyl group, and a 2,2-difluorocyclopropylmethyl group; C2 to C6 alkenyl groups optionally having one or more atoms or groups selected from group X such as a vinyl group, a 1-propenyl group, a 2-propenyl group, a 1-methylvinyl group, a 2-methyl-1-propenyl group, a 1-butenyl group, a 2-butenyl group, a 3-butenyl group, a 1-pentenyl group, a 1-hexenyl group, a 1,1-difluoroallyl group and a pentafluoroallyl group; and C2 to C6 alkynyl groups optionally having one or more atoms or groups selected from group X such as an ethynyl group, a propargyl group, a 2-butynyl group, a 3-butynyl group, a 1-pentynyl group, a 1-hexynyl group and a 4,4,4-trifluoro-2-butynyl group, and the "C1 to C6 chain hydrocarbon group optionally having one or more atoms or groups selected from group X" is selected in the range of each specified number of carbon atoms.

The notation of the "C3 to C6 alicyclic hydrocarbon group optionally having one or more atoms or groups selected from group Y" in the compound of the present invention represents a cyclic nonaromatic hydrocarbon group comprising a carbon atom number of 3 to 6, in which a hydrogen atom bound to the carbon atom is optionally substituted by an atom or group selected from group Y, and at that time, when having two or more atoms or groups selected from group Y, the atoms or groups selected from group Y may be the same or different from each other.

Examples of the "C3 to C6 alicyclic hydrocarbon group optionally having one or more atoms or groups selected from group Y" include a cyclopropyl group, a cyclobutyl group, a cyclopentyl group, a cyclohexyl group, a 1-cyclohexenyl group, a 2-cyclohexenyl group, a 3-cyclohexenyl group, a 1-methylcyclohexyl group, a 2-methylcyclohexyl group, a 3-methylcyclohexyl group, a 4-methylcyclohexyl group, a 2-methoxylcyclohexyl group, a 3-methoxylcyclohexyl group, a 4-methoxylcyclohexyl group, a 1-fluorocyclohexyl group, a 2-fluorocyclohexyl group, a 3-fluorocyclohexyl group, and a 4-fluorocyclohexyl group.

The notation of the "C1 to C6 chain hydrocarbon group optionally having one or more halogen atoms" in the compound of the present invention represents a straight-chain or branched-chain hydrocarbon group comprising a carbon atom number of 1 to 6, in which a hydrogen atom bound to the carbon atom is optionally substituted by a halogen atom, and at that time, when having two or more halogen atoms, those halogen atoms may be the same or different from each other.

Examples of the "C1 to C6 chain hydrocarbon group optionally having one or more halogen atoms" include C1 to C6 alkyl groups optionally having one or more halogen atoms such as a methyl group, an ethyl group, a propyl group, an isopropyl group, a butyl group, an isobutyl group, a sec-butyl group, a tert-butyl group, a pentyl group, a neopentyl group, a hexyl group, a trifluoromethyl group, a trichloromethyl group, a 2-fluoroethyl group, a 2,2-difluoroethyl group, a 2,2,2-trifluoroethyl group, a pentafluoroethyl group and a heptafluoroisopropyl group; C2 to C6 alkenyl groups optionally having one or more halogen atoms such as a vinyl group, a 1-propenyl group, a 2-propenyl group, a 1-methylvinyl group, a 2-methyl-1-propenyl group, a 1-butenyl group, a 2-butenyl group, a 3-butenyl group, a 1-pentenyl group, a 1-hexenyl group, a 1,1-difluoroallyl group and a pentafluoroallyl group; and C2 to C6 alkynyl groups optionally having one or more halogen atoms such as an ethynyl group, a propargyl group, a 2-butynyl group, a 3-butynyl group, a 1-pentynyl group, a 1-hexynyl group and a 4,4,4-trifluoro-2-butynyl group, and the "C1 to C6 chain hydrocarbon group optionally having one or more halogen atoms" is selected in the range of each specified number of carbon atoms.

The notation of the "phenyl group optionally having one or more atoms or groups selected from group Z" in the compound of the present invention represents a phenyl group in which a hydrogen atom bound to the carbon atom is optionally substituted by an atom or group selected from group Z, and at that time, when having two or more atoms or groups selected from group Z, the atoms or groups selected from group Z may be the same or different from each other.

Examples of the "phenyl group optionally having one or more atoms or groups selected from group Z" include a phenyl group, a 2-fluorophenyl group, a 3-fluorophenyl group, a 4-fluorophenyl group, a 2,3-difluorophenyl group, a 2,4-difluorophenyl group, a 2,5-difluorophenyl group, a 2,6-difluorophenyl group, a 3,4-difluorophenyl group, a 3,5-difluorophenyl group, a 2,3,4,5,6-pentafluorophenyl group, a 2-chlorophenyl group, a 3-chlorophenyl group, a 4-chlorophenyl group, a 2-bromophenyl group, a 3-bromophenyl group, a 4-bromophenyl group, a 2-iodophenyl group, a 3-iodophenyl group, a 4-iodophenyl group, a 2-trifluoromethylphenyl group, a 3-trifluoromethylphenyl group, a 4-trifluoromethylphenyl group, a 2-trifluoromethoxyphenyl group, a 3-trifluoromethoxyphenyl group, a 4-trifluoromethoxyphenyl group, a 2-trifluoromethylsulfanylphenyl group, a 3-trifluoromethylsulfanylphenyl group, a 4-trifluoromethylsulfanylphenyl group, a 4-methoxycarbonylphenyl group, a 4-nitrophenyl group, a 4-cyanophenyl group, a 4-methylaminophenyl group, a 4-dimethylaminophenyl group, a 4-methylsulfinylphenyl group, a 4-methylsulfonylphenyl group, a 4-acetylphenyl group, and a 4-methoxycarbonylphenyl group.

The notation of the "heterocyclic group" in the "6-membered heterocyclic group optionally having one or more atoms or groups selected from group Z" in the compound of the present invention represents a heterocyclic compound residue containing one or more atoms selected from the group consisting of a nitrogen atom, an oxygen atom and a sulfur atom, other than a carbon atom, in the cyclic structure, and at that time, when having two or more atoms or groups selected from group Z, the atoms or groups selected from group Z may be the same or different from each other.

In addition, a 6-membered heterocyclic group means a 6-membered aromatic heterocyclic group or a 6-membered nonaromatic heterocyclic group in the compound of the present invention.

Examples of the "6-membered heterocyclic group optionally having one or more atoms or groups selected from group Z" include 6-membered nonaromatic heterocyclic groups optionally having one or more atoms or groups selected from group Z such as a piperidyl group, a morpholinyl group and a thiomorpholinyl group; and 6-membered aromatic heterocyclic groups optionally having one or more atoms or groups selected from selected from group Z such as a pyrazinyl group, a 4-pyrimidinyl group, a 5-pyrimidinyl group, a 2-pyridinyl group, a 3-pyridyl group, a 4-pyridyl group, a 3-fluoro-2-pyridyl group, a 4-fluoro-2-pyridyl group, a 5-fluoro-2-pyridyl group, a 6-fluoro-2-pyridyl group, a 2-pyrimidinyl group, a 3-chloro-5-trifluoromethylpyridin-2-yl group and a 5-trifluoromethylpyridin-2-yl group.

The notation of the "heterocyclic group" in the "5- or 6-membered heterocyclic group optionally having one or more atoms or groups selected from group Z" in the compound of the present invention represents a heterocyclic compound residue containing one or more atoms selected from the group consisting of a nitrogen atom, an oxygen atom and a sulfur atom, other than a carbon atom, in the cyclic structure, and at that time, when having two or more atoms or groups selected from group Z, the atoms or groups selected from group Z may be the same or different from each other.

In addition, a 5- or 6-membered heterocyclic group means a 5- or 6-membered aromatic heterocyclic group or a 5- or 6-membered nonaromatic heterocyclic group.

Examples of the "5- or 6-membered heterocyclic group optionally having one or more atoms or groups selected from group Z" include 5- or 6-membered nonaromatic heterocyclic groups optionally having one or more atoms or groups selected from group Z such as a pyrrolidin-1-yl group, a 3,3,4,4-tetrafluoropyrrolidin-1-yl group, a tetrahydrofuran-2-yl group, a piperidyl group, a morpholinyl group and a thiomorpholinyl group; and 5- or 6-membered aromatic heterocyclic groups optionally having one or more atoms or groups selected from group Z such as a 2-pyrrolyl group, a 2-furyl group, a 3-furyl group, a 5-pyrazolyl group, a 4-pyrazolyl group, a 1-pyrrolyl group, a 1-methyl-2-pyrrolyl group, a 2-methylsulfanyl-1-pyrrolyl group, a 2-methylsulfinyl-1-pyrrolyl group, a 2-methylsulfonyl-1-pyrrolyl group, a 2-methylamino-1-pyrrolyl group, a 2-dimethylamino-1-pyrrolyl group, a 5-bromo-2-furyl group, a 5-nitro-2-furyl group, a 5-cyano-2-furyl group, a 5-methoxy-2-furyl group, a 5-acetyl-2-furyl group, a 5-methoxycarbonyl-2-furyl group, a 2-methyl-3-furyl group, a 2,5-dimethyl-3-furyl group, a 2,4-dimethyl-3-furyl group, a 5-methyl-2-thienyl group, a 3-methyl-2-thienyl group, a 1-methyl-3-trifluoromethyl-5-pyrazolyl group, a 5-chloro-1,3-dimethyl-4-pyrazolyl group, a pyrazol-1-yl group, a 3-chloro-pyrazol-1-yl group, a 3-bromopyrazol-1-yl group, a 4-chloropyrazol-1-yl group, a 4-bromopyrazol-1-yl group, an imidazole-1-yl group, a 1,2,4-triazole-1-yl group, a 3-chloro-1,2,4-triazole-1-yl group, a 1,2,3,4-tetrazol-1-yl group, a 1,2,3,5-tetrazol-1-yl group, a 2-thienyl group, a 3-thienyl group, a 3-trifluoromethyl-1,2,4-triazol-1-yl group, a 4-trifluoromethylpyrazol-1-yl group, a pyrazinyl group, a 4-pyrimidinyl group, a 5-pyrimidinyl group, a 2-pyridyl group, a 3-pyridyl group, a 4-pyridyl group, a 3-fluoro-2-pyridyl group, a 4-fluoro-2-pyridyl group, a 5-fluoro-2-pyridyl group, a 6-fluoro-2-pyridyl group, a 2-pyrimidinyl group, a 3-chloro-5-trifluoromethylpyridin-2-yl group and a 5-trifluoromethylpyridin-2-yl group.

Examples of the "C1 to C6 chain hydrocarbon group having one phenyl group (wherein the phenyl group may have one or more atoms or groups selected from group Z)" in the compound of the present invention include a phenylmethyl group, a 4-chlorophenylmethyl group, and a 4-trifluoromethylphenylmethyl group. At that time, when having two or more atoms or groups selected from group Z, the atoms or groups selected from group Z may be the same or different from each other.

Examples of the "C1 to C6 chain hydrocarbon group having one 5- or 6-membered heterocyclic group (wherein the 5- or 6-membered heterocyclic group may have one or more atoms or groups selected from group Z)" in the compound of the present invention include C1 to C6 alkyl groups having a 5- or 6-membered nonaromatic heterocyclic group such as a tetrahydrofuran-2-ylmethyl group, a tetrahydropyran-2-ylmethyl group and a tetrahydropyran-3-ylmethyl group; and C1 to C6 alkyl groups having a 5- or 6-membered aromatic heterocyclic group such as a thiozol-5-ylmethyl group, a 2-chlorothiozol-5-ylmethyl group, a pyridin-3-ylmethyl group, a 6-chloropyridin-3-ylmethyl group and a 6-trifluoromethylpyridin-3-ylmethyl group. At that time, when having two or more atoms or groups selected from group Z, the atoms or groups selected from group Z may be the same or different from each other.

Examples of the "5- or 6-membered aromatic heterocyclic group (wherein the 5- or 6-membered aromatic heterocyclic group may have one or more atoms or groups selected from the group consisting of halogen atoms, C1 to C3 alkyl groups optionally having a halogen atom, and C1 to C3 alkoxy groups optionally having a halogen atom.)" in the compound of the present invention include a 2-pyrrolyl group, a 2-furyl group, a 3-furyl group, a 5-pyrazolyl group, a 4-pyrazolyl group, a 1-pyrrolyl group, a 1-methyl-2-pyrrolyl group, a 5-bromo-2-furyl group, a 5-methoxy-2-furyl group, a 2-methyl-3-furyl group, a 2,5-dimethyl-3-furyl group, a 2,4-dimethyl-3-furyl group, a 5-methyl-2-thienyl group, a 3-methyl-2-thienyl group, a 1-methyl-3-trifluoromethyl-5-pyrazolyl group, a 5-chloro-1,3-dimethyl-4-pyrazolyl group, a pyrazol-1-yl group, a 3-chloro-pyrazol-1-yl group, a 3-bromopyrazol-1-yl group, a 4-chloropyrazol-1-yl group, a 4-bromopyrazol-1-yl group, an imidazol-1-yl group, a 1,2,4-triazol-1-yl group, a 3-chloro-1,2,4-triazol-1-yl group, a 1,2,3,4-tetrazol-1-yl group, a 1,2,3,5-tetrazol-1-yl group, a 2-thienyl group, a 3-thienyl group, a 3-trifluoromethyl-1,2,4-triazol-1-yl group, a 4-trifluoromethylpyrazol-1-yl group, a pyrazinyl group, a 4-pyrimidinyl group, a 5-pyrimidinyl group, a 2-pyridyl group, a 3-pyridyl group, a 4-pyridyl group, a 3-fluoro-2-pyridyl group, a 4-fluoro-2-pyridyl group, a 5-fluoro-2-pyridyl group, a 6-fluoro-2-pyridyl group, a 2-pyrimidinyl group, a 3-chloro-5-trifluoromethylpyridin-2-yl group and a 5-trifluoromethylpyridin-2-yl group.

Examples of the "C1 to C6 alkyl group having one 5- or 6-membered aromatic heterocyclic group (wherein the 5- or 6-membered aromatic heterocyclic group may have one or more atoms or groups selected from the group consisting of halogen atoms, C1 to C3 alkyl groups optionally having a halogen atom, and C1 to C3 alkoxy groups optionally having a halogen atom.)" in the compound of the present invention include a thiazol-5-ylmethyl group, a 2-chlorothiazol-5-ylmethyl group, a pyridin-3-ylmethyl group, a 6-chloropyridin-3-ylmethyl group and a 6-trifluoromethylpyridin-3-ylmethyl group.

Examples of the "C1 to C6 alkyl group optionally having one or more atoms or groups selected from the group consisting of halogen atoms and a cyclolpropyl group (wherein the cyclolpropyl group may have one or more halogen atoms or one or more C1 to C3 alkyl groups)" in the compound of the present invention include a methyl group, an ethyl group, a propyl group, an isopropyl group, a butyl group, an isobutyl group, a sec-butyl group, a tert-butyl group, a pentyl group, a neopentyl group, a hexyl group, a trifluoromethyl group, a trichloromethyl group, a 2-fluoroethyl group, a 2,2-difluoroethyl group, a 2,2,2,-trifluoroethyl group, a pentafluoroethyl group, a heptafluoroisopropyl group, a cyclopropylmethyl group, a 2-cyclopropylethyl group, a 1-cyclopropylethyl group, and a 1-methylcyclopropylmethyl group.

Examples of the "C1 to C6 chain hydrocarbon group optionally having one or more atoms or groups selected from group W" in the compound of the present invention include C1 to C6 alkyl groups optionally having one or more atoms or groups selected from group W such as a methyl group, an ethyl group, a propyl group, an isopropyl group, a butyl group, an isobutyl group, a sec-butyl group, a tert-butyl group, a pentyl group, a neopentyl group, a hexyl group, a trifluoromethyl group, a trichloromethyl group, a 2-fluoroethyl group, a 2,2-difluoroethyl group, a 2,2,2,-trifluoroethyl group, a pentafluoroethyl group, a methoxymethyl group, an ethoxymethyl group, a propyloxymethyl group, an isopropyloxymethyl group, a butyloxymethyl group, a sec-butyloxymethyl group, an isobutyloxymethyl group, a tert-butyloxymethyl group, a methoxyethyl group, an ethoxyethyl group, a propyloxyethyl group, an isopropyloxyethyl group, a butyloxyethyl group, a sec-butyloxyethyl group, an isobutyloxyethyl group, a tert-butyloxyethyl group, a methylsulfanylethyl group, an ethylsulfanylethyl group, a methylsulfinylethyl group, a methylsulfonylethyl group, a methoxycarbonylmethyl group, a methoxycarbonylethyl group, a 2-cyanoethyl group, a propyl-2-one group, a cyclopropylmethyl group and a cyclohexylmethyl group; C2 to C6 alkenyl groups optionally having one or more atoms or groups selected from group W such as a vinyl group, a 1-propenyl group, a 2-propenyl group, a 1-methylvinyl group, a 2-methyl-1-propenyl group, a 1-butenyl group, a 2-butenyl group, a 3-butenyl group, a 1-pentenyl group, a 1-hexenyl group, a 1,1-difluoroallyl group and a pentafluoroallyl group; and C2 to C6 alkynyl groups optionally having one or more atoms or groups selected from group W such as an ethynyl group, a propargyl group, a 2-butynyl group, a 3-butynyl group, a 1-pentynyl group, a 1-hexynyl group and a 4,4,4-trifluoro-2-butynyl group. At that time, when having two or more atoms or groups selected from group W, the atoms or groups selected from group W may be the same or different from each other.

Examples of the "C1 to C6 alkoxy groups optionally having one or more halogen atoms" in the compound of the present invention include a methoxy group, a trifluoromethoxy group, an ethoxygroup, a 2,2,2-trifluoroethoxygroup, a propoxygroup, an isopropoxy group, a butoxy group, an isobutoxy group, a sec-butoxy group, a tert-butoxy group, a pentyloxy group, and a hexyloxy group.

Examples of the "C2 to C6 alkenyloxy groups optionally having one or more halogen atoms" in the compound of the present invention include a 2-propenyloxy group, a 2-methyl-2-propenyloxy group, a 2-butenyloxy group, a 3-butenyloxy group, a 2-pentenyloxy group, a 2-hexenyloxy group, a 3,3-difluoroallyloxy group, and a 3,3-dichloroallyloxy group.

Examples of the "C2 to C6 alkynyloxy groups optionally having one or more halogen atoms" in the compound of the present invention include a propargyloxy group, a 2-butynyloxy group, a 3-butynyloxy group, a 2-pentynyloxy group, a 2-hexynyloxy group, and a 4,4,4-trifluoro-2-butynyloxy group.

Examples of the "C1 to C6 alkylsulfanyl groups optionally having one or more halogen atoms" in the compound of the present invention include a methylsulfanyl group, an ethylsulfanyl group, a propylsulfanyl group, an isopropylsulfanyl group, a butylsulfanyl group, a pentylsulfanyl group, a hexylsulfanyl group, a trifluoromethylsulfanyl group, a 2,2,2-trifluoroethylsulfanyl group, and a pentafluoroethylsulfanyl group.

Examples of the "C1 to C6 alkylsulfinyl groups optionally having one or more halogen atoms" in the compound of the present invention include a methylsulfinyl group, an ethylsulfinyl group, a propylsulfinyl group, an isopropylsulfinyl group, a butylsulfinyl group, a pentylsulfinyl group, a hexylsulfinyl group, a trifluoromethylsulfinyl group, a 2,2,2-trifluoroethylsulfinyl group, and a pentafluoroethylsulfinyl group.

Examples of the "C1 to C6 alkylsulfonyl groups optionally having one or more halogen atoms" in the compound of the present invention include a methylsulfonyl group, an ethylsulfonyl group, a propylsulfonyl group, an isopropylsulfonyl group, a butylsulfonyl group, a pentylsulfonyl group, a hexylsulfonyl group, a trifluoromethylsulfonyl group, a 2,2,2-trifluoroethylsulfonyl group, and a pentafluoroethylsulfonyl group.

Examples of the "C2 to C6 alkylcarbonyl groups optionally having one or more halogen atoms" in the compound of the present invention include an acetyl group, a propionyl group, a butyryl group, a pentanoyl group, a hexanoyl group, and a trifluoroacetyl group.

Examples of the "C2 to C6 alkoxycarbonyl groups optionally having one or more halogen atoms" in the compound of the present invention include a methoxycarbonyl group, an ethoxycarbonyl group, a propoxycarbonyl group, a butoxycarbonyl group, a pentyloxycarbonyl group, a tert-butoxycarbonyl group, and a 2,2,2-trifluoroethoxycarbonyl group.

Examples of the "C1 to C6 alkylamino groups optionally having one or more halogen atoms" in the compound of the present invention include a methylamino group, an ethylamino group, a 2,2,2-trifluoroethylamino group, a propylamino group, an isopropylamino group, and a butylamino group.

Examples of the "C2 to C8 dialkylamino groups optionally having one or more halogen atoms" in the compound of the present invention include a dimethylamino group, a diethylamino group, a bis(2,2,2-trifluoroethyl)amino group, and a dipropylamino group.

Examples of the "C3 to C6 cycloalkyl groups optionally having one or more halogen atoms" in the compound of the present invention include a cyclopropyl group, a 2,2-difluorocyclopropyl group, a 2,2-dichlorocyclopropyl group, a 2,2-dibromocyclopropyl group, a cyclobutyl group, a cyclopentyl group, and a cyclohexyl group.

Examples of the "C3 to C6 cycloalkyl groups optionally having one or more halogen atoms or one or more C1 to C3 alkyl groups" in the compound of the present invention include a cyclopropyl group, a 1-methylcyclopropyl group, a 2-methylcyclopropyl group, a 1-fluorocyclopropyl group, a 2,2-difluorocyclopropyl group, a 2,2-dichlorocyclopropyl group, a 2,2-bromocyclopropyl group, a cyclobutyl group, a cyclopentyl group, and a cyclohexyl group.

Examples of the "C4 to C9 cyclopropylalkyl groups (wherein the cyclopropyl group optionally has one or more halogen atoms or one or more C1 to C3 alkyl groups)" in the compound of the present invention include a cyclopropylmethyl group, a 2-cyclopropylethyl group, a 1-cyclopropylethyl group, and a 1-methylcyclopropyl group.

Examples of the "C1 to C6 perfluoroalkyl group" in the compound of the present invention include a trifluoromethyl group, a pentafluoroethyl group, a heptafluoropropyl group, and a heptafluoroisopropyl group.

Examples of the "C1 to C6 alkyl group optionally having one or more halogen atoms" in the compound of the present invention include a methyl group, an ethyl group, a propyl group, an isopropyl group, a butyl group, an isobutyl group, a sec-butyl group, a tert-butyl group, a pentyl group, a neopentyl group, a hexyl group, a fluoromethyl group, a chloromethyl group, a bromomethyl group, an iodomethyl group, a difluoromethyl group, a dichloromethyl group, a trifluoromethyl group, a chlorodifluoromethyl group, a bromodifluoromethyl group, a trichloromethyl group, a 2-fluoroethyl group, a 2-chloroethyl group, a 2-bromoethyl group, a 2,2-difluoroethyl group, a 2,2,2-trifluoroethyl group, a pentafluoroethyl group, a heptafluoropropyl group, and a heptafluoroisopropyl group.

Examples of the "C2 to C6 alkenyl group optionally having one or more halogen atoms" in the compound of the present invention include a vinyl group, a 1-propenyl group, a 2-propenyl group, a 1-methylvinyl group, a 2-methyl-1-propenyl group, a 1-butenyl group, a 2-butenyl group, a 3-butenyl group, a 1-pentenyl group, a 1-hexenyl group, a 1,1-difluoroallyl group, and a pentafluoroallyl group.

Examples of the "C2 to C6 alkynyl group optionally having one or more halogen atoms" in the compound of the present invention include an ethynyl group, a propargyl group, a 2-butynyl group, a 3-butynyl group, a 1-pentynyl group, a 1-hexynyl group, and a 4,4,4-trifluoro-2-butynyl group.

Examples of the "C3 to C6 alkenyl group optionally having one or more halogen atoms" in the compound of the present invention include a 1-propenyl group, a 2-propenyl group, a 1-methylvinyl group, a 2-methyl-1-propenyl group, a 1-butenyl group, a 2-butenyl group, a 3-butenyl group, a 1-pentenyl group, a 1-hexenyl group, a 1,1-difluoroallyl group, and a pentafluoroallyl group.

Examples of the "C3 to C6 alkynyl group optionally having one or more halogen atoms" in the compound of the present invention include a propargyl group, a 2-butynyl group, a 3-butynyl group, a 1-pentynyl group, a 1-hexynyl group, and a 4,4,4-trifluoro-2-butynyl group.

Examples of the "C2 to C6 alkoxyalkyl group optionally having one or more halogen atoms" in the compound of the present invention include a methoxymethyl group, an ethoxymethyl group, a 1-(methoxy)ethyl group, a 2-(methoxy)ethyl group, a 1-(ethoxy)ethyl group, and a 2-(ethoxy)ethyl group.

Examples of the "pyridyl group (wherein the pyridyl group optionally has one or more atoms or substituents selected from the group consisting of halogen atoms, C1 to C3 alkyl groups optionally having a halogen atom, and C1 to C3 alkoxy groups optionally having a halogen atom.)" in the compound of the present invention include a 2-pyridyl group, a 3-pyridyl group, 4-pyridyl group, a 5-trifluoromethyl-2-pyridyl group, and a 3-chloro-5-trifluoromethyl-2-pyridyl group.

Examples of the "pyrimidinyl group (wherein the pyrimidinyl group optionally has one or more atoms or substituents selected from the group consisting of halogen atoms, C1 to C3 alkyl groups optionally having a halogen atom, and C1 to C3 alkoxy groups optionally having a halogen atom.)" in the compound of the present invention include a 2-pyrimidinyl group, a 4-pyrimidinyl group, a 5-pyrimidinyl group, and a 2-chloro-4-pyrimidinyl group.

Examples of the "C1 to C6 alkyl group having one thiazolyl group (wherein the thiazolyl group optionally has one or more atoms or substituents selected from the group consisting of halogen atoms, C1 to C3 alkyl groups optionally having a halogen atom, and C1 to C3 alkoxy groups optionally having a halogen atom.)" in the compound of the present invention include a (thiazol-5-yl)methyl group, a (2-chlorothiazol-5-yl) methyl group, and a 1-(2-chlorothiazol-5-yl)ethyl group.

Examples of the "C1 to C6 alkyl group having one pyridyl group (wherein the pyridyl group optionally has one or more atoms or substituents selected from the group consisting of halogen atoms, C1 to C3 alkyl groups optionally having a halogen atom, and C1 to C3 alkoxy groups optionally having a halogen atom.)" in the compound of the present invention include a (pyridin-5-yl)methyl group, a (2-chloropyridin-5-yl)methyl group, a 1-(2-chloropyridin-5-yl)ethyl group, and a (2-trifluoromethylpyridin-5-yl)methyl group.

Examples of the compound of the present invention include the following compounds.

In the formula (1), compounds wherein $A^1$ is $=CR^6—$;

In the formula (1), compounds wherein $A^1$ is $=CR^6—$, $G^1$ is a nitrogen atom, and $G^2$ is $=CR^5—$;

In the formula (1), compounds wherein $A^1$ is $=CR^6—$, $G^1$ is a nitrogen atom, $G^2$ is $=CR^5—$, and $A^2$ is $=CR^7—$;

In the formula (1), compounds wherein $A^1$ is $=CR^6—$, $G^1$ is $=CR^5—$, and $G^2$ is a nitrogen atom;

In the formula (1), compounds wherein $A^1$ is $=CR^6—$, and $G^1$ and $G^2$ are a nitrogen atom;

In the formula (1), compounds wherein $A^1$ is a nitrogen atom;

In the formula (1), compounds wherein $A^1$ is a nitrogen atom, and $A^2$ is $=CR^7—$;

In the formula (1), compounds wherein

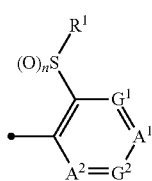

is J1 to J6 as shown below

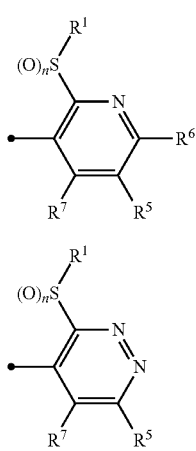

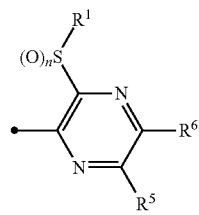

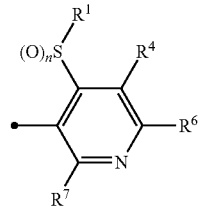

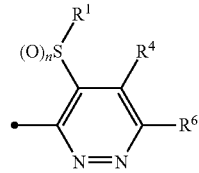

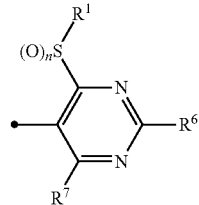

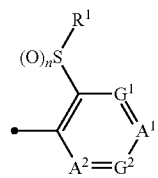

wherein symbols represent the same meaning as in the formula (1);

In the formula (1), compounds wherein

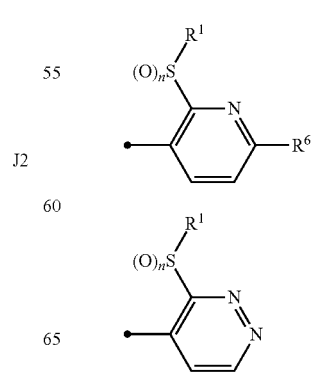

is J1' to J6' as shown below

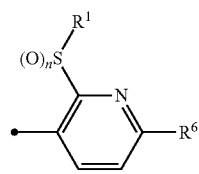

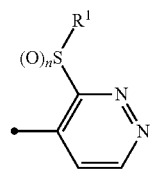

-continued

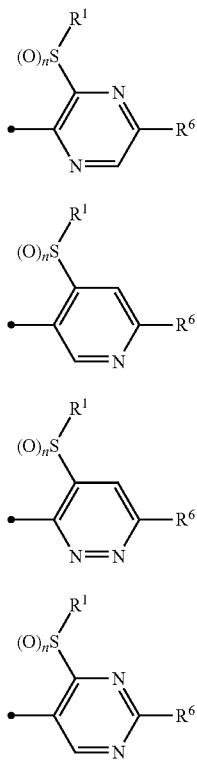

wherein symbols represent the same meaning as in the formula (1);

In the formula (1), compounds wherein $R^1$ is a C1 to C6 chain hydrocarbon group optionally having one or more atoms or groups selected from group X;

In the formula (1), compounds wherein $R^1$ is a C1 to C6 alkyl group optionally having one or more atoms or groups selected from halogen atoms and a cyclopropyl group (wherein the cyclopropyl group optionally has one or more halogen atoms or one or more C1 to C3 alkyl groups), a C2 to C6 alkenyl group optionally having one or more halogen atoms, or a C2 to C6 alkynyl group optionally having one or more halogen atoms;

In the formula (1), compounds wherein $R^1$ is a C1 to C6 alkyl group optionally having one or more atoms or groups selected from halogen atoms and a cyclopropyl group (wherein the cyclopropyl group optionally has one or more halogen atoms or one or more C1 to C3 alkyl groups);

In the formula (1), compounds wherein $R^1$ is a C1 to C6 alkyl group, a C1 to C6 haloalkyl group, or a C4 to C9 cyclopropylalkyl group (wherein the cyclopropyl group optionally has one or more halogen atoms or one or more C1 to C3 alkyl groups);

In the formula (1), compounds wherein $R^1$ is a C2 to C6 alkyl group, a C1 to C6 haloalkyl group, or a C4 to C9 cyclopropylalkyl group (wherein the cyclopropyl group optionally has one or more halogen atoms or one or more C1 to C3 alkyl groups);

In the formula (1), compounds wherein $R^1$ is a methyl group, an ethyl group, a propyl group, an isopropyl group, a trifluoromethyl group, a 2,2,2-trifluoroethyl group, or a cyclopropylmethyl group;

In the formula (1), compounds wherein $R^1$ is an ethyl group or a cyclopropylmethyl group;

In the formula (1), compounds wherein $R^1$ is an ethyl group;

In the formula (1), compounds wherein $R^2$ is a C1 to C6 chain hydrocarbon group optionally having one or more atoms or groups selected from group X, $-OR^{11}$, $-S(O)_mR^{11}$, $-SF_5$, a halogen atom, or a hydrogen atom;

In the formula (1), compounds wherein $R^2$ is a C1 to C6 chain hydrocarbon group optionally having one or more atoms or groups selected from group X, $-OR^{11}$, $-S(O)_mR^{11}$, $-SF_5$, or a halogen atom;

In the formula (1), compounds wherein $R^2$ is a C1 to C6 alkyl group optionally having one or more halogen atoms, $-OR^{11}$ (wherein $R^{11}$ is a C1 to C6 alkyl group optionally having one or more halogen atoms), $-S(O)_mR^{11}$ (wherein $R^{11}$ is a C1 to C6 alkyl group optionally having one or more halogen atoms), $-SF_5$ or a halogen atom;

In the formula (1), compounds wherein $R^2$ is a C1 to C6 haloalkyl group, $-OR^{11}$ (wherein $R^{11}$ is a C1 to C6 haloalkyl group), $-S(O)_mR^{11}$ (wherein $R^{11}$ is a C1 to C6 haloalkyl group), $-SF_5$ or a halogen atom;

In the formula (1), compounds wherein $R^2$ is a C1 to C6 haloalkyl group, $-OR^1$ (wherein $R^{11}$ is a C1 to C6 haloalkyl group), $-S(O)_mR^{11}$ (wherein $R^{11}$ is a C1 to C6 haloalkyl group) or $-SF_5$;

In the formula (1), compounds wherein $R^2$ is a C1 to C6 haloalkyl group, $-OR^1$ (wherein $R^{11}$ is a C1 to C6 haloalkyl group), $-S(O)_mR^{11}$ (wherein $R^1$ is a C1 to C6 haloalkyl group) or a halogen atom;

In the formula (1), compounds wherein $R^2$ is a C1 to C6 haloalkyl group, $-OR^{11}$ (wherein $R^{11}$ is a C1 to C6 haloalkyl group) or $-S(O)_mR^{11}$ (wherein $R^{11}$ is a C1 to C6 haloalkyl group);

In the formula (1), compounds wherein $R^2$ is a C1 to C6 perfluoroalkyl group, $-OR^{11}$ (wherein $R^{11}$ is a C1 to C6 perfluoroalkyl group) or $-S(O)_mR^1$ (wherein $R^{11}$ is a C1 to C6 perfluoroalkyl group);

In the formula (1), compounds wherein $R^2$ is a trifluoromethyl group, $-CF_2CF_3$, $-CF_2CF_2CF_3$, $-CF(CF_3)_2$, $-OCF_3$, $-OCF_2CF_3$, $-SCF_3$, $-S(O)CF_3$, $-S(O)_2CF_3$, $-SCF_2CF_3$, $-S(O)CF_2CF_3$, $-S(O)_2CF_2CF_3$, $SF_5$, a fluorine atom, a chlorine atom, a bromine atom, or an iodine atom;

In the formula (1), compounds wherein $R^3$ is a C1 to C6 chain hydrocarbon group optionally having one or more atoms or groups selected from group X, $-OR^1$, $-S(O)_mR^{11}$, $-SF_5$, a halogen atom, or a hydrogen atom;

In the formula (1), compounds wherein $R^3$ is a hydrogen atom;

In the formula (1), compounds wherein, when $G^1$ is $=CR^4-$, $R^4$ is a C1 to C6 chain hydrocarbon group optionally having one or more atoms or groups selected from group X, a phenyl group optionally having one or more atoms or groups selected from group Z, a 5- or 6-membered heterocyclic group optionally having one or more atoms or groups selected from group Z, $-OR^{13}$, $-S(O)_mR^{13}$, $-SF_5$, a cyano group, a nitro group, a halogen atom, or a hydrogen atom;

In the formula (1), compounds wherein, when $G^1$ is $=CR^4-$, $R^4$ is a halogen atom or a hydrogen atom;

In the formula (1), compounds wherein, when $G^1$ is $=CR^4-$, $R^4$ is a hydrogen atom;

In the formula (1), compounds wherein, when $G^2$ is $=CR^5-$, $R^5$ is a C1 to C6 chain hydrocarbon group optionally having one or more atoms or groups selected from group X, a phenyl group optionally having one or more atoms or groups selected from group Z, a 5- or 6-membered heterocyclic group optionally has one or more atoms or groups selected from group Z, —OR$^{13}$, —S(O)$_m$R$^{13}$, —SF$_5$, a cyano group, a nitro group, a halogen atom, or a hydrogen atom;

In the formula (1), compounds wherein, when G$^2$ is =CR$^5$—, R$^5$ is a halogen atom or a hydrogen atom;

In the formula (1), compounds wherein, when G$^2$ is =CR$^5$—, R$^5$ is a hydrogen atom;

In the formula (1), compounds wherein, when A$^1$ is =CR$^6$—, R$^6$ is a C1 to C6 chain hydrocarbon group optionally having one or more atoms or groups selected from group X, a phenyl group optionally having one or more atoms or groups selected from group Z, a 5- or 6-membered heterocyclic group optionally has one or more atoms or groups selected from group Z, —OR$^{13}$, —S(O)$_m$R$^{13}$, —SF$_5$, a cyano group, a nitro group, a halogen atom, or a hydrogen atom;

In the formula (1), compounds wherein, when A$^1$ is =CR$^6$—, R$^6$ is a C1 to C6 alkyl group optionally having one or more halogen atoms, a C2 to C6 alkenyl group optionally having one or more halogen atoms, a C2 to C6 alkynyl group optionally having one or more halogen atoms, a 5- or 6-membered aromatic heterocyclic group (wherein the 5- or 6-membered aromatic heterocyclic group optionally has one or more atoms or substituents selected from a group consisting of halogen atoms, C1 to C3 alkyl groups optionally having a halogen atom and C1 to C3 alkoxy groups optionally having a halogen atom), —OR$^{13}$ (wherein R$^{13}$ is a C1 to C6 alkyl group optionally having one or more halogen atoms), —S(O)$_m$R$^{13}$ (wherein R$^{13}$ is a C1 to C6 alkyl group optionally having one or more halogen atoms), a cyano group, a nitro group, a halogen atom, or a hydrogen atom;

In the formula (1), compounds wherein, when A$^1$ is =CR$^6$—, R$^6$ is a C1 to C6 alkyl group optionally having one or more halogen atoms, a C2 to C6 alkenyl group optionally having one or more halogen atoms, a C2 to C6 alkynyl group optionally having one or more halogen atoms, a pyridyl group (wherein the pyridyl group optionally has one or more atoms or substituents selected from the group consisting of halogen atoms, C1 to C3 alkyl groups optionally having a halogen atom, and C1 to C3 alkoxy groups optionally having a halogen atom), a pyrimidinyl group (wherein the pyrimidinyl group optionally has one or more atoms or substituents selected from the group consisting of halogen atoms, C1 to C3 alkyl groups optionally having a halogen atom, and C1 to C3 alkoxy groups optionally having a halogen atom), —OR$^{13}$ (wherein R$^{13}$ is a C1 to C6 alkyl group optionally having one or more halogen atoms), —S(O)$_m$R$^{13}$ (wherein R$^{13}$ is a C1 to C6 alkyl group optionally having one or more halogen atoms), a halogen atom, or a hydrogen atom;

In the formula (1), compounds wherein, when A$^1$ is =CR$^6$—, R$^6$ is a C1 to C6 alkyl group optionally having one or more halogen atoms, —OR$^{13}$ (wherein R$^{13}$ is a C1 to C6 alkyl group optionally having one or more halogen atoms), —S(O)$_m$R$^{13}$ (wherein R$^{13}$ is a C1 to C6 alkyl group optionally having one or more halogen atoms), a halogen atom, or a hydrogen atom;

In the formula (1), compounds wherein, when A$^1$ is =CR$^6$—, R$^6$ is a methyl group, a fluoromethyl group, a difluoromethyl group, a trifluoromethyl group, an ethyl group, an ethenyl group, an ethynyl group, a fluoromethyl group, a difluoromethyl group, a trifluoromethyl group, —CF$_2$CF$_3$, —CF$_2$CF$_2$CF$_3$, —CF(CF$_3$)$_2$, —CF$_2$CF$_2$CF$_2$CF$_3$, —OCF$_3$, —OCF$_2$CF$_3$, —SCF$_3$, —S(O)CF$_3$, —S(O)$_2$CF$_3$, —SCF$_2$CF$_3$, —S(O)CF$_2$CF$_3$, —S(O)$_2$CF$_2$CF$_3$, a 2-pyridyl group, a 5-trifluoromethyl-2-pyridyl group, a 2-pyrimidinyl group, a fluorine atom, a chlorine atom, a bromine atom, an iodine atom, or a hydrogen atom;

In the formula (1), compounds wherein, when A$^1$ is =CR$^6$—, R$^6$ is a methyl group, a fluoromethyl group, a difluoromethyl group, a trifluoromethyl group, an ethyl group, an ethenyl group, an ethynyl group, a fluoromethyl group, a difluoromethyl group, a trifluoromethyl group, —CF$_2$CF$_3$, —CF$_2$CF$_2$CF$_3$, —CF(CF$_3$)$_2$, —CF$_2$CF$_2$CF$_2$CF$_3$, —OCF$_3$, —OCF$_2$CF$_3$, —SCF$_3$, —S(O)CF$_3$, —S(O)$_2$CF$_3$, —SCF$_2$CF$_3$, —S(O) CF$_2$CF$_3$, —S(O)$_2$CF$_2$CF$_3$, a fluorine atom, a chlorine atom, a bromine atom, an iodine atom, or a hydrogen atom;

In the formula (1), compounds wherein, when A$^1$ is =CR$^6$—, R$^6$ is a methyl group, a fluoromethyl group, a difluoromethyl group, a trifluoromethyl group, an ethyl group, an ethenyl group, an ethynyl group, a fluoromethyl group, a difluoromethyl group, a trifluoromethyl group, —CF$_2$CF$_3$, —CF$_2$CF$_2$CF$_3$, —CF(CF$_3$)$_2$, —CF$_2$CF$_2$CF$_2$CF$_3$, —OCF$_3$, —OCF$_2$CF$_3$, —SCF$_3$, —S(O)CF$_3$, —S(O)$_2$CF$_3$, —SCF$_2$CF$_3$, —S(O) CF$_2$CF$_3$, —S(O)$_2$CF$_2$CF$_3$, a fluorine atom, a chlorine atom, a bromine atom, or an iodine atom;

In the formula (1), compounds wherein, when A$^2$ is =CR$^7$—, R$^7$ is a C1 to C6 chain hydrocarbon group optionally having one or more atoms or groups selected from group X, a phenyl group optionally having one or more atoms or groups selected from group Z, a 5- or 6-membered heterocyclic group optionally having one or more atoms or groups selected from group Z, —OR$^{13}$, —S(O)$_m$R$^{13}$, —SF$_5$, a cyano group, a nitro group, a halogen atom, or a hydrogen atom;

In the formula (1), compounds wherein, when A$^2$ is =CR$^7$—, R$^7$ is a halogen atom or a hydrogen atom;

In the formula (1), compounds wherein, when A$^2$ is =CR$^7$—, R$^7$ is a hydrogen atom;

In the formula (1), compounds wherein A$^2$ is a nitrogen atom;

In the formula (1), compounds wherein, when A$^3$ is —NR$^8$—, R$^8$ is a C1 to C6 chain hydrocarbon group optionally having one or more atoms or groups selected from group W, a C1 to C6 chain hydrocarbon group having one phenyl group (wherein the phenyl group optionally has one or more atoms or groups selected from group Z), a C1 to C6 chain hydrocarbon group having one 5- or 6-membered heterocyclic group (wherein the 5- or 6-membered heterocyclic group optionally has one or more atoms or groups selected from group Z), or a hydrogen atom;

In the formula (1), compounds wherein, when A$^3$ is —NR$^8$—, R$^8$ is a C1 to C6 alkyl group optionally having one or more halogen atoms, a C3 to C6 alkenyl group optionally having one or more halogen atoms, a C3 to C6 alkynyl group optionally having one or more halogen atoms, a C1 to C6 alkyl group optionally having one 5- or 6-membered aromatic heterocyclic group (wherein the 5- or 6-membered aromatic heterocyclic group optionally has one or more atoms or substituents selected from a group consisting of halogen atoms, C1 to C3 alkyl groups optionally having a halogen atom and C1 to C3 alkoxy groups optionally having a halogen atom), a C2 to C6 alkoxyalkyl group optionally having one or more halogen atoms, or a hydrogen atom;

In the formula (1), compounds wherein, when A$^3$ is —NR$^8$—, R$^8$ is a C1 to C6 alkyl group optionally having one or more halogen atoms, a C3 to C6 alkenyl group optionally having one or more halogen atoms, a C3 to C6 alkynyl group optionally having one or more halogen atoms, or a C1 to C6 alkyl group having one 5- or 6-membered aromatic heterocyclic group (wherein the 5- or 6-membered aromatic heterocyclic group optionally has one or more atoms or substituents selected from a group consisting of halogen atoms, C1 to C3 alkyl groups optionally having a halogen atom and C1 to C3 alkoxy groups optionally having a halogen atom);

In the formula (1), compounds wherein, when A$^3$ is —NR$^8$—, R$^8$ is a C1 to C6 alkyl group optionally having one or more halogen atoms, a C3 to C6 alkenyl group optionally having one or more halogen atoms, a C3 to C6 alkynyl group optionally having one or more halogen atoms, a C1 to C6 alkyl group having one thiazolyl group (wherein the thiazolyl group optionally has one or more atoms or substituents selected from the group consisting of halogen atoms, C1 to C3 alkyl groups optionally having a halogen atom, and C1 to C3 alkoxy groups optionally having a halogen atom), a C1 to C6 alkyl group having one pyridyl group (wherein the pyridyl group optionally has one or more atoms or substituents selected from the group consisting of halogen atoms, C1 to C3 alkyl groups optionally having a halogen atom, and C1 to C3 alkoxy groups optionally having a halogen atom), a C2 to C6 alkoxyalkyl group optionally having one or more halogen atoms, or a hydrogen atom;

In the formula (1), compounds wherein, when $A^3$ is $—NR^8—$, $R^8$ is a methyl group, an ethyl group, a propyl group, an allyl group, a propargyl group, a (2-chlorthiazol-5-yl)methyl group, a (2-chloropyridin-5-yl)methyl group, a hydrogen atom, a methoxymethyl group, an ethoxymethyl group, a 1-(methoxy)ethyl group, or a 1-(ethoxy)ethyl group;

In the formula (1), compounds wherein, when $A^3$ is $—NR^8—$, $R^8$ is a methyl group, an ethyl group, a propyl group, an allyl group, a propargyl group, a (2-chlorthiazol-5-yl)methyl group, or a (2-chloropyridin-5-yl)methyl group;

In the formula (1), compounds wherein, when $A^3$ is $—NR^8—$, $R^8$ is a methyl group or a propargyl group;

In the formula (1), compounds wherein, when $A^3$ is $—NR^8—$, $R^8$ is a hydrogen atom or a C2 to C6 alkoxyalkyl group optionally having one or more halogen atoms;

In the formula (1), compounds wherein, when $A^3$ is $—NR^8—$, $R^8$ is a hydrogen atom, a methoxymethyl group, an ethoxymethyl group, a 1-(methoxy)ethyl group, or a 1-(ethoxy)ethyl group;

In the formula (1), compounds wherein, when $A^4$ is $=CR^9—$, $R^9$ is a C1 to C6 chain hydrocarbon group optionally having one or more halogen atoms, $—OR^{16}$, $—S(O)_mR^{16}$, a halogen atom, or a hydrogen atom;

In the formula (1), compounds wherein, when $A^4$ is $=CR^9—$, $R^9$ is a C1 to C6 alkyl group optionally having one or more halogen atoms, $—OR^{16}$ (wherein $R^{16}$ is a C1 to C6 alkyl group optionally having one or more halogen atoms), $—S(O)_mR^{16}$ (wherein $R^{16}$ is a C1 to C6 alkyl group optionally having one or more halogen atoms), a halogen atom, or a hydrogen atom;

In the formula (1), compounds wherein, when $A^4$ is $=CR^9—$, $R^9$ is a halogen atom or a hydrogen atom;

In the formula (1), compounds wherein, when $A^4$ is $=CR^9—$, $R^9$ is a hydrogen atom;

In the formula (1), compounds wherein, when $A^4$ is a nitrogen atom;

In the formula (1), compounds wherein, when $A^5$ is $=CR^{10}—$, $R^{10}$ is a C1 to C6 chain hydrocarbon group optionally having one or more halogen atoms, a halogen atom, or a hydrogen atom;

In the formula (1), compounds wherein, when $A^5$ is $=CR^{10}—$, $R^{10}$ is a C1 to C6 alkyl group optionally having one or more halogen atoms, $—OR^{16}$ (wherein $R^{16}$ is a C1 to C6 alkyl group optionally having one or more halogen atoms), $—S(O)_mR^{16}$ (wherein $R^{16}$ is a C1 to C6 alkyl group optionally having one or more halogen atoms), a halogen atom, or a hydrogen atom;

In the formula (1), compounds wherein, when $A^5$ is $=CR^{10}—$, $R^{10}$ is a halogen atom, or a hydrogen atom;

In the formula (1), compounds wherein, when $A^5$ is $=CR^{10}—$, $R^{10}$ is a fluorine atom, a chlorine atom, a bromine atom, an iodine atom, or a hydrogen atom;

In the formula (1), compounds wherein, when $A^5$ is $=CR^{10}—$, $R^{10}$ is a fluorine atom or a hydrogen atom;

In the formula (1), compounds wherein, when $A^5$ is a nitrogen atom;

In the formula (1), compounds wherein, when $A^3$ is $—NR^8—$;

In the formula (1), compounds wherein, when $A^3$ is a sulfur atom;

In the formula (1), compounds wherein, when $A^3$ is an oxygen atom;

In the formula (1), compounds wherein, when $A^4$ is $=CR^9—$ (especially, $=CH—$);

In the formula (1), compounds wherein, when $A^4$ is $=CR^9—$ (especially, $=CH—$), and $A^5$ is a nitrogen atom;

In the formula (1), compounds wherein, when $A^4$ is $=CR^9—$ (especially, $=CH—$), and $A^5$ is $=CR^1—$ (especially, $=CH—$);

In the formula (1), compounds wherein $R^3$ is a hydrogen atom, and $A^4$ is $=CR^9—$ (especially, $=CH—$);

In the formula (1), compounds wherein $R^3$ is a hydrogen atom, and $R^5$ is a nitrogen atom;

In the formula (1), compounds wherein $R^3$ is a hydrogen atom, $A^4$ is $=CR^9—$ (especially, $=CH—$), and $A^5$ is $=CR^{10}—$ (especially, $=CH—$);

In the formula (1), compounds wherein $R^3$ is a hydrogen atom, $A^4$ is $=CR^9—$ (especially, $=CH—$), and $A^5$ is a nitrogen atom;

In the formula (1), compounds wherein $R^3$ is a hydrogen atom, $A^4$ is $=CR^9—$ (especially, $=CH—$), $A^5$ is a nitrogen atom, and

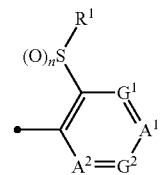

in the formula (1) is J1' to J6' as shown below,

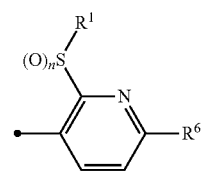
J1'

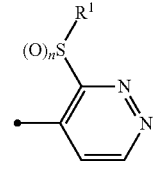
J2'

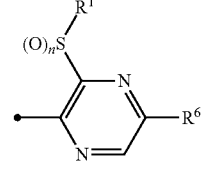
J3'

-continued

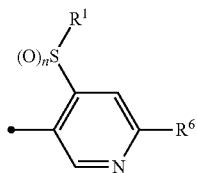
J4'

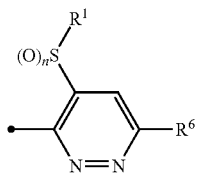
J5'

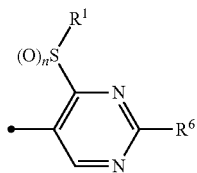
J6' wherein symbols represent the same meaning as in the formula (1); and

In the formula (1), compounds wherein $R^3$ is a hydrogen atom,
$G^1$ is a hydrogen atom or =CH—,
$G^2$ is a hydrogen atom or =CH—,
$A^1$ is a nitrogen atom or =CR$^6$—, $R^6$ is a C1 to C6 alkyl group optionally having one or more halogen atoms, —OR$^{13}$ (wherein R$^{13}$ is a C1 to C6 alkyl group optionally having one or more halogen atoms), —S(O)$_m$R$^{13}$ (wherein R$^{13}$ is a C1 to C6 alkyl group optionally having one or more halogen atoms), a halogen atom, or a hydrogen atom,
$A^2$ is a nitrogen atom or =CH—,
$A^3$ represents —NR$^8$—, an oxygen atom, or a sulfur atom, R$^8$ is a C1 to C6 alkyl group optionally having one or more halogen atoms, a C3 to C6 alkenyl group optionally having one or more halogen atoms, a C3 to C6 alkynyl group optionally having one or more halogen atoms, a C2 to C6 alkoxyalkyl group optionally having one or more halogen atoms, or a hydrogen atom,
$A^4$ is =CR$^9$— (especially, =CH—), and
$A^5$ is a nitrogen atom.

Next, the method for producing the compound of the present invention will be described.

The compound of the present invention and an intermediate compound can be produced, for example, according to the following (Production Method 1) to (Production Method 27).
(Production Method 1)

The compound of the present invention in which n is 1 or 2 in the formula (1) can be produced by oxidizing the compound of the present invention in which n is 0.

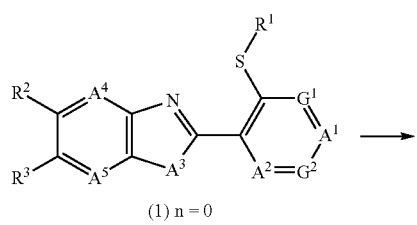
(1) n = 0

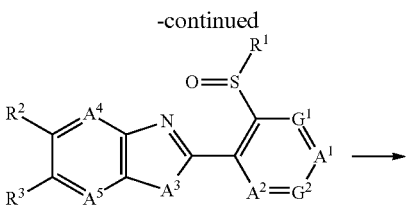
(1) n = 1

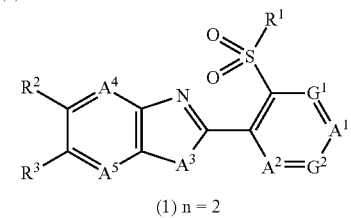
(1) n = 2 wherein symbols represent the same meaning as in the formula (1).

The compound of the present invention (1-n1) in which n is 1 in the formula (1) can be produced by subjecting the compound of the present invention (1-n0) in which n is 0 to an oxidation reaction.

The reaction is usually carried out in the presence of a solvent. Examples of the solvent include aliphatic halogenated hydrocarbons such as dichloromethane and chloroform, alcohols such as methanol and ethanol, acetic acid, water, and mixtures thereof.

Examples of the oxidizing agent used in the oxidation reaction include sodiumperiodate and m-chloroperbenzoic acid.

In the reaction, the oxidizing agent is usually used in a ratio of 1 to 3 mol, based on 1 mol of 1 mol of the compound of the present invention (1-n0). Preferably, the oxidizing agent is used in a ratio of 1 to 1.2 mol, based on 1 mol of the compound of the present invention (1-n0).

The reaction temperature is usually within the range of –20 to 80° C. The reaction time is usually within the range of 0.1 to 12 hours.

After completion of the reaction, the compound of the present invention (1-n1) can be isolated by subjecting it to normal post-process operations. The isolated compound of the present invention (1-n1) also can be further purified by chromatography, recrystallization, or the like.

The compound of the present invention (1-n2) in which n is 2 in the formula (1) can be produced by allowing the compound of the present invention (1-n1) in which n is 1 to react with an oxidizing agent.

The reaction is usually carried out in the presence of a solvent. Examples of the solvent include aliphatic halogenated hydrocarbons such as dichloromethane and chloroform, alcohols such as methanol and ethanol, acetic acid, water, and mixtures thereof.

Examples of the oxidizing agent include m-chloroperbenzoic acid and aqueous hydrogen peroxide.

In the reaction, the oxidizing agent is usually used in a ratio of 1 to 4 mol, based on 1 mol of the compound of the present invention (1-n1). Preferably, the oxidizing agent is used in a ratio of 1 to 2 mol, based on 1 mol of the compound of the present invention (1-n1).

The reaction temperature is usually within the range of –20 to 120° C. The reaction time is usually within the range of 0.1 to 12 hours.

After completion of the reaction, the compound of the present invention (1-n2) can be isolated by subjecting it to normal post-process operations. The compound of the present invention (1-n2) also can be further purified by chromatography, recrystallization, or the like.

The compound of the present invention (1-n2) in which n is 2 in the formula (1) can be produced by a one step reaction (one pot) by allowing the compound of the present invention (1-n0) in which n is 0 to react with an oxidizing agent.

The reaction is usually carried out in the presence of a solvent. Examples of the solvent include aliphatic halogenated hydrocarbons such as dichloromethane and chloroform, alcohols such as methanol and ethanol, acetic acid, water, and mixtures thereof.

Examples of the oxidizing agent include m-chloroperbenzoic acid and aqueous hydrogen peroxide.

In the reaction, the oxidizing agent is usually used in a ratio of 2 to 5 mol, based on 1 mol of the compound of the present invention (1-n0). Preferably, the oxidizing agent is used in a ratio of 2 to 3 mol, based on 1 mol of the compound of the present invention (1-n0).

The reaction temperature is usually within the range of 0 to 120° C. The reaction time is usually within the range of 0.1 to 12 hours.

After completion of the reaction, the compound of the present invention (1-n2) can be isolated by subjecting it to normal post-process operations. The isolated compound of the present invention (1-n2) also can be further purified by chromatography, recrystallization, or the like.

(Production Method 2)

The compound of the present invention can be produced by allowing the intermediate compound (M1) to react with the intermediate compound (M2) or the intermediate compound (M3) to produce the intermediate compound (M4), then condensing the obtained intermediate compound (M4) between the molecules.

wherein symbols represents the same meaning as in formula (1).

The intermediate compound (M4) can be produced by allowing the intermediate compound (M1) to react with the intermediate compound (M2), in the presence of a condensing agent.

The reaction is usually carried out in the presence of a solvent. Examples of the solvent include ethers such as 1,4-dioxane, diethyl ether, tetrahydrofuran (hereinafter, referred to as THF) and tert-butyl methyl ether, halogenated hydrocarbons such as dichloromethane, chloroform, carbon tetrachloride, 1,2-dichloroethane and chlorobenzene, aromatic hydrocarbons such as toluene, benzene and xylene, esters such as ethyl acetate and butyl acetate, nitriles such as acetonitrile, aprotic polar solvents such as N,N-dimethylformamide (hereinafter, referred to as DMF), N-methyl pyrrolidone (hereinafter, referred to as NMP), 1,3-dimethyl-2-imidazolidinone (hereinafter, referred to as DMI) and dimethyl sulfoxide (hereinafter, referred to as DMSO), nitrogen-containing aromatic compounds such as pyridine and quinolone, and mixtures thereof.

Examples of the condensing agent include carbodiimides such as 1-ethyl-3-(3-dimethylaminopropyl) carbodiimide hydrochloride (hereinafter, referred to as EDCI hydrochloride) and 1,3-dicyclohexylcarbodiimide and benzotriazol-1-yloxy-tris(dimethylamino)phosphonium hexafluorophosphate (hereinafter, referred to as BOP reagent).

The reaction can be also carried out by adding a catalyst, as necessary. Examples of the catalyst include 1-hydroxybenzotriazole (hereinafter, referred to as HOBt).

In the reaction, the intermediate compound (M2) is usually used in a ratio of 1 to 3 mol, the condensing agent is usually used in a ratio of 1 to 5 mol, and the catalyst is usually used in a ratio of 0.01 to 1 mol, based on 1 mol of the intermediate compound (M1).

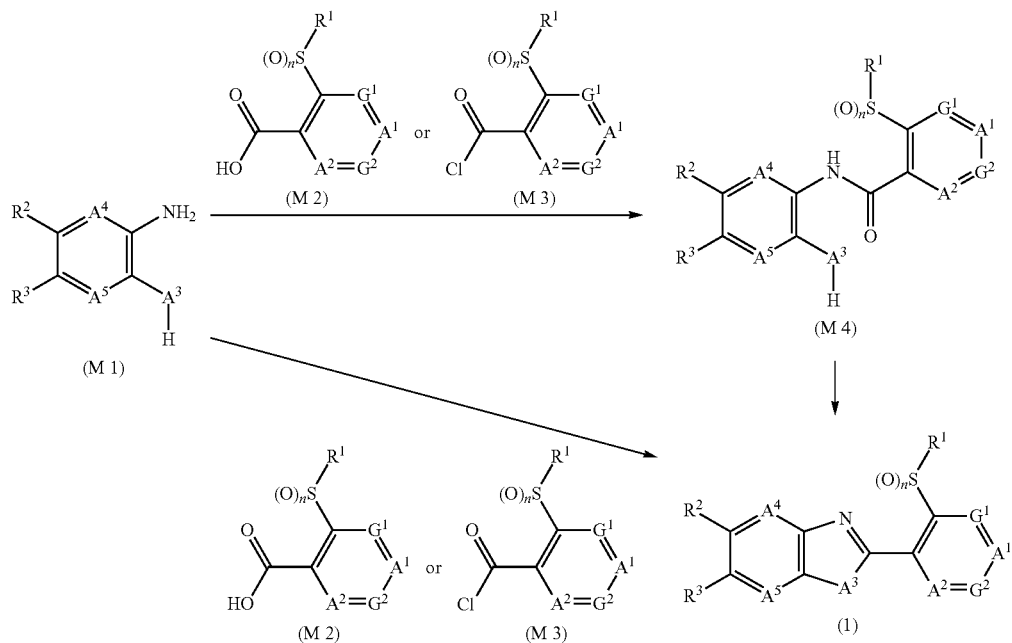

The reaction temperature is usually within the range of 0 to 120° C. The reaction time is usually within the range of 0.1 to 24 hours.

After completion of the reaction, the intermediate compound (M4) can be isolated by subjecting it to normal post-process operations. The isolated intermediate compound (M4) also can be further purified by recrystallization, chromatography, or the like.

In addition, the intermediate compound (M4) can be produced by allowing the intermediate compound (M1) to react with the intermediate compound (M3).

The reaction is usually carried out in the presence of a solvent. Examples of the solvent include ethers such as THF, ethylene glycol dimethyl ether, tert-butyl methyl ether and 1,4-dioxane, aliphatic hydrocarbons such as hexane, heptane and octane, aromatic hydrocarbons such as toluene and xylene, halogenated hydrocarbons such as chlorobenzene, esters such as ethyl acetate and butyl acetate, nitriles such as acetonitrile, aprotic polar solvents such as DMF, NMP, DMI and DMSO, and mixtures thereof.

The reaction can be also carried out by adding a base, as necessary. Examples of the base include alkali metal carbonates such as sodium carbonate and potassium carbonate, tertiary amines such as triethylamine and N,N-diisopropylethylamine, and nitrogen-containing aromatic compounds such as pyridine and 4-dimethylaminopyridine.

In the reaction, the intermediate compound (M3) is usually used in a ratio of 1 to 3 mol, and the base is usually used in a ratio of 1 to 10 mol, based on 1 mol of the intermediate compound (M1).

The reaction temperature is usually within the range of –20 to 100° C. The reaction time is usually within the range of 0.1 to 24 hours.

After completion of the reaction, the intermediate compound (M4) can be isolated by subjecting it to normal post-process operations. The isolated intermediate compound (M4) also can be further purified by recrystallization, chromatography, or the like.

The compound of the present invention (1) can be produced by intramolecular condensation of the intermediate compound (M4).

The reaction is usually carried out in the presence of a solvent. Examples of the solvent include ethers such as 1,4-dioxane, diethyl ether, THF and tert-butyl methyl ether, halogenated hydrocarbons such as dichloromethane, chloroform, carbon tetrachloride, 1,2-dichloroethane and chlorobenzene, aromatic hydrocarbons such as toluene, benzene and xylene, esters such as ethyl acetate and butyl acetate, nitriles such as acetonitrile, aprotic polar solvents such as DMF, NMP, DMI and DMSO, nitrogen-containing aromatic compounds such as pyridine and quinoline, and mixtures thereof.

The reaction can use a condensing agent, an acid, a base or a chlorinating agent, as necessary.

Examples of the condensing agent include a mixture of acetic anhydride, trifluoroacetic anhydride, EDCI hydrochloride, a mixture of triphenylphosphine, a base and carbon tetrachloride or carbon tetrabromide, and a mixture of triphenylphosphine and azodiesters such as diethyl azodicarboxylate.

Examples of the acid include sulfonic acids such as p-toluenesolufonic acid, carboxylic acids such as acetic acid, and polyphosphoric acid.

Examples of the base include nitrogen-containing heterocyclic compounds such as pyridine, picoline, 2,6-lutidine, 1,8-diazabicyclo[5.4.0]-7-undecene and 1,5-diazabicyclo[4.3.0]-5-nonene, tertiary amines such as triethylamine and N,N-diisopropylethylamine, and inorganic bases such as tripotassium phosphate, potassium carbonate and sodium hydride.

Examples of the chlorinating agent include phosphorus oxychloride.

In the reaction, when a condensing agent is used, the condensing agent is usually used in a ratio of 1 to 5 mol, when an acid is used, the acid is usually used in a ratio of 0.1 to 5 mol, when a base is used, the base is usually used in a ratio of 1 to 5 mol, and when a chlorinating agent is used, the chlorinating agent is usually used in a ratio of 1 to 5 mol, based on 1 mol of the intermediate compound (M4).

The reaction temperature is usually within the range of 0 to 200° C. The reaction time is usually within the range of 0.1 to 24 hours.

After completion of the reaction, the compound of the present invention (1) can be isolated by subjecting it to normal post-process operations. The isolated compound of the present invention (1) also can be further purified by recrystallization, chromatography, or the like.

The compound of the present invention (1) can be produced by a one step reaction (one pot) by allowing the intermediate compound (M1) to react with the intermediate compound (M2), in the presence of a condensing agent.

The reaction is usually carried out in the presence of a solvent. Examples of the solvent include ethers such as 1,4-dioxane, diethyl ether, THF and tert-butyl methyl ether, halogenated hydrocarbons such as dichloromethane, chloroform, carbon tetrachloride, 1,2-dichloroethane and chlorobenzene, aromatic hydrocarbons such as toluene, benzene and xylene, esters such as ethyl acetate and butyl acetate, nitriles such as acetonitrile, aprotic polar solvents such as DMF, NMP, DMI and DMSO, nitrogen-containing aromatic compounds such as pyridine and quinoline, and mixtures thereof.

Examples of the condensing agent include carbodiimides such as EDCI hydrochloride and 1,3-dicyclohexylcarbodiimide, and BOP reagent.

The reaction can be also carried out by adding a catalyst, as necessary. Examples of the catalyst include HOBt.

In the reaction, the intermediate compound (M2) is usually used in a ratio of 1 to 2 mol, the condensing agent is usually used in a ratio of 1 to 5 mol, and the catalyst is usually used in a ratio of 0.01 to 1 mol, based on 1 mol of the intermediate compound (M1).

The reaction temperature is usually within the range of 0 to 200° C. The reaction time is usually within the range of 0.1 to 24 hours.

After completion of the reaction, the compound of the present invention (1) can be isolated by subjecting it to normal post-process operations. The isolated compound of the present invention (1) also can be further purified by recrystallization, chromatography, or the like.

Also, the compound of the present invention (1) can be produced by a one step reaction (one pot) by allowing the intermediate compound (M1) to react with the intermediate compound (M3).

The reaction is usually carried out in the presence or absence of a solvent. Examples of the solvent include ethers such as THF, ethylene glycol dimethyl ether, tert-butyl methyl ether and 1,4-dioxane, aliphatic hydrocarbons such as hexane, heptane and octane, aromatic hydrocarbons such as toluene and xylene, halogenated hydrocarbons such as chlorobenzene, esters such as ethyl acetate and butyl acetate, nitriles such as acetonitrile, aprotic polar solvents such as DMF, NMP, DMI and DMSO, and mixtures thereof.

The reaction can be also carried out by adding a base, as necessary. Examples of the base include alkali metal carbonates such as sodium carbonate and potassium carbonate, tertiary amines such as triethylamine and N,N-diisopropylethylamine, and nitrogen-containing aromatic compounds such as pyridine and 4-dimethylaminopyridine.

In the reaction, the intermediate compound (M3) is usually used in a ratio of 1 to 3 mol, and the base is usually used in a ratio of 1 to 10 mol, based on 1 mol of the intermediate compound (M1).

The reaction temperature is usually within the range of 20 to 200° C. The reaction time is usually within the range of 0.1 to 24 hours.

After completion of the reaction, the compound of the present invention (1) can be isolated by subjecting it to normal-process operations. The isolated compound of the present invention (1) also can be further purified by recrystallization, chromatography, or the like.

(Production Method 3)

Compound (M5) is reacted with the intermediate compound (M2) or the intermediate compound (M3) to produce the intermediate compound (M6), then the obtained intermediate compound (M6) is reacted with a sulfurizing agent, whereby the compound of the present invention (P1) in which $A^3$ is a sulfur atom, and $A^5$ is a nitrogen atom in the formula (1) can be produced.

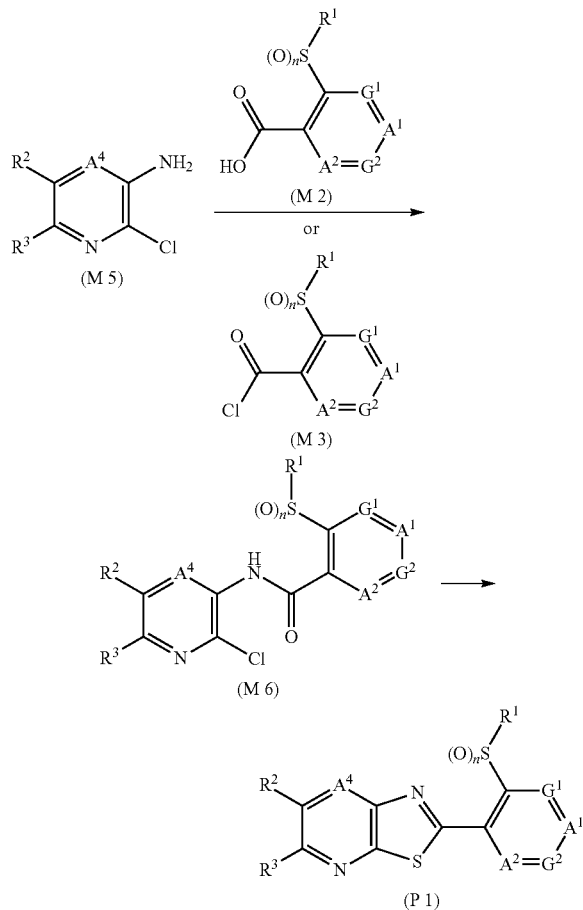

wherein symbols represent the same meaning as in the formula (1).

The intermediate compound (M6) can be produced by allowing the compound (M5) to react with the intermediate compound (M2), in the presence of a condensing agent.

The reaction is usually carried out in the presence or absence of a solvent. Examples of the solvent include ethers such as THF, ethylene glycol dimethyl ether, tert-butyl methyl ether and 1,4-dioxane, aliphatic hydrocarbons such as hexane, heptane and octane, aromatic hydrocarbons such as toluene and xylene, halogenated hydrocarbons such as chlorobenzene, esters such as ethyl acetate and butyl acetate, nitriles such as acetonitrile, aprotic polar solvents such as DMF, NMP, DMI and DMSO, nitrogen-containing aromatic compounds such as pyridine and quinoline, and mixtures thereof.

Examples of the condensing agent include carbodiimides such as EDCI hydrochloride and 1,3-dicyclohexylcarbodiimide, and BOP reagent.

The reaction can be also carried out by adding a catalyst, as necessary. Examples of the catalyst include HOBt.

In the reaction, the intermediate compound (M2) is usually used in a ratio of 1 to 3 mol, the condensing agent is usually used in a ratio of 1 to 5 mol, and the catalyst is usually used in a ratio of 0.01 to 1 mol, based on 1 mol of the compound (M5).

The reaction temperature is usually within the range of 0 to 200° C. The reaction time is usually within the range of 0.1 to 24 hours.

After completion of the reaction, the compound of the present invention (M6) can be isolated by subjecting it to normal post-process operations. The isolated compound of the present invention (M6) also can be further purified by recrystallization, chromatography, or the like.

Also, the intermediate compound (M6) can be produced by allowing the compound (M5) to react with the intermediate compound (M3).

The reaction is usually carried out in the presence or absence of a solvent. The reaction can be also carried out by adding a base, as necessary. Examples of the solvent include ethers such as THF, ethylene glycol dimethyl ether, tert-butyl methyl ether and 1,4-dioxane, aliphatic hydrocarbons such as hexane, heptane and octane, aromatic hydrocarbons such as toluene and xylene, halogenated hydrocarbons such as chlorobenzene, esters such as ethyl acetate and butyl acetate, nitriles such as acetonitrile, aprotic polar solvents such as DMF, NMP, DMI and DMSO, nitrogen-containing aromatic compounds such as pyridine and quinoline, and mixtures thereof.

Examples of the base include alkali metal carbonates such as sodium carbonate and potassium carbonate, tertiary amines such as triethylamine and N,N-diisopropylethylamine, and nitrogen-containing aromatic compounds such as pyridine and 4-dimethylaminopyridine.

In the reaction, the intermediate compound (M3) is usually used in a ratio of 1 to 3 mol, and the base is usually used in a ratio of 1 to 5 mol, based on 1 mol of the compound (M5).

The reaction temperature is usually within the range of 0 to 200° C. The reaction time is usually within the range of 0.1 to 24 hours.

After completion of the reaction, the compound of the present invention (M6) can be isolated by subjecting it to normal post-process operations. The isolated compound of the present invention (M6) also can be further purified by recrystallization, chromatography, or the like.

The compound of the present invention (P1) can be produced by allowing the compound (M6) to react with a sulfurizing agent.

The reaction is usually carried out in the presence or absence of a solvent. Examples of the solvent include ethers such as 1,4-dioxane, diethyl ether, tetrahydrofuran, tert-butyl methyl ether and diglyme, halogenated hydrocarbons such as dichloromethane, chloroform, carbon tetrachloride, 1,2- dichloroethane and chlorobenzene, aromatic hydrocarbons such as toluene, benzene and xylene, nitriles such as acetonitrile, nitrogen-containing aromatic compounds such as pyridine, picoline and lutidine, and mixtures thereof.

Examples of the sulfurizing agent include diphosphorus pentasulfide and Lawesson's reagent (2,4-bis-(4-methoxyphenyl)-1,3-dithia-2,4-diphosphetane-2,4-disulfide).

In the reaction, the sulfurizing agent is usually used in a ratio of 1 to 3 mol, based on 1 mol of the intermediate compound (M6).

The reaction temperature is usually within the range of 0 to 200° C. The reaction time is usually within the range of 1 to 24 hours.

After completion of the reaction, the compound of the present invention (P1) can be isolated by subjecting it to normal post-process operations. The isolated compound of the present invention (P1) also can be further purified by recrystallization, chromatography, or the like.

(Production Method 4)

The compound of the present invention can be produced by allowing the intermediate compound (M1) to react with the intermediate compound (M7), in the presence of an oxidizing agent.

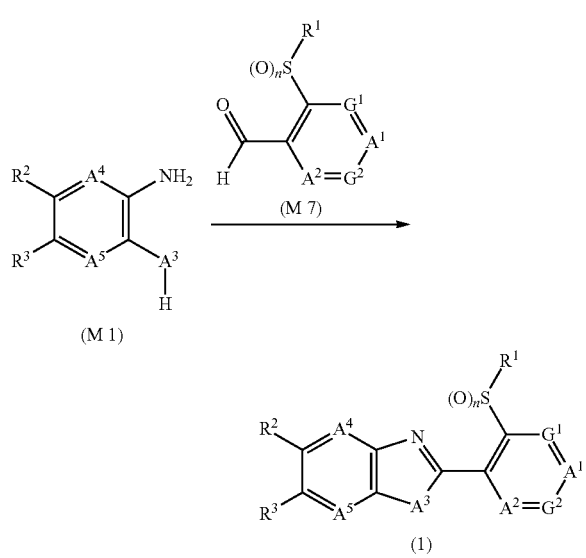

wherein symbols represent the same meaning as in the formula (1).

The reaction is usually carried out in the presence of a solvent. Examples of the solvent include alcohols such as methanol and ethanol, ethers such as 1,4-dioxane, diethyl ether, THF and tert-butyl methyl ether, halogenated hydrocarbons such as dichloromethane, chloroform, carbon tetrachloride, 1,2-dichloroethane and chlorobenzene, aromatic hydrocarbons such as toluene, benzene and xylene, esters such as ethyl acetate and butyl acetate, nitriles such as acetonitrile, aprotic polar solvents such as DMF, NMP, DMI and DMSO, nitrogen-containing aromatic compounds such as pyridine and quinoline, and mixtures thereof.

Examples of the oxidizing agent include oxygen, copper (II) chloride, and 2,3-dichloro-5,6-dicyano-p-benzoquinone.

The reaction can be also carried out by adding an acid, as necessary. Examples of the acid include sulfonic acids such as p-toluenesolufonic acid, carboxylic acids such as acetic acid, and polyphosphoric acid.

The reaction can be also carried out by adding a sulfite, as necessary. Examples of the sulfite include sulfites such as sodium bisulfite and sodium disulfite.

In the reaction, the intermediate compound (M7) is usually used in a ratio of 1 to 2 mol, the acid is usually used in a ratio of 0.1 to 2 mol, the sulfite is usually used in a ratio of 1 to 5 mol, and the oxidizing agent is usually used in a ratio of 1 to 5 mol, based on 1 mol of the intermediate compound (M1).

The reaction temperature is usually within the range of 0 to 200° C. The reaction time is usually within the range of 0.1 to 24 hours.

After completion of the reaction, the compound of the present invention (1) can be isolated by subjecting it to normal post-process operations. The isolated compound of the present invention (1) also can be further purified by recrystallization, chromatography, or the like.

(Production Method 5)

The compound of the present invention (1) in which n is 0 in the formula (1) can be produced by allowing the intermediate compound (M8) to react with the intermediate compound (M9), in the presence of a base.

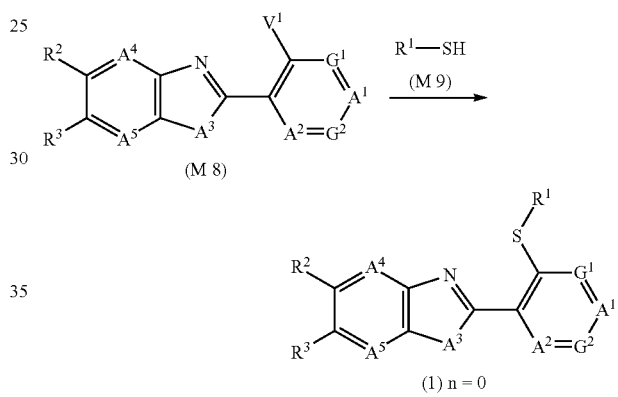

wherein $V^1$ represents a halogen atom, and other symbols represent the same meaning as in the formula (1).

The reaction is usually carried out in the presence of a solvent. Examples of the solvent include ethers such as THF, ethylene glycol dimethyl ether, tert-butyl methyl ether and 1,4-dioxane, aromatic hydrocarbons such as toluene and xylene, nitriles such as acetonitrile, aprotic polar solvents such as DMF, NMP, DMI and DMSO, water, and mixtures thereof.

Examples of the base include alkali metal carbonates such as sodium carbonate and potassium carbonate, alkali metal hydrides such as sodium hydride, and potassium tert-butoxide.

In the reaction, the intermediate compound (M9) is usually used in a ratio of 1 to 10 mol, and the base is usually used in a ratio of 1 to 10 mol, based on 1 mol of the intermediate compound (M8).

The reaction temperature is usually within the range of 0 to 150° C. The reaction time is usually within the range of 0.5 to 24 hours.

After completion of the reaction, the compound of the present invention (1) can be isolated by subjecting it to normal post-process operations. The isolated compound of the present invention (1) also can be further purified by recrystallization, chromatography, or the like.

In the reaction, $V^1$ is preferably a fluorine atom or a chlorine atom.

(Production Method 6)

The intermediate compound (M1) is reacted with the compound (M10) or the compound (M11) to produce the intermediate compound (M12), then the obtained intermediate compound (M12) is condensed in the molecule, whereby the intermediate compound (M8) can be produced.

wherein $V^1$ represents a halogen atom, and other symbols represent the same meaning as in the formula (1).

place of the intermediate compound (M2), in accordance with the method of Production Method 2.

Also, the intermediate compound (M8) can be produced by a one step reaction (one pot), using the compound (M11) in place of the intermediate compound (M3), in accordance with the method of Production Method 2.

In the reaction, $V^1$ is preferably a fluorine atom or a chlorine atom.

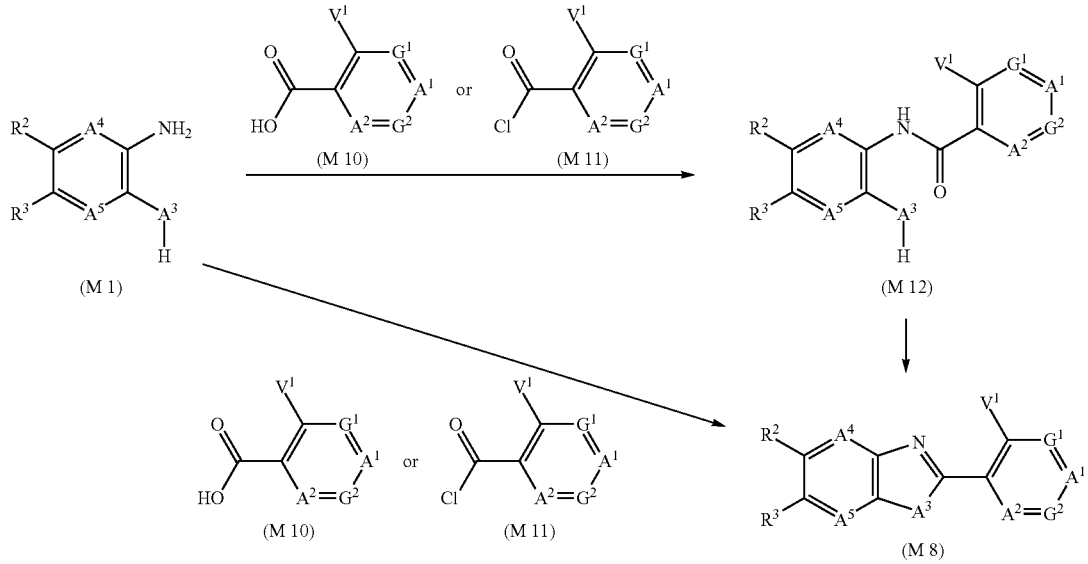

The intermediate compound (M12) can be produced, using the compound (M10) in place of the intermediate compound (M2), in accordance with the method of Production Method 2.

The intermediate compound (M12) can be produced, using the compound (M11) in place of the intermediate compound (M3), in accordance with the method of Production Method 2.

The intermediate compound (M8) can be produced, using the intermediate compound (M12) in place of the intermediate compound (M4), in accordance with the method of Production Method 2.

Also, the intermediate compound (M8) can be produced by a one step reaction (one pot), using the compound (M10) in (Production Method 7)

The intermediate compound (M4) in which n is 0 in the formula (M4) can be produced by allowing the intermediate compound (M12) to react with the compound (M9). In addition, the compound of the present invention (1) in which n is 0 in the formula (1) can be produced by condensing the obtained intermediate compound (M4).

wherein $V^1$ represents a halogen atom, and other symbols represent the same meaning as in the formula (1).

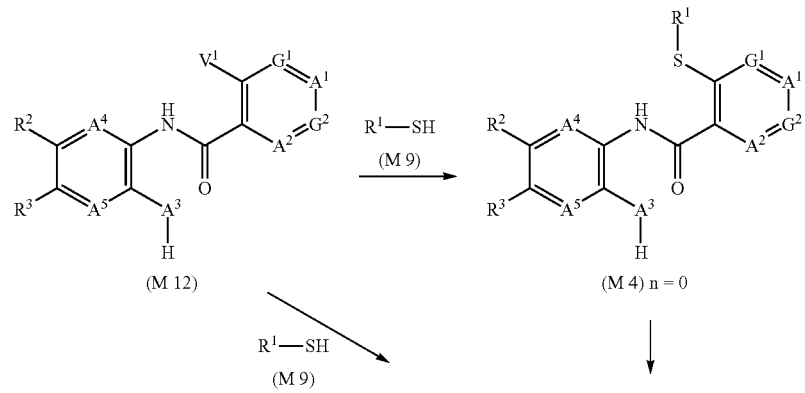

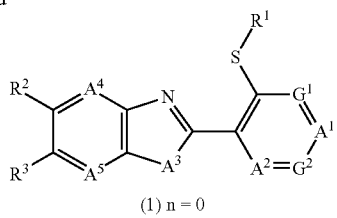

(1) n = 0

The intermediate compound (M4) n=0 can be produced, using the intermediate compound (M12) in place of the intermediate compound (M8), in accordance with the method of Production Method 5.

The compound of the present invention (1) n=0 can be produced, using the intermediate compound (M4) n=0 in place of the intermediate compound (M4), in accordance with the method of Production Method 2.

Also, the compound of the present invention (1) n=0 can be produced by a one step reaction (one pot), using the intermediate compound (M12) in place of the intermediate compound (M8), in accordance with the method of Production Method 5.

In the reaction, $V^1$ is preferably a fluorine atom or a chlorine atom.

(Production Method 8)

The compound of the present invention (1) in which n is 0 in the formula (1) can be produced by allowing the intermediate compound (M13) or the intermediate compound (M13') that is a disulfide body thereof to react with the compound (M14), in the presence of a base.

Examples of the base include hydrides of alkali metals or alkaline earth metals such as sodium hydride, potassium hydride and calcium hydride, inorganic bases such as sodium carbonate and potassium carbonate, or organic bases such as triethylamine.

When the intermediate compound (M13') that is a disulfide body is used, the reaction is usually carried out in the presence of a reducing agent. Examples of the reducing agent include sodium hydroxymethanesulfinate.

In the reaction, the compound (M14) is usually used in a ratio of 1 to 10 mol, and the base is usually used in a ratio of 1 to 10 mol, based on 1 mol of the intermediate compound (M13). Also, when the intermediate compound (M13') that is a disulfide body is used, the compound (M14) is usually used in a ratio of 2 to 10 mol, the base is usually used in a ratio of 2 to 10 mol, and the reducing agent is usually used in a ratio of 1 to 5 mol, based on 1 mol of the intermediate compound (M13').

The reaction temperature is usually within the range of 0 to 100° C. The reaction time is usually within the range of 0.1 to 24 hours.

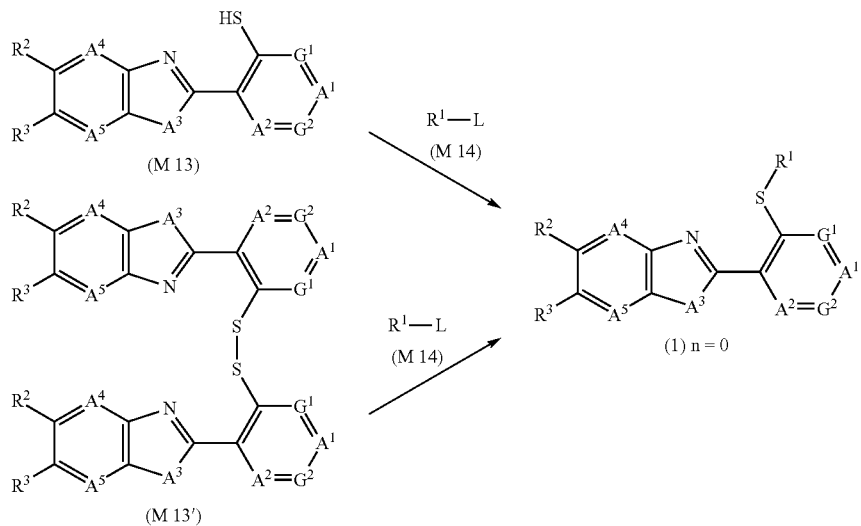

wherein L represents a leaving group such as a chlorine atom, a bromine atom, an iodine atom, a trifluoromethanesulfonyloxy group or a methanesulfonyloxy group, and other symbols represent the same meaning as in the formula (1).

The reaction is usually carried out in the presence of a solvent. Examples of the solvent include ethers such as THF, ethylene glycol dimethyl ether, tert-butyl methyl ether and 1,4-dioxane, aromatic hydrocarbons such as toluene and xylene, nitriles such as acetonitrile, aprotic polar solvents such as DMF, NMP, DMI and DMSO, and mixtures thereof.

After completion of the reaction, the compound of the present invention (1) in which n is 0 can be isolated by subjecting it to normal post-process operations. The isolated compound of the present invention (1) in which n is 0 also can be further purified by chromatography, recrystallization, or the like.

(Production Method 9)

The compound of the present invention (1) in which n is 0 in the formula (1) can be produced by allowing the intermediate compound (M13') to react with the compound (M14'-1) or the compound (M14'-2).

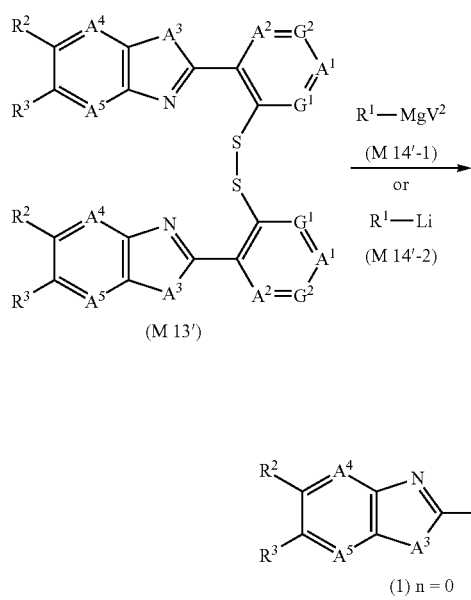

(M 13′)

$R^1$—$MgV^2$ (M 14′-1)

or $R^1$—Li (M 14′-2)

(1) n = 0 wherein $V^2$ represents a chlorine atom, a bromine atom or an iodine atom, and other symbols represent the same meaning as in the formula (1).

The reaction is usually carried out in the presence of a solvent. Examples of the solvent include ethers such as THF, diethyl ether, ethylene glycol dimethyl ether, tert-butyl methyl ether and 1,4-dioxane, aromatic hydrocarbons such as toluene and xylene, and mixtures thereof.

In the reaction, the compound (M14′-1) is usually used in a ratio of 1 to 5 mol, based on 1 mol of the intermediate compound (M13′). Also, when the compound (M14′-2) is used, the compound (M14′-2) is usually used in a ratio of 1 to 5 mol, based on 1 mol of the intermediate compound (M13′).

The reaction temperature is usually within the range of –80 to 100° C. The reaction time is usually within the range of 0.1 to 24 hours.

After completion of the reaction, the compound of the present invention (1) in which n is 0 can be isolated by subjecting it to normal post-process operations. The isolated compound of the present invention (1) in which n is 0 also can be further purified by chromatography, recrystallization, or the like.

(Production Method 10)

The intermediate compound (M13) can be produced by allowing the intermediate compound (M8) to react with a sulfurizing agent. In addition, the intermediate compound (M13′) that is a disulfide body thereof can be produced by oxidizing the intermediate compound (M13).

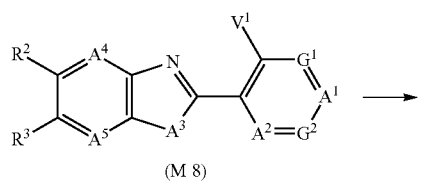

(M 8)

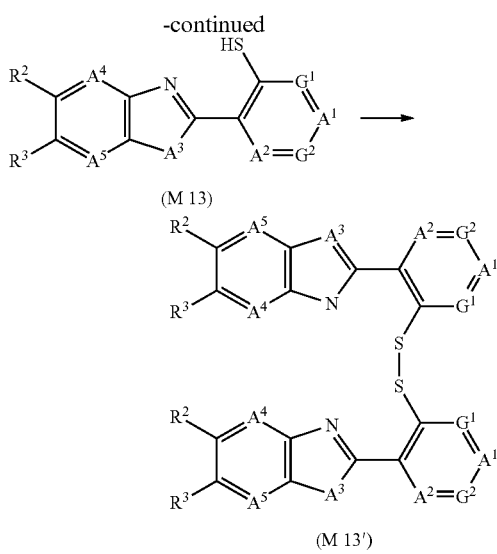

(M 13)

(M 13′)

wherein $V^1$ represents a halogen atom, and other symbols represent the same meaning as in the formula (1).

The intermediate compound (M13) can be produced, using sodium sulfide, sodium hydrogen sulfide or hydrogen sulfide in place of the compound (M9), in accordance with the method of Production Method 5.

Here, the reaction from the intermediate compound (M13) to the intermediate compound (M13′) is likely to occur, and the intermediate compound (M13′) is sometimes produced during synthesis of the intermediate compound (M13).

In the reaction, $V^1$ is preferably a fluorine atom or a chlorine atom.

The intermediate compound (M13′) can be produced by allowing the intermediate compound (M13) to react, in the presence of an oxidizing agent.

The reaction is usually carried out in the presence of a solvent. Examples of the solvent include water, alcohols such as methanol and ethanol, ethers such as THF, ethylene glycol dimethyl ether, tert-butyl methyl ether and 1,4-dioxane, aromatic hydrocarbons such as toluene and xylene, nitriles such as acetonitrile, aprotic polar solvents such as DMF, NMP, DMI and DMSO, carboxylic acids such as acetic acid, and mixtures thereof.

Examples of the oxidizing agent include oxygen, iodine, aqueous hydrogen peroxide, and potassium ferricyanide.

In the reaction, the oxidizing agent is usually used in a ratio of 0.5 to 10 mol, based on 1 mol of the intermediate compound (M13).

The reaction temperature is usually within the range of 0 to 100° C. The reaction time is usually within the range of 0.1 to 24 hours.

After completion of the reaction, the intermediate compound (13′) can be isolated by subjecting it to normal post-process operations. The isolated intermediate compound (13′) also can be further purified by chromatography, recrystallization, or the like.

(Production Method 11)

The compound of the present invention (P3) in which $A^3$ is —$NR^{8′}$— in the formula (1) can be produced by allowing the compound of the present invention (2) in which $A^3$ is —NH— in the formula (1) to react with the compound (M15), in the presence of a base.

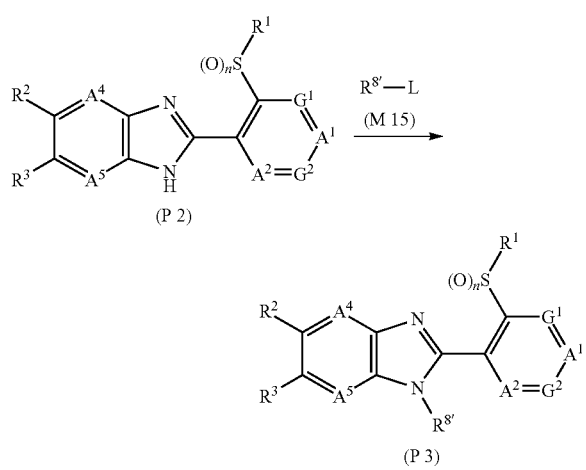

wherein $R^{8'}$ represents any of $R^8$ in the formula (1) other than a hydrogen atom, L represents a leaving group such as a chlorine atom, a bromine atom, an iodine atom, a trifluoromethanesulfonyloxy group or a methanesulfonyloxy group, and other symbols represent the same meaning as in the formula (1).

The reaction is usually carried out in the presence of a solvent. Examples of the solvent include ethers such as THF, ethylene glycol dimethyl ether, tert-butyl methyl ether and 1,4-dioxane, aromatic hydrocarbons such as toluene and xylene, nitriles such as acetonitrile, aprotic polar solvents such as DMF, NMP, DMI and DMSO, and mixtures thereof.

Examples of the base include hydrides of alkali metals or alkaline earth metals such as sodium hydride, potassium hydride and calcium hydride, inorganic bases such as sodium carbonate and potassium carbonate, or organic bases such as triethylamine.

In the reaction, the compound (M15) is usually used in a ratio of 1 to 5 mol, and the base is usually used in a ratio of 1 to 3 mol, based on 1 mol of the compound of the present invention (P2).

The reaction temperature is usually within the range of 0 to 100° C. The reaction time is usually within the range of 0.1 to 24 hours.

After completion of the reaction, the compound of the present invention (P3) can be isolated by subjecting it to normal post-process operations. The isolated compound of the present invention (P3) also can be further purified by chromatography, recrystallization, or the like.

(Production Method 12)

The intermediate compound (M2) can be produced by hydrolyzing the intermediate compound (M16).

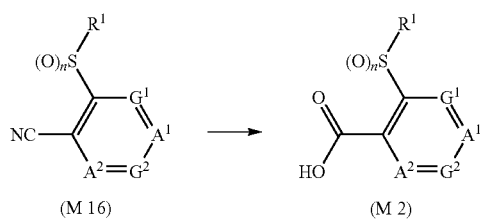

wherein symbols represent the same meaning as in the formula (1).

When hydrolyzed by an acid, the reaction is usually carried out using an aqueous solution of an acid as a solvent. Examples of the acid include mineral acids such as hydrochloric acid, nitric acid, phosphoric acid and sulfuric acid, carboxylic acids such as acetic acid and trifluoroacetic acid.

The reaction temperature is usually within the range of 0 to 100° C. The reaction time is usually within the range of 0.1 to 24 hours.

After completion of the reaction, the intermediate compound (M2) can be isolated by subjecting it to normal post-process operations. The isolated intermediate compound (M2) also can be further purified by chromatography, recrystallization, or the like.

When hydrolyzed by a base, the reaction is usually carried out in the presence of a solvent. Examples of the solvent include ethers such as THF, ethylene glycol dimethyl ether, tert-butyl methyl ether and 1,4-dioxane, alcohols such as methanol and ethanol, water, and mixtures thereof.

Examples of the base include alkali metal hydroxides such as sodium hydroxide and potassium hydroxide.

In the reaction, the base is usually used in a ratio of 1 to 10 mol, based on 1 mol of the intermediate compound (M16).

The reaction temperature is usually within range of 0 to 120° C. The reaction time is usually within the range of 0.1 to 24 hours.

After completion of the reaction, the intermediate compound (M2) can be isolated by subjecting it to normal post-process operations. The isolated intermediate compound (M2) also can be further purified by chromatography, recrystallization, or the like.

(Production Method 13)

The intermediate compound (M3) can be produced by allowing the intermediate compound (M2) to react with a chlorinating agent.

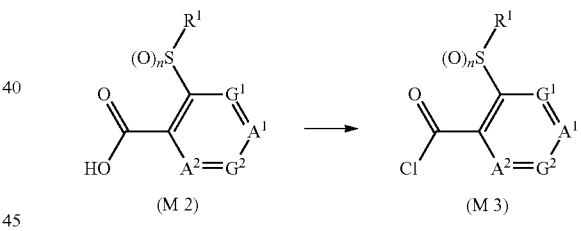

wherein symbols represent the same meaning as in the formula (1).

The reaction is usually carried out in the presence of a solvent. Examples of the solvent include ethers such as THF, ethylene glycol dimethyl ether, tert-butyl methyl ether and 1,4-dioxane, aromatic hydrocarbons such as toluene and xylene, aliphatic halogenated hydrocarbons such as dichloromethane and chloroform, and mixtures thereof.

Examples of the chlorinating agent include thionyl chloride, oxalyl dichloride and phosphorus oxychloride.

The reaction can be also carried out by adding a catalyst, as necessary. Examples of the catalyst include DMF.

In the reaction, the chlorinating agent is usually used in a ratio of 1 to 5 mol, and the catalyst is usually used in a ratio of 0.001 to 0.1 mol, based on 1 mol of the intermediate compound (M2).

The reaction temperature is usually within the range of 0 to 100° C. The reaction time is usually within the range of 0.1 to 24 hours.

After completion of the reaction, the intermediate compound (M3) can be isolated by distilling the solvent.

(Production Method 14)

The intermediate compound (M2), the intermediate compound (M7) or the intermediate compound (M16) can be produced by allowing intermediate compound (M10) to react with intermediate compound (M17) or intermediate compound (M18) to react with the intermediate compound (M9), respectively, and oxidizing the obtained compound as necessary.

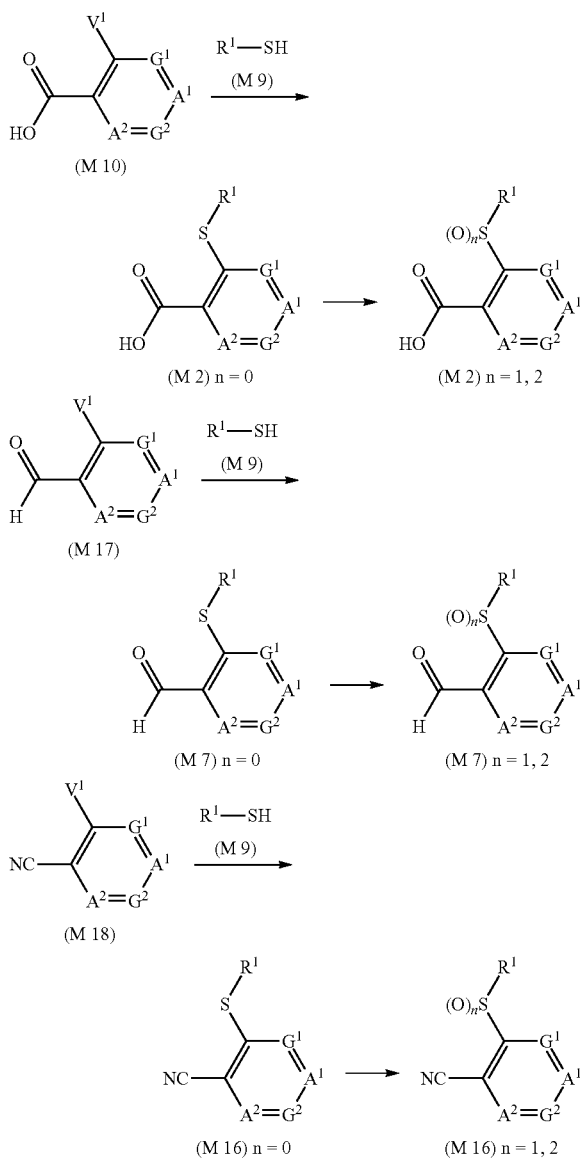

wherein $V^1$ represents a halogen atom, and other symbols represent the same meaning as in the formula (1).

The intermediate compound (M2) in which n is 0 can be produced, using the compound (M10) in place of the intermediate compound (M8), in accordance with the method of Production Method 5.

The intermediate compound (M7) in which n is 0 can be produced, using the compound (M17) in place of the intermediate compound (M8), in accordance with the method of Production Method 5.

The intermediate compound (M16) in which n is 0 can be produced, using the compound (M18) in place of the intermediate compound (M8), in accordance with the method of Production Method 5.

The intermediate compound (M2) in which n is 1 or 2 can be produced, using the intermediate compound (M2) in which n is 0 in place of the compound of the present invention (1) in which n is 0, in accordance with the method of Production Method 1.

The intermediate compound (M7) in which n is 1 or 2 can be produced, using the intermediate compound (M7) in which n is 0 in place of the compound of the present invention (1) in which n is 0, in accordance with the method of Production Method 1.

The intermediate compound (M16) in which n is 1 or 2 can be produced, using the intermediate compound (M16) in which n is 0 in place of the compound of the present invention (1) in which n is 0, in accordance with the method of Production Method 1.

In the reaction, $V^1$ is preferably a fluorine atom or a chlorine atom.

(Production Method 15)

The intermediate compound (M21) can be produced by allowing an organic lithium compound produced by allowing the compound (M19) to react with a lithium amide reagent, to react with the compound (M20).

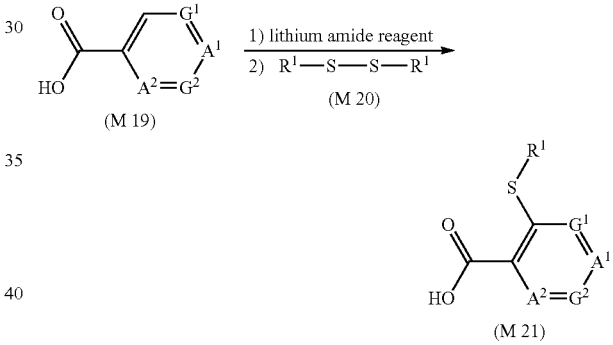

wherein symbols represent the same meaning as in the formula (1).

The reaction is usually carried out in the presence of a solvent. Examples of the solvent include ethers such as THF, diethyl ether, ethylene glycol dimethyl ether, tert-butyl methyl ether and 1,4-dioxane, aromatic hydrocarbons such as toluene and xylene, and mixtures thereof.

The lithium amide reagent includes lithium 2,2,6,6-tetramethylpiperidide, lithium diisopropylamide, and lithium hexamethyldisilazide.

In the reaction, the lithium amide reagent is usually used in a ratio of 2 to 3 mol, and the compound (M20) is usually used in a ratio of 2 to 5 mol, based on 1 mol of the compound (M19).

The reaction temperature in the reaction of the compound (M19) with the lithium amide reagent is usually within the range of −80 to 30° C. The reaction time is usually within the range of 0.1 to 24 hours.

The reaction temperature in the reaction of the reaction intermediate with the compound (M20) is usually within the range of −80 to 30° C. The reaction time is usually within the range of 0.1 to 24 hours.

After completion of the reaction, the intermediate compound (M21) can be isolated by subjecting it to normal post-process operations. The intermediate compound (M21) also can be further purified by chromatography, recrystallization, or the like.

(Production Method 16)

The intermediate compound (M27) can be produced according to the following scheme.

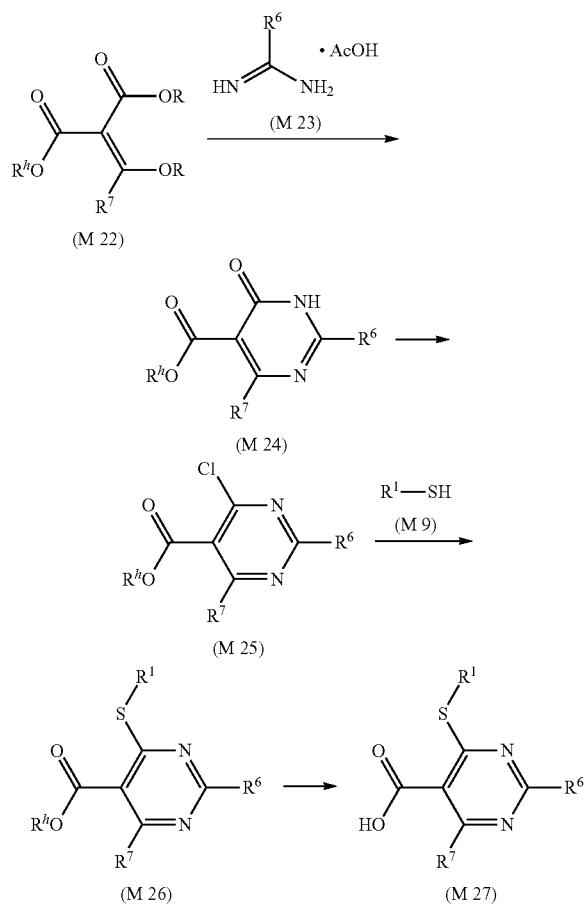

wherein $R^h$ represents a methyl group or an ethyl groups, and other symbols represent the same meaning as in the formula (1).

The intermediate compound (M24) can be produced by allowing the compound (M22) to react with the compound (M23).

The reaction is usually carried out in the presence of a solvent. Examples of the solvent include alcohols such as methanol and ethanol, acetic acid, water, and mixtures thereof.

In the reaction, the compound (M23) is usually used in a ratio of 1 to 3 mol, based on 1 mol of the compound (M22).

The reaction temperature is usually within the range of 0 to 100° C. The reaction time is usually within the range of 0.1 to 24 hours.

After completion of the reaction, the intermediate compound (M24) can be isolated by subjecting it to normal post-process operations. The intermediate compound (M24) also can be further purified by chromatography, recrystallization, or the like.

The intermediate compound (M25) can be produced by allowing the intermediate compound (M24) to react in the presence of a chlorinating agent.

The reaction is usually carried out in the presence of a solvent. Examples of the solvent include ethers such as THF, diethyl ether, ethylene glycol dimethyl ether, tert-butyl methyl ether and 1,4-dioxane, aromatic hydrocarbons such as toluene and xylene, and mixtures thereof.

Examples of the chlorinating agent include phosphorus oxychloride and thionyl chloride.

The reaction can be also carried out by adding a base, as necessary. Examples of the base include tertiary amines such as N,N-diisopropylethylamine, and pyridine, quinoline, N,N-dimethylaniline, and the like.

In the reaction, the chlorinating agent is usually used in a ratio of 1 to 3 mol, and the base is usually used in a ratio of 1 to 3 mol, based on 1 mol of the intermediate compound (M24).

The reaction temperature is usually within the range of 0 to 100° C. The reaction time is usually within the range of 0.1 to 24 hours.

After completion of the reaction, the intermediate compound (M25) can be isolated by subjecting it to normal post-process operations. The isolated intermediate compound (M25) also can be further purified by chromatography, recrystallization, or the like.

The intermediate compound (M26) can be produced, using the intermediate compound (M25) in place of the intermediate compound (M8), in accordance with the method of Production Method 5.

The intermediate compound (M27) can be produced by hydrolyzing the intermediate compound (M26).

When hydrolyzed by an acid, the reaction is usually carried out using an aqueous solution of an acid as a solvent.

Examples of the acid include mineral acids such as hydrochloric acid, nitric acid, phosphoric acid and sulfuric acid, carboxylic acid such as acetic acid and trifluoroacetic acid.

The reaction temperature is usually within the range of 0 to 100° C. The reaction time is usually within the range of 0.1 to 24 hours.

After completion of the reaction, the intermediate compound (M27) can be isolated by subjecting it to normal post-process operations. The isolated intermediate compound (M27) also can be further purified by recrystallization, chromatography, or the like.

Hydrolysis with a base is usually carried out in the presence of a solvent. Examples of the solvent include ethers such as THF, ethylene glycol dimethyl ether, tert-butyl methyl ether and 1,4-dioxane, alcohols such as methanol and ethanol, water, and mixtures thereof.

Examples of the base used in hydrolysis include alkali metal hydroxides such as sodium hydroxide and potassium hydroxide.

In the reaction, the base is usually used in a ratio of 1 to 10 mol, based on 1 mol of the intermediate compound (M26).

The reaction temperature is usually within the range of 0 to 120° C. The reaction time is usually within the range of 0.1 to 24 hours.

After completion of the reaction, the intermediate compound (M26) can be isolated by subjecting it to normal post-process operations. The isolated intermediate compound (M26) also can be further purified by chromatography, recrystallization, or the like.

(Production Method 17)

The intermediate compound (M31) can be produced by nitrating the compound (M28) or allowing the compound (M29) to react with the compound (M30). The intermediate compound (M1) in which $A^3$ is $—NR^8—$ in the formula (M1) can be produced by reducing the intermediate compound (M31) obtained above.

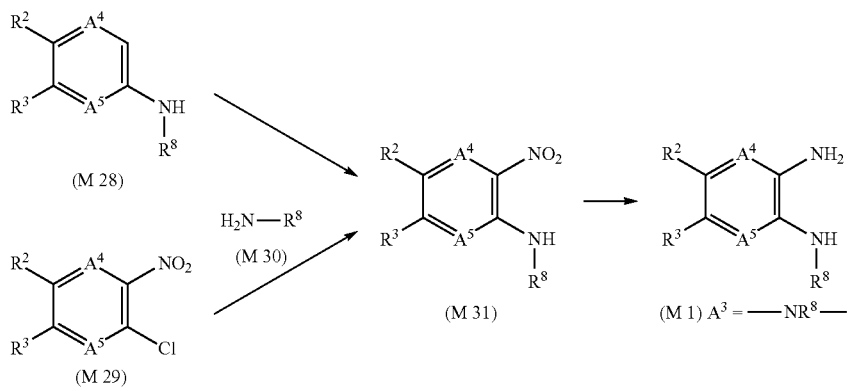

wherein symbols represent the same meaning as in the formula (1).

The intermediate compound (M31) can be produced by allowing the compound (M28) to react with a nitrating agent.

The reaction is usually carried out in the presence of a solvent. Examples of the solvent include aliphatic halogenated hydrocarbons such as dichloromethane and chloroform, acetic acid, concentrated sulfuric acid, concentrated nitric acid, water, and mixtures thereof.

Examples of the nitrating agent include concentrated nitric acid and fuming nitric acid.

In the reaction, the nitrating agent is usually used in a ratio of 1 to 3 mol, based on 1 mol of the compound (M28).

The reaction temperature is usually within the range of −10 to 120° C. The reaction time is usually within the range of 0.1 to 24 hours.

After completion of the reaction, the intermediate compound (M31) can be isolated by subjecting it to normal post-process operations. The isolated intermediate compound (M31) also can be further purified by chromatography, recrystallization, or the like.

In addition, when $R^8$ is a hydrogen atom in the formula (M31), the compound in which $R^8$ is other than a hydrogen atom in the formula (M31) can be produced, using the intermediate compound (M31) in which $R^8$ is a hydrogen atom in place of the compound (P2), in accordance with the method of Production Method 11.

The intermediate compound (M31) can be produced by allowing the compound (M29) to react with the compound (M30).

The reaction is usually carried out in the presence of a solvent. Examples of the solvent include ethers such as THF, ethylene glycol dimethyl ether, tert-butyl methyl ether and 1,4-dioxane, aromatic hydrocarbons such as toluene and xylene, halogenated hydrocarbons such as dichloromethane, chloroform and chlorobenzene, nitriles such as acetonitrile, aprotic polar solvents such as DMF, NMP, DMI and DMSO, and mixtures thereof.

The reaction can be also carried out by adding a base, as necessary. Examples of the base include of alkali metal hydrides such as sodium hydride, alkali metal carbonates such as sodium carbonate and potassium carbonate, tertiary amines such as triethylamine and N,N-diisopropylethylamine, and nitrogen-containing aromatic compounds such as pyridine and 4-dimethylaminopyridine.

In the reaction, the compound (M30) is usually used in a ratio of 1 to 10 mol, and the base is usually used in a ratio of 1 to 10 mol, based on 1 mol of the compound (M29).

The reaction temperature is usually within the range of 0 to 150° C. The reaction time is usually within the range of 0.5 to 24 hours.

After completion of the reaction, the intermediate compound (M31) can be isolated by subjecting it to normal post-process operations. The isolated intermediate compound (M31) also can be further purified by chromatography, recrystallization, or the like.

The intermediate compound (M1) in which $A^3$ is —$NR^8$— can be produced by allowing the intermediate compound (M31) to react with hydrogen, in the presence of a hydrogenation catalyst.

The reaction is usually carried out in the presence of a solvent, usually in a hydrogen atmosphere of 1 to 100 atmospheric pressure. Examples of the solvent include ethers such as THF, ethylene glycol dimethyl ether, tert-butyl methyl ether and 1,4-dioxane, esters such as ethyl acetate and butyl acetate, alcohols such as methanol and ethanol, water, and mixtures thereof.

Examples of the hydrogenation catalyst include transition metals and compounds thereof such as palladium carbon, palladium hydroxide, Raney nickel and platinum oxide.

The reaction can be also carried out by adding an acid, a base or the like, as necessary. Examples of the acid include acetic acid and hydrochloric acid, and examples of the base include tertiary amines such as triethylamine and magnesium oxide.

In the reaction, hydrogen is usually used in a ratio of 3 mol or more, the hydrogenation catalyst is usually used in a ratio of 0.001 to 0.5 mol, the acid is usually used in a ratio of 0.001 to 10 mol, and the base is usually used in a ratio of 1 to 10 mol, based on 1 mol of the intermediate compound (M31).

The reaction temperature is usually within the range of −20 to 100° C. The reaction time is usually within the range of 0.1 to 24 hours.

After completion of the reaction, the intermediate compound (M1) in which $A^3$ is —$NR^8$— can be isolated by subjecting it to normal post-process operations. The isolated intermediate compound (M1) in which $A^3$ is —$NR^8$— also can be further purified by chromatography, recrystallization, or the like.

Also, the intermediate compound (M31) can be also produced by acetylating the compound (M28) as shown below to produce the intermediate compound (M28'), then nitrating the obtained intermediate compound (M28') to produce the intermediate compound (M31'), and hydrolyzing the obtained intermediate compound (M31').

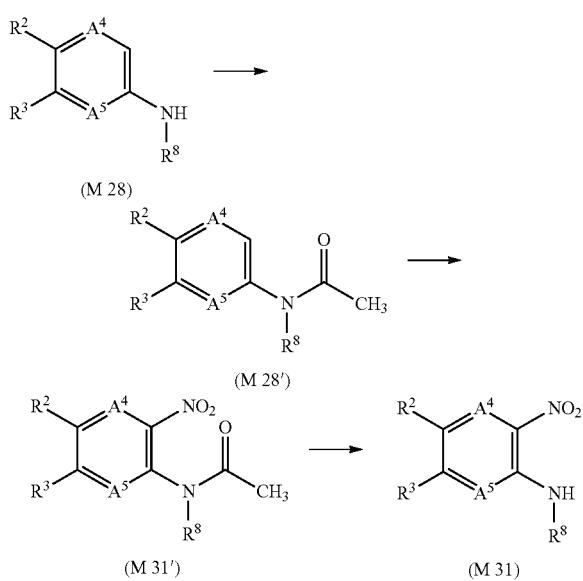

(M 28)

(M 28')

(M 31')    (M 31)

wherein symbols represent the same meaning as in the formula (1).

The intermediate compound (M28') can be produced by allowing the compound (M28) to react with an acylating agent.

The reaction is usually carried out in the presence of a solvent or using an acylating agent as a solvent. Examples of the solvent include aliphatic halogenated hydrocarbons such as dichloromethane and chloroform, ethers such as THF, ethylene glycol dimethyl ether, tert-butyl methyl ether and 1,4-dioxane, aromatic hydrocarbons such as toluene and xylene, nitriles such as acetonitrile, aprotic polar solvents such as DMF, NMP, DMI and DMSO, acetic anhydride, and mixtures thereof.

Examples of the acylating agent include acetic anhydride and p-acetoxynitrobenzene.

The reaction can be also carried out by adding a base, as necessary. Examples of the base include tertiary amines such as triethylamine and N,N-diisopropylethylamine, and nitrogen-containing aromatic compounds such as pyridine and 4-dimethylaminopyridine.

In the reaction, the acetylating agent is usually used in a ratio of 1 mol or more, and the base is usually used in a ratio of 1 to 10 mol, based on 1 mol of the intermediate compound (M28).

The reaction temperature is usually within the range of 0 to 150° C. The reaction time is usually within the range of 0.5 to 24 hours.

After completion of the reaction, the intermediate compound (M28') can be isolated by subjecting it to normal post-process operations. The isolated intermediate compound (M28') also can be further purified by chromatography, recrystallization, or the like.

The intermediate compound (M31') can be produced, using the intermediate compound (M28') in place of the intermediate compound (M28), in accordance with the method of Production Method 17.

The intermediate compound (M31) can be produced by hydrolyzing the intermediate compound (M31'), in the presence of an acid or a base.

When hydrolyzed by an acid, the reaction is usually carried out using an aqueous solution of an acid as a solvent.

Examples of the acid include mineral acids such as hydrochloric acid and sulfuric acid, carboxylic acids such as acetic acid and trifluoroacetic acid.

The reaction temperature is usually within the range of 0 to 100° C. The reaction time is usually within the range of 0.1 to 24 hours.

After completion of the reaction, the intermediate compound (M31) can be isolated by subjecting it to normal post-process operations. The isolated intermediate compound (M31) also can be further purified by chromatography, recrystallization, or the like.

When hydrolyzed by a base, the reaction is usually carried out in the presence of a solvent. Examples of the solvent include ethers such as THF, ethylene glycol dimethyl ether, tert-butyl methyl ether and 1,4-dioxane, alcohols such as methanol and ethanol, water, and mixtures thereof.

Examples of the base include alkali metal hydroxides such as sodium hydroxide and potassium hydroxide and hydrazine.

In the reaction, the base is usually used in a ratio of 1 to 10 mol, based on 1 mol of the intermediate compound (M31').

The reaction temperature is usually within the range of 0 to 120° C. The reaction time is usually within the range of 0.1 to 24 hours.

After completion of the reaction, the intermediate compound (M31) can be isolated by subjecting it to normal post-process operations. The isolated intermediate compound (M31) also can be further purified by chromatography, recrystallization, or the like.

(Production Method 18)

The intermediate compound (M1) in which $A^3$ is —$NR^8$— in the formula (M1) can be produced by brominating the compound (M28) to produce the intermediate compound (M32), then aminating the obtained intermediate compound (M32).

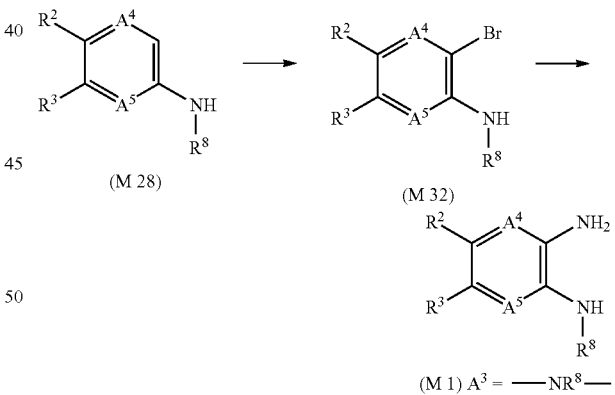

(M 28)    (M 32)

(M 1) $A^3$ = —$NR^8$— wherein symbols represent the same meaning as in the formula (1).

The intermediate compound (M32) can be produced by allowing the compound (M28) to react with a brominating agent.

The reaction is usually carried out in the presence of a solvent. Examples of the solvent include water, acetic acid, ethers such as 1,4-dioxane, diethyl ether and THF, esters such as ethyl acetate and butyl acetate, halogenated hydrocarbons such as dichloromethane, chloroform, carbon tetrachloride and 1,2-dichloroethane, nitriles such as acetonitrile, aprotic polar solvents such as DMF and NMP, and mixtures thereof.

Examples of the brominating agent include N-bromosuccinimide and bromine.

The reaction can be also carried out by adding a base, as necessary. Examples of the base include alkali metal bicarbonates such as sodium bicarbonate and alkali metal carbonates such as potassium carbonate.

The brominating agent is usually used in a ratio of 1 to 3 mol, and the base is usually used in a ratio of 1 to 3 mol, based on 1 mol of the compound (M28).

The reaction temperature is usually within the range of −10 to 100° C. The reaction time is usually within the range of 0.1 to 24 hours.

After completion of the reaction, the intermediate compound (M32) can be isolated by subjecting it to normal post-process operations. The isolated intermediate compound (M32) also can be further purified by recrystallization, chromatography, or the like.

The intermediate compound (M1) in which $A^3$ is —$NR^8$— can be produced by allowing the intermediate compound (M32) to react with an aminating agent, in the presence of copper or a copper compound.

The reaction is usually carried out in the presence of a solvent. Examples of the solvent include water, alcohols such as methanol and ethanol, ethers such as 1,4-dioxane, diethyl ether and THF, esters such as ethyl acetate and butyl acetate, halogenated hydrocarbons such as dichloromethane, chloroform, carbon tetrachloride and 1,2-dichloroethane, nitriles such as acetonitrile, aprotic polar solvents such as DMF, NMP, DMI and DMSO, nitrogen-containing aromatic compounds such as pyridine and quinoline, and mixtures thereof.

Examples of the aminating agent include ammonia, aqueous ammonia, and lithium amide.

Examples of the copper compound used in the reaction include copper(I) iodide, copper(I) oxide, copper(II) oxide, acetylacetone copper(II), copper(II) acetate, and copper(II) sulfate.

The reaction can be also carried out by adding a ligand as necessary. Examples of the ligand include acetylacetone, salen, and phenanthroline.

The reaction can be also carried out by adding a base as necessary.

Examples of the base used in the reaction include nitrogen-containing heterocyclic compounds such as pyridine, picoline, 2,6-lutidine, 1,8-diazabicyclo[5.4.0]-7-undecene and 1,5-diazabicyclo[4.3.0]-5-nonene, tertiary amines such as triethylamine and N,N-diisopropylethylamine, and inorganic bases such as tripotassium phosphate, potassium carbonate, cesium carbonate and sodium hydroxide.

The aminating agent is usually used in a ratio of 1 to 5 mol, copper or the copper compound is usually used in a ratio of 0.02 to 0.5 mol, the ligand is usually used in a ratio of 0.02 to 2 mol, and the base is usually used in a ratio of 1 to 5 mol, based on 1 mol of the intermediate compound (M32).

The reaction temperature is usually within the range of 30 to 200° C. The reaction time is usually within the range of 0.1 to 24 hours.

After completion of the reaction, the intermediate compound (M1) in which $A^3$ is —$NR^8$— can be isolated by subjecting it to normal post-process operations. The isolated intermediate compound (M1) in which $A^3$ is —NR— also can be further purified by recrystallization, chromatography, or the like.
(Production Method 19)

The compound of the present invention (1) in which $A^3$ is an oxygen atom in the formula (M1) can be produced by nitrating the compound (M33) to produce the intermediate compound (M34), then reducing the obtained intermediate compound (M34).

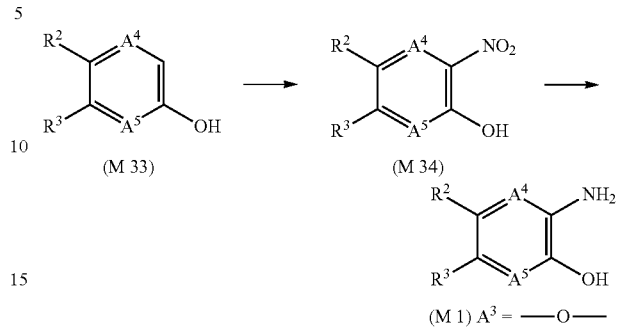

wherein symbols represent the same meaning as in the formula (1).

The intermediate compound (M34) can be produced, using the compound (M33) in place of the compound (M28), in accordance with the method of Production Method 17.

The intermediate compound (M1) in which $A^3$ is an oxygen atom can be produced, using the intermediate compound (M34) in place of the intermediate compound (M31), in accordance with the method of Production Method 17.
(Production Method 20)

The intermediate compound (M1) in which $A^3$ is a sulfur atom in the formula (M1) can be produced by allowing the compound (M29) to react with a sulfurizing agent, to produce the intermediate compound (M35), followed by allowing the obtained intermediate compound (M35) to react with a reducing agent.

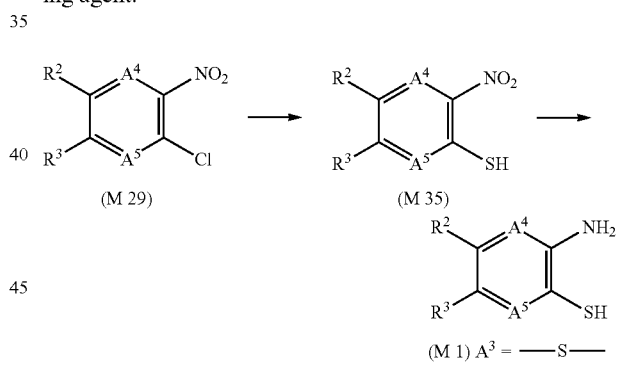

wherein symbols represent the same meaning as in the formula (1).

The intermediate compound (M35) can be produced by allowing the compound (M29) to react with thiourea, in the presence of a base.

The reaction is usually carried out in the presence of a solvent. Examples of the solvent include alcohols such as methanol and ethanol, water, and mixtures thereof.

Examples of the base include alkali metal hydroxides such as sodium hydroxide and potassium hydroxide.

In the reaction, thiourea is usually used in a ratio of 1 to 3 mol, and the base is usually used in a ratio of 1 to 10 mol, based on 1 mol of the compound (M29).

The reaction temperature is usually within the range of 0 to 100° C. The reaction time is usually within the range of 0.1 to 24 hours.

After completion of the reaction, the intermediate compound (M35) can be isolated by subjecting it to normal post-process operations. The isolated intermediate compound (M35) also can be further purified by chromatography, recrystallization, or the like.

The intermediate compound (M1) in which $A^3$ is a sulfur atom can be produced by allowing the intermediate compound (M35) to react with a reducing agent.

The reduction reaction can be carried out, for example, in the presence of metal powder such as iron powder and zinc powder; an acid such as hydrochloric acid and acetic acid; and water.

The reaction is usually carried out in the presence of a solvent. Examples of the solvent include ethers such as THF, ethylene glycol dimethyl ether, tert-butyl methyl ether and 1,4-dioxane, esters such as ethyl acetate and butyl acetate, alcohols such as methanol and ethanol, acid amides such as DMF and NMP, and mixtures thereof.

The reducing agent includes metal powder such as iron powder and zinc powder and tin dichloride.

In the reaction, the metal powder or tin dichloride is usually used in a ratio of 3 to 10 mol, based on 1 mol of the intermediate compound (M35).

The reaction temperature is usually within the range of 0 to 100° C. The reaction time is usually within the range of 0.1 to 24 hours.

After completion of the reaction, the intermediate compound (M1) in which $A^3$ is a sulfur atom can be isolated by subjecting it to normal post-process operations. The isolated intermediate compound (M1) in which $A^3$ is a sulfur atom also can be further purified by chromatography, recrystallization, or the like.

(Production Method 21)

The compound of the present invention (P5) in which $G^1$ is a nitrogen atom, $G^2$ is =CH—, $A^1$ is a nitrogen atom, and $A^2$ is =CR$^7$— in the formula (1) can be produced from the compound of the present invention (P4).

spheric pressure. Examples of the solvent include ethers such as THF, ethylene glycol dimethyl ether, tert-butyl methyl ether and 1,4-dioxane, esters such as ethyl acetate and butyl acetate, alcohols such as methanol and ethanol, water, and mixtures thereof.

Examples of the hydrogenation catalyst include palladium carbon and palladium hydroxide.

The reaction can be also carried out by adding an acid, a base or the like, as necessary. Examples of the acid include acetic acid and hydrochloric acid, and examples of the base include alkali metal carbonates such as potassium carbonate, alkali metal hydrides such as sodium hydride, tertiary amines such as triethylamine and N,N-diisopropylethylamine, sodium acetate and magnesium oxide.

In the reaction, hydrogen is usually used in a ratio of 1 mol or more, the hydrogenation catalyst is usually used in a ratio of 0.001 to 0.5 mol, the acid is usually used in a ratio of 0.001 to 10 mol, and the base is usually used in a ratio of 1 to 10 mol, based on 1 mol of the compound of the present invention (P4).

The reaction temperature is usually within the range of −20 to 100° C. The reaction time is usually within the range of 0.1 to 24 hours.

After completion of the reaction, the intermediate compound (M36) can be isolated by subjecting it to normal post-process operations. The isolated intermediate compound (M36) also can be further purified by chromatography, recrystallization, or the like. Also, after completion of the present reaction, the intermediate compound (M36) can be subjected to the next reaction without isolation.

The compound of the present invention (P5) can be produced by allowing the intermediate compound (M36) to react with an oxidizing agent.

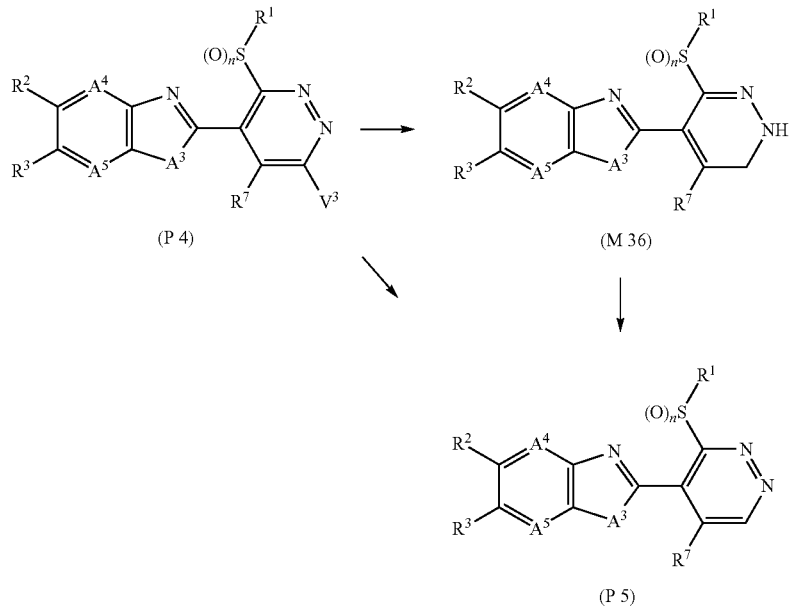

wherein $V^3$ represents a chlorine atom or a bromine atom, and other symbols represent the same meaning as in the formula (1).

The intermediate compound (M36) can be produced by allowing the compound of the present invention (P4) to react with hydrogen, in the presence of a hydrogenation catalyst.

The reaction is usually carried out in the presence of a solvent, usually in a hydrogen atmosphere of 1 to 100 atmo- The reaction is usually carried out in the presence of a solvent. Examples of the solvent include aliphatic halogenated hydrocarbons such as dichloromethane and chloroform, alcohols such as methanol and ethanol, acetic acid, water, and mixtures thereof.

Examples of the oxidizing agent include 2,3-dichloro-5,6-dicyano-p-benzoquinone, potassium ferricyanide, potassium permanganate, and chromium (VI) oxide.

In the reaction, the oxidizing agent is usually used in a ratio of 1 to 3 mol, based on 1 mol of the intermediate compound (M36).

The reaction temperature is usually within the range of −20 to 80° C. The reaction time is usually within the range of 0.1 to 12 hours.

After completion of the reaction, the compound of the present invention (P5) can be isolated by subjecting it to normal post-process operations. The isolated compound of the present invention (P5) also can be further purified by chromatography, recrystallization, or the like.

The compound of the present invention (P5) can be produced by allowing the compound of the present invention (P4) to react with hydrogen, in the presence of a hydrogenation catalyst.

The reaction is usually carried out in the presence of a solvent, usually in a hydrogen atmosphere of 1 to 100 atmospheric pressure. Examples of the solvent include ethers such as THF, ethylene glycol dimethyl ether, tert-butyl methyl ether and 1,4-dioxane, esters such as ethyl acetate and butyl acetate, alcohols such as methanol and ethanol, water, and mixtures thereof.

Examples of the hydrogenation catalyst include palladium carbon and palladium hydroxide.

The reaction can be also carried out by adding an acid, a base or the like, as necessary. Examples of the acid include acetic acid and hydrochloric acid, and examples of the base include alkali metal carbonates such as potassium carbonate, alkali metal hydrides such as sodium hydride, tertiary amines such as triethylamine and N,N-diisopropylethylamine, sodium acetate and magnesium oxide.

In the reaction, hydrogen is usually used in a ratio of 1 mol or more, the hydrogenation catalyst is usually used in a ratio of 0.001 to 0.5 mol, the acid is usually used in a ratio of 0.001 to 10 mol, and the base is usually used in a ratio of 1 to 10 mol, based on 1 mol of the compound of the present invention (P4).

The reaction temperature is usually within the range of −20 to 100° C. The reaction time is usually within the range of 0.1 to 24 hours.

After completion of the reaction, the compound of the present invention (P5) can be isolated by subjecting it to normal post-process operations. The isolated compound of the present invention (P5) also can be further purified by chromatography, recrystallization, or the like.

(Production Method 22)

The compound of the present invention (P7) in which $R^2$ is a C1 to C6 perfluoroalkyl group in the formula (1) can be produced by allowing the compound of the present invention (P6) in which $R^3$ is a halogen atom in the formula (1) to react with compound (M37) or compound (M37'), in the presence of copper or a copper compound.

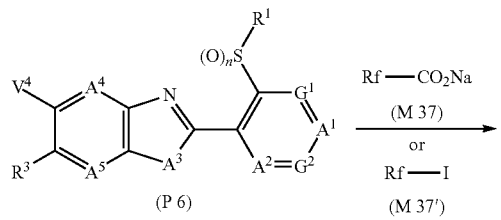

-continued

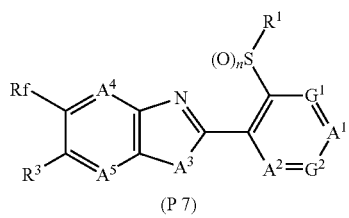

wherein $V^4$ represents a halogen atom, Rf represents a C1 to C6 perfluoroalkyl group, and other symbols represent the same meaning as in the formula (1).

The reaction is usually carried out in the presence of a solvent. Examples of the solvent include aromatic hydrocarbons such as toluene and xylene, acid amides such as DMF and NMP, and mixtures thereof.

Examples of the copper compound include copper(I) iodide.

When the compound (M37) is used in the reaction, the compound (M37) is usually used in a ratio of 1 to 10 mol, and copper or the copper compound is usually used in a ratio of 0.5 to 10 mol, based on 1 mol of the compound of the present invention (P6). The reaction temperature is usually within the range of 100 to 200° C., and the reaction time is usually within the range of 0.5 to 48 hours.

When the compound (M37') is used in the reaction, potassium fluoride may be added. The compound (M37') is usually used in a ratio of 1 to 10 mol, copper or the copper compound is usually used in a ratio of 0.1 to 10 mol, and potassium fluoride is usually used in a ratio of 0.1 to 5 mol, based on 1 mol of the compound of the present invention (P6). The reaction temperature is usually within the range of 0 to 150° C., and the reaction time is usually within the range of 0.5 to 48 hours.

After completion of the reaction, the compound of the present invention (P7) can be isolated by subjecting it to normal post-process operations. The isolated compound of the present invention (P7) also can be further purified by chromatography, recrystallization, or the like.

In the reaction, $V^4$ is preferably a bromine atom or an iodide atom.

(Production Method 23)

The compound of the present invention (P8) in which $R^2$ is —SH in the formula (1) can be produced by allowing the compound of the present invention (P6) to react with a sulfurizing agent. Also, the intermediate compound (P8') that is the disulfide body thereof can be produced by oxidizing the compound of the present invention (P8).

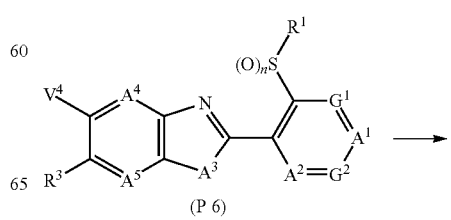

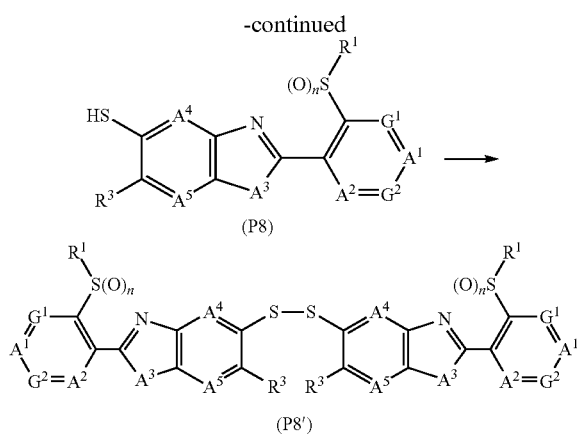

(P8)

(P8')

wherein $V^4$ represents a halogen atom, and other symbols represent the same meaning as in the formula (1).

The compound of the present invention (P8) can be produced by allowing the compound of the present invention (P6) to react with a thiolating agent, in the presence of a catalyst.

The reaction is usually carried out in the presence of a solvent. Examples of the solvent include aromatic hydrocarbons such as toluene and xylene, aprotic polar solvents such as DMF, NMP, DMI and DMSO, and mixtures thereof.

Examples of the thiolating agent include sodium sulfide, sodium sulfide nonahydrate, and thiourea.

Examples of the catalyst include copper(I) chloride, copper(I) bromide, and copper(I) iodide.

The reaction can be also carried out by adding a ligand as necessary. Examples of the ligand include acetylacetone, salen, and phenanthroline.

The reaction can be also carried out by adding a base, as necessary. Examples of the base include potassium carbonate, cesium carbonate, tripotassium phosphate, and triethylamine.

The thiolating agent is usually used in a ratio of 1 to 10 mol, the catalyst is usually used in a ratio of 0.1 to 5 mol, the ligand is usually used in a ratio of 0.1 to 5 mol, and the base is usually used in a ratio of 1 to 2 mol, based on 1 mol of the compound of the present invention (P6).

The reaction temperature is usually within the range of 50 to 200° C. The reaction time is usually within the range of 0.5 to 24 hours.

After completion of the reaction, the compound of the present invention (P8) can be isolated by subjecting it to normal post-process operations. The isolated compound of the present invention (P8) also can be further purified by chromatography, recrystallization, or the like.

In the reaction, $V^4$ is preferably a bromine atom or an iodide atom.

Here, the reaction from the compound of the present invention (P5) to the intermediate compound (P8') is likely to occur, and the intermediate compound (P8') is produced in some cases during synthesis of the compound of the present invention (P8).

The intermediate compound (P8') can be produced by allowing the compound of the present invention (P8) to react with an oxidizing agent.

The reaction is usually carried out in the presence of a solvent. Examples of the solvent include water, alcohols such as methanol and ethanol, ethers such as THF, ethylene glycol dimethyl ether, tert-butyl methyl ether and 1,4-dioxane, aromatic hydrocarbons such as toluene and xylene, nitriles such as acetonitrile, aprotic polar solvents such as DMF, NMP, DMI and DMSO, carboxylic acids such as acetic acid, and mixtures thereof.

Examples of the oxidizing agent include oxygen atom, iodine, aqueous hydrogen peroxide, and potassium ferricyanide.

In the reaction, the oxidizing agent is usually used in a ratio of 0.5 to 10 mol, based on 1 mol of the compound of the present invention (P8).

The reaction temperature is usually within the range of 0 to 100° C. The reaction time is usually within the range of 0.1 to 24 hours.

After completion of the reaction, the compound of the present invention (P8') can be isolated by subjecting it to normal post-process operations. The isolated compound of the present invention (P8') also can be further purified by chromatography, recrystallization, or the like.

Also, the compound of the present invention (P8) can be produced by thioesterifying the compound of the present invention (P6) as shown below to produce the intermediate compound (P8-1), then hydrolyzing the obtained intermediate compound (P8-1).

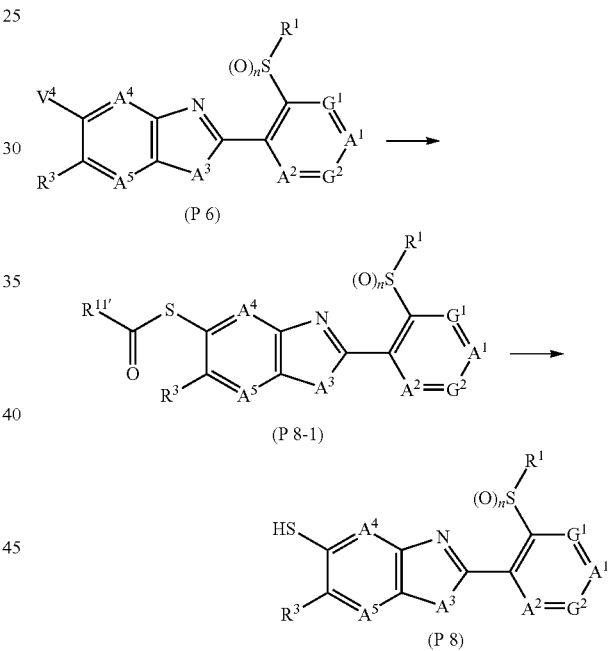

wherein $V^4$ represents a halogen atom, $R^{11'}$ represents any of $R^{11}$ in the formula (1) other than a hydrogen atom, and other symbols represent the same meaning as in the formula (1).

The intermediate compound (P8-1) can be produced by allowing the compound of the present invention (P6) to react with a thioesterifying agent, in the presence of a catalyst.

The reaction is usually carried out in the presence of a solvent. Examples of the solvent include aromatic hydrocarbons such as toluene and xylene, aprotic polar solvents such as DMF, NMP, DMI and DMSO, and mixtures thereof.

Examples of the thioesterifying agent include thiobenzoic acid and the like.

Examples of the catalyst include copper(I) chloride, copper(I) bromide, and copper(I) iodide.

The reaction can be also carried out by adding a ligand as necessary. Examples of the ligand include acetylacetone, salen, and phenanthroline.

The reaction can be also carried out in the presence of a base, as necessary. Examples of the base include potassium carbonate, cesium carbonate, tripotassium phosphate, and triethylamine.

In the reaction, the thioesterifying agent is usually used in a ratio of 1 to 10 mol, the catalyst usually used in a ratio of 0.1 to 5 mol, the ligand is usually used in a ratio of 0.1 to 5 mol, and the base is usually used in a ratio of 1 to 2 mol, based on 1 mol of the compound of the present invention (P6).

The reaction temperature is usually within the range of 50 to 200° C. The reaction time is usually within the range of 0.5 to 24 hours.

After completion of the reaction, the intermediate compound (P8-1) can be isolated by subjecting it to normal post-process operations. The isolated intermediate compound (P8-1) also can be further purified by chromatography, recrystallization, or the like.

In the reaction, $V^4$ is preferably a bromine atom or an iodide atom.

The compound of the present invention (P8) can be produced by hydrolyzing the intermediate compound (P8-1).

In the reaction, the base is usually used in a ratio of 1 to 10 mol, based on 1 mol of the intermediate compound (P8-1).

The reaction temperature of base hydrolysis is usually within the range of 0 to 120° C. The reaction time is usually within the range of 0.1 to 24 hours.

After completion of the reaction, the compound of the present invention (P8) can be isolated by subjecting it to normal post-process operations. The isolated compound of the present invention (P8) also can be further purified by chromatography, recrystallization, or the like.

(Production Method 24)

The compound of the present invention (P9-m0) in which $R^2$ is $—S(O)_m R^{11'}$, and m is 0 can be produced by allowing the intermediate compound (P8) or the intermediate compound (P8') that is a disulfide body thereof to react with the compound (M38) in the presence of a base. The compound of the present invention (P9) in which $R^2$ is $—S(O)_m R^{11'}$, and m is 1 or 2 in the formula (1) can be produced by oxidizing the compound of the present invention (P9-m0) in which m is 0.

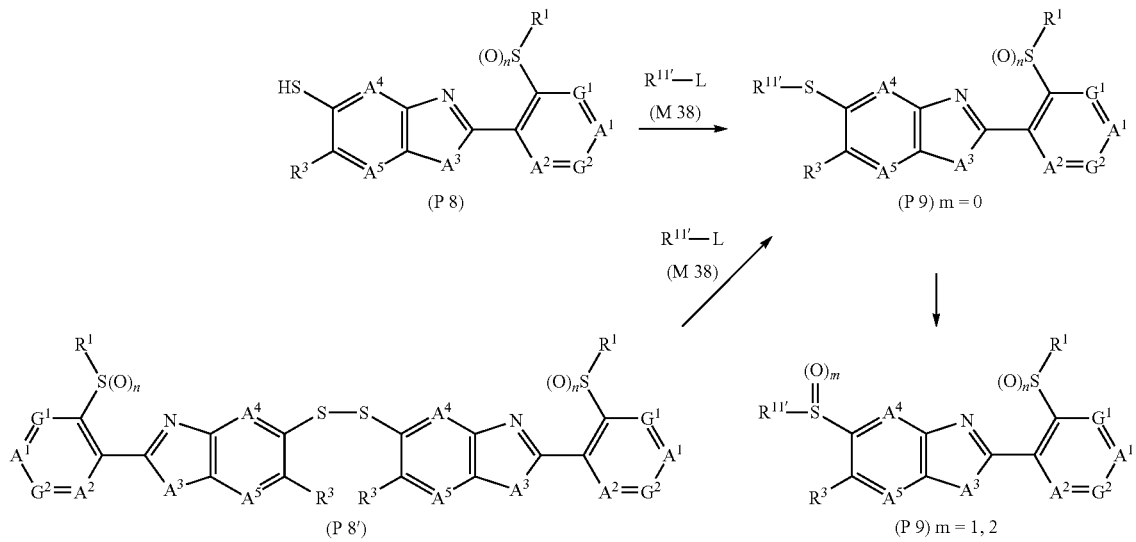

When hydrolyzed by an acid, the reaction is usually carried out using an aqueous solution of an acid as a solvent. Examples of the acid include mineral acids such as hydrochloric acid, nitric acid, phosphoric acid and sulfuric acid, carboxylic acids such as acetic acid and trifluoroacetic acid.

The reaction temperature of acid hydrolysis is usually within the range of 0 to 100° C. The reaction time is usually within the range of 0.1 to 24 hours.

After completion of the reaction, the compound of the present invention (P8) can be isolated by subjecting it to normal post-process operations. The isolated compound of the present invention (P8) also can be further purified by chromatography, recrystallization, or the like.

When hydrolyzed by a base, the reaction is usually carried out in the presence of a solvent. Examples of the solvent include ethers such as THF, ethylene glycol dimethyl ether, tert-butyl methyl ether and 1,4-dioxane, alcohols such as methanol and ethanol, water, and mixtures thereof.

Examples of the base include alkali metal hydroxides such as sodium hydroxide and potassium hydroxide.

wherein $R^{11'}$ represents any of $R^{11}$ in the formula (1) other than a hydrogen atom, L represents a leaving group such as a chlorine atom, a bromine atom, an iodine atom, a trifluoromethanesulfonyloxy group or a methanesulfonyloxy group, and other symbols represent the same meaning as in the formula (1).

The reaction is usually carried out in the presence of a solvent. Examples of the solvent include ethers such as THF, ethylene glycol dimethyl ether, tert-butyl methyl ether and 1,4-dioxane, aromatic hydrocarbons such as toluene and xylene, nitriles such as acetonitrile, aprotic polar solvents such as DMF, NMP, DMI and DMSO, and mixtures thereof.

Examples of the base include hydrides of alkali metals or alkaline earth metals such as sodium hydride, potassium hydride and calcium hydride, inorganic bases such as sodium carbonate and potassium carbonate, or organic bases such as triethylamine.

When the intermediate compound (P8') that is a disulfide body is used, the reaction is usually carried out in the presence of a reducing agent. Examples of the reducing agent include sodium hydroxymethanesulfinate.

In the reaction, the compound (M38) is usually used in a ratio of 1 to 10 mol, and the base is usually used in a ratio of 1 to 10 mol, based on 1 mol of the compound of the present invention (P8).

When the intermediate compound (M8') that is a disulfide body is used, the compound (M38) is usually used in a ratio of 2 to 5 mol, the base is usually used in a ratio of 2 to 5 mol, and the reducing agent is usually used in a ratio of 1 to 5 mol, based on 1 mol of the intermediate compound (P8').

The reaction temperature is usually within the range of 0 to 100° C. The reaction time is usually within the range of 0.1 to 24 hours.

After completion of the reaction, the compound of the present invention (P9-m0) in which m is 0 can be isolated by subjecting it to normal post-process operations. The isolated compound of the present invention (P9-m0) in which m is 0 also can be further purified by chromatography, recrystallization, or the like.

In addition, among the compounds of the present invention (P9-m0) in which m is 0, a compound in which $R^{11'}$ is a C1 to C6 perfluoroalkyl can be produced by allowing the intermediate compound (P8'), perfluoroalkyl iodide and a reducing agent to react.

The reaction is usually carried out in the presence of a solvent. Examples of the solvent include ethers such as THF, ethylene glycol dimethyl ether, tert-butyl methyl ether and 1,4-dioxane, aromatic hydrocarbons such as toluene and xylene, nitriles such as acetonitrile, aprotic polar solvents such as DMF, NMP, DMI and DMSO, and mixtures thereof.

Examples of the reducing agent include tetrakis(dimethylamino)ethylene.

Examples of the perfluoroalkyl iodide include trifluoromethane iodide, pentafluoroethane iodide, and heptafluoro-2-iodopropane.

In the reaction, perfluoroalkyl iodide is usually used in a ratio of 2 to 10 mol, and the reducing agent is usually used in a ratio of 1 to 5 mol, based on 1 mol of the intermediate compound (P8').

The reaction temperature is usually within the range of −80 to 50° C. The reaction time is usually within the range of 0.1 to 24 hours.

After completion of the reaction, the compound of the present invention (P9-m0) in which m is 0 can be isolated by subjecting it to normal post-process operations. The isolated compound of the present invention (P9-m0) in which m is 0 also can be further purified by chromatography, recrystallization, or the like.

In the compound of the present invention (P9), the compound of the present invention in which m is 1 or 2 can be produced by allowing the compound of the present invention (P9-m0) in which m is 0 to react, in the presence of an oxidizing agent.

The reaction is usually carried out in the presence of a solvent. Examples of the solvent include aliphatic halogenated hydrocarbons such as dichloromethane and chloroform, alcohols such as methanol and ethanol, acetic acid, water, and mixtures thereof.

Examples of the oxidizing agent include m-chloroperbenzoic acid and aqueous hydrogen peroxide.

The reaction can be also carried out, in the presence of a catalyst, as necessary. Examples of the catalyst include sodium tungstate.

In the reaction, the oxidizing agent is usually used in a ratio of 1 to 5 mol, and the catalyst is usually used in a ratio of 0.01 to 0.5 mol, based on 1 mol of the compound of the present invention (P9-m0) in which m is 0.

In the compound in which m is 1, the oxidizing agent is usually used in a ratio of 0.8 to 1.2 mol, based on 1 mol of the compound of the present invention (P9-m0) in which m is 0, and in the compound in which m is 2, the oxidizing agent is usually used in a ratio of 1.8 to 5 mol, based on 1 mol of the compound of the present invention (P9-m0) in which m is 0.

The reaction temperature is usually within the range of −20 to 120° C. The reaction time is usually within the range of 0.1 to 24 hours.

After completion of the reaction, the compound of the present invention (P9) in which m is 1 or 2 can be isolated by subjecting it to normal post-process operations. The isolated compound of the present invention (P9) in which m is 1 or 2 also can be further purified by chromatography, recrystallization, or the like.

(Production Method 25)

The compound of the present invention (P10) in which $R^2$ is —OH in the formula (1) can be produced from the compound of the present invention (P6) through the intermediate compound (210').

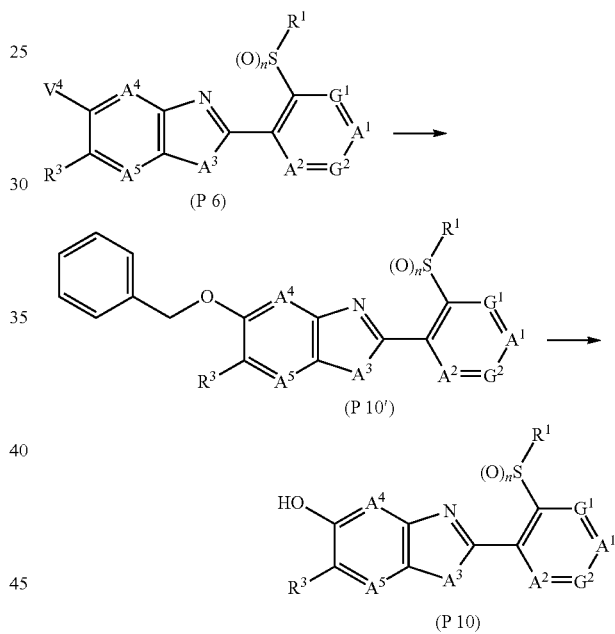

wherein $V^4$ represents a halogen atom, and other symbols represent the same meaning as in the formula (1).

The intermediate compound (P10') can be produced by allowing the compound of the present invention (P6) to react with benzyl alcohol, in the presence of a base.

The reaction is usually carried out in the presence of a solvent or using benzyl alcohol as a solvent. Examples of the solvent include aromatic hydrocarbons such as toluene and xylene, aprotic polar solvents such as DMF, NMP, DMI and DMSO, and mixtures thereof.

The reaction can be also carried out by adding a catalyst, as necessary. Examples of the catalyst include copper(I) chloride, copper(I) bromide, and copper(I) iodide.

The reaction can be also carried out by adding a ligand as necessary. Examples of the ligand include acetylacetone, salen, and phenanthroline.

The reaction is usually carried out in the presence of a base. Examples of the base include potassium carbonate, cesium carbonate, and tripotassium phosphate.

In the reaction, benzyl alcohol is usually used in a ratio of 1 to 10 mol, the catalyst is usually used in a ratio of 0.1 to 5 mol, the ligand is usually used in a ratio of 0.1 to 5 mol, and the base is usually used in a ratio of 1 to 2 mol, based on 1 mol of the compound of the present invention (P6).

The reaction temperature is usually within the range of 50 to 200° C. The reaction time is usually within the range of 0.5 to 24 hours.

After completion of the reaction, the intermediate compound (P10') can be isolated by subjecting it to normal post-process operations. The isolated intermediate compound (P10') also can be further purified by chromatography, recrystallization, or the like.

In the reaction, $V^4$ is preferably a bromine atom or an iodine atom.

The compound of the present invention (P10) can be produced by allowing the intermediate compound (P10') to react with hydrogen, in the presence of a hydrogenation catalyst.

The reaction is usually carried out in the presence of a solvent, usually in a hydrogen atmosphere of 1 to 100 atmospheric pressure. Examples of the solvent include ethers such as THF, ethylene glycol dimethyl ether, tert-butyl methyl ether and 1,4-dioxane, esters such as ethyl acetate and butyl acetate, alcohols such as methanol and ethanol, water, and mixtures thereof.

Examples of the hydrogenation catalyst include transition metal compounds such as palladium carbon, palladium hydroxide, and platinum oxide.

The reaction can be also carried out by adding an acid, a base or the like, as necessary. Examples of the acid include acetic acid and hydrochloric acid, and examples of the base include tertiary amines such as triethylamine, and magnesium oxide.

In the reaction, hydrogen is usually used in a ratio of 1 mol or more, the hydrogenation catalyst is usually used in a ratio of 0.001 to 0.5 mol, the acid is usually used in a ratio of 0.001 to 10 mol, and the base is usually used in a ratio of 1 to 10 mol, based on 1 mol of the intermediate compound (P10').

The reaction temperature is usually within the range of −20 to 100° C. The reaction time is usually within the range of 0.1 to 24 hours.

After completion of the reaction, the compound of the present invention (P10) can be isolated by subjecting it to normal post-process operations. The isolated compound of the present invention (P10) also can be further purified by chromatography, recrystallization, or the like.

(Production Method 26)

The compound of the present invention (P11) in which $R^2$ is $-OR^{11'}$ in the formula (1) can be produced by allowing the compound of the present invention (P10) to react with the compound (M38), in the presence of a base.

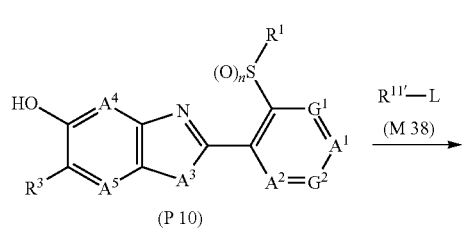

(P 10)

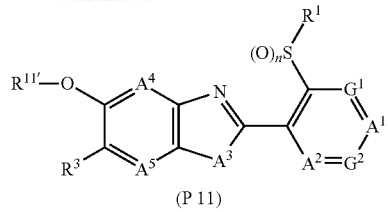

(P 11)

wherein $R^{11'}$ represents any of $R^{11}$ in the formula (1) other than a hydrogen atom, L represents a leaving group such as a chlorine atom, a bromine atom, an iodine atom, a trifluoromethanesulfonyloxy group or a methanesulfonyloxy group, and other symbols represent the same meaning as in the formula (1).

The reaction is usually carried out in the presence of a solvent. Examples of the solvent include ethers such as THF, ethylene glycol dimethyl ether, tert-butyl methyl ether and 1,4-dioxane, aromatic hydrocarbons such as toluene and xylene, nitriles such as acetonitrile, aprotic polar solvents such as DMF, NMP, DMI and DMSO, and mixtures thereof.

Examples of the base include hydrides of alkali metals or alkaline earth metals such as sodium hydride, potassium hydride and calcium hydride, inorganic bases such as sodium carbonate and potassium carbonate, or organic bases such as triethylamine.

In the reaction, the compound (M38) is usually used in a ratio of 1 to 10 mol, and the base is usually used in a ratio of 1 to 10 mol, based on 1 mol of the compound of the present invention (P10).

The reaction temperature is usually within the range of 0 to 100° C. The reaction time is usually within the range of 0.1 to 24 hours.

After completion of the reaction, the compound of the present invention (P11) can be isolated by subjecting it to normal post-process operations. The isolated compound of the present invention (P11) also can be further purified by chromatography, recrystallization, or the like.

Also, among the compounds of the present invention (P11), the compound of the present invention (P11) in which $R^{11'}$ is a trifluoromethyl group can be produced according to the following production method.

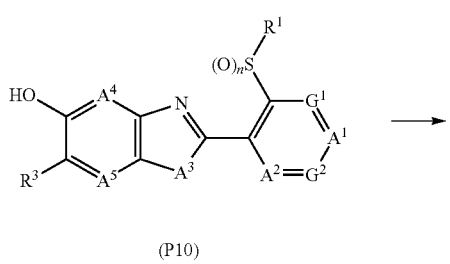

(P10)

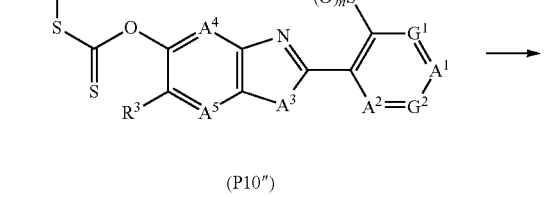

(P10'')

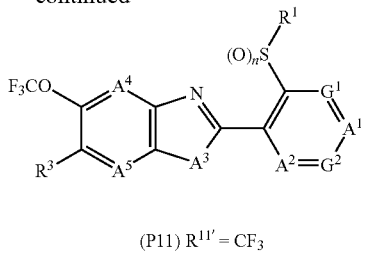

(P11) R$^{11'}$ = CF$_3$ wherein symbols represent the same meaning as in the formula (1).

The intermediate compound (P10'') can be produced by allowing the compound of the present invention (P10) to react with a base, carbon disulfide and a methylating agent.

The reaction is usually carried out in the presence of a solvent. Examples of the solvent include aprotic polar solvents such as DMF, NMP, DMI and DMSO.

Examples of the base include alkali metal hydrides such as sodium hydride.

Examples of the methylating agent include methyl iodide.

In the reaction, the base is usually used in a ratio of 1 to 2 mol, carbon disulfide is usually used in a ratio of 1 to 10 mol, and the methylating agent is usually used in a ratio of 1 to 10 mol, based on 1 mol of the compound of the present invention (P10).

The reaction temperature is usually within the range of 0 to 100° C. The reaction time is usually within the range of 0.5 to 24 hours.

After completion of the reaction, the intermediate compound (P10'') can be isolated by subjecting it to normal post-process operations. The isolated intermediate compound (P10'') also can be further purified by chromatography, recrystallization, or the like.

Among the compounds of the present invention (P11), the compound of the present invention (P11) in which R$^{11'}$ is a trifluoromethyl group can be produced by allowing the intermediate compound (P10'') to react with a fluorinating agent, in the presence of a base.

The reaction is usually carried out in the presence of a solvent. Examples of the solvent include halogenated hydrocarbons such as dichloromethane, chloroform, carbon tetrachloride, and 1,2-dichloroethane.

Examples of the base include 1,3-dibromo-5,5-dimethylhydantoin.

Examples of the fluorinating agent include tetra-n-butylammonium fluoride and hydrogen fluoride pyridine complex.

In the reaction, the base is usually used in a ratio of 1 to 10 mol, and the fluorinating agent is usually used in a ratio of 1 to 10 mol, based on 1 mol of the intermediate compound (P10'').

The reaction temperature is usually within the range of −80 to 50° C. The reaction time is usually within the range of 0.5 to 24 hours.

After completion of the reaction, the compound of the present invention (P11) in which R$^{11'}$ is a trifluoromethyl group can be isolated by subjecting it to normal post-process operations. The isolated compound of the present invention (P11) in which R$^{11'}$ is a trifluoromethyl group also can be further purified by chromatography, recrystallization, or the like.

(Production Method 27)

Among the compounds of the present invention and the above-described intermediate compounds, a compound having a nitrogen-containing heterocyclic group having a lone pair of electrons on the nitrogen atom is reacted with an oxidizing agent, whereby an N-oxide in which the nitrogen atom is oxidized can be manufactured in some cases.

Examples of the nitrogen-containing heterocyclic group include a pyridine ring, and condensed rings containing a pyridine ring.

The reaction can be carried out by a known method, and is carried out using an oxidizing agent such as m-chloroperbenzoic acid or hydrogen peroxide, in a solvent, for example, a halogenated hydrocarbon such as dichloromethane, chloroform or chlorobenzene, an alcohol such as methanol or ethanol, acetic acid, water, and mixtures thereof.

Examples of the intermediate compound (M4) include following compounds.

Compounds according to the formula (M4) represented by formula (M4-1)

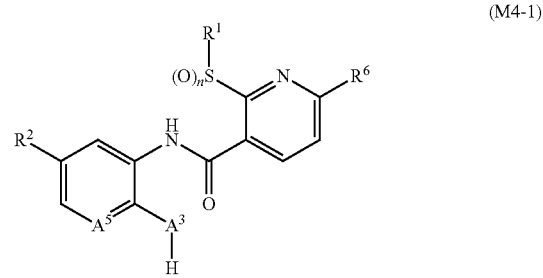

(M4-1)

wherein symbols represent the same meaning as in the formula (1);
In the formula (M4-1), compounds wherein A$^3$ is —NR$^8$—, and R$^8$ is a methyl group;
In the formula (M4-1), compounds wherein A$^3$ is —NR$^8$—, and R$^8$ is a propargyl group;
In the formula (M4-1), compounds wherein A$^3$ is an oxygen atom;
In the formula (M4-1), compounds wherein A$^3$ is a sulfur atom; compounds according to the formula (M4) represented by formula (M4-2)

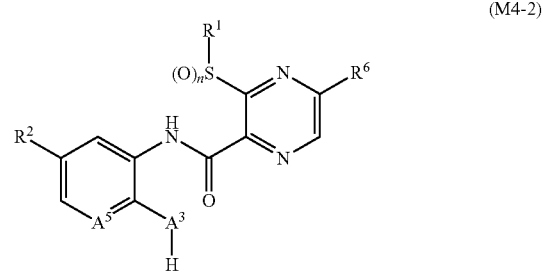

(M4-2)

wherein symbols represent the same meaning as in the formula (1);
In the formula (M4-2), compounds wherein A$^3$ is —NR$^8$—, and R$^8$ is a methyl group;
In the formula (M4-2), compounds wherein A$^3$ is —NR$^8$—, and R$^8$ is a propargyl group;
In the formula (M4-2), compounds wherein A$^3$ is an oxygen atom;
In the formula (M4-2), compounds wherein A$^3$ is a sulfur atom; compounds according to the formula (M4) represented by formula (M4-3)

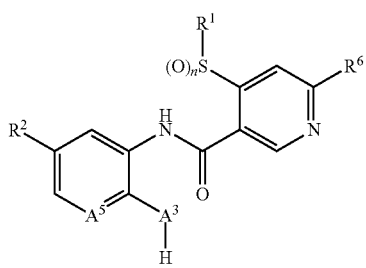

(M4-3)

wherein symbols represent the same meaning as in the formula (1);
In the formula (M4-3), compounds wherein $A^3$ is —$NR^8$—, and $R^8$ is a methyl group;
In the formula (M4-3), compounds wherein $A^3$ is —$NR^8$—, and $R^8$ is a propargyl group;
In the formula (M4-3), compounds wherein $A^3$ is an oxygen atom;
In the formula (M4-3), compounds wherein $A^3$ is a sulfur atom; compounds according to the formula (M4) represented by formula (M4-4)

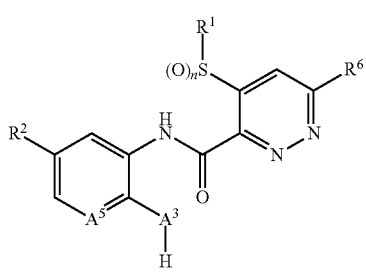

(M4-4)

wherein symbols represent the same meaning as in the formula (1);
In the formula (M4-4), compounds wherein $A^3$ is —$NR^8$—, and $R^8$ is a methyl group;
In the formula (M4-4), compounds wherein $A^3$ is —$NR^8$—, and $R^8$ is a propargyl group;
In the formula (M4-4), compounds wherein $A^3$ is an oxygen atom;
In the formula (M4-4), compounds wherein $A^3$ is a sulfur atom; compounds according to the formula (M4) represented by formula (M4-5)

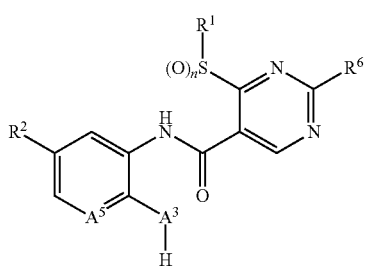

(M4-5)

wherein symbols represent the same meaning as in the formula (1);
In the formula (M4-5), compounds wherein $A^3$ is —$NR^8$—, and $R^8$ is a methyl group;
In the formula (M4-5), compounds wherein $A^3$ is —$NR^8$—, and $R^8$ is a propargyl group;
In the formula (M4-5), compounds wherein $A^3$ is an oxygen atom;
In the formula (M4-5), compounds wherein $A^3$ is a sulfur atom; compounds according to the formula (M4) represented by formula (M4-6)

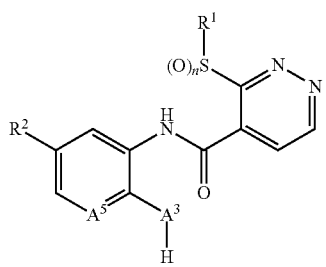

(M4-6)

wherein symbols represent the same meaning as in the formula (1);
In the formula (M4-6), compounds wherein $A^3$ is —$NR^8$—, and $R^8$ is a methyl group;
In the formula (M4-6), compounds wherein $A^3$ is —$NR^8$—, and $R^8$ is a propargyl group;
In the formula (M4-6), compounds wherein $A^3$ is an oxygen atom;
In the formula (M4-6), compounds wherein $A^3$ is a sulfur atom;
Examples of the intermediate compound (M8) include following compounds.
Compounds according to the formula (M8) represented by formula (M8-1)

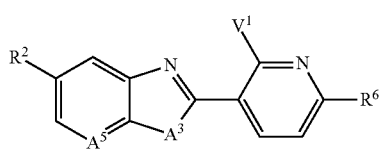

(M8-1)

wherein $V^1$ represents a halogen atom, and other symbols represent the same meaning as in the formula (1);
In the formula (M8-1), compounds wherein $A^3$ is —$NR^8$—, and $R^8$ is a methyl group;
In the formula (M8-1), compounds wherein $A^3$ is —$NR^8$—, and $R^8$ is a propargyl group;
In the formula (M8-1), compounds wherein $A^3$ is an oxygen atom;
In the formula (M8-1), compounds wherein $A^3$ is a sulfur atom; compounds according to the formula (M8) represented by formula (M8-2)

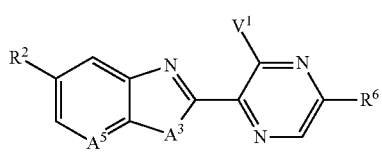

(M8-2)

wherein $V^1$ represents a halogen atom, and other symbols represent the same meaning as in the formula (1);

In the formula (M8-2), compounds wherein $A^3$ is —$NR^8$—, and $R^8$ is a methyl group;
In the formula (M8-2), compounds wherein $A^3$ is —$NR^8$—, and $R^8$ is a propargyl group;
In the formula (M8-2), compounds wherein $A^3$ is an oxygen atom;
In the formula (M8-2), compounds wherein $A^3$ is a sulfur atom; compounds according to the formula (M8) represented by formula (M8-3)

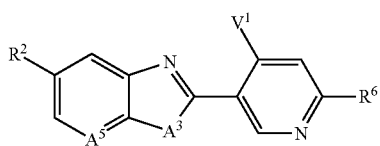

(M8-3)

wherein $V^1$ represents a halogen atom, and other symbols represent the same meaning as in the formula (1);
In the formula (M8-3), compounds wherein $A^3$ is —$NR^8$—, and $R^8$ is a methyl group;
In the formula (M8-3), compounds wherein $A^3$ is —$NR^8$—, and $R^8$ is a propargyl group;
In the formula (M8-3), compounds wherein $A^3$ is an oxygen atom;
In the formula (M8-3), compounds wherein $A^3$ is a sulfur atom; compounds according to the formula (M8) represented by formula (M8-4)

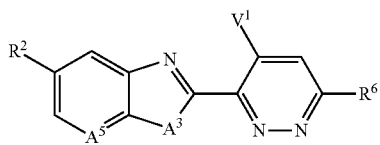

(M8-4)

wherein $V^1$ represents a halogen atom, and other symbols represent the same meaning as in the formula (1);
In the formula (M8-4), compounds wherein $A^3$ is —$NR^8$—, and $R^8$ is a methyl group;
In the formula (M8-4), compounds wherein $A^3$ is —$NR^8$—, and $R^8$ is a propargyl group;
In the formula (M8-4), compounds wherein $A^3$ is an oxygen atom;
In the formula (M8-4), compounds wherein $A^3$ is a sulfur atom; compounds according to the formula (M8) represented by formula (M8-5)

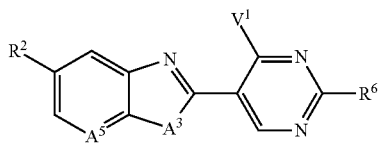

(M8-5)

wherein $V^1$ represents a halogen atom, and other symbols represent the same meaning as in the formula (1);
In the formula (M8-5), compounds wherein $A^3$ is —$NR^8$—, and $R^8$ is a methyl group;
In the formula (M8-5), compounds wherein $A^3$ is —$NR^8$—, and $R^8$ is a propargyl group;

In the formula (M8-5), compounds wherein $A^3$ is an oxygen atom;
In the formula (M8-5), compounds wherein $A^3$ is a sulfur atom; compounds according to the formula (M8) represented by formula (M8-6)

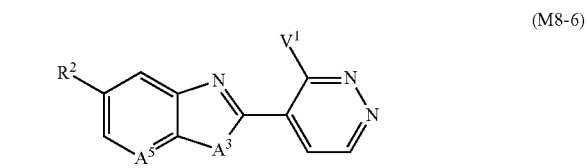

(M8-6)

wherein $V^1$ represents a halogen atom, and other symbols represent the same meaning as in the formula (1);
In the formula (M8-6), compounds wherein $A^3$ is —$NR^8$—, and $R^8$ is a methyl group;
In the formula (M8-6), compounds wherein $A^3$ is —$NR^8$—, and $R^8$ is a propargyl group;
In the formula (M8-6), compounds wherein $A^3$ is an oxygen atom;
In the formula (M8-6), compounds wherein $A^3$ is a sulfur atom;
Examples of the intermediate compound (M12) include following compounds.
Compounds according to the formula (M12) represented by formula (M12-1)

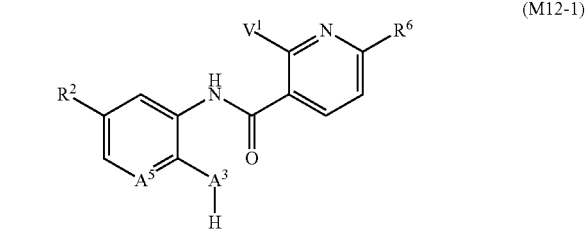

(M12-1)

wherein $V^1$ represents a halogen atom, and other symbols represent the same meaning as in the formula (1);
In the formula (M12-1), compounds wherein $A^3$ is —$NR^8$—, and $R^8$ is a methyl group;
In the formula (M12-1), compounds wherein $A^3$ is —$NR^8$—, and $R^8$ is a propargyl group;
In the formula (M12-1), compounds wherein $A^3$ is an oxygen atom;
In the formula (M12-1), compounds wherein $A^3$ is a sulfur atom; compounds according to the formula (M12) represented by formula (M12-2)

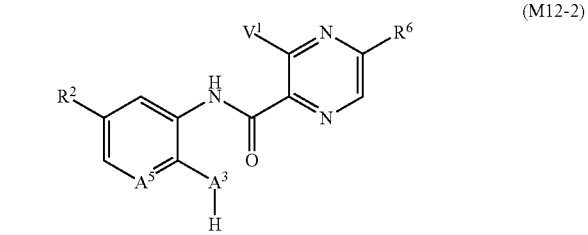

(M12-2)

wherein $V^1$ represents a halogen atom, and other symbols represent the same meaning as in the formula (1);

In the formula (M12-2), compounds wherein $A^3$ is —$NR^8$—, and $R^8$ is a methyl group;

In the formula (M12-2), compounds wherein $A^3$ is —$NR^8$—, and $R^8$ is a propargyl group;

In the formula (M12-2), compounds wherein $A^3$ is an oxygen atom;

In the formula (M12-2), compounds wherein $A^3$ is a sulfur atom; compounds according to the formula (M12) represented by formula (M12-3)

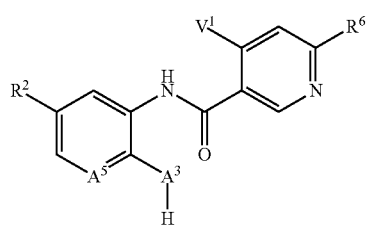

(M12-3)

wherein $V^1$ represents a halogen atom, and other symbols represent the same meaning as in the formula (1);

In the formula (M12-3), compounds wherein $A^3$ is —$NR^8$—, and $R^8$ is a methyl group;

In the formula (M12-3), compounds wherein $A^3$ is —$NR^8$—, and $R^8$ is a propargyl group;

In the formula (M12-3), compounds wherein $A^3$ is an oxygen atom;

In the formula (M12-3), compounds wherein $A^3$ is a sulfur atom; compounds according to the formula (M12) represented by formula (M12-4)

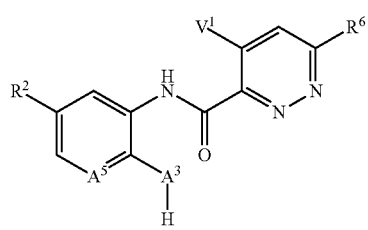

(M12-4)

wherein $V^1$ represents a halogen atom, and other symbols represent the same meaning as in the formula (1);

In the formula (M12-4), compounds wherein $A^3$ is —$NR^8$—, and $R^8$ is a methyl group;

In the formula (M12-4), compounds wherein $A^3$ is —$NR^8$—, and $R^8$ is a propargyl group;

In the formula (M12-4), compounds wherein $A^3$ is an oxygen atom;

In the formula (M12-4), compounds wherein $A^3$ is a sulfur atom; compounds according to the formula (M12) represented by formula (M12-5)

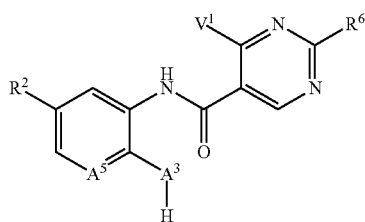

(M12-5)

wherein $V^1$ represents a halogen atom, and other symbols represent the same meaning as in the formula (1);

In the formula (M12-5), compounds wherein $A^3$ is —$NR^8$—, and $R^8$ is a methyl group;

In the formula (M12-5), compounds wherein $A^3$ is —$NR^8$—, and $R^8$ is a propargyl group;

In the formula (M12-5), compounds wherein $A^3$ is an oxygen atom;

In the formula (M12-5), compounds wherein $A^3$ is a sulfur atom; compounds according to the formula (M12) represented by formula (M12-6)

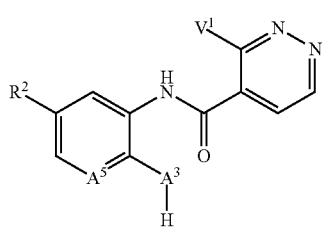

(M12-6)

wherein $V^1$ represents a halogen atom, and other symbols represent the same meaning as in the formula (1);

In the formula (M12-6), compounds wherein $A^3$ is —$NR^8$—, and $R^8$ is a methyl group;

In the formula (M12-6), compounds wherein $A^3$ is —$NR^8$—, and $R^8$ is a propargyl group;

In the formula (M12-6), compounds wherein $A^3$ is an oxygen atom;

In the formula (M12-6), compounds wherein $A^3$ is a sulfur atom;

Next, specific examples of the compound of the present invention are shown below.

In formula (A-1),

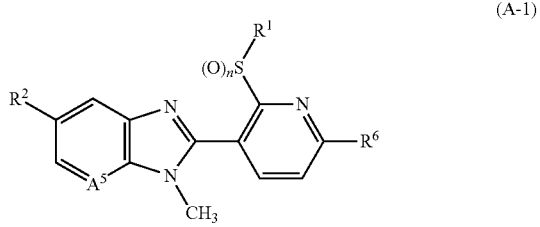

(A-1)

wherein symbols represent the same meaning as in the formula (1), the compounds of the present invention wherein $R^6$ is a hydrogen atom, and $R^1$, $R^2$, $A^5$ and n are the combinations shown in [Table 1] to [Table 10].

TABLE 1

| R¹ | R² | A⁵ | n |
|---|---|---|---|
| Me | CF₃ | =N— | 0 |
| Me | CF₃ | =N— | 1 |
| Me | CF₃ | =N— | 2 |
| Me | CF₂CF₃ | =N— | 0 |
| Me | CF₂CF₃ | =N— | 1 |
| Me | CF₂CF₃ | =N— | 2 |
| Me | CF(CF₃)₂ | =N— | 0 |
| Me | CF(CF₃)₂ | =N— | 1 |
| Me | CF(CF₃)₂ | =N— | 2 |
| Me | OCF₃ | =N— | 0 |
| Me | OCF₃ | =N— | 1 |
| Me | OCF₃ | =N— | 2 |
| Me | SCF₃ | =N— | 0 |
| Me | SCF₃ | =N— | 1 |
| Me | SCF₃ | =N— | 2 |
| Me | S(O)CF₃ | =N— | 0 |
| Me | S(O)CF₃ | =N— | 1 |
| Me | S(O)CF₃ | =N— | 2 |
| Me | S(O)₂CF₃ | =N— | 0 |
| Me | S(O)₂CF₃ | =N— | 1 |
| Me | S(O)₂CF₃ | =N— | 2 |
| Et | CF₃ | =N— | 0 |
| Et | CF₃ | =N— | 1 |
| Et | CF₃ | =N— | 2 |
| Et | CF₂CF₃ | =N— | 0 |
| Et | CF₂CF₃ | =N— | 1 |
| Et | CF₂CF₃ | =N— | 2 |
| Et | CF(CF₃)₂ | =N— | 0 |
| Et | CF(CF₃)₂ | =N— | 1 |
| Et | CF(CF₃)₂ | =N— | 2 |

TABLE 2

| R¹ | R² | A⁵ | n |
|---|---|---|---|
| Et | OCF₃ | =N— | 0 |
| Et | OCF₃ | =N— | 1 |
| Et | OCF₃ | =N— | 2 |
| Et | SCF₃ | =N— | 0 |
| Et | SCF₃ | =N— | 1 |
| Et | SCF₃ | =N— | 2 |
| Et | S(O)CF₃ | =N— | 0 |
| Et | S(O)CF₃ | =N— | 1 |
| Et | S(O)CF₃ | =N— | 2 |
| Et | S(O)₂CF₃ | =N— | 0 |
| Et | S(O)₂CF₃ | =N— | 1 |
| Et | S(O)₂CF₃ | =N— | 2 |
| Pr | CF₃ | =N— | 0 |
| Pr | CF₃ | =N— | 1 |
| Pr | CF₃ | =N— | 2 |
| Pr | CF₂CF₃ | =N— | 0 |
| Pr | CF₂CF₃ | =N— | 1 |
| Pr | CF₂CF₃ | =N— | 2 |
| Pr | CF(CF₃)₂ | =N— | 0 |
| Pr | CF(CF₃)₂ | =N— | 1 |
| Pr | CF(CF₃)₂ | =N— | 2 |
| Pr | OCF₃ | =N— | 0 |
| Pr | OCF₃ | =N— | 1 |
| Pr | OCF₃ | =N— | 2 |
| Pr | SCF₃ | =N— | 0 |
| Pr | SCF₃ | =N— | 1 |
| Pr | SCF₃ | =N— | 2 |
| Pr | S(O)CF₃ | =N— | 0 |
| Pr | S(O)CF₃ | =N— | 1 |
| Pr | S(O)CF₃ | =N— | 2 |

TABLE 3

| R¹ | R² | A⁵ | n |
|---|---|---|---|
| Pr | S(O)₂CF₃ | =N— | 0 |
| Pr | S(O)₂CF₃ | =N— | 1 |
| Pr | S(O)₂CF₃ | =N— | 2 |
| iPr | CF₃ | =N— | 0 |
| iPr | CF₃ | =N— | 1 |
| iPr | CF₃ | =N— | 2 |
| iPr | CF₂CF₃ | =N— | 0 |
| iPr | CF₂CF₃ | =N— | 1 |
| iPr | CF₂CF₃ | =N— | 2 |
| iPr | CF(CF₃)₂ | =N— | 0 |
| iPr | CF(CF₃)₂ | =N— | 1 |
| iPr | CF(CF₃)₂ | =N— | 2 |
| iPr | OCF₃ | =N— | 0 |
| iPr | OCF₃ | =N— | 1 |
| iPr | OCF₃ | =N— | 2 |
| iPr | SCF₃ | =N— | 0 |
| iPr | SCF₃ | =N— | 1 |
| iPr | SCF₃ | =N— | 2 |
| iPr | S(O)CF₃ | =N— | 0 |
| iPr | S(O)CF₃ | =N— | 1 |
| iPr | S(O)CF₃ | =N— | 2 |
| iPr | S(O)₂CF₃ | =N— | 0 |
| iPr | S(O)₂CF₃ | =N— | 1 |
| iPr | S(O)₂CF₃ | =N— | 2 |
| CH₂cyPr | CF₃ | =N— | 0 |
| CH₂cyPr | CF₃ | =N— | 1 |
| CH₂cyPr | CF₃ | =N— | 2 |
| CH₂cyPr | CF₂CF₃ | =N— | 0 |
| CH₂cyPr | CF₂CF₃ | =N— | 1 |
| CH₂cyPr | CF₂CF₃ | =N— | 2 |

TABLE 4

| R¹ | R² | A⁵ | n |
|---|---|---|---|
| CH₂cyPr | CF(CF₃)₂ | =N— | 0 |
| CH₂cyPr | CF(CF₃)₂ | =N— | 1 |
| CH₂cyPr | CF(CF₃)₂ | =N— | 2 |
| CH₂cyPr | OCF₃ | =N— | 0 |
| CH₂cyPr | OCF₃ | =N— | 1 |
| CH₂cyPr | OCF₃ | =N— | 2 |
| CH₂cyPr | SCF₃ | =N— | 0 |
| CH₂cyPr | SCF₃ | =N— | 1 |
| CH₂cyPr | SCF₃ | =N— | 2 |
| CH₂cyPr | S(O)CF₃ | =N— | 0 |
| CH₂cyPr | S(O)CF₃ | =N— | 1 |
| CH₂cyPr | S(O)CF₃ | =N— | 2 |
| CH₂cyPr | S(O)₂CF₃ | =N— | 0 |
| CH₂cyPr | S(O)₂CF₃ | =N— | 1 |
| CH₂cyPr | S(O)₂CF₃ | =N— | 2 |
| CF₃ | CF₃ | =N— | 0 |
| CF₃ | CF₃ | =N— | 1 |
| CF₃ | CF₃ | =N— | 2 |
| CF₃ | CF₂CF₃ | =N— | 0 |
| CF₃ | CF₂CF₃ | =N— | 1 |
| CF₃ | CF₂CF₃ | =N— | 2 |
| CF₃ | CF(CF₃)₂ | =N— | 0 |
| CF₃ | CF(CF₃)₂ | =N— | 1 |
| CF₃ | CF(CF₃)₂ | =N— | 2 |
| CF₃ | OCF₃ | =N— | 0 |
| CF₃ | OCF₃ | =N— | 1 |
| CF₃ | OCF₃ | =N— | 2 |
| CF₃ | SCF₃ | =N— | 0 |
| CF₃ | SCF₃ | =N— | 1 |
| CF₃ | SCF₃ | =N— | 2 |

TABLE 5

| R¹ | R² | A⁵ | n |
|---|---|---|---|
| CF₃ | S(O)CF₃ | =N— | 0 |
| CF₃ | S(O)CF₃ | =N— | 1 |
| CF₃ | S(O)CF₃ | =N— | 2 |
| CF₃ | S(O)₂CF₃ | =N— | 0 |
| CF₃ | S(O)₂CF₃ | =N— | 1 |
| CF₃ | S(O)₂CF₃ | =N— | 2 |

TABLE 5-continued

| R$^1$ | R$^2$ | A$^5$ | n |
|---|---|---|---|
| CH$_2$CF$_3$ | CF$_3$ | =N— | 0 |
| CH$_2$CF$_3$ | CF$_3$ | =N— | 1 |
| CH$_2$CF$_3$ | CF$_3$ | =N— | 2 |
| CH$_2$CF$_3$ | CF$_2$CF$_3$ | =N— | 0 |
| CH$_2$CF$_3$ | CF$_2$CF$_3$ | =N— | 1 |
| CH$_2$CF$_3$ | CF$_2$CF$_3$ | =N— | 2 |
| CH$_2$CF$_3$ | CF(CF$_3$)$_2$ | =N— | 0 |
| CH$_2$CF$_3$ | CF(CF$_3$)$_2$ | =N— | 1 |
| CH$_2$CF$_3$ | CF(CF$_3$)$_2$ | =N— | 2 |
| CH$_2$CF$_3$ | OCF$_3$ | =N— | 0 |
| CH$_2$CF$_3$ | OCF$_3$ | =N— | 1 |
| CH$_2$CF$_3$ | OCF$_3$ | =N— | 2 |
| CH$_2$CF$_3$ | SCF$_3$ | =N— | 0 |
| CH$_2$CF$_3$ | SCF$_3$ | =N— | 1 |
| CH$_2$CF$_3$ | SCF$_3$ | =N— | 2 |
| CH$_2$CF$_3$ | S(O)CF$_3$ | =N— | 0 |
| CH$_2$CF$_3$ | S(O)CF$_3$ | =N— | 1 |
| CH$_2$CF$_3$ | S(O)CF$_3$ | =N— | 2 |
| CH$_2$CF$_3$ | S(O)$_2$CF$_3$ | =N— | 0 |
| CH$_2$CF$_3$ | S(O)$_2$CF$_3$ | =N— | 1 |
| CH$_2$CF$_3$ | S(O)$_2$CF$_3$ | =N— | 2 |

TABLE 6

| R$^1$ | R$^2$ | A$^5$ | n |
|---|---|---|---|
| Me | CF$_3$ | =CH— | 0 |
| Me | CF$_3$ | =CH— | 1 |
| Me | CF$_3$ | =CH— | 2 |
| Me | CF$_2$CF$_3$ | =CH— | 0 |
| Me | CF$_2$CF$_3$ | =CH— | 1 |
| Me | CF$_2$CF$_3$ | =CH— | 2 |
| Me | CF(CF$_3$)$_2$ | =CH— | 0 |
| Me | CF(CF$_3$)$_2$ | =CH— | 1 |
| Me | CF(CF$_3$)$_2$ | =CH— | 2 |
| Me | OCF$_3$ | =CH— | 0 |
| Me | OCF$_3$ | =CH— | 1 |
| Me | OCF$_3$ | =CH— | 2 |
| Me | SCF$_3$ | =CH— | 0 |
| Me | SCF$_3$ | =CH— | 1 |
| Me | SCF$_3$ | =CH— | 2 |
| Me | S(O)CF$_3$ | =CH— | 0 |
| Me | S(O)CF$_3$ | =CH— | 1 |
| Me | S(O)CF$_3$ | =CH— | 2 |
| Me | S(O)$_2$CF$_3$ | =CH— | 0 |
| Me | S(O)$_2$CF$_3$ | =CH— | 1 |
| Me | S(O)$_2$CF$_3$ | =CH— | 2 |
| Et | CF$_3$ | =CH— | 0 |
| Et | CF$_3$ | =CH— | 1 |
| Et | CF$_3$ | =CH— | 2 |
| Et | CF$_2$CF$_3$ | =CH— | 0 |
| Et | CF$_2$CF$_3$ | =CH— | 1 |
| Et | CF$_2$CF$_3$ | =CH— | 2 |
| Et | CF(CF$_3$)$_2$ | =CH— | 0 |
| Et | CF(CF$_3$)$_2$ | =CH— | 1 |
| Et | CF(CF$_3$)$_2$ | =CH— | 2 |

TABLE 7

| R$^1$ | R$^2$ | A$^5$ | n |
|---|---|---|---|
| Et | OCF$_3$ | =CH— | 0 |
| Et | OCF$_3$ | =CH— | 1 |
| Et | OCF$_3$ | =CH— | 2 |
| Et | SCF$_3$ | =CH— | 0 |
| Et | SCF$_3$ | =CH— | 1 |
| Et | SCF$_3$ | =CH— | 2 |
| Et | S(O)CF$_3$ | =CH— | 0 |
| Et | S(O)CF$_3$ | =CH— | 1 |
| Et | S(O)CF$_3$ | =CH— | 2 |
| Et | S(O)$_2$CF$_3$ | =CH— | 0 |
| Et | S(O)$_2$CF$_3$ | =CH— | 1 |
| Et | S(O)$_2$CF$_3$ | =CH— | 2 |

TABLE 7-continued

| R$^1$ | R$^2$ | A$^5$ | n |
|---|---|---|---|
| Pr | CF$_3$ | =CH— | 0 |
| Pr | CF$_3$ | =CH— | 1 |
| Pr | CF$_3$ | =CH— | 2 |
| Pr | CF$_2$CF$_3$ | =CH— | 0 |
| Pr | CF$_2$CF$_3$ | =CH— | 1 |
| Pr | CF$_2$CF$_3$ | =CH— | 2 |
| Pr | CF(CF$_3$)$_2$ | =CH— | 0 |
| Pr | CF(CF$_3$)$_2$ | =CH— | 1 |
| Pr | CF(CF$_3$)$_2$ | =CH— | 2 |
| Pr | OCF$_3$ | =CH— | 0 |
| Pr | OCF$_3$ | =CH— | 1 |
| Pr | OCF$_3$ | =CH— | 2 |
| Pr | SCF$_3$ | =CH— | 0 |
| Pr | SCF$_3$ | =CH— | 1 |
| Pr | SCF$_3$ | =CH— | 2 |
| Pr | S(O)CF$_3$ | =CH— | 0 |
| Pr | S(O)CF$_3$ | =CH— | 1 |
| Pr | S(O)CF$_3$ | =CH— | 2 |

TABLE 8

| R$^1$ | R$^2$ | A$^5$ | n |
|---|---|---|---|
| Pr | S(O)$_2$CF$_3$ | =CH— | 0 |
| Pr | S(O)$_2$CF$_3$ | =CH— | 1 |
| Pr | S(O)$_2$CF$_3$ | =CH— | 2 |
| iPr | CF$_3$ | =CH— | 0 |
| iPr | CF$_3$ | =CH— | 1 |
| iPr | CF$_3$ | =CH— | 2 |
| iPr | CF$_2$CF$_3$ | =CH— | 0 |
| iPr | CF$_2$CF$_3$ | =CH— | 1 |
| iPr | CF$_2$CF$_3$ | =CH— | 2 |
| iPr | CF(CF$_3$)$_2$ | =CH— | 0 |
| iPr | CF(CF$_3$)$_2$ | =CH— | 1 |
| iPr | CF(CF$_3$)$_2$ | =CH— | 2 |
| iPr | OCF$_3$ | =CH— | 0 |
| iPr | OCF$_3$ | =CH— | 1 |
| iPr | OCF$_3$ | =CH— | 2 |
| iPr | SCF$_3$ | =CH— | 0 |
| iPr | SCF$_3$ | =CH— | 1 |
| iPr | SCF$_3$ | =CH— | 2 |
| iPr | S(O)CF$_3$ | =CH— | 0 |
| iPr | S(O)CF$_3$ | =CH— | 1 |
| iPr | S(O)CF$_3$ | =CH— | 2 |
| iPr | S(O)$_2$CF$_3$ | =CH— | 0 |
| iPr | S(O)$_2$CF$_3$ | =CH— | 1 |
| iPr | S(O)$_2$CF$_3$ | =CH— | 2 |
| CH$_2$cyPr | CF$_3$ | =CH— | 0 |
| CH$_2$cyPr | CF$_3$ | =CH— | 1 |
| CH$_2$cyPr | CF$_3$ | =CH— | 2 |
| CH$_2$cyPr | CF$_2$CF$_3$ | =CH— | 0 |
| CH$_2$cyPr | CF$_2$CF$_3$ | =CH— | 1 |
| CH$_2$cyPr | CF$_2$CF$_3$ | =CH— | 2 |

TABLE 9

| R$^1$ | R$^2$ | A$^5$ | n |
|---|---|---|---|
| CH$_2$cyPr | CF(CF$_3$)$_2$ | =CH— | 0 |
| CH$_2$cyPr | CF(CF$_3$)$_2$ | =CH— | 1 |
| CH$_2$cyPr | CF(CF$_3$)$_2$ | =CH— | 2 |
| CH$_2$cyPr | OCF$_3$ | =CH— | 0 |
| CH$_2$cyPr | OCF$_3$ | =CH— | 1 |
| CH$_2$cyPr | OCF$_3$ | =CH— | 2 |
| CH$_2$cyPr | SCF$_3$ | =CH— | 0 |
| CH$_2$cyPr | SCF$_3$ | =CH— | 1 |
| CH$_2$cyPr | SCF$_3$ | =CH— | 2 |
| CH$_2$cyPr | S(O)CF$_3$ | =CH— | 0 |
| CH$_2$cyPr | S(O)CF$_3$ | =CH— | 1 |
| CH$_2$cyPr | S(O)CF$_3$ | =CH— | 2 |
| CH$_2$cyPr | S(O)$_2$CF$_3$ | =CH— | 0 |
| CH$_2$cyPr | S(O)$_2$CF$_3$ | =CH— | 1 |
| CH$_2$cyPr | S(O)$_2$CF$_3$ | =CH— | 2 |

TABLE 9-continued

| R$^1$ | R$^2$ | A$^5$ | n |
|---|---|---|---|
| CF$_3$ | CF$_3$ | =CH— | 0 |
| CF$_3$ | CF$_3$ | =CH— | 1 |
| CF$_3$ | CF$_3$ | =CH— | 2 |
| CF$_3$ | CF$_2$CF$_3$ | =CH— | 0 |
| CF$_3$ | CF$_2$CF$_3$ | =CH— | 1 |
| CF$_3$ | CF$_2$CF$_3$ | =CH— | 2 |
| CF$_3$ | CF(CF$_3$)$_2$ | =CH— | 0 |
| CF$_3$ | CF(CF$_3$)$_2$ | =CH— | 1 |
| CF$_3$ | CF(CF$_3$)$_2$ | =CH— | 2 |
| CF$_3$ | OCF$_3$ | =CH— | 0 |
| CF$_3$ | OCF$_3$ | =CH— | 1 |
| CF$_3$ | OCF$_3$ | =CH— | 2 |
| CF$_3$ | SCF$_3$ | =CH— | 0 |
| CF$_3$ | SCF$_3$ | =CH— | 1 |
| CF$_3$ | SCF$_3$ | =CH— | 2 |

TABLE 10

| R$^1$ | R$^2$ | A$^5$ | n |
|---|---|---|---|
| CF$_3$ | S(O)CF$_3$ | =CH— | 0 |
| CF$_3$ | S(O)CF$_3$ | =CH— | 1 |
| CF$_3$ | S(O)CF$_3$ | =CH— | 2 |
| CF$_3$ | S(O)$_2$CF$_3$ | =CH— | 0 |
| CF$_3$ | S(O)$_2$CF$_3$ | =CH— | 1 |
| CF$_3$ | S(O)$_2$CF$_3$ | =CH— | 2 |
| CH$_2$CF$_3$ | CF$_3$ | =CH— | 0 |
| CH$_2$CF$_3$ | CF$_3$ | =CH— | 1 |
| CH$_2$CF$_3$ | CF$_3$ | =CH— | 2 |
| CH$_2$CF$_3$ | CF$_2$CF$_3$ | =CH— | 0 |
| CH$_2$CF$_3$ | CF$_2$CF$_3$ | =CH— | 1 |
| CH$_2$CF$_3$ | CF$_2$CF$_3$ | =CH— | 2 |
| CH$_2$CF$_3$ | CF(CF$_3$)$_2$ | =CH— | 0 |
| CH$_2$CF$_3$ | CF(CF$_3$)$_2$ | =CH— | 1 |
| CH$_2$CF$_3$ | CF(CF$_3$)$_2$ | =CH— | 2 |
| CH$_2$CF$_3$ | OCF$_3$ | =CH— | 0 |
| CH$_2$CF$_3$ | OCF$_3$ | =CH— | 1 |
| CH$_2$CF$_3$ | OCF$_3$ | =CH— | 2 |
| CH$_2$CF$_3$ | SCF$_3$ | =CH— | 0 |
| CH$_2$CF$_3$ | SCF$_3$ | =CH— | 1 |
| CH$_2$CF$_3$ | SCF$_3$ | =CH— | 2 |
| CH$_2$CF$_3$ | S(O)CF$_3$ | =CH— | 0 |
| CH$_2$CF$_3$ | S(O)CF$_3$ | =CH— | 1 |
| CH$_2$CF$_3$ | S(O)CF$_3$ | =CH— | 2 |
| CH$_2$CF$_3$ | S(O)$_2$CF$_3$ | =CH— | 0 |
| CH$_2$CF$_3$ | S(O)$_2$CF$_3$ | =CH— | 1 |
| CH$_2$CF$_3$ | S(O)$_2$CF$_3$ | =CH— | 2 |

(In [Table 1] to [Table 10] above, Me represents a methyl group, Et represents an ethyl group, Pr represents a n-propyl group, iPr represents an isopropyl group, and cyPr represents a cyclopropyl group.)

In the formula (A-1), compounds wherein R$^6$ is a fluorine atom, and R$^1$, R$^2$, A$^5$ and n are the combinations shown in [Table 1] to [Table 10].

In the formula (A-1), compounds wherein R$^6$ is a chlorine atom, and R$^1$, R$^2$, A$^5$ and n are the combinations shown in [Table 1] to [Table 10].

In the formula (A-1), compounds wherein R$^6$ is a bromine atom, and R$^1$, R$^2$, A$^5$ and n are the combinations shown in [Table 1] to [Table 10].

In the formula (A-1), compounds wherein R$^6$ is a trifluoromethyl group, and R$^1$, R$^2$, A$^5$ and n are the combinations shown in [Table 1] to [Table 10].

In the formula (A-1), compounds wherein R$^6$ is a pentafluoroethyl group, and R$^1$, R$^2$, A$^5$ and n are the combinations shown in [Table 1] to [Table 10].

In the formula (A-1), compounds wherein R$^6$ is a trifluoromethoxy group, and R$^1$, R$^2$, A$^5$ and n are the combinations shown in [Table 1] to [Table 10].

In the formula (A-1), compounds wherein R$^6$ is a trifluoromethylsulfanyl group, and R$^1$, R$^2$, A$^5$ and n are the combinations shown in [Table 1] to [Table 10].

In the formula (A-1), compounds wherein R$^6$ is a trifluoromethylsulfinyl group, and R$^1$, R$^2$, A$^5$ and n are the In the formula (A-1), compounds wherein R$^6$ is a trifluoromethylsulfonyl group, and R$^1$, R$^2$, A$^5$ and n are the combinations shown in [Table 1] to [Table 10].

In formula (A-2),

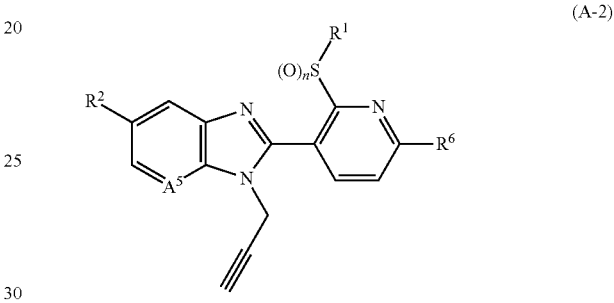

(A-2)

wherein symbols represent the same meaning as in the formula (1), compounds wherein R$^6$ is a hydrogen atom, and R$^1$, R$^2$, A$^5$ and n are the combinations shown in [Table 1] to [Table 10].

In the formula (A-2), compounds wherein R$^6$ is a fluorine atom, and R$^1$, R$^2$, A$^5$ and n are the combinations shown in [Table 1] to [Table 10].

In the formula (A-2), compounds wherein R$^6$ is a chlorine atom, and R$^1$, R$^2$, A$^5$ and n are the combinations shown in [Table 1] to [Table 10].

In the formula (A-2), compounds wherein R$^6$ is a bromine atom, and R$^1$, R$^2$, A$^5$ and n are the combinations shown in [Table 1] to [Table 10].

In the formula (A-2), compounds wherein R$^6$ is a trifluoromethyl group, and R$^1$, R$^2$, A$^5$ and n are the combinations shown in [Table 1] to [Table 10].

In the formula (A-2), compounds wherein R$^6$ is a pentafluoroethyl group, and R$^1$, R$^2$, A$^5$ and n are the combinations shown in [Table 1] to [Table 10].

In the formula (A-2), compounds wherein R$^6$ is a trifluoromethoxy group, and R$^1$, R$^2$, A$^5$ and n are the combinations shown in [Table 1] to [Table 10].

In the formula (A-2), compounds wherein R$^6$ is a trifluoromethylsulfanyl group, and R$^1$, R$^2$, A$^5$ and n are the combinations shown in [Table 1] to [Table 10].

In the formula (A-2), compounds wherein R$^6$ is a trifluoromethylsulfinyl group, and R$^1$, R$^2$, A$^5$ and n are the combinations shown in [Table 1] to [Table 10].

In the formula (A-2), compounds wherein R$^6$ is a trifluoromethylsulfonyl group, and R$^1$, R$^2$, A$^5$ and n are the combinations shown in [Table 1] to [Table 10].

In formula (A-3), (A-3)

wherein symbols represent the same meaning as in the formula (1),
compounds wherein $R^6$ is a hydrogen atom, and $R^1$, $R^2$, $A^5$ and n are the combinations shown in [Table 1] to [Table 10].
In the formula (A-3), compounds wherein $R^6$ is a fluorine atom, and $R^1$, $R^2$, $A^5$ and n are the combinations shown in [Table 1] to [Table 10].
In the formula (A-3), compounds wherein $R^6$ is a chlorine atom, and $R^1$, $R^2$, $A^5$ and n are the combinations shown in [Table 1] to [Table 10].
In the formula (A-3), compounds wherein $R^6$ is a bromine atom, and $R^1$, $R^2$, $A^5$ and n are the combinations shown in [Table 1] to [Table 10].
In the formula (A-3), compounds wherein $R^6$ is a trifluoromethyl group, and $R^1$, $R^2$, $A^5$ and n are the combinations shown in [Table 1] to [Table 10].
In the formula (A-3), compounds wherein $R^6$ is a pentafluoroethyl group, and $R^1$, $R^2$, $A^5$ and n are the combinations shown in [Table 1] to [Table 10].
In the formula (A-3), compounds wherein $R^6$ is a trifluoromethoxy group, and $R^1$, $R^2$, $A^5$ and n are the combinations shown in [Table 1] to [Table 10].
In the formula (A-3), compounds wherein $R^6$ is a trifluoromethylsulfanyl group, and $R^1$, $R^2$, $A^5$ and n are the combinations shown in [Table 1] to [Table 10].
In the formula (A-3), compounds wherein $R^6$ is a trifluoromethylsulfinyl group, and $R^1$, $R^2$, $A^5$ and n are the combinations shown in [Table 1] to [Table 10].
In the formula (A-3), compounds wherein $R^6$ is a trifluoromethylsulfonyl group, and $R^1$, $R^2$, $A^5$ and n are the combinations shown in [Table 1] to [Table 10].
In formula (A-4), (A-4)

wherein symbols represent the same meaning as in the formula (1),
compounds wherein $R^6$ is a hydrogen atom, and $R^1$, $R^2$, $A^5$ and n are the combinations shown in [Table 1] to [Table 10].
In the formula (A-4), compounds wherein $R^6$ is a fluorine atom, and $R^1$, $R^2$, $A^5$ and n are the combinations shown in [Table 1] to [Table 10].
In the formula (A-4), compounds wherein $R^6$ is a chlorine atom, and $R^1$, $R^2$, $A^5$ and n are the combinations shown in [Table 1] to [Table 10].
In the formula (A-4), compounds wherein $R^6$ is a bromine atom, and $R^1$, $R^2$, $A^5$ and n are the combinations shown in [Table 1] to [Table 10].
In the formula (A-4), compounds wherein $R^6$ is a trifluoromethyl group, and $R^1$, $R^2$, $A^5$ and n are the combinations shown in [Table 1] to [Table 10].
In the formula (A-4), compounds wherein $R^6$ is a pentafluoroethyl group, and $R^1$, $R^2$, $A^5$ and n are the combinations shown in [Table 1] to [Table 10].
In the formula (A-4), compounds wherein $R^6$ is a trifluoromethoxy group, and $R^1$, $R^2$, $A^5$ and n are the combinations shown in [Table 1] to [Table 10].
In the formula (A-4), compounds wherein $R^6$ is a trifluoromethylsulfanyl group, and $R^1$, $R^2$, $A^5$ and n are the combinations shown in [Table 1] to [Table 10].
In the formula (A-4), compounds wherein $R^6$ is a trifluoromethylsulfinyl group, and $R^1$, $R^2$, $A^5$ and n are the combinations shown in [Table 1] to [Table 10].
In the formula (A-4), compounds wherein $R^6$ is a trifluoromethylsulfonyl group, and $R^1$, $R^2$, $A^5$ and n are the combinations shown in [Table 1] to [Table 10].
In formula (A-5), (A-5)

wherein symbols represent the same meaning as in the formula (1),
compounds wherein $R^6$ is a hydrogen atom, and $R^1$, $R^2$, $A^5$ and n are the combinations shown in [Table 1] to [Table 10].
In the formula (A-5), compounds wherein $R^6$ is a fluorine atom, and $R^1$, $R^2$, $A^5$ and n are the combinations shown in [Table 1] to [Table 10].
In the formula (A-5), compounds wherein $R^6$ is a chlorine atom, and $R^1$, $R^2$, $A^5$ and n are the combinations shown in [Table 1] to [Table 10].
In the formula (A-5), compounds wherein $R^6$ is a bromine atom, and $R^1$, $R^2$, $A^5$ and n are the combinations shown in [Table 1] to [Table 10].
In the formula (A-5), compounds wherein $R^6$ is a trifluoromethyl group, and $R^1$, $R^2$, $A^5$ and n are the combinations shown in [Table 1] to [Table 10].
In the formula (A-5), compounds wherein $R^6$ is a pentafluoroethyl group, and $R^1$, $R^2$, $A^5$ and n are the combinations shown in [Table 1] to [Table 10].
In the formula (A-5), compounds wherein $R^6$ is a trifluoromethoxy group, and $R^1$, $R^2$, $A^5$ and n are the combinations shown in [Table 1] to [Table 10].
In the formula (A-5), compounds wherein $R^6$ is a trifluoromethylsulfanyl group, and $R^1$, $R^2$, $A^5$ and n are the combinations shown in [Table 1] to [Table 10].
In the formula (A-5), compounds wherein $R^6$ is a trifluoromethylsulfinyl group, and $R^1$, $R^2$, $A^5$ and n are the combinations shown in [Table 1] to [Table 10].

In the formula (A-5), compounds wherein $R^6$ is a trifluoromethylsulfonyl group, and $R^1$, $R^2$, $A^5$ and n are the combinations shown in [Table 1] to [Table 10].

In formula (A-6), $$\text{(A-6)}$$

wherein symbols represent the same meaning as in the formula (1), compounds wherein $R^6$ is a hydrogen atom, and $R^1$, $R^2$, $A^5$ and n are the combinations shown in [Table 1] to [Table 10].

In the formula (A-6), compounds wherein $R^6$ is a fluorine atom, and $R^1$, $R^2$, $A^5$ and n are the combinations shown in [Table 1] to [Table 10].

In the formula (A-6), compounds wherein $R^6$ is a chlorine atom, and $R^1$, $R^2$, $A^5$ and n are the combinations shown in [Table 1] to [Table 10].

In the formula (A-6), compounds wherein $R^6$ is a bromine atom, and $R^1$, $R^2$, $A^5$ and n are the combinations shown in [Table 1] to [Table 10].

In the formula (A-6), compounds wherein $R^6$ is a trifluoromethyl group, and $R^1$, $R^2$, $A^5$ and n are the combinations shown in [Table 1] to [Table 10].

In the formula (A-6), compounds wherein $R^6$ is a pentafluoroethyl group, and $R^1$, $R^2$, $A^5$ and n are the combinations shown in [Table 1] to [Table 10].

In the formula (A-6), compounds wherein $R^6$ is a trifluoromethoxy group, and $R^1$, $R^2$, $A^5$ and n are the combinations shown in [Table 1] to [Table 10].

In the formula (A-6), compounds wherein $R^6$ is a trifluoromethylsulfanyl group, and $R^1$, $R^2$, $A^5$ and n are the combinations shown in [Table 1] to [Table 10].

In the formula (A-6), compounds wherein $R^6$ is a trifluoromethylsulfinyl group, and $R^1$, $R^2$, $A^5$ and n are the combinations shown in [Table 1] to [Table 10].

In the formula (A-6), compounds wherein $R^6$ is a trifluoromethylsulfonyl group, and $R^1$, $R^2$, $A^5$ and n are the combinations shown in [Table 1] to [Table 10].

In formula (A-7), $$\text{(A-7)}$$

wherein symbols represent the same meaning as in the formula (1), compounds wherein $R^6$ is a hydrogen atom, and $R^1$, $R^2$, $A^5$ and n are the combinations shown in [Table 1] to [Table 10].

In the formula (A-7), compounds wherein $R^6$ is a fluorine atom, and $R^1$, $R^2$, $A^5$ and n are the combinations shown in [Table 1] to [Table 10].

In the formula (A-7), compounds wherein $R^6$ is a chlorine atom, and $R^1$, $R^2$, $A^5$ and n are the combinations shown in [Table 1] to [Table 10].

In the formula (A-7), compounds wherein $R^6$ is a bromine atom, and $R^1$, $R^2$, $A^5$ and n are the combinations shown in [Table 1] to [Table 10].

In the formula (A-7), compounds wherein $R^6$ is a trifluoromethyl group, and $R^1$, $R^2$, $A^5$ and n are the combinations shown in [Table 1] to [Table 10].

In the formula (A-7), compounds wherein $R^6$ is a pentafluoroethyl group, and $R^1$, $R^2$, $A^5$ and n are the combinations shown in [Table 1] to [Table 10].

In the formula (A-7), compounds wherein $R^6$ is a trifluoromethoxy group, and $R^1$, $R^2$, $A^5$ and n are the combinations shown in [Table 1] to [Table 10].

In the formula (A-7), compounds wherein $R^6$ is a trifluoromethylsulfanyl group, and $R^1$, $R^2$, $A^5$ and n are the combinations shown in [Table 1] to [Table 10].

In the formula (A-7), compounds wherein $R^6$ is a trifluoromethylsulfinyl group, and $R^1$, $R^2$, $A^5$ and n are the combinations shown in [Table 1] to [Table 10].

In the formula (A-7), compounds wherein $R^6$ is a trifluoromethylsulfonyl group, and $R^1$, $R^2$, $A^5$ and n are the combinations shown in [Table 1] to [Table 10].

In formula (B-1), $$\text{(B-1)}$$

wherein symbols represent the same meaning as in the formula (1), compounds wherein $R^6$ is a hydrogen atom, and $R^1$, $R^2$, $A^5$ and n are the combinations shown in [Table 1] to [Table 10].

In the formula (B-1), compounds wherein $R^6$ is a fluorine atom, and $R^1$, $R^2$, $A^5$ and n are the combinations shown in [Table 1] to [Table 10].

In the formula (B-1), compounds wherein $R^6$ is a chlorine atom, and $R^1$, $R^2$, $A^5$ and n are the combinations shown in [Table 1] to [Table 10].

In the formula (B-1), compounds wherein $R^6$ is a bromine atom, and $R^1$, $R^2$, $A^5$ and n are the combinations shown in [Table 1] to [Table 10].

In the formula (B-1), compounds wherein $R^6$ is a trifluoromethyl group, and $R^1$, $R^2$, $A^5$ and n are the combinations shown in [Table 1] to [Table 10].

In the formula (B-1), compounds wherein $R^6$ is a pentafluoroethyl group, and $R^1$, $R^2$, $A^5$ and n are the combinations shown in [Table 1] to [Table 10].

In the formula (B-1), compounds wherein $R^6$ is a trifluoromethoxy group, and $R^1$, $R^2$, $A^5$ and n are the combinations shown in [Table 1] to [Table 10].

In the formula (B-1), compounds wherein $R^6$ is a trifluoromethylsulfanyl group, and $R^1$, $R^2$, $A^5$ and n are the combinations shown in [Table 1] to [Table 10].

In the formula (B-1), compounds wherein $R^6$ is a trifluoromethylsulfinyl group, and $R^1$, $R^2$, $A^5$ and n are the combinations shown in [Table 1] to [Table 10].

In the formula (B-1), compounds wherein $R^6$ is a trifluoromethylsulfonyl group, and $R^1$, $R^2$, $A^5$ and n are the combinations shown in [Table 1] to [Table 10].

In formula (B-2),

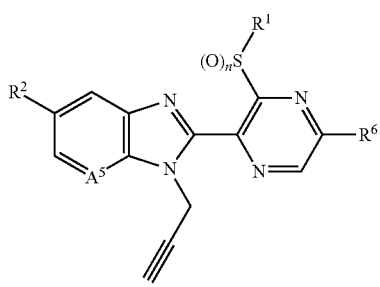

wherein symbols represent the same meaning as in the formula (1),
compounds wherein $R^6$ is a hydrogen atom, and $R^1$, $R^2$, $A^5$ and n are the combinations shown in [Table 1] to [Table 10].
In the formula (B-2), compounds wherein $R^6$ is a fluorine atom, and $R^1$, $R^2$, $A^5$ and n are the combinations shown in [Table 1] to [Table 10].
In the formula (B-2), compounds wherein $R^6$ is a chlorine atom, and $R^1$, $R^2$, $A^5$ and n are the combinations shown in [Table 1] to [Table 10].
In the formula (B-2), compounds wherein $R^6$ is a bromine atom, and $R^1$, $R^2$, $A^5$ and n are the combinations shown in [Table 1] to [Table 10].
In the formula (B-2), compounds wherein $R^6$ is a trifluoromethyl group, and $R^1$, $R^2$, $A^5$ and n are the combinations shown in [Table 1] to [Table 10].
In the formula (B-2), compounds wherein $R^6$ is a pentafluoroethyl group, and $R^1$, $R^2$, $A^5$ and n are the combinations shown in [Table 1] to [Table 10].
In the formula (B-2), compounds wherein $R^6$ is a trifluoromethoxy group, and $R^1$, $R^2$, $A^5$ and n are the combinations shown in [Table 1] to [Table 10].
In the formula (B-2), compounds wherein $R^6$ is a trifluoromethylsulfanyl group, and $R^1$, $R^2$, $A^5$ and n are the combinations shown in [Table 1] to [Table 10].
In the formula (B-2), compounds wherein $R^6$ is a trifluoromethylsulfinyl group, and $R^1$, $R^2$, $A^5$ and n are the combinations shown in [Table 1] to [Table 10].
In the formula (B-2), compounds wherein $R^6$ is a trifluoromethylsulfonyl group, and $R^1$, $R^2$, $A^5$ and n are the combinations shown in [Table 1] to [Table 10].
In formula (B-3),

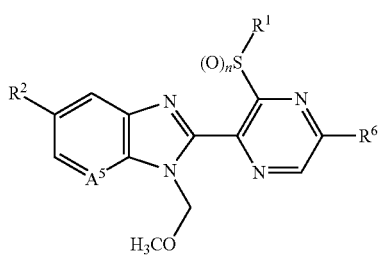

wherein symbols represent the same meaning as in the formula (1),
compounds wherein $R^6$ is a hydrogen atom, and $R^1$, $R^2$, $A^5$ and n are the combinations shown in [Table 1] to [Table 10].
In the formula (B-3), compounds wherein $R^6$ is a fluorine atom, and $R^1$, $R^2$, $A^5$ and n are the combinations shown in [Table 1] to [Table 10].
In the formula (B-3), compounds wherein $R^6$ is a chlorine atom, and $R^1$, $R^2$, $A^5$ and n are the combinations shown in [Table 1] to [Table 10].
In the formula (B-3), compounds wherein $R^6$ is a bromine atom, and $R^1$, $R^2$, $A^5$ and n are the combinations shown in [Table 1] to [Table 10].
In the formula (B-3), compounds wherein $R^6$ is a trifluoromethyl group, and $R^1$, $R^2$, $A^5$ and n are the combinations shown in [Table 1] to [Table 10].
In the formula (B-3), compounds wherein $R^6$ is a pentafluoroethyl group, and $R^1$, $R^2$, $A^5$ and n are the combinations shown in [Table 1] to [Table 10].
In the formula (B-3), compounds wherein $R^6$ is a trifluoromethoxy group, and $R^1$, $R^2$, $A^5$ and n are the combinations shown in [Table 1] to [Table 10].
In the formula (B-3), compounds wherein $R^6$ is a trifluoromethylsulfanyl group, and $R^1$, $R^2$, $A^5$ and n are the combinations shown in [Table 1] to [Table 10].
In the formula (B-3), compounds wherein $R^6$ is a trifluoromethylsulfinyl group, and $R^1$, $R^2$, $A^5$ and n are the combinations shown in [Table 1] to [Table 10].
In the formula (B-3), compounds wherein $R^6$ is a trifluoromethylsulfonyl group, and $R^1$, $R^2$, $A^5$ and n are the combinations shown in [Table 1] to [Table 10].
In formula (B-4),

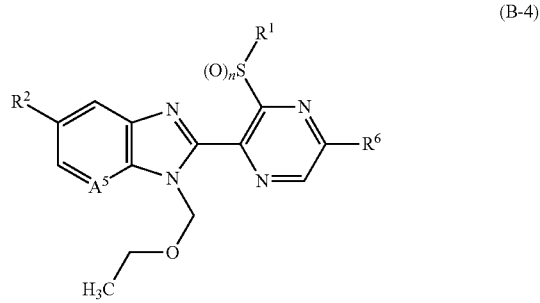

wherein symbols represent the same meaning as in the formula (1),
compounds wherein $R^6$ is a hydrogen atom, and $R^1$, $R^2$, $A^5$ and n are the combinations shown in [Table 1] to [Table 10].
In the formula (B-4), compounds wherein $R^6$ is a fluorine atom, and $R^1$, $R^2$, $A^5$ and n are the combinations shown in [Table 1] to [Table 10].
In the formula (B-4), compounds wherein $R^6$ is a chlorine atom, and $R^1$, $R^2$, $A^5$ and n are the combinations shown in [Table 1] to [Table 10].
In the formula (B-4), compounds wherein $R^6$ is a bromine atom, and $R^1$, $R^2$, $A^5$ and n are the combinations shown in [Table 1] to [Table 10].
In the formula (B-4), compounds wherein $R^6$ is a trifluoromethyl group, and $R^1$, $R^2$, $A^5$ and n are the combinations shown in [Table 1] to [Table 10].
In the formula (B-4), compounds wherein $R^6$ is a pentafluoroethyl group, and $R^1$, $R^2$, $A^5$ and n are the combinations shown in [Table 1] to [Table 10].
In the formula (B-4), compounds wherein $R^6$ is a trifluoromethoxy group, and $R^1$, $R^2$, $A^5$ and n are the combinations shown in [Table 1] to [Table 10].

In the formula (B-4), compounds wherein $R^6$ is a trifluoromethylsulfanyl group, and $R^1$, $R^2$, $A^5$ and n are the combinations shown in [Table 1] to [Table 10].
In the formula (B-4), compounds wherein $R^6$ is a trifluoromethylsulfinyl group, and $R^1$, $R^2$, $A^5$ and n are the combinations shown in [Table 1] to [Table 10].
In the formula (B-4), compounds wherein $R^6$ is a trifluoromethylsulfonyl group, and $R^1$, $R^2$, $A^5$ and n are the combinations shown in [Table 1] to [Table 10].

In formula (B-5), (B-5)

wherein symbols represent the same meaning as in the formula (1),
compounds wherein $R^6$ is a hydrogen atom, and $R^1$, $R^2$, $A^5$ and n are the combinations shown in [Table 1] to [Table 10].
In the formula (B-5), compounds wherein $R^6$ is a fluorine atom, and $R^1$, $R^2$, $A^5$ and n are the combinations shown in [Table 1] to [Table 10].
In the formula (B-5), compounds wherein $R^6$ is a chlorine atom, and $R^1$, $R^2$, $A^5$ and n are the combinations shown in [Table 1] to [Table 10].
In the formula (B-5), compounds wherein $R^6$ is a bromine atom, and $R^1$, $R^2$, $A^5$ and n are the combinations shown in [Table 1] to [Table 10].
In the formula (B-5), compounds wherein $R^6$ is a trifluoromethyl group, and $R^1$, $R^2$, $A^5$ and n are the combinations shown in [Table 1] to [Table 10].
In the formula (B-5), compounds wherein $R^6$ is a pentafluoroethyl group, and $R^1$, $R^2$, $A^5$ and n are the combinations shown in [Table 1] to [Table 10].
In the formula (B-5), compounds wherein $R^6$ is a trifluoromethoxy group, and $R^1$, $R^2$, $A^5$ and n are the combinations shown in [Table 1] to [Table 10].
In the formula (B-5), compounds wherein $R^6$ is a trifluoromethylsulfanyl group, and $R^1$, $R^2$, $A^5$ and n are the combinations shown in [Table 1] to [Table 10].
In the formula (B-5), compounds wherein $R^6$ is a trifluoromethylsulfinyl group, and $R^1$, $R^2$, $A^5$ and n are the combinations shown in [Table 1] to [Table 10].
In the formula (B-5), compounds wherein $R^6$ is a trifluoromethylsulfonyl group, and $R^1$, $R^2$, $A^5$ and n are the combinations shown in [Table 1] to [Table 10].

In formula (B-6), (B-6)

wherein symbols represent the same meaning as in the formula (1),
compounds wherein $R^6$ is a hydrogen atom, and $R^1$, $R^2$, $A^5$ and n are the combinations shown in [Table 1] to [Table 10].
In the formula (B-6), compounds wherein $R^6$ is a fluorine atom, and $R^1$, $R^2$, $A^5$ and n are the combinations shown in [Table 1] to [Table 10].
In the formula (B-6), compounds wherein $R^6$ is a chlorine atom, and $R^1$, $R^2$, $A^5$ and n are the combinations shown in [Table 1] to [Table 10].
In the formula (B-6), compounds wherein $R^6$ is a bromine atom, and $R^1$, $R^2$, $A^5$ and n are the combinations shown in [Table 1] to [Table 10].
In the formula (B-6), compounds wherein $R^6$ is a trifluoromethyl group, and $R^1$, $R^2$, $A^5$ and n are the combinations shown in [Table 1] to [Table 10].
In the formula (B-6), compounds wherein $R^6$ is a pentafluoroethyl group, and $R^1$, $R^2$, $A^5$ and n are the combinations shown in [Table 1] to [Table 10].
In the formula (B-6), compounds wherein $R^6$ is a trifluoromethoxy group, and $R^1$, $R^2$, $A^5$ and n are the combinations shown in [Table 1] to [Table 10].
In the formula (B-6), compounds wherein $R^6$ is a trifluoromethylsulfanyl group, and $R^1$, $R^2$, $A^5$ and n are the combinations shown in [Table 1] to [Table 10].
In the formula (B-6), compounds wherein $R^6$ is a trifluoromethylsulfinyl group, and $R^1$, $R^2$, $A^5$ and n are the combinations shown in [Table 1] to [Table 10].
In the formula (B-6), compounds wherein $R^6$ is a trifluoromethylsulfonyl group, and $R^1$, $R^2$, $A^5$ and n are the combinations shown in [Table 1] to [Table 10].

In formula (B-7), (B-7)

wherein symbols represent the same meaning as in the formula (1),
compounds wherein $R^6$ is a hydrogen atom, and $R^1$, $R^2$, $A^5$ and n are the combinations shown in [Table 1] to [Table 10].
In the formula (B-7), compounds wherein $R^6$ is a fluorine atom, and $R^1$, $R^2$, $A^5$ and n are the combinations shown in [Table 1] to [Table 10].
In the formula (B-7), compounds wherein $R^6$ is a chlorine atom, and $R^1$, $R^2$, $A^5$ and n are the combinations shown in [Table 1] to [Table 10].
In the formula (B-7), compounds wherein $R^6$ is a bromine atom, and $R^1$, $R^2$, $A^5$ and n are the combinations shown in [Table 1] to [Table 10].
In the formula (B-7), compounds wherein $R^6$ is a trifluoromethyl group, and $R^1$, $R^2$, $A^5$ and n are the combinations shown in [Table 1] to [Table 10].
In the formula (B-7), compounds wherein $R^6$ is a pentafluoroethyl group, and $R^1$, $R^2$, $A^5$ and n are the combinations shown in [Table 1] to [Table 10].
In the formula (B-7), compounds wherein $R^6$ is a trifluoromethoxy group, and $R^1$, $R^2$, $A^5$ and n are the combinations shown in [Table 1] to [Table 10].
In the formula (B-7), compounds wherein $R^6$ is a trifluoromethylsulfanyl group, and $R^1$, $R^2$, $A^5$ and n are the combinations shown in [Table 1] to [Table 10].

In the formula (B-7), compounds wherein $R^6$ is a trifluoromethylsulfinyl group, and $R^1$, $R^2$, $A^5$ and n are the combinations shown in [Table 1] to [Table 10].

In the formula (B-7), compounds wherein $R^6$ is a trifluoromethylsulfonyl group, and $R^1$, $R^2$, $A^5$ and n are the combinations shown in [Table 1] to [Table 10].

In formula (C-1), (C-1)

wherein symbols represent the same meaning as in the formula (1), compounds wherein $R^6$ is a hydrogen atom, and $R^1$, $R^2$, $A^5$ and n are the combinations shown in [Table 1] to [Table 10].

In the formula (C-1), compounds wherein $R^6$ is a fluorine atom, and $R^1$, $R^2$, $A^5$ and n are the combinations shown in [Table 1] to [Table 10].

In the formula (C-1), compounds wherein $R^6$ is a chlorine atom, and $R^1$, $R^2$, $A^5$ and n are the combinations shown in [Table 1] to [Table 10].

In the formula (C-1), compounds wherein $R^6$ is a bromine atom, and $R^1$, $R^2$, $A^5$ and n are the combinations shown in [Table 1] to [Table 10].

In the formula (C-1), compounds wherein $R^6$ is a trifluoromethyl group, and $R^1$, $R^2$, $A^5$ and n are the combinations shown in [Table 1] to [Table 10].

In the formula (C-1), compounds wherein $R^6$ is a pentafluoroethyl group, and $R^1$, $R^2$, $A^5$ and n are the combinations shown in [Table 1] to [Table 10].

In the formula (C-1), compounds wherein $R^6$ is a trifluoromethoxy group, and $R^1$, $R^2$, $A^5$ and n are the combinations shown in [Table 1] to [Table 10].

In the formula (C-1), compounds wherein $R^6$ is a trifluoromethylsulfanyl group, and $R^1$, $R^2$, $A^5$ and n are the combinations shown in [Table 1] to [Table 10].

In the formula (C-1), compounds wherein $R^6$ is a trifluoromethylsulfinyl group, and $R^1$, $R^2$, $A^5$ and n are the combinations shown in [Table 1] to [Table 10].

In the formula (C-1), compounds wherein $R^6$ is a trifluoromethylsulfonyl group, and $R^1$, $R^2$, $A^5$ and n are the combinations shown in [Table 1] to [Table 10].

In formula (C-2), (C-2)

wherein symbols represent the same meaning as in the formula (1), compounds wherein $R^6$ is a hydrogen atom, and $R^1$, $R^2$, $A^5$ and n are the combinations shown in [Table 1] to [Table 10].

In the formula (C-2), compounds wherein $R^6$ is a fluorine atom, and $R^1$, $R^2$, $A^5$ and n are the combinations shown in [Table 1] to [Table 10].

In the formula (C-2), compounds wherein $R^6$ is a chlorine atom, and $R^1$, $R^2$, $A^5$ and n are the combinations shown in [Table 1] to [Table 10].

In the formula (C-2), compounds wherein $R^6$ is a bromine atom, and $R^1$, $R^2$, $A^5$ and n are the combinations shown in [Table 1] to [Table 10].

In the formula (C-2), compounds wherein $R^6$ is a trifluoromethyl group, and $R^1$, $R^2$, $A^5$ and n are the combinations shown in [Table 1] to [Table 10].

In the formula (C-2), compounds wherein $R^6$ is a pentafluoroethyl group, and $R^1$, $R^2$, $A^5$ and n are the combinations shown in [Table 1] to [Table 10].

In the formula (C-2), compounds wherein $R^6$ is a trifluoromethoxy group, and $R^1$, $R^2$, $A^5$ and n are the combinations shown in [Table 1] to [Table 10].

In the formula (C-2), compounds wherein $R^6$ is a trifluoromethylsulfanyl group, and $R^1$, $R^2$, $A^5$ and n are the combinations shown in [Table 1] to [Table 10].

In the formula (C-2), compounds wherein $R^6$ is a trifluoromethylsulfinyl group, and $R^1$, $R^2$, $A^5$ and n are the combinations shown in [Table 1] to [Table 10].

In the formula (C-2), compounds wherein $R^6$ is a trifluoromethylsulfonyl group, and $R^1$, $R^2$, $A^5$ and n are the combinations shown in [Table 1] to [Table 10].

In formula (C-3), (C-3)

wherein symbols represent the same meaning as in the formula (1), compounds wherein $R^6$ is a hydrogen atom, and $R^1$, $R^2$, $A^5$ and n are the combinations shown in [Table 1] to [Table 10].

In the formula (C-3), compounds wherein $R^6$ is a fluorine atom, and $R^1$, $R^2$, $A^5$ and n are the combinations shown in [Table 1] to [Table 10].

In the formula (C-3), compounds wherein $R^6$ is a chlorine atom, and $R^1$, $R^2$, $A^5$ and n are the combinations shown in [Table 1] to [Table 10].

In the formula (C-3), compounds wherein $R^6$ is a bromine atom, and $R^1$, $R^2$, $A^5$ and n are the combinations shown in [Table 1] to [Table 10].

In the formula (C-3), compounds wherein $R^6$ is a trifluoromethyl group, and $R^1$, $R^2$, $A^5$ and n are the combinations shown in [Table 1] to [Table 10].

In the formula (C-3), compounds wherein $R^6$ is a pentafluoroethyl group, and $R^1$, $R^2$, $A^5$ and n are the combinations shown in [Table 1] to [Table 10].

In the formula (C-3), compounds wherein $R^6$ is a trifluoromethoxy group, and $R^1$, $R^2$, $A^5$ and n are the combinations shown in [Table 1] to [Table 10].

In the formula (C-3), compounds wherein $R^6$ is a trifluoromethylsulfanyl group, and $R^1$, $R^2$, $A^5$ and n are the combinations shown in [Table 1] to [Table 10].

In the formula (C-3), compounds wherein $R^6$ is a trifluoromethylsulfinyl group, and $R^1$, $R^2$, $A^5$ and n are the combinations shown in [Table 1] to [Table 10].

In the formula (C-3), compounds wherein $R^6$ is a trifluoromethylsulfonyl group, and $R^1$, $R^2$, $A^5$ and n are the combinations shown in [Table 1] to [Table 10].

In formula (C-4),

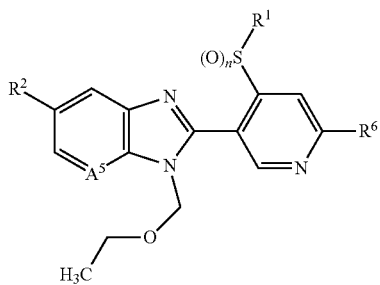

(C-4)

wherein symbols represent the same meaning as in the formula (1), compounds wherein $R^6$ is a hydrogen atom, and $R^1$, $R^2$, $A^5$ and n are the combinations shown in [Table 1] to [Table 10].

In the formula (C-4), compounds wherein $R^6$ is a fluorine atom, and $R^1$, $R^2$, $A^5$ and n are the combinations shown in [Table 1] to [Table 10].

In the formula (C-4), compounds wherein $R^6$ is a chlorine atom, and $R^1$, $R^2$, $A^5$ and n are the combinations shown in [Table 1] to [Table 10].

In the formula (C-4), compounds wherein $R^6$ is a bromine atom, and $R^1$, $R^2$, $A^5$ and n are the combinations shown in [Table 1] to [Table 10].

In the formula (C-4), compounds wherein $R^6$ is a trifluoromethyl group, and $R^1$, $R^2$, $A^5$ and n are the combinations shown in [Table 1] to [Table 10].

In the formula (C-4), compounds wherein $R^6$ is a pentafluoroethyl group, and $R^1$, $R^2$, $A^5$ and n are the combinations shown in [Table 1] to [Table 10].

In the formula (C-4), compounds wherein $R^6$ is a trifluoromethoxy group, and $R^1$, $R^2$, $A^5$ and n are the combinations shown in [Table 1] to [Table 10].

In the formula (C-4), compounds wherein $R^6$ is a trifluoromethylsulfanyl group, and $R^1$, $R^2$, $A^5$ and n are the combinations shown in [Table 1] to [Table 10].

In the formula (C-4), compounds wherein $R^6$ is a trifluoromethylsulfinyl group, and $R^1$, $R^2$, $A^5$ and n are the combinations shown in [Table 1] to [Table 10].

In the formula (C-4), compounds wherein $R^6$ is a trifluoromethylsulfonyl group, and $R^1$, $R^2$, $A^5$ and n are the combinations shown in [Table 1] to [Table 10].

In formula (C-5),

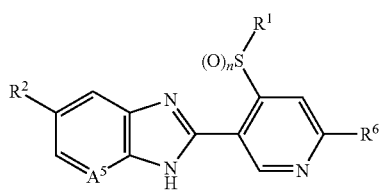

(C-5)

wherein symbols represent the same meaning as in the formula (1), compounds wherein $R^6$ is a hydrogen atom, and $R^1$, $R^2$, $A^5$ and n are the combinations shown in [Table 1] to [Table 10].

In the formula (C-5), compounds wherein $R^6$ is a fluorine atom, and $R^1$, $R^2$, $A^5$ and n are the combinations shown in [Table 1] to [Table 10].

In the formula (C-5), compounds wherein $R^6$ is a chlorine atom, and $R^1$, $R^2$, $A^5$ and n are the combinations shown in [Table 1] to [Table 10].

In the formula (C-5), compounds wherein $R^6$ is a bromine atom, and $R^1$, $R^2$, $A^5$ and n are the combinations shown in [Table 1] to [Table 10].

In the formula (C-5), compounds wherein $R^6$ is a trifluoromethyl group, and $R^1$, $R^2$, $A^5$ and n are the combinations shown in [Table 1] to [Table 10].

In the formula (C-5), compounds wherein $R^6$ is a pentafluoroethyl group, and $R^1$, $R^2$, $A^5$ and n are the combinations shown in [Table 1] to [Table 10].

In the formula (C-5), compounds wherein $R^6$ is a trifluoromethoxy group, and $R^1$, $R^2$, $A^5$ and n are the combinations shown in [Table 1] to [Table 10].

In the formula (C-5), compounds wherein $R^6$ is a trifluoromethylsulfanyl group, and $R^1$, $R^2$, $A^5$ and n are the combinations shown in [Table 1] to [Table 10].

In the formula (C-5), compounds wherein $R^6$ is a trifluoromethylsulfinyl group, and $R^1$, $R^2$, $A^5$ and n are the combinations shown in [Table 1] to [Table 10].

In the formula (C-5), compounds wherein $R^6$ is a trifluoromethylsulfonyl group, and $R^1$, $R^2$, $A^5$ and n are the combinations shown in [Table 1] to [Table 10].

In formula (C-6),

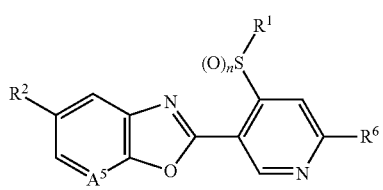

(C-6)

wherein symbols represent the same meaning as in the formula (1), compounds wherein $R^6$ is a hydrogen atom, and $R^1$, $R^2$, $A^5$ and n are the combinations shown in [Table 1] to [Table 10].

In the formula (C-6), compounds wherein $R^6$ is a fluorine atom, and $R^1$, $R^2$, $A^5$ and n are the combinations shown in [Table 1] to [Table 10].

In the formula (C-6), compounds wherein $R^6$ is a chlorine atom, and $R^1$, $R^2$, $A^5$ and n are the combinations shown in [Table 1] to [Table 10].

In the formula (C-6), compounds wherein $R^6$ is a bromine atom, and $R^1$, $R^2$, $A^5$ and n are the combinations shown in [Table 1] to [Table 10].

In the formula (C-6), compounds wherein $R^6$ is a trifluoromethyl group, and $R^1$, $R^2$, $A^5$ and n are the combinations shown in [Table 1] to [Table 10].

In the formula (C-6), compounds wherein $R^6$ is a pentafluoroethyl group, and $R^1$, $R^2$, $A^5$ and n are the combinations shown in [Table 1] to [Table 10].

In the formula (C-6), compounds wherein $R^6$ is a trifluoromethoxy group, and $R^1$, $R^2$, $A^5$ and n are the combinations shown in [Table 1] to [Table 10].

In the formula (C-6), compounds wherein $R^6$ is a trifluoromethylsulfanyl group, and $R^1$, $R^2$, $A^5$ and n are the combinations shown in [Table 1] to [Table 10].

In the formula (C-6), compounds wherein $R^6$ is a trifluoromethylsulfinyl group, and $R^1$, $R^2$, $A^5$ and n are the combinations shown in [Table 1] to [Table 10].

In the formula (C-6), compounds wherein $R^6$ is a trifluoromethylsulfonyl group, and $R^1$, $R^2$, $A^5$ and n are the combinations shown in [Table 1] to [Table 10].

In formula (C-7), (C-7)

wherein symbols represent the same meaning as in the formula (1), compounds wherein $R^6$ is a hydrogen atom, and $R^1$, $R^2$, $A^5$ and n are the combinations shown in [Table 1] to [Table 10].

In the formula (C-7), compounds wherein $R^6$ is a fluorine atom, and $R^1$, $R^2$, $A^5$ and n are the combinations shown in [Table 1] to [Table 10].

In the formula (C-7), compounds wherein $R^6$ is a chlorine atom, and $R^1$, $R^2$, $A^5$ and n are the combinations shown in [Table 1] to [Table 10].

In the formula (C-7), compounds wherein $R^6$ is a bromine atom, and $R^1$, $R^2$, $A^5$ and n are the combinations shown in [Table 1] to [Table 10].

In the formula (C-7), compounds wherein $R^6$ is a trifluoromethyl group, and $R^1$, $R^2$, $A^5$ and n are the combinations shown in [Table 1] to [Table 10].

In the formula (C-7), compounds wherein $R^6$ is a pentafluoroethyl group, and $R^1$, $R^2$, $A^5$ and n are the combinations shown in [Table 1] to [Table 10].

In the formula (C-7), compounds wherein $R^6$ is a trifluoromethoxy group, and $R^1$, $R^2$, $A^5$ and n are the combinations shown in [Table 1] to [Table 10].

In the formula (C-7), compounds wherein $R^6$ is a trifluoromethylsulfanyl group, and $R^1$, $R^2$, $A^5$ and n are the combinations shown in [Table 1] to [Table 10].

In the formula (C-7), compounds wherein $R^6$ is a trifluoromethylsulfinyl group, and $R^1$, $R^2$, $A^5$ and n are the combinations shown in [Table 1] to [Table 10].

In the formula (C-7), compounds wherein $R^6$ is a trifluoromethylsulfonyl group, and $R^1$, $R^2$, $A^5$ and n are the combinations shown in [Table 1] to [Table 10].

In formula (D-1), (D-1)

wherein symbols represent the same meaning as in the formula (1), compounds wherein $R^6$ is a hydrogen atom, and $R^1$, $R^2$, $A^5$ and n are the combinations shown in [Table 1] to [Table 10].

In the formula (D-1), compounds wherein $R^6$ is a fluorine atom, and $R^1$, $R^2$, $A^5$ and n are the combinations shown in [Table 1] to [Table 10].

In the formula (D-1), compounds wherein $R^6$ is a chlorine atom, and $R^1$, $R^2$, $A^5$ and n are the combinations shown in [Table 1] to [Table 10].

In the formula (D-1), compounds wherein $R^6$ is a bromine atom, and $R^1$, $R^2$, $A^5$ and n are the combinations shown in [Table 1] to [Table 10].

In the formula (D-1), compounds wherein $R^6$ is a trifluoromethyl group, and $R^1$, $R^2$, $A^5$ and n are the combinations shown in [Table 1] to [Table 10].

In the formula (D-1), compounds wherein $R^6$ is a pentafluoroethyl group, and $R^1$, $R^2$, $A^5$ and n are the combinations shown in [Table 1] to [Table 10].

In the formula (D-1), compounds wherein $R^6$ is a trifluoromethoxy group, and $R^1$, $R^2$, $A^5$ and n are the combinations shown in [Table 1] to [Table 10].

In the formula (D-1), compounds wherein $R^6$ is a trifluoromethylsulfanyl group, and $R^1$, $R^2$, $A^5$ and n are the combinations shown in [Table 1] to [Table 10].

In the formula (D-1), compounds wherein $R^6$ is a trifluoromethylsulfinyl group, and $R^1$, $R^2$, $A^5$ and n are the combinations shown in [Table 1] to [Table 10].

In the formula (D-1), compounds wherein $R^6$ is a trifluoromethylsulfonyl group, and $R^1$, $R^2$, $A^5$ and n are the combinations shown in [Table 1] to [Table 10].

In formula (D-2), (D-2)

wherein symbols represent the same meaning as in the formula (1), compounds wherein $R^6$ is a hydrogen atom, and $R^1$, $R^2$, $A^5$ and n are the combinations shown in [Table 1] to [Table 10].

In the formula (D-2), compounds wherein $R^6$ is a fluorine atom, and $R^1$, $R^2$, $A^5$ and n are the combinations shown in [Table 1] to [Table 10].

In the formula (D-2), compounds wherein $R^6$ is a chlorine atom, and $R^1$, $R^2$, $A^5$ and n are the combinations shown in [Table 1] to [Table 10].

In the formula (D-2), compounds wherein $R^6$ is a bromine atom, and $R^1$, $R^2$, $A^5$ and n are the combinations shown in [Table 1] to [Table 10].

In the formula (D-2), compounds wherein $R^6$ is a trifluoromethyl group, and $R^1$, $R^2$, $A^5$ and n are the combinations shown in [Table 1] to [Table 10].

In the formula (D-2), compounds wherein $R^6$ is a pentafluoroethyl group, and $R^1$, $R^2$, $A^5$ and n are the combinations shown in [Table 1] to [Table 10].

In the formula (D-2), compounds wherein $R^6$ is a trifluoromethoxy group, and $R^1$, $R^2$, $A^5$ and n are the combinations shown in [Table 1] to [Table 10].

In the formula (D-2), compounds wherein $R^6$ is a trifluoromethylsulfanyl group, and $R^1$, $R^2$, $A^5$ and n are the combinations shown in [Table 1] to [Table 10].

In the formula (D-2), compounds wherein $R^6$ is a trifluoromethylsulfinyl group, and $R^1$, $R^2$, $A^5$ and n are the combinations shown in [Table 1] to [Table 10].

In the formula (D-2), compounds wherein $R^6$ is a trifluoromethylsulfonyl group, and $R^1$, $R^2$, $A^5$ and n are the combinations shown in [Table 1] to [Table 10].

In formula (D-3), (D-3)

wherein symbols represent the same meaning as in the formula (1), compounds wherein $R^6$ is a hydrogen atom, and $R^1$, $R^2$, $A^5$ and n are the combinations shown in [Table 1] to [Table 10].

In the formula (D-3), compounds wherein $R^6$ is a fluorine atom, and $R^1$, $R^2$, $A^5$ and n are the combinations shown in [Table 1] to [Table 10].

In the formula (D-3), compounds wherein $R^6$ is a chlorine atom, and $R^1$, $R^2$, $A^5$ and n are the combinations shown in [Table 1] to [Table 10].

In the formula (D-3), compounds wherein $R^6$ is a bromine atom, and $R^1$, $R^2$, $A^5$ and n are the combinations shown in [Table 1] to [Table 10].

In the formula (D-3), compounds wherein $R^6$ is a trifluoromethyl group, and $R^1$, $R^2$, $A^5$ and n are the combinations shown in [Table 1] to [Table 10].

In the formula (D-3), compounds wherein $R^6$ is a pentafluoroethyl group, and $R^1$, $R^2$, $A^5$ and n are the combinations shown in [Table 1] to [Table 10].

In the formula (D-3), compounds wherein $R^6$ is a trifluoromethoxy group, and $R^1$, $R^2$, $A^5$ and n are the combinations shown in [Table 1] to [Table 10].

In the formula (D-3), compounds wherein $R^6$ is a trifluoromethylsulfanyl group, and $R^1$, $R^2$, $A^5$ and n are the combinations shown in [Table 1] to [Table 10].

In the formula (D-3), compounds wherein $R^6$ is a trifluoromethylsulfinyl group, and $R^1$, $R^2$, $A^5$ and n are the combinations shown in [Table 1] to [Table 10].

In the formula (D-3), compounds wherein $R^6$ is a trifluoromethylsulfonyl group, and $R^1$, $R^2$, $A^5$ and n are the combinations shown in [Table 1] to [Table 10].

In formula (D-4), (D-4)

wherein symbols represent the same meaning as in the formula (1), compounds wherein $R^6$ is a hydrogen atom, and $R^1$, $R^2$, $A^5$ and n are the combinations shown in [Table 1] to [Table 10].

In the formula (D-4), compounds wherein $R^6$ is a fluorine atom, and $R^1$, $R^2$, $A^5$ and n are the combinations shown in [Table 1] to [Table 10].

In the formula (D-4), compounds wherein $R^6$ is a chlorine atom, and $R^1$, $R^2$, $A^5$ and n are the combinations shown in [Table 1] to [Table 10].

In the formula (D-4), compounds wherein $R^6$ is a bromine atom, and $R^1$, $R^2$, $A^5$ and n are the combinations shown in [Table 1] to [Table 10].

In the formula (D-4), compounds wherein $R^6$ is a trifluoromethyl group, and $R^1$, $R^2$, $A^5$ and n are the combinations shown in [Table 1] to [Table 10].

In the formula (D-4), compounds wherein $R^6$ is a pentafluoroethyl group, and $R^1$, $R^2$, $A^5$ and n are the combinations shown in [Table 1] to [Table 10].

In the formula (D-4), compounds wherein $R^6$ is a trifluoromethoxy group, and $R^1$, $R^2$, $A^5$ and n are the combinations shown in [Table 1] to [Table 10].

In the formula (D-4), compounds wherein $R^6$ is a trifluoromethylsulfanyl group, and $R^1$, $R^2$, $A^5$ and n are the combinations shown in [Table 1] to [Table 10].

In the formula (D-4), compounds wherein $R^6$ is a trifluoromethylsulfinyl group, and $R^1$, $R^2$, $A^5$ and n are the combinations shown in [Table 1] to [Table 10].

In the formula (D-4), compounds wherein $R^6$ is a trifluoromethylsulfonyl group, and $R^1$, $R^2$, $A^5$ and n are the combinations shown in [Table 1] to [Table 10].

In formula (D-5), (D-5)

wherein symbols represent the same meaning as in the formula (1), compounds wherein $R^6$ is a hydrogen atom, and $R^1$, $R^2$, $A^5$ and n are the combinations shown in [Table 1] to [Table 10].

In the formula (D-5), compounds wherein $R^6$ is a fluorine atom, and $R^1$, $R^2$, $A^5$ and n are the combinations shown in [Table 1] to [Table 10].
In the formula (D-5), compounds wherein $R^6$ is a chlorine atom, and $R^1$, $R^2$, $A^5$ and n are the combinations shown in [Table 1] to [Table 10].
In the formula (D-5), compounds wherein $R^6$ is a bromine atom, and $R^1$, $R^2$, $A^5$ and n are the combinations shown in [Table 1] to [Table 10].
In the formula (D-5), compounds wherein $R^6$ is a trifluoromethyl group, and $R^1$, $R^2$, $A^5$ and n are the combinations shown in [Table 1] to [Table 10].
In the formula (D-5), compounds wherein $R^6$ is a pentafluoroethyl group, and $R^1$, $R^2$, $A^5$ and n are the combinations shown in [Table 1] to [Table 10].
In the formula (D-5), compounds wherein $R^6$ is a trifluoromethoxy group, and $R^1$, $R^2$, $A^5$ and n are the combinations shown in [Table 1] to [Table 10].
In the formula (D-5), compounds wherein $R^6$ is a trifluoromethylsulfanyl group, and $R^1$, $R^2$, $A^5$ and n are the combinations shown in [Table 1] to [Table 10].
In the formula (D-5), compounds wherein $R^6$ is a trifluoromethylsulfinyl group, and $R^1$, $R^2$, $A^5$ and n are the combinations shown in [Table 1] to [Table 10].
In the formula (D-5), compounds wherein $R^6$ is a trifluoromethylsulfonyl group, and $R^1$, $R^2$, $A^5$ and n are the combinations shown in [Table 1] to [Table 10].

In formula (D-6), (D-6)

wherein symbols represent the same meaning as in the formula (1),
compounds wherein $R^6$ is a hydrogen atom, and $R^1$, $R^2$, $A^5$ and n are the combinations shown in [Table 1] to [Table 10].
In the formula (D-6), compounds wherein $R^6$ is a fluorine atom, and $R^1$, $R^2$, $A^5$ and n are the combinations shown in [Table 1] to [Table 10].
In the formula (D-6), compounds wherein $R^6$ is a chlorine atom, and $R^1$, $R^2$, $A^5$ and n are the combinations shown in [Table 1] to [Table 10].
In the formula (D-6), compounds wherein $R^6$ is a bromine atom, and $R^1$, $R^2$, $A^5$ and n are the combinations shown in [Table 1] to [Table 10].
In the formula (D-6), compounds wherein $R^6$ is a trifluoromethyl group, and $R^1$, $R^2$, $A^5$ and n are the combinations shown in [Table 1] to [Table 10].
In the formula (D-6), compounds wherein $R^6$ is a pentafluoroethyl group, and $R^1$, $R^2$, $A^5$ and n are the combinations shown in [Table 1] to [Table 10].
In the formula (D-6), compounds wherein $R^6$ is a trifluoromethoxy group, and $R^1$, $R^2$, $A^5$ and n are the combinations shown in [Table 1] to [Table 10].
In the formula (D-6), compounds wherein $R^6$ is a trifluoromethylsulfanyl group, and $R^1$, $R^2$, $A^5$ and n are the combinations shown in [Table 1] to [Table 10].
In the formula (D-6), compounds wherein $R^6$ is a trifluoromethylsulfinyl group, and $R^1$, $R^2$, $A^5$ and n are the combinations shown in [Table 1] to [Table 10].
In the formula (D-6), compounds wherein $R^6$ is a trifluoromethylsulfonyl group, and $R^1$, $R^2$, $A^5$ and n are the combinations shown in [Table 1] to [Table 10].

In formula (D-7), (D-7)

wherein symbols represent the same meaning as in the formula (1),
compounds wherein $R^6$ is a hydrogen atom, and $R^1$, $R^2$, $A^5$ and n are the combinations shown in [Table 1] to [Table 10].
In the formula (D-7), compounds wherein $R^6$ is a fluorine atom, and $R^1$, $R^2$, $A^5$ and n are the combinations shown in [Table 1] to [Table 10].
In the formula (D-7), compounds wherein $R^6$ is a chlorine atom, and $R^1$, $R^2$, $A^5$ and n are the combinations shown in [Table 1] to [Table 10].
In the formula (D-7), compounds wherein $R^6$ is a bromine atom, and $R^1$, $R^2$, $A^5$ and n are the combinations shown in [Table 1] to [Table 10].
In the formula (D-7), compounds wherein $R^6$ is a trifluoromethyl group, and $R^1$, $R^2$, $A^5$ and n are the combinations shown in [Table 1] to [Table 10].
In the formula (D-7), compounds wherein $R^6$ is a pentafluoroethyl group, and $R^1$, $R^2$, $A^5$ and n are the combinations shown in [Table 1] to [Table 10].
In the formula (D-7), compounds wherein $R^6$ is a trifluoromethoxy group, and $R^1$, $R^2$, $A^5$ and n are the combinations shown in [Table 1] to [Table 10].
In the formula (D-7), compounds wherein $R^6$ is a trifluoromethylsulfanyl group, and $R^1$, $R^2$, $A^5$ and n are the combinations shown in [Table 1] to [Table 10].
In the formula (D-7), compounds wherein $R^6$ is a trifluoromethylsulfinyl group, and $R^1$, $R^2$, $A^5$ and n are the combinations shown in [Table 1] to [Table 10].
In the formula (D-7), compounds wherein $R^6$ is a trifluoromethylsulfonyl group, and $R^1$, $R^2$, $A^5$ and n are the combinations shown in [Table 1] to [Table 10].

In formula (E-1), (E-1)

wherein symbols represent the same meaning as in the formula (1),
compounds wherein $R^6$ is a hydrogen atom, and $R^1$, $R^2$, $A^5$ and n are the combinations shown in [Table 1] to [Table 10].
In the formula (E-1), compounds wherein $R^6$ is a fluorine atom, and $R^1$, $R^2$, $A^5$ and n are the combinations shown in [Table 1] to [Table 10].

In the formula (E-1), compounds wherein $R^6$ is a chlorine atom, and $R^1$, $R^2$, $A^5$ and n are the combinations shown in [Table 1] to [Table 10].

In the formula (E-1), compounds wherein $R^6$ is a bromine atom, and $R^1$, $R^2$, $A^5$ and n are the combinations shown in [Table 1] to [Table 10].

In the formula (E-1), compounds wherein $R^6$ is a trifluoromethyl group, and $R^1$, $R^2$, $A^5$ and n are the combinations shown in [Table 1] to [Table 10].

In the formula (E-1), compounds wherein $R^6$ is a pentafluoroethyl group, and $R^1$, $R^2$, $A^5$ and n are the combinations shown in [Table 1] to [Table 10].

In the formula (E-1), compounds wherein $R^6$ is a trifluoromethoxy group, and $R^1$, $R^2$, $A^5$ and n are the combinations shown in [Table 1] to [Table 10].

In the formula (E-1), compounds wherein $R^6$ is a trifluoromethylsulfanyl group, and $R^1$, $R^2$, $A^5$ and n are the combinations shown in [Table 1] to [Table 10].

In the formula (E-1), compounds wherein $R^6$ is a trifluoromethylsulfinyl group, and $R^1$, $R^2$, $A^5$ and n are the combinations shown in [Table 1] to [Table 10].

In the formula (E-1), compounds wherein $R^6$ is a trifluoromethylsulfonyl group, and $R^1$, $R^2$, $A^5$ and n are the combinations shown in [Table 1] to [Table 10].

In formula (E-2), (E-2)

wherein symbols represent the same meaning as in the formula (1), compounds wherein $R^6$ is a hydrogen atom, and $R^1$, $R^2$, $A^5$ and n are the combinations shown in [Table 1] to [Table 10].

In the formula (E-2), compounds wherein $R^6$ is a fluorine atom, and $R^1$, $R^2$, $A^5$ and n are the combinations shown in [Table 1] to [Table 10].

In the formula (E-2), compounds wherein $R^6$ is a chlorine atom, and $R^1$, $R^2$, $A^5$ and n are the combinations shown in [Table 1] to [Table 10].

In the formula (E-2), compounds wherein $R^6$ is a bromine atom, and $R^1$, $R^2$, $A^5$ and n are the combinations shown in [Table 1] to [Table 10].

In the formula (E-2), compounds wherein $R^6$ is a trifluoromethyl group, and $R^1$, $R^2$, $A^5$ and n are the combinations shown in [Table 1] to [Table 10].

In the formula (E-2), compounds wherein $R^6$ is a pentafluoroethyl group, and $R^1$, $R^2$, $A^5$ and n are the combinations shown in [Table 1] to [Table 10].

In the formula (E-2), compounds wherein $R^6$ is a trifluoromethoxy group, and $R^1$, $R^2$, $A^5$ and n are the combinations shown in [Table 1] to [Table 10].

In the formula (E-2), compounds wherein $R^6$ is a trifluoromethylsulfanyl group, and $R^1$, $R^2$, $A^5$ and n are the combinations shown in [Table 1] to [Table 10].

In the formula (E-2), compounds wherein $R^6$ is a trifluoromethylsulfinyl group, and $R^1$, $R^2$, $A^5$ and n are the combinations shown in [Table 1] to [Table 10].

In the formula (E-2), compounds wherein $R^6$ is a trifluoromethylsulfonyl group, and $R^1$, $R^2$, $A^5$ and n are the combinations shown in [Table 1] to [Table 10].

In formula (E-3), (E-3)

wherein symbols represent the same meaning as in the formula (1), compounds wherein $R^6$ is a hydrogen atom, and $R^1$, $R^2$, $A^5$ and n are the combinations shown in [Table 1] to [Table 10].

In the formula (E-3), compounds wherein $R^6$ is a fluorine atom, and $R^1$, $R^2$, $A^5$ and n are the combinations shown in [Table 1] to [Table 10].

In the formula (E-3), compounds wherein $R^6$ is a chlorine atom, and $R^1$, $R^2$, $A^5$ and n are the combinations shown in [Table 1] to [Table 10].

In the formula (E-3), compounds wherein $R^6$ is a bromine atom, and $R^1$, $R^2$, $A^5$ and n are the combinations shown in [Table 1] to [Table 10].

In the formula (E-3), compounds wherein $R^6$ is a trifluoromethyl group, and $R^1$, $R^2$, $A^5$ and n are the combinations shown in [Table 1] to [Table 10].

In the formula (E-3), compounds wherein $R^6$ is a pentafluoroethyl group, and $R^1$, $R^2$, $A^5$ and n are the combinations shown in [Table 1] to [Table 10].

In the formula (E-3), compounds wherein $R^6$ is a trifluoromethoxy group, and $R^1$, $R^2$, $A^5$ and n are the combinations shown in [Table 1] to [Table 10].

In the formula (E-3), compounds wherein $R^6$ is a trifluoromethylsulfanyl group, and $R^1$, $R^2$, $A^5$ and n are the combinations shown in [Table 1] to [Table 10].

In the formula (E-3), compounds wherein $R^6$ is a trifluoromethylsulfinyl group, and $R^1$, $R^2$, $A^5$ and n are the combinations shown in [Table 1] to [Table 10].

In the formula (E-3), compounds wherein $R^6$ is a trifluoromethylsulfonyl group, and $R^1$, $R^2$, $A^5$ and n are the combinations shown in [Table 1] to [Table 10].

In formula (E-4), (E-4)

wherein symbols represent the same meaning as in the formula (1), compounds wherein $R^6$ is a hydrogen atom, and $R^1$, $R^2$, $A^5$ and n are the combinations shown in [Table 1] to [Table 10]
In the formula (E-4), compounds wherein $R^6$ is a fluorine atom, and $R^1$, $R^2$, $A^5$ and n are the combinations shown in [Table 1] to [Table 10].
In the formula (E-4), compounds wherein $R^6$ is a chlorine atom, and $R^1$, $R^2$, $A^5$ and n are the combinations shown in [Table 1] to [Table 10].
In the formula (E-4), compounds wherein $R^6$ is a bromine atom, and $R^1$, $R^2$, $A^5$ and n are the combinations shown in [Table 1] to [Table 10]
In the formula (E-4), compounds wherein $R^6$ is a trifluoromethyl group, and $R^1$, $R^2$, $A^5$ and n are the combinations shown in [Table 1] to [Table 10].
In the formula (E-4), compounds wherein $R^6$ is a pentafluoroethyl group, and $R^1$, $R^2$, $A^5$ and n are the combinations shown in [Table 1] to [Table 10].
In the formula (E-4), compounds wherein $R^6$ is a trifluoromethoxy group, and $R^1$, $R^2$, $A^5$ and n are the combinations shown in [Table 1] to [Table 10].
In the formula (E-4), compounds wherein $R^6$ is a trifluoromethylsulfanyl group, and $R^1$, $R^2$, $A^5$ and n are the combinations shown in [Table 1] to [Table 10].
In the formula (E-4), compounds wherein $R^6$ is a trifluoromethylsulfinyl group, and $R^1$, $R^2$, $A^5$ and n are the combinations shown in [Table 1] to [Table 10].
In the formula (E-4), compounds wherein $R^6$ is a trifluoromethylsulfonyl group, and $R^1$, $R^2$, $A^5$ and n are the combinations shown in [Table 1] to [Table 10].

In formula (E-5), (E-5)

wherein symbols represent the same meaning as in the formula (1),
compounds wherein $R^6$ is a hydrogen atom, and $R^1$, $R^2$, $A^5$ and n are the combinations shown in [Table 1] to [Table 10].
In the formula (E-5), compounds wherein $R^6$ is a fluorine atom, and $R^1$, $R^2$, $A^5$ and n are the combinations shown in [Table 1] to [Table 10].
In the formula (E-5), compounds wherein $R^6$ is a chlorine atom, and $R^1$, $R^2$, $A^5$ and n are the combinations shown in [Table 1] to [Table 10].
In the formula (E-5), compounds wherein $R^6$ is a bromine atom, and $R^1$, $R^2$, $A^5$ and n are the combinations shown in [Table 1] to [Table 10].
In the formula (E-5), compounds wherein $R^6$ is a trifluoromethyl group, and $R^1$, $R^2$, $A^5$ and n are the combinations shown in [Table 1] to [Table 10].
In the formula (E-5), compounds wherein $R^6$ is a pentafluoroethyl group, and $R^1$, $R^2$, $A^5$ and n are the combinations shown in [Table 1] to [Table 10].
In the formula (E-5), compounds wherein $R^6$ is a trifluoromethoxy group, and $R^1$, $R^2$, $A^5$ and n are the combinations shown in [Table 1] to [Table 10].
In the formula (E-5), compounds wherein $R^6$ is a trifluoromethylsulfanyl group, and $R^1$, $R^2$, $A^5$ and n are the combinations shown in [Table 1] to [Table 10].
In the formula (E-5), compounds wherein $R^6$ is a trifluoromethylsulfinyl group, and $R^1$, $R^2$, $A^5$ and n are the combinations shown in [Table 1] to [Table 10].
In the formula (E-5), compounds wherein $R^6$ is a trifluoromethylsulfonyl group, and $R^1$, $R^2$, $A^5$ and n are the combinations shown in [Table 1] to [Table 10].

In formula (E-6), (E-6)

wherein symbols represent the same meaning as in the formula (1),
compounds wherein $R^6$ is a hydrogen atom, and $R^1$, $R^2$, $A^5$ and n are the combinations shown in [Table 1] to [Table 10].
In the formula (E-6), compounds wherein $R^6$ is a fluorine atom, and $R^1$, $R^2$, $A^5$ and n are the combinations shown in [Table 1] to [Table 10].
In the formula (E-6), compounds wherein $R^6$ is a chlorine atom, and $R^1$, $R^2$, $A^5$ and n are the combinations shown in [Table 1] to [Table 10].
In the formula (E-6), compounds wherein $R^6$ is a bromine atom, and $R^1$, $R^2$, $A^5$ and n are the combinations shown in [Table 1] to [Table 10].
In the formula (E-6), compounds wherein $R^6$ is a trifluoromethyl group, and $R^1$, $R^2$, $A^5$ and n are the combinations shown in [Table 1] to [Table 10].
In the formula (E-6), compounds wherein $R^6$ is a pentafluoroethyl group, and $R^1$, $R^2$, $A^5$ and n are the combinations shown in [Table 1] to [Table 10].
In the formula (E-6), compounds wherein $R^6$ is a trifluoromethoxy group, and $R^1$, $R^2$, $A^5$ and n are the combinations shown in [Table 1] to [Table 10].
In the formula (E-6), compounds wherein $R^6$ is a trifluoromethylsulfanyl group, and $R^1$, $R^2$, $A^5$ and n are the combinations shown in [Table 1] to [Table 10].
In the formula (E-6), compounds wherein $R^6$ is a trifluoromethylsulfinyl group, and $R^1$, $R^2$, $A^5$ and n are the combinations shown in [Table 1] to [Table 10].
In the formula (E-6), compounds wherein $R^6$ is a trifluoromethylsulfonyl group, and $R^1$, $R^2$, $A^5$ and n are the combinations shown in [Table 1] to [Table 10].

In formula (E-7), (E-7)

wherein symbols represent the same meaning as in the formula (1),
compounds wherein $R^6$ is a hydrogen atom, and $R^1$, $R^2$, $A^5$ and n are the combinations shown in [Table 1] to [Table 10].
In the formula (E-7), compounds wherein $R^6$ is a fluorine atom, and $R^1$, $R^2$, $A^5$ and n are the combinations shown in [Table 1] to [Table 10].

In the formula (E-7), compounds wherein $R^6$ is a chlorine atom, and $R^1$, $R^2$, $A^5$ and n are the combinations shown in [Table 1] to [Table 10].

In the formula (E-7), compounds wherein $R^6$ is a bromine atom, and $R^1$, $R^2$, $A^5$ and n are the combinations shown in [Table 1] to [Table 10].

In the formula (E-7), compounds wherein $R^6$ is a trifluoromethyl group, and $R^1$, $R^2$, $A^5$ and n are the combinations shown in [Table 1] to [Table 10].

In the formula (E-7), compounds wherein $R^6$ is a pentafluoroethyl group, and $R^1$, $R^2$, $A^5$ and n are the combinations shown in [Table 1] to [Table 10].

In the formula (E-7), compounds wherein $R^6$ is a trifluoromethoxy group, and $R^1$, $R^2$, $A^5$ and n are the combinations shown in [Table 1] to [Table 10].

In the formula (E-7), compounds wherein $R^6$ is a trifluoromethylsulfanyl group, and $R^1$, $R^2$, $A^5$ and n are the combinations shown in [Table 1] to [Table 10].

In the formula (E-7), compounds wherein $R^6$ is a trifluoromethylsulfinyl group, and $R^1$, $R^2$, $A^5$ and n are the combinations shown in [Table 1] to [Table 10].

In the formula (E-7), compounds wherein $R^6$ is a trifluoromethylsulfonyl group, and $R^1$, $R^2$, $A^5$ and n are the combinations shown in [Table 1] to [Table 10].

In formula (F-1),

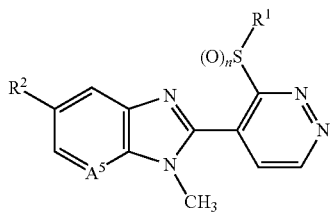

(F-1)

wherein symbols represent the same meaning as in the formula (1), compounds wherein $R^1$, $R^2$, $A^5$ and n are the combinations shown in [Table 1] to [Table 10].

In formula (F-2),

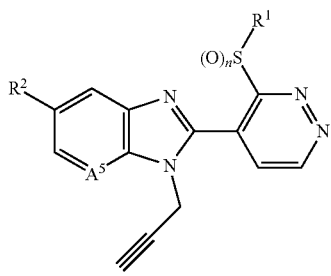

(F-2)

wherein symbols represent the same meaning as in the formula (1), compounds wherein $R^1$, $R^2$, $A^5$ and n are the combinations shown in [Table 1] to [Table 10].

In formula (F-3),

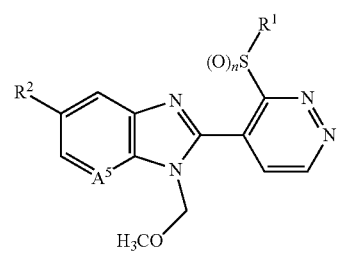

(F-3)

wherein symbols represent the same meaning as in the formula (1), compounds wherein $R^1$, $R^2$, $A^5$ and n are the combinations shown in [Table 1] to [Table 10].

In formula (F-4), (F-4)

wherein symbols represent the same meaning as in the formula (1), compounds wherein $R^1$, $R^2$, $A^5$ and n are the combinations shown in [Table 1] to [Table 10].

In formula (F-5), (F-5)

wherein symbols represent the same meaning as in the formula (1), compounds wherein $R^1$, $R^2$, $A^5$ and n are the combinations shown in [Table 1] to [Table 10].

In formula (F-6), (F-6)

wherein symbols represent the same meaning as in the formula (1), compounds wherein R¹, R², A⁵ and n are the combinations shown in [Table 1] to [Table 10].

In formula (F-7),

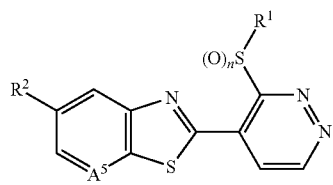

(F-7)

wherein symbols represent the same meaning as in the formula (1),
compounds wherein R¹, R², A⁵ and n are the combinations shown in [Table 1] to [Table 10].

Examples of the pest on which the composition of the present invention has an effect include arthropod pests such as pest insects and pest mites and nematoda. Specifically, examples of the pests include those shown below.

Hemiptera: Delphacidae such as *Laodelphax striatellus*, *Nilaparvata lugens*, and *Sogatella furcifera*, Deltocephalidae such as *Nephotettix cincticeps*, *Nephotettix virescens*, and *Empoasca onukii*, Aphididae such as *Aphis gossypii*, *Myzus persicae*, *Brevicoryne brassicae*, *Aphis spiraecola*, *Macrosiphum euphorbiae*, *Aulacorthum solani*, *Rhopalosiphum padi*, *Toxoptera citricidus*, and *Hyalopterus pruni*, Pentatomidae such as *Nezara antennata*, *Riptortus clavetus*, *Leptocorisa chinensis*, *Eysarcoris parvus*, and *Halyomorpha mista*, Aleyrodidae such as *Trialeurodes vaporariorum*, *Bemisia tabaci*, *Dialeurodes citri*, and *Aleurocanthus spiniferus*, Coccidae such as *Aonidiella aurantii*, *Comstockaspis perniciosa*, *Unaspis citri*, *Ceroplastes rubens*, *Icerya purchasi*, *Planococcus kraunhiae*, *Pseudococcus longispinis*, and *Pseudaulacaspis pentagona*, Tingidae, Cimicoidea such as *Cimex lectularius*, and Psyliidae.

Lepidoptera: Pyralidae such as *Chilo suppressalis*, *Tryporyza incertulas*, *Cnaphalocrocis medinalis*, *Notarcha derogata*, *Plodia interpunctella*, *Ostrinia furnacalis*, *Hellula undalis*, and *Pediasia teterrellus*, Noctuidae such as *Spodoptera litura*, *Spodoptera exigua*, *Pseudaletia separata*, *Mamestra brassicae*, *Agrotis ipsilon*, *Plusia nigrisigna*, *Trichoplusia* spp., *Heliothis* spp., and *Helicoverpa* spp., Pieridae such as *Pieris rapae*, *Adoxophyes* spp., Tortricidae such as *Grapholita molesta*, *Leguminivora glycinivorella*, *Matsumuraeses azukivora*, *Adoxophyes orana fasciata*, *Adoxophyes honmai*., *Homona magnanima*, *Archips fuscocupreanus*, and *Cydia pomonella*, Gracillariidae such as *Caloptilia theivora* and *Phyllonorycter ringoneella*, Carposinidae such as *Carposina niponensis*, Lyonetiidae such as *Lyonetia* spp., Lymantriidae such as *Lymantria* spp. and *Euproctis* spp., Yponomeutidae such as *Plutella xylostella*, Gelechiidae such as *Pectinophora gossypiella* and *Phthorimaea operculella*, Arctiidae such as *Hyphantria cunea*, and Tineidae such as *Tinea translucens* and *Tineola bisselliella*.

Thysanoptera: Thripidae such as *Frankliniella occidentalis*, *Thrips parmi*, *Scirtothrips dorsalis*, *Thrips tabaci*, and *Frankliniella intonsa*.

Diptera: Culex such as *Culex pipiens pallens*, *Culex tritaeniorhynchus*, and *Culex quinquefasciatus*, *Aedes* spp. such as *Aedes aegypti* and *Aedes albopictus*, *Anopheles* spp. such as *Anopheles sinensis*, Chironomidae, Muscidae such as *Musca domestica* and *Muscina stabulans*, Calliphoridae, Sarcophagidae, Fanniidae, Anthomyiidae such as *Delia platura* and *Delia antiqua*, Agromyzidae such as *Agromyza oryzae*, *Hydrellia griseola*, *Liriomyza sativae*, *Liriomyza trifolii*, and *Chromatomyia horticola*, Chloropidae such as *Chlorops oryzae*, Tephritidae such as *Dacus cucurbitae* and *Ceratitis capitata*, Drosophilidae, Phoridae such as *Megaselia spiracularis*, Psychodidae such as *Clogmia albipunctata*, Sciaridae, Simuliidae, Tabanidae such as *Tabanus trigonus*, Stomoxys, and Stomoxyidae.

Coleoptera: Corn rootworm such as *Diabrotica virgifera virgifera* and *Diabrotica undecimpunctata howardi*, Scarabaeidae such as *Anomala cuprea*, *Anomala rufocuprea*, and *Popillia japonica*, Curculionidae such as *Sitophilus zeamais*, *Lissorhoptrus oryzophilus*, *Callosobruchuys chienensis*, *Echinocnemus squameus*, *Anthonomus grandis*, and *Sphenophorus venatus*, Tenebrionidae such as *Tenebrio molitor* and *Tribolium castaneum*, Chrysomelidae such as *Oulema oryzae*, *Aulacophora femoralis*, *Phyllotreta striolata*, and *Leptinotarsa decemlineata*, Dermestidae such as *Anthrenus verbasci* and *Dermestes maculates*, Anobiidae such as *Lasioderma serricorne*, Epilachna such as *Epilachna vigintioctopunctata*, Lyctidae such as *Lyctus brunneus* and *Tomicus piniperda*, Bostrychidae, Ptinidae, Cerambycidae such as *Anoplophora malasiaca*, *Agriotes* spp., and *Paederus fuscipes*.

Orthoptera: *Locusta migratoria*, *Gryllotalpa africana*, *Oxya yezoensis*, *Oxya japonica*, and Grylloidea.

Siphonaptera: *Ctenocephalides felis*, *Ctenocephalides canis*, *Pulex irritans*, *Xenopsylla cheopis*, and the like.

Anoplura: *Pediculus humanus corporis*, *Pediculus humanus humanus*, *Phthirus pubis*, *Haematopinus eurysternus*, *Dalmalinia ovis*, *Haematopinus suis*, *Linognathus setosus*, and the like.

Mallophaga: *Dalmalinia ovis*, *Dalmalinia bovis*, *Menopon gallinae*, *Trichodectes canis*, *Felicola subrostrata*, and the like Hymenoptera: Formicidae such as *Monomorium pharaosis*, *Formica fusca japonica*, *Ochetellus glaber*, *Pristomyrmex pungens*, *Pheidole noda*, *Acromyrmex* spp., *Solenopsis* spp., and *Linepithema humile*, Vespidae, Bethylidae, and Tenthredinidae such as *Athalia rosae* and *Athalia japonica*.

Nematoda: Aphelenchoidesbesseyi, Nothotylenchus acris, *Meloidogyne incognita*, *Meloidogyne hapla*, *Meloidogyne javanica*, *Heterodera glycines*, *Globodera rostochiensis*, *Pratylenchus coffeae*, and *Pratylenchus neglectus*.

Blattodea: *Blattella germanica*, *Periplaneta fuliginosa*, *Periplaneta americana*, *Periplaneta brunnea*, and *Blatta orientalis*.

Isoptera: *Reticulitermes speratus*, *Coptotermes formosanus*, *Incisitermes minor*, *Cryptotermes domesticus*, *Odontotermes formosanus*, *Neotermes koshunensis*, *Glyptotermes satsumensis*, *Glyptotermes nakajimai*, *Glyptotermes fuscus*, *Glyptotermes kodamai*, *Glyptotermes kushimensis*, *Hodotermopsis japonica*, *Coptotermes guangzhoensis*, *Reticulitermes miyatakei*, *Reticulitermes flaviceps amamianus*, *Reticulitermes* sp., *Nasutitermes takasagoensis*, *Pericapritermes nitobei*, *Sinocapritermes mushae*, and the like.

Acarina: Tetranychidae such as *Tetranychus urticae*, *Tetranychus kanzawai*, *Panonychus citri*, *Panonychus ulmi*, and *Oligonychus* spp., Eriophyidae such as *Aculops pelekassi*, *Phyllocoptruta citri*, *Aculops lycopersici*, *Calacarus carinatus*, *Acaphylla theavagrans*, *Eriophyes chibaensis*, and *Aculus schlechtendali*, Tarsonemidae such as *Polyphagotarsonemus latus*, Tenuipalpidae such as *Brevipalpus phoenicis*, Tuckerellidae, Metastigmata such as *Haemaphysalis longicornis*, *Haemaphysalis flava*, *Dermacentor taiwanicus*, *Dermacentor variabilis*, *Ixodes ovatus*, *Ixodes persulcatus*, *Ixodes scapularis*, *Amblyomma americanum*, *Boophilus microplus*, and *Rhipicephalus sanguineus*, Acaridae such as

*Tyrophagus putrescentiae* and *Tyrophagus similis*, Pyroglyphidae such as *Dermatophagoides farinae* and *Dermatophagoides ptrenyssnus*, Cheyletidae such as *Cheyletus eruditus, Cheyletus malaccensis, Cheyletus moorei*, and *Cheyletiella yasguri*, Sarcoptidae such as *Octodectes cynotis* and Sacroptes *scabiei*, Demodicidae such as *Demodex canis*, Listrophoridae, Oribatei, Dermanyssidae such as *Ornithonyssus bacoti, Ornithonyssus sylvairum*, and *Dermanyssus gallinae*, Trombiculidae such as *Leptotrombidium akamushi*, Arachnida such as *Chiracanthium japonicum* and *Latrodectus hasseltii*, and the like.

Chilopoda: *Thereuonema hilgendorfi, Scolopendra subspinipes*, and the like.

Diplopoda: *Oxidus gracilis, Nedyopus tambanus*, and the like.

Isopoda: *Armadillidium vulgare*, and the like.

Gastropoda: *Limaxmarginatus, Limax flavus*, and the like.

The pest control agent of the present invention contains the compound of the present invention and an inert carrier. The pest control agent of the present invention is usually obtained by mixing the compound of the present invention and an inert carrier such as a solid carrier, a liquid carrier or a gaseous carrier, and adding a surfactant or other auxiliaries for formulation as necessary, to be formulated into emulsifiable concentrates, oil formulations, dust formulations, granules, wettable powders, flowables, microcapsule formulations, aerosols, fumigants, poisonous baits, resin formulations, shampoo agent, paste formulation, foam agent, carbon dioxide preparation, tablet, and the like. These formulations may be processed into mosquito repellent coil, electric mosquito repellent mat, mosquito repellent liquid formulation, smoking agent, fumigant, sheet formulation, spot-on agent, or oral treatment agent, and used.

The pest control agent of the present invention usually contains the compound of the present invention in an amount of 0.01 to 95% by weight.

Examples of the solid carrier which is used in the formulation include fine powder and granules of clays (kaolin clay, diatomaceous earth, bentonite, Fubasami clay, acid clay, etc.), synthetic hydrated silicon oxide, talc, ceramics, other inorganic minerals (sericite, quartz, sulfur, activated carbon, calcium carbonate, hydrated silica, etc.), fine powder and granulated substances of chemical fertilizers (ammonium sulfate, ammonium phosphate, ammonium nitrate, urea, ammonium chloride, etc.) and the like, polyester resins such as synthetic resins (polyester resins such as polypropylene, polyacrylonitrile, polymethylmethacrylate and polyethylene terephthalate, nylon resins such as nylon-6, nylon-11 and nylon-66, polyamide resin, polyvinyl chloride, polyvinylidene chloride, vinyl chloride-propylene copolymer, and the like).

Examples of the liquid carrier include water, alcohols (methanol, ethanol, isopropyl alcohol, butanol, hexanol, benzyl alcohol, ethylene glycol, propylene glycol, phenoxyethanol, etc.), ketones (acetone, methyl ethyl ketone, cyclohexanone, etc.), aromatic hydrocarbons (toluene, xylene, ethylbenzene, dodecylbenzene, phenylxylylethane, methylnaphthalene, etc.), aliphatic hydrocarbons (hexane, cyclohexane, kerosene, light oil, etc.), esters (ethyl acetate, butyl acetate, isopropyl myristate, ethyl oleate, diisopropyl adipate, diisobutyl adipate, propylene glycol monomethyl ether acetate, etc.), nitriles (acetonitrile, isobutyronitrile, etc.), ethers (diisopropyl ether, 1,4-dioxane, ethylene glycol dimethyl ether, diethylene glycol dimethyl ether, diethylene glycol monomethyl ether, propylene glycol monomethyl ether, dipropylene glycol monomethyl ether, 3-methoxy-3-methyl-1-butanol, etc.), acid amides (DMF, N,N-dimethylacetamide, etc.), halogenated hydrocarbons (dichloromethane, trichloroethane, carbon tetrachloride, etc.), sulfoxides (DMSO, etc.), and propylene carbonate and vegetable oils (soybean oil, cottonseed oil, etc.).

Examples of the gaseous carrier include fluorocarbon, butane gas, LPG (liquefied petroleum gas), dimethyl ether, and carbon dioxide.

Examples of the surfactant include nonionic surfactants such as polyoxyethylene alkyl ether, polyoxyethylene alkylaryl ether and polyethylene glycol fatty acid ester, and anionic surfactants such as alkylsulfates, alkylbenzene sulfonates and alkylsulfates.

The other auxiliaries for formulation include such as fixing agents, dispersants, colorants and stabilizers, specifically, for example, casein, gelatin, polysaccharides (starch, arabic gum, cellulose derivatives, alginic acid, etc.), lignin derivatives, bentonite, synthetic water-soluble polymers (polyvinyl alcohol, polyvinyl pyrrolidone, polyacrylic acid, etc.), PAP (isopropyl acid phosphate), BHT (2,6-di-tert-butyl-4-methylphenol) and BHA (mixtures of 2-tert-butyl-4-methoxyphenol and 3-tert-butyl-4-methoxyphenol).

Examples of a base material of the resin formulation include vinyl chloride polymer, polyurethane and the like, and a plasticizer such as ester phthalates (dimethyl phthalate, dioctyl phthalate, etc.), ester adipates or stearic acid may be added to these base materials as necessary. The resin formulation is obtained by kneading a compound into the base material using an ordinary kneading apparatus, then molding it by injection molding, extrusion molding, press molding or the like, and can be processed into a plate, film, taped, reticular or string resin formulation by further undergoing molding or cutting step as necessary. These resin formulation is processed into, for example, a collar for animal, an ear tag for animal, a sheet formulation, an induction cord, and a gardening pole.

Examples of a base material of the poisonous bait include grain powder, vegetable oil, sugar, crystalline cellulose and the like, and further, an antioxidant such as dibutylhydroxytoluene and nordihydroguaiaretic acid, a preservative such as dehydroacetic acid, a substance for preventing accidental ingestion by children and pets such as red pepper powder, a pest attractant such as cheese flavor, onion flavor and peanut oil or the like are added as necessary.

The method for controlling pests of the present invention is carried out by applying an effective amount of the composition of the present invention to a pest directly and/or a pest-infested area (plants, soil, in-house, animal body, etc.). In the method for controlling pests of the present invention, the compound is usually used in the form of the pest control agent of the present invention.

When the pest control agent of the present invention is used in pest controlling in the agricultural field, the application amount is usually 1 to 10000 g per the amount of the compound of the present invention per 10000 $m^2$. When the pest control agent of the present invention is formulated into an emulsifiable concentrate, a wettable powder, a flowable or the like, the pest control agent is usually diluted with water for an application so as to have a concentration of the active ingredient of 0.01 to 10000 ppm, and dust formulations, granules and the like are usually applied as they are.

These formulations and formulation solutions diluted with water may be directly treated by being sprayed on a pest or a plant such as crops which should be protected from pests, and also may be treated on a soil in order to control a pest that infests in the soil of cultivated land.

Also, the resin formulation processed into a sheet or string can be also treated by a method such as winding it around crops, spreading it in the vicinity of crops, or spreading it to the soil around crop roots.

When the pest control agent of the present invention is used in controlling the pest that inhabits in the house, the application amount is usually 0.01 to 1000 mg in an amount of the compound of the present invention per 1 m² of an area to be treated, in the case of using it on a planar area, and is usually 0.01 to 500 mg in an amount of the compound of the present invention per 1 m² of a space to be treated, in the case of using it in a space. When the pest control agent of the present invention is formulated into an emulsifiable concentrate, a wettable powder, a flowable or the like, the pest control agent is usually diluted with water for an application so as to have a concentration of the active ingredient of 0.1 to 10000 ppm, and oil formulations, aerosols, fumigants, poisonous baits and the like are applied as they are.

When the arthropod pest control agent of the present invention is used in the control of external parasites on livestock such as cows, horses, pigs, sheep, goats and chickens, and small animals such as dogs, cats, rats and mice, veterinary known methods can be applied to the animals. As specific methods, the formulation is administered, for example, by way of a tablet, mixing in feed, a suppository and injection (intramuscular, subcutaneous, intravenous, intraperitoneal injections, etc.), when systemic control is intended, and the formulation is used, for example, by way of spraying an oil solution or aqueous solution, pour-on or spot-on treatment, washing an animal with a shampoo formulation, or putting a collar or ear tag made of a resin formulation on to an animal, when non-systemic control is intended. The amount of the compound of the present invention when administered to an animal body is usually in the range from 0.1 to 1000 mg per 1 kg of the weight of an animal.

The pest control agent of the present invention can be used in the farmland where the following "crops" are grown.

Crops: corn, rice, wheat, barley, rye, oat, sorghum, cotton, soybean, peanut, sarrazin, sugar beet, rapeseed, sunflower, sugar cane, tobacco, etc.

Vegetables: Solanaceae vegetables (eggplant, tomato, green pepper, hot pepper, potato, etc.), Cucurbitaceae vegetables (cucumber, pumpkin, zucchini, watermelon, melon, etc.), Cruciferae vegetables (Japanese radish, turnip, horseradish, kohlrabi, Chinese cabbage, cabbage, brown mustard, broccoli, cauliflower, etc.), Compositae vegetables (burdock, garland chrysanthemum, artichoke, lettuce, etc.), Liliaceae vegetables (Welsh onion, onion, garlic, asparagus, etc.), Umbelliferae vegetables (carrot, parsley, celery, parsnip, etc.), Chenopodiaceae vegetables (spinach, Swiss chard, etc.), Labiatae vegetables (Japanese mint, mint, basil, etc.), strawberry, sweat potato, yam, aroid, etc.

Fruit trees: pomaceous fruits (apple, common pear, Japanese pear, Chinese quince, quince, etc.), stone fleshy fruits (peach, plum, nectarine, Japanese plum, cherry, apricot, prune, etc.), citrus plants (Satsuma mandarin, orange, lemon, lime, grapefruits, etc.), nuts (chestnut, walnut, hazel nut, almond, pistachio, cashew nut, macadamia nut, etc.), berry fruits (blueberry, cranberry, blackberry, raspberry, etc.), grape, persimmon, olive, loquat, banana, coffee, date, coconut, oil palm, etc.

Trees other than fruit trees: tea, mulberry, flowering trees and shrubs (azalea, camellia, hydrangea, sasanqua, *Illicium religiosum*, cherry tree, tulip tree, crape myrtle, fragrant olive, etc.), street trees (ash tree, birch, dogwood, eucalyptus, ginkgo, lilac, maple tree, oak, poplar, cercis, Chinese sweet gum, plane tree, zelkova, Japanese arborvitae, fir tree, Japanese hemlock, needle juniper, pine, spruce, yew, elm, horsechestnut, etc.), sweet viburnum, *Podocarpus macrophyllus*, Japanese cedar, Japanese cypress, croton, spindle tree, Chainese howthorn, etc.

Lawn: zoysia (Japanese lawn grass, mascarene grass, etc.), Bermuda grass (*Cynodon dactylon*, etc.), bent grass (creeping bent grass, *Agrostis stolonifera, Agrostis tenuis*, etc.), bluegrass (Kentucky bluegrass, rough bluegrass, etc.), fescue (tall fescue, chewing fescue, creeping fescue, etc.), ryegrass (darnel, perennial ryegrass, etc.), cocksfoot, timothy grass, etc.

Others: flowers (rose, carnation, chrysanthemum, *Eustoma grandiflorum* Shinners (prairie gentian), gypsophila, gerbera, pot marigold, salvia, petunia, verbena, tulip, aster, gentian, lily, pansy, cyclamen, orchid, lily of the valley, lavender, stock, ornamental kale, primula, poinsttia, gladiolus, cattleya, daisy, cymbidium, begonia, etc.), bio-fuel plants (Jatropha, curcas, safflower, Camelina alyssum, switchgrass, miscanthus, reed canary grass, *Arundo donax*, kenaf, cassava, willow, algae, etc.), foliage plants, etc.

The "crops" also contains genetically modified crops.

The pest control agent of the present invention can be used as a mixture with or in combination with other insecticide, miticide, nematicide, fungicide, plant growth regulator, herbicide or synergist. Examples of the active ingredient of said insecticide, miticide, nematicide, fungicide, plant growth regulator, herbicide and synergist are shown below.

Active Ingredients of Insecticide (1) Organic Phosphorus Compounds acephate, Aluminium phosphide, butathiofos, cadusafos, chlorethoxyfos, chlorfenvinphos, chlorpyrifos, chlorpyrifos-methyl, cyanophos: CYAP, diazinon, DCIP (dichlorodiisopropyl ether), dichlofenthion: ECP, dichlorvos: DDVP, dimethoate, dimethylvinphos, disulfoton, EPN, ethion, ethoprophos, etrimfos, fenthion: MPP, fenitrothion: MEP, fosthiazate, formothion, Hydrogen phosphide, isofenphos, isoxathion, malathion, mesulfenfos, methidathion: DMTP, monocrotophos, naled: BRP, oxydeprofos: ESP, parathion, phosalone, phosmet: PMP, pirimiphos-methyl, pyridafenthion, quinalphos, phenthoate: PAP, profenofos, propaphos, prothiofos, pyraclorfos, salithion, sulprofos, tebupirimfos, temephos, tetrachlorvinphos, terbufos, thiometon, trichlorphon: DEP, vamidothion, phorate, and cadusafos.

(2) Carbamate Compounds alanycarb, bendiocarb, benfuracarb, BPMC, carbaryl, carbofuran, carbosulfan, cloethocarb, ethiofencarb, fenobucarb, fenothiocarb, fenoxycarb, furathiocarb, isoprocarb: MIPC, metolcarb, methomyl, methiocarb, NAC, oxamyl, pirimicarb, propoxur: PHC, XMC, thiodicarb, xylylcarb, and aldicarb.

(3) Pyrethroid Compounds acrinathrin, allethrin, benfluthrin, beta-cyfluthrin, bifenthrin, cycloprothrin, cyfluthrin, cyhalothrin, cypermethrin, deltamethrin, esfenvalerate, ethofenprox, fenpropathrin, fenvalerate, flucythrinate, flufenoprox, flumethrin, fluvalinate, halfenprox, imiprothrin, permethrin, prallethrin, pyrethrins, resmethrin, sigma-cypermethrin, silafluofen, tefluthrin, tralomethrin, transfluthrin, tetramethrin, phenothrin, cyphenothrin, alpha-cypermethrin, zeta-cypermethrin, lambda-cyhalothrin, gamma-cyhalothrin, furamethrin, tau-fluvalinate, metofluthrin, profluthrin, dimefluthrin, 2,3,5,6-tetrafluoro-4-(methoxymethyl)benzyl (EZ)-(1RS, 3RS; 1RS, 3SR)-2,2-dimethyl-3-prop-1-enylcyclopropanecarboxylate, 2,3,5,6-tetrafluoro-4-methylbenzyl (EZ)-(1RS, 3RS; 1RS, 3SR)-2,2-dimethyl-3-prop-1-enylcyclopropanecarboxylate, and 2,3,5,6-tetrafluoro-4-(methoxymethyl)benzyl(1RS, 3RS; 1RS, 3SR)-2,2-dimethyl-3-(2-methyl-1-propenyl)cyclopropanecarbox ylate, 2,3,5,6-tetrafluoro-4-(methoxymethyl)benzyl(EZ)-(1RS, 3RS; 1RS, 3SR)-2,2-dimethyl-3-(2-cyano-1-propenyl)cyclopropanecarboxy late.

(4) Nereistoxin Compounds cartap, bensultap, thiocyclam, monosultap, and bisultap.

(5) Neonicotinoid Compounds imidacloprid, nitenpyram, acetamiprid, thiamethoxam, thiacloprid, dinotefuran, and clothianidin.

(6) Benzoyl Urea Compounds chlorfluazuron, bistrifluron, diafenthiuron, diflubenzuron, fluazuron, flucycloxuron, flufenoxuron, hexaflumuron, lufenuron, novaluron, noviflumuron, teflubenzuron, triflumuron, and triazuron.

(7) Phenylpyrazole-Based Compounds acetoprole, ethiprole, fipronil, vaniliprole, pyriprole, and pyrafluprole.

(8) Bt Toxins

Living spores derived from *Bacillus thuringiensis* and produced crystalline toxins and mixtures thereof.

(9) Hydrazine Compounds chromafenozide, halofenozide, methoxyfenozide, and tebufenozide.

(10) Organic Chlorine Compounds aldrin, dieldrin, dienochlor, endosulfan, and methoxychlor.

(11) Other Active Ingredients of Insecticide machine oil, nicotine-sulfate; avermectin-B, bromopropylate, buprofezin, chlorphenapyr, cyantraniliprole, cyromazine, D-D(1,3-Dichloropropene), emamectin-benzoate, fenazaquin, flupyrazofos, hydroprene, methoprene, indoxacarb, metoxadiazone, milbemycin-A, pymetrozine, pyridalyl, pyriproxyfen, spinosad, sulfluramid, tolfenpyrad, triazamate, flubendiamide, lepimectin, Arsenic acid, benclothiaz, Calcium cyanamide, Calcium polysulfide, chlordane, DDT, DSP, flufenerim, flonicamid, flurimfen, formetanate, metam-ammonium, metam-sodium, Methyl bromide, Potassium oleate, protrifenbute, spiromesifen, sulfoxaflor, Sulfur, metaflumizone, spirotetramat, pyrifluquinazone, spinetoram, chlorantraniliprole, tralopyril, cyantraniliprole, compounds represented by the following formula (K)

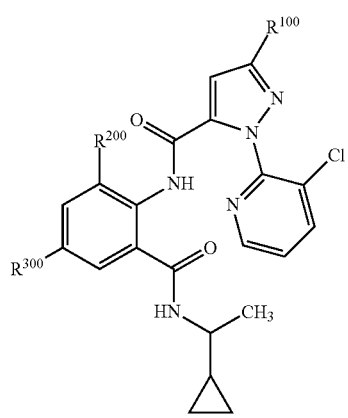

(K)

wherein $R^{100}$ represents chlorine, bromine or a trifluoromethyl group, $R^{200}$ represents chlorine, bromine or a methyl group, and $R^{300}$ represents chlorine, bromine or a cyano group, and compounds represented by the following formula (L)

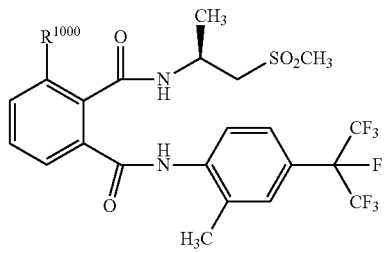

(L)

wherein $R^{1000}$ represents chlorine, bromine or iodine.

Active ingredients of Miticide acequinocyl, amitraz, benzoximate, bifenaate, bromopropylate, chinomethionat, chlorobenzilate, CPCBS (chlorfenson), clofentezine, cyflumetofen, kelthane (dicofol), etoxazole, fenbutatin oxide, fenothiocarb, fenpyroximate, fluacrypyrim, fluproxyfen, hexythiazox, propargite: BPPS, polynactins, pyridaben, Pyrimidifen, tebufenpyrad, tetradifon, spirodiclofen, spiromesifen, spirotetramat, amidoflumet, and cyenopyrafen.

Active ingredients of Nematicide

DCIP, fosthiazate, levamisol, methyisothiocyanate, morantel tartarate, and imicyafos.

Active ingredients of Fungicide azole fungicidal compounds such as propiconazole, prothioconazole, triadimenol, prochloraz, penconazole, tebuconazole, flusilazole, diniconazole, bromuconazole, epoxiconazole, difenoconazole, cyproconazole, metconazole, triflumizole, tetraconazole, myclobutanil, fenbuconazole, hexaconazole, fluquinconazole, triticonazole, bitertanol, imazalil, and flutriafol; Cyclic amine fungicidal compounds such as fenpropimorph, tridemorph, and fenpropidin; Benzimidazole fungicidal compounds such as carbendezim, benomyl, thiabendazole, and thiophanate-methyl; procymidone; cyprodinil; pyrimethanil; diethofencarb; thiuram; fluazinam; mancozeb; iprodione; vinclozolin; chlorothalonil; captan; mepanipyrim; fenpiclonil; fludioxonil; dichlofluanid; folpet; kresoxim-methyl; azoxystrobin; trifloxystrobin; fluoxastrobin; picoxystrobin; pyraclostrobin; dimoxystrobin; pyribencarb; spiroxamine; quinoxyfen; fenhexamid; famoxadone; fenamidone; zoxamide; ethaboxam; amisulbrom; iprovalicarb; benthiavalicarb; cyazofamid; mandipropamid; boscalid; penthiopyrad; metrafenone; fluopiran; bixafen; cyflufenamid; proquinazid; isotianil and tiadinil.

Active ingredients of Herbicide (1) Phenoxy Fatty Acid Herbicidal Compounds 2,4-PA, MCP, MCPB, phenothiol, mecoprop, fluroxypyr, triclopyr, clomeprop, and naproanilide.

(2) Benzoate Herbicidal Compounds 2,3,6-TBA, dicamba, clopyralid, picloram, aminopyralid, quinclorac, and quinmerac.

(3) Urea Herbicidal Compounds diuron, linuron, chlortoluron, isoproturon, fluometuron, isouron, tebuthiuron, methabenzthiazuron, cumyluron, daimuron, and methyl-daimuron.

(4) Triazine Herbicidal Compounds atrazine, ametoryn, cyanazine, simazine, propazine, simetryn, dimethametryn, prometryn, metribuzin, triaziflam, and indaziflam.

(5) Bipyridinium Herbicidal Compounds
paraquat, and diquat.
(6) Hydroxybenzonitrile Herbicidal Compounds
bromoxynil, and ioxynil.
(7) Dinitroaniline Herbicidal Compounds
Pendimethalin, Prodiamine, and Trifluralin.
(8) Organophosphorus Herbicidal Compounds
amiprofos-methyl, butamifos, bensulide, piperophos, anilofos, glyphosate, glufosinate, glufosinate-P, and bialaphos.
(9) Carbamate Herbicidal Compounds
di-allate, tri-allate, EPTC, butylate, benthiocarb, esprocarb, molinate, dimepiperate, swep, chlorpropham, phenmedipham, phenisopham, pyributicarb, and asulam.
(10) Acid Amide Herbicidal Compounds
propanil, propyzamide, bromobutide, and etobenzanid.
(11) Chloroacetanilide Herbicidal Compounds
acetochlor, alachlor, butachlor, dimethenamid, propachlor, metazachlor, metolachlor, pretilachlor, thenylchlor, and pethoxamid.
(12) Diphenyl Ether Herbicidal Compounds
acifluorfen-sodium, bifenox, oxyfluorfen, lactofen, fomesafen, chlomethoxynil, and aclonifen.
(13) Cyclic Imide Herbicidal Compounds
oxadiazon, cinidon-ethyl, carfentrazone-ethyl, surfentrazone, flumiclorac-pentyl, flumioxazin, pyraflufen-ethyl, oxadiargyl, pentoxazone, fluthiacet-methyl, butafenacil, benzfendizone, bencarbazone, and saflufenacil.
(14) Pyrazole Herbicidal Compounds
benzofenap, pyrazolate, pyrazoxyfen, topramezone, and pyrasulfotole.
(15) Triketone Herbicidal Compounds
isoxaflutole, benzobicyclon, sulcotrione, mesotrione, tembotrione, and tefuryltrione.
(16) Aryloxyphenoxypropionate Herbicidal Compounds
clodinafop-propargyl, cyhalofop-butyl, diclofop-methyl, fenoxaprop-ethyl, fluazifop-butyl, haloxyfop-methyl, and quizalofop-ethyl, metamifop.
(17) Trione Oxime Herbicidal Compounds
alloxydim-sodium, sethoxydim, butroxydim, clethodim, cloproxydim, cycloxydim, tepraloxydim, tralkoxydim, and profoxydim.
(18) Sulfonyl Urea Herbicidal Compounds
chlorsulfuron, sulfometuron-methyl, metsulfuron-methyl, chlorimuron-ethyl, tribenuron-methyl, triasulfuron, metsulfuron-methyl, thifensulfuron-methyl, pyrazosulfuron-ethyl, primisulfuron-methyl, nicosulfuron, amidosulfuron, cinosulfuron, imazosulfuron, rimsulfuron, halosulfuron-methyl, prosulfuron, ethametsulfuron-methyl, triflusulfuron-methyl, flazasulfuron, cyclosulfamuron, flupyrsulfuron, sulfosulfuron, azimsulfuron, ethoxysulfuron, oxasulfuron, iodosulfuron-methyl-sodium, foramsulfuron, mesosulfuron-methyl, trifloxysulfuron, tritosulfuron, orthosulfamuron, flucetosulfuron, and propyrisulfuron.
(19) Imidazolinone Herbicidal Compounds
imazamethabenz-methyl, imazamethapyr, imazamox, imazapyr, imazaquin, and imazethapyr.
(20) Sulfonamide Herbicidal Compounds
flumetsulam, metosulam, diclosulam, florasulam, cloransulam-methyl, penoxsulam, and pyroxsulam.
(21) Pyrimidinyloxybenzoate Herbicidal Compounds
pyrithiobac-sodium, bispyribac-sodium, pyriminobac-methyl, pyribenzoxim, pyriftalid, and pyrimisulfan.
(22) Other Herbicidal Compounds
bentazon, bromacil, terbacil, chlorthiamid, isoxaben, dinoseb, amitrole, cinmethylin, tridiphane, dalapon, diflufenzopyr-sodium, dithiopyr, thiazopyr, flucarbazone-sodium, propoxycarbazone-sodium, mefenacet, flufenacet, fentrazamide, cafenstrole, indanofan, oxaziclomefone, benfuresate, ACN, pyridate, chloridazon, norflurazon, flurtamone, diflufenican, picolinafen, beflubutamid, clomazone, amicarbazone, pinoxaden, pyraclonil, pyroxasulfone, thiencarbazone-methyl, aminocyclopyrachlor, ipfencarbazone, and methiozolin.

Active ingredients of Plant Growth Regulator
hymexazol, paclobutrazol, uniconazole-P, inabenfide, prohexadione-calcium, aviglycine, naphthalene acetamide, abscisic acid, indolebutyric acid, ethychlozate, ethephon, cloxyfonac, chlormequat, dichlorprop, gibberellins, prohydrojasmon, benzyladenine, forchlorfenuron, maleic hydrazide, calcium peroxide, mepiquat-chloride and 4-chlorophenoxyacetic acid.

Active ingredients of Synergist
piperonyl butoxide, sesamex, sulfoxide, N-(2-ethylhexyl)-8,9,10-trinorborn-5-ene-2,3-dicarboximide (MGK 264), N-declyimidazole), WARF-antiresistant, TBPT, TPP, IBP, PSCP, CH$_3$I, t-phenylbutenone, diethylmaleate, DMC, FDMC, ETP, and ETN.

EXAMPLES

Hereinbelow, the present invention will be further described in detail byproduction examples, reference examples, formulation examples, test examples, and the like. However, the present invention is not limited to these examples.

First, the production examples for the production of the compounds of the present invention are shown below.

Production Example 1 (1)

A mixture of 0.96 g of N$^2$-methyl-5-trifluoromethylpyridine-2,3-diamine, 0.95 g of 2-chloronicotinic acid, 0.85 g of EDCI hydrochloride and 10 ml of pyridine was heated and stirred at 120° C. for 3 hours. Water was poured to the reaction mixture cooled to room temperature, and the mixture was extracted with ethyl acetate. The organic layer was dried over anhydrous magnesium sulfate, and then concentrated under reduced pressure. The resulting residue was applied to a silica gel column chromatography to obtain 1.02 g of 2-(2-chloropyridin-3-yl)-3-methyl-6-trifluoromethyl-3H-imidazo[4,5-b]pyridine. 2-(2-Chloropyridin-3-yl)-3-methyl-6-trifluoromethyl-3H-imidazo[4,5-b]pyridine

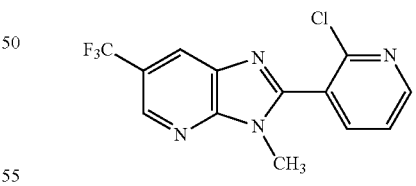

$^1$H-NMR (CDCl$_3$) δ: 8.77-8.76 (1H, m), 8.66 (1H, dd), 8.36-8.35 (1H, m), 7.97 (1H, dd), 7.50 (1H, dd), 3.86 (3H, s).

Production Example 1 (2)

A DMF solution of 0.86 g of 2-(2-chloropyridin-3-yl)-3-methyl-6-trifluoromethyl-3H-imidazo[4,5-b]pyridine was added dropwise to a mixture of 0.46 g of ethyl mercaptan sodium salt (80%) and 9 ml of DMF under ice cooling, then the mixture was heated to room temperature, and stirred at room temperature for 1 hour. A saturated aqueous sodium bicarbonate solution was poured to the reaction mixture, and the mixture was extracted with ethyl acetate. The combined organic layer was dried over anhydrous magnesium sulfate, and then concentrated under reduced pressure. The resulting residue was applied to a silica gel column chromatography to obtain 0.71 g of 2-(2-ethanesulfanylpyridin-3-yl)-3-methyl-6-trifluoromethyl-3H-imidazo[4,5-b]pyridine (hereinafter, referred to as Compound of Present Invention 1).

Compound of Present Invention 1

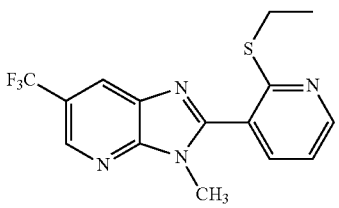 [SMILES: CCSc1ncccc1-c1nc2cc(C(F)(F)F)cnc2n1C]

$^1$H-NMR (CDCl$_3$) δ: 8.74-8.72 (1H, m), 8.64 (1H, dd), 8.35-8.33 (1H, m), 7.67 (1H, dd), 7.19 (1H, dd), 3.83 (3H, s), 3.24 (2H, q), 1.34 (3H, t).

Production Examples 2 and 3

0.57 g of 3-chloroperoxybenzoic acid (purity of 69% or more) was added to a mixture of 0.55 g of 2-(2-ethanesulfanylpyridin-3-yl)-3-methyl-6-trifluoromethyl-3H-imidazo[4,5-b]pyridine and 8 ml of chloroform under ice cooling, then the mixture was heated to room temperature, and stirred for 30 minutes. A saturated aqueous sodium bicarbonate solution and a saturated aqueous sodium thiosulfate solution were poured to the reaction mixture, and the mixture was extracted with chloroform. The combined organic layer was dried over anhydrous magnesium sulfate, and then concentrated under reduced pressure. The resulting residue was applied to a silica gel column chromatography to obtain 0.22 g of 2-(2-ethanesulfinylpyridin-3-yl)-3-methyl-6-trifluoromethyl-3H-imidazo[4,5-b]pyridine (hereinafter, referred to as Compound of Present Invention 2) and 0.32 g of 2-(2-ethanesulfonylpyridin-3-yl)-3-methyl-6-trifluoromethyl-3H-imidazo[4,5-b]pyridine (hereinafter, referred to as Compound of Present Invention 3).

Compound of Present Invention 2

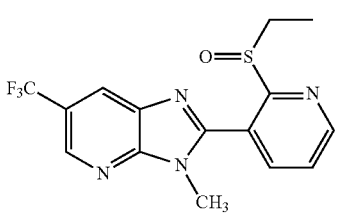 [SMILES: CCS(=O)c1ncccc1-c1nc2cc(C(F)(F)F)cnc2n1C]

$^1$H-NMR (CDCl$_3$) δ: 8.99 (1H, dd), 8.77-8.74 (1H, m), 8.33-8.32 (1H, m), 7.97 (1H, dd), 7.64 (1H, dd), 3.88 (3H, s), 3.41-3.30 (1H, m), 3.29-3.19 (1H, m), 1.34 (3H, t).

Compound of Present Invention 3

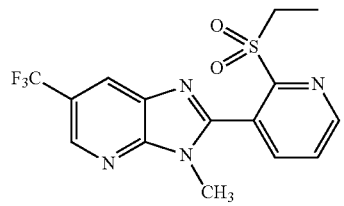 [SMILES: CCS(=O)(=O)c1ncccc1-c1nc2cc(C(F)(F)F)cnc2n1C]

$^1$H-NMR (CDCl$_3$) δ: 8.99 (1H, dd), 8.76-8.74 (1H, m), 8.32-8.30 (1H, m), 8.03 (1H, dd), 7.78 (1H, dd), 3.81 (3H, s), 3.51 (2H, q), 1.31 (3H, t).

Production Example 4 (1)

A mixture of 0.42 g of N$^2$-methyl-5-trifluoromethylpyridine-2,3-diamine, 0.50 g of 2-chloro-6-trifluoromethylpyridine-3-carboxylic acid, 0.64 g of EDCI hydrochloride, 30 mg of HOBt and 2.5 ml of pyridine was stirred at room temperature for 7 hours. Water was poured to the reaction mixture, and the precipitated solid was filtered. The resulting solid was washed with water and n-hexane, and then dried to obtain 0.81 g of 2-chloro-6-trifluoromethylpyridine-3-carboxylic acid (2-methylamino-5-trifluoromethylpyridin-3-yl)-amide. 2-Chloro-6-trifluoromethylpyridine-3-carboxylic acid (2-methylamino-5-trifluoromethylpyridin-3-yl)-amide

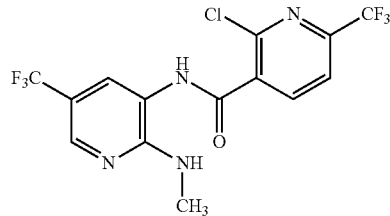 [SMILES: CNc1ncc(C(F)(F)F)cc1NC(=O)c1ccc(C(F)(F)F)nc1Cl]

$^1$H-NMR (CDCl$_3$) δ: 8.45-8.39 (2H, m), 8.00 (1H, brs), 7.82 (1H, d), 7.76 (1H, s), 5.07 (1H, brs), 3.09 (3H, d).

Production Example 4 (2)

256 mg of ethyl mercaptan sodium salt (80%) was added to a mixture of 810 mg of 2-chloro-6-trifluoromethylpyridine-3-carboxylic acid (2-methylamino-5-trifluoromethylpyridin-3-yl)-amide, 4 ml of DMF and 1 ml of THF under ice cooling, then the mixture was heated to room temperature, and stirred for 3 hours. Water was poured to the reaction mixture, and the precipitated solid was filtered. The resulting solid was washed with water and n-hexane, and then dried to obtain 705 mg of 2-ethylsulfanyl-6-trifluoromethylpyridine-3-carboxylic acid (2-methylamino-5-trifluoromethylpyridin-3-yl)-amide. 2-Ethylsulfanyl-6-trifluoromethylpyridine-3-carboxylic acid (2-methylamino-5-trifluoromethylpyridin-3-yl)-amide

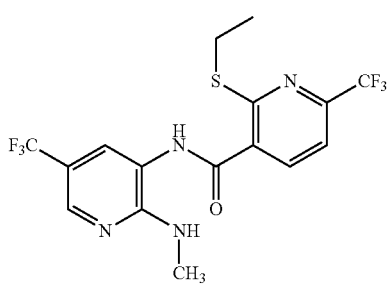 [SMILES: CCSc1nc(C(F)(F)F)ccc1C(=O)Nc1cc(C(F)(F)F)cnc1NC]

¹H-NMR (CDCl₃) δ: 8.40 (1H, s), 8.18 (1H, d), 7.84 (1H, brs), 7.76 (1H, s), 7.52 (1H, d), 5.23 (1H, brs), 3.37 (2H, q), 3.09 (3H, d), 1.45 (3H, t).

Production Example 4 (3)

A mixture of 703 mg of 2-ethylsulfanyl-6-trifluoromethylpyridine-3-carboxylic acid (2-methylamino-5-trifluoromethylpyridin-3-yl)-amide, 630 mg of p-toluenesolufonic acid-hydrate, 2.5 ml of DMF and 0.5 ml of toluene was heated and stirred at 150° C. for 2 hours. A saturated aqueous sodium bicarbonate solution was poured to the cooled reaction mixture, and the precipitated solid was filtered. The resulting solid was washed with water and n-hexane, and then dried to obtain 616 mg of 2-(2-ethylsulfanyl-6-trifluoromethylpyridin-3-yl)-3-methyl-6-trifluoromethyl-3H-imidazo[4,5-b]pyridine (hereinafter, referred to as Compound of Present Invention 4).

Compound of Present Invention 4

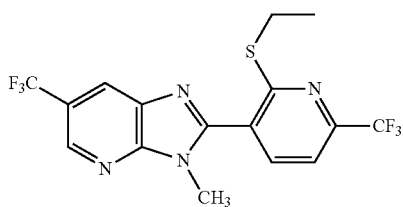

¹H-NMR (CDCl₃) δ: 8.76 (1H, d), 8.37 (1H, d), 7.83 (1H, d), 7.54 (1H, d), 3.85 (3H, s), 3.26 (2H, q), 1.37 (3H, t).

Production Example 5

542 mg of 3-chloroperoxybenzoic acid (purity of 65% or more) was added to a mixture of 416 mg of 2-(2-ethylsulfanyl-6-trifluoromethylpyridin-3-yl)-3-methyl-6-trifluoromethyl-3H-imidazo[4,5-b]pyridine and 5 ml of chloroform, and the mixture was stirred at room temperature for 1 hour, then allowed to stand at room temperature overnight. A 10% aqueous sodium thiosulfate solution was poured to the reaction mixture, and the mixture was extracted with chloroform. The organic layer was washed with a saturated aqueous sodium bicarbonate solution and dried over anhydrous magnesium sulfate, then concentrated under reduced pressure to obtain 452 mg of 2-(2-ethylsulfonyl-6-trifluoromethylpyridin-3-yl)-3-methyl-6-trifluoromethyl-3H-imidazo[4,5-b]pyridine (hereinafter, referred to as Compound of Present Invention 5).

Compound of Present Invention 5

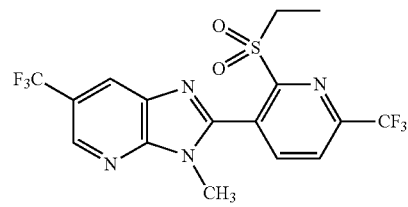

¹H-NMR (CDCl₃) δ: 8.77 (1H, d), 8.35 (1H, d), 8.26 (1H, d), 8.12 (1H, d), 3.84 (3H, s), 3.59 (2H, q), 1.35 (3H, t).

Production Example 6 (1)

A mixture of 2.59 g of 3-ethylsulfanylpyridazine-2-carboxylic acid ethyl ester, 5 ml of a 5 M aqueous sodium hydroxide solution, and 8 ml of methanol was stirred at 85° C. for 4 hours. Concentrated hydrochloric acid was poured to the cooled reaction mixture, and the precipitated solid was filtered. The resulting solid was washed with water and dried to obtain 612 mg of 3-ethylsulfanylpyridazine-2-carboxylic acid. 3-Ethylsulfanylpyridazine-2-carboxylic acid

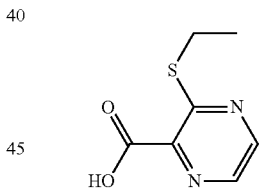

¹H-NMR (DMSO-D₆) δ: 8.38 (1H, d), 8.16 (1H, d), 2.98 (2H, q), 1.23 (3H, t).

Production Example 6 (2)

A mixture of 618 mg of N²-methyl-5-trifluoromethylpyridine-2,3-diamine, 612 mg of 3-ethylsulfanylpyridazine-2-carboxylic acid, 958 mg of EDCI hydrochloride, 45 mg of HOBt and 5 ml of pyridine was stirred at 60° C. for 4 hours. Water was poured to the cooled reaction mixture, and the mixture was extracted with ethyl acetate. The organic layer was washed with water, and then dried over anhydrous magnesium sulfate and concentrated under reduced pressure to obtain 1.15 g of 3-ethylsulfanylpyrazine-2-carboxylic acid (2-methylamino-5-trifluoromethylpyridin-3-yl)-amide.
3-Ethylsulfanylpyrazine-2-carboxylic acid (2-methylamino-5-trifluoromethylpyridin-3-yl)-amide

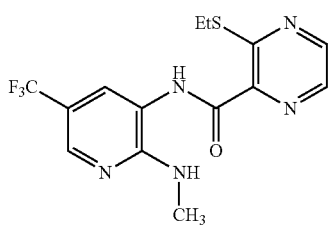

¹H-NMR (CDCl₃) δ: 9.35 (1H, brs), 8.63 (1H, d), 8.35 (1H, d), 8.24 (1H, d), 7.90 (1H, d), 5.01 (1H, brs), 3.19 (2H, q), 3.08 (3H, d), 1.39 (3H, t).

Production Example 6 (3)

A mixture of 1.15 g of 3-ethylsulfanylpyrazine-2-carboxylic acid (2-methylamino-5-trifluoromethylpyridin-3-yl)-amide, 1.23 g of p-toluenesolufonic acid-hydrate and 5 ml of NMP was heated and stirred at 150° C. for 2 hours. A saturated aqueous sodium bicarbonate solution was poured to the cooled reaction mixture, and the mixture was extracted with ethyl acetate. The organic layer was washed with water, then dried over anhydrous magnesium sulfate and concentrated under reduced pressure. The resulting residue was applied to a silica gel column chromatography to obtain 631 mg of 2-(3-ethylsulfanylpyrazin-2-yl)-3-methyl-6-trifluoromethyl-3H-imidazo[4,5-b]pyridine (hereinafter, referred to as Compound of Present Invention 6).

Compound of Present Invention 6

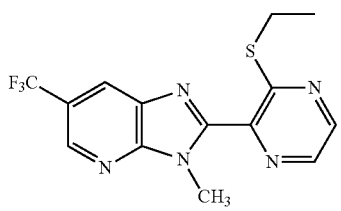

¹H-NMR (CDCl₃) δ: 8.75 (1H, d), 8.52 (1H, d), 8.44 (1H, d), 8.39 (1H, d), 4.14 (3H, s), 3.21 (2H, q), 1.39 (3H, t).

Production Examples 7 and 8

467 mg of 3-chloroperoxybenzoic acid (purity of 65% or more) was added to a mixture of 425 mg of 2-(3-ethylsulfanylpyrazin-2-yl)-3-methyl-6-trifluoromethyl-3H-imidazo[4,5-b]pyridine and 8 ml of chloroform under ice cooling. The mixture was heated to room temperature and stirred at room temperature for 1 hour. A saturated aqueous sodium bicarbonate solution was poured to the reaction mixture, and the mixture was extracted with chloroform. The organic layer was washed with water and dried over anhydrous magnesium sulfate, and then concentrated under reduced pressure to obtain 205 mg of 2-(3-ethylsulfinylpyrazin-2-yl)-3-methyl-6-trifluoromethyl-3H-imidazo[4,5-b]pyridine (hereinafter, referred to as Compound of Present Invention 7) and 230 mg of 2-(3-ethylsulfonylpyrazin-2-yl)-3-methyl-6-trifluoromethyl-3H-imidazo[4,5-b]pyridine (hereinafter, referred to as Compound of Present Invention 8).

Compound of Present Invention 7

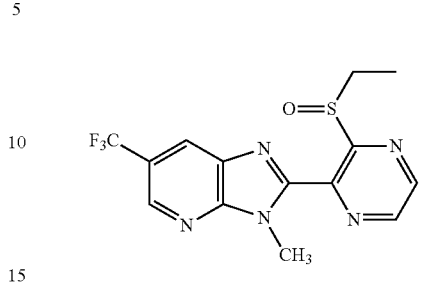

¹H-NMR (DMSO-D₆) δ: 9.07 (1H, d), 9.03 (1H, d), 8.92 (1H, d), 8.75 (1H, d), 4.16 (3H, s), 3.57-3.45 (1H, m), 3.17-3.06 (1H, m), 1.37 (3H, q).

Compound of Present Invention 8

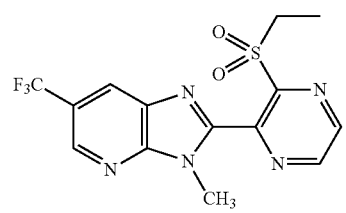

¹H-NMR (CDCl₃) δ: 9.00 (1H, d), 8.95 (1H, d), 8.79 (1H, d), 8.36 (1H, d), 3.97 (3H, s), 3.80 (2H, q), 1.45 (3H, t).

Production Example 9 (1)

A mixture of 524 mg of N²-methyl-5-trifluoromethylpyridine-2,3-diamine, 500 mg of 4-chloronicotinic acid, 790 mg of EDCI hydrochloride, 37 mg of HOBt and 4 ml of pyridine was stirred at room temperature for 4 hours. Water was poured to the reaction mixture, and the precipitated solid was filtered. The resulting solid was washed with water and n-hexane and then dried to obtain 828 mg of 4-chloropyridine-3-carboxylic acid (2-methylamino-5-trifluoromethylpyridin-3-yl)-amide. 4-chloropyridine-3-carboxylic acid (2-methylamino-5-trifluoromethylpyridin-3-yl)-amide

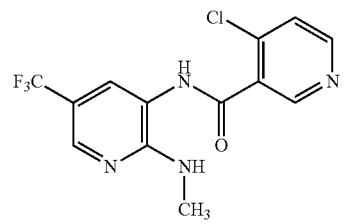 [SMILES: CNc1ncc(C(F)(F)F)cc1NC(=O)c1cnccc1Cl]

¹H-NMR (CDCl₃) δ: 9.02 (1H, brs), 8.65 (1H, s), 8.41 (1H, s), 7.79-7.73 (2H, m), 7.46 (1H, d), 5.13 (1H, brs), 3.08 (3H, d).

Production Example 9 (2)

289 mg of ethyl mercaptan sodium salt (80%) was added to a mixture of 828 mg of 4-chloropyridine-3-carboxylic acid (2-methylamino-5-trifluoromethylpyridin-3-yl)-amide and 4 ml of DMF was added under ice cooling, then the mixture was heated to room temperature, and stirred for 3 hours. Water was poured to the reaction mixture, and the precipitated solid was filtered. The resulting solid was washed with water and n-hexane and then dried to obtain 700 mg of 4-ethylsulfanylpyridine-3-carboxylic acid (2-methylamino-5-trifluoromethylpyridin-3-yl)-amide. 4-Ethylsulfanylpyridine-3-carboxylic acid (2-methylamino-5-trifluoromethylpyridin-3-yl)-amide

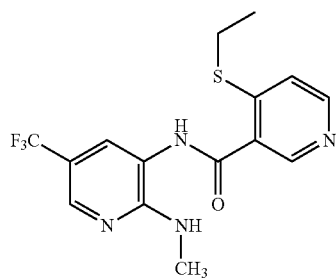 [SMILES: CCSc1ccncc1C(=O)Nc1cc(C(F)(F)F)cnc1NC]

$^1$H-NMR (CDCl$_3$) δ: 8.77 (1H, s), 8.50 (1H, d), 8.38 (1H, s), 7.83 (1H, brs), 7.78 (1H, s), 7.23 (1H, d), 5.33 (1H, brs), 3.11-3.02 (5H, m), 1.44 (3H, t).

Production Example 9 (3)

A mixture of 700 mg of 4-ethylsulfanylpyridine-3-carboxylic acid (2-methylamino-5-trifluoromethylpyridin-3-yl)-amide, 704 mg of p-toluenesolufonic acid-hydrate and 3.5 ml of NMP was heated and stirred at 150° C. for 2 hours. A saturated aqueous sodium bicarbonate solution was poured to the cooled reaction mixture, and the precipitated solid was filtered. The resulting solid was washed with water and n-hexane and then dried to obtain 650 mg of 2-(4-ethylsulfanylpyridin-3-yl)-3-methyl-6-trifluoromethyl-3H-imidazo[4,5-b]pyridine (hereinafter, referred to as Compound of Present Invention 9).

Compound of Present Invention 9

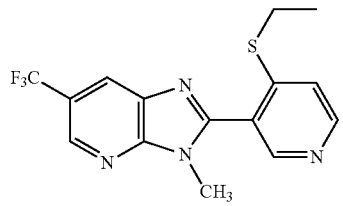 [SMILES: CCSc1ccncc1-c1nc2cc(C(F)(F)F)cnc2n1C]

$^1$H-NMR (CDCl$_3$) δ: 8.74 (1H, d), 8.62 (1H, d), 8.54 (1H, s), 8.36 (1H, d), 7.30 (1H, d), 3.83 (3H, s), 3.03 (2H, q), 1.37 (3H, t).

Production Examples 10 and 11

448 mg of 3-chloroperoxybenzoic acid (purity of 65% or more) was added to a mixture of 420 mg of 2-(4-ethylsulfanylpyridin-3-yl)-3-methyl-6-trifluoromethyl-3H-imidazo[4,5-b]pyridine and 9 ml of chloroform under ice cooling. The mixture was stirred at 0° C. for 1 hour, then stirred at room temperature for 30 minutes. A saturated aqueous sodium bicarbonate solution was poured to the reaction mixture, and the mixture was extracted with chloroform. The organic layer was washed with water and then dried over anhydrous magnesium sulfate and concentrated under reduced pressure. The resulting residue was applied to a silica gel column chromatography to obtain 215 mg of 2-(4-ethylsulfinylpyridin-3-yl)-3-methyl-6-trifluoromethyl-3H-imidazo[4,5-b]pyridine (hereinafter, referred to as Compound of Present Invention 10) and 211 mg of 2-(4-ethylsulfonylpyridin-3-yl)-3-methyl-6-trifluoromethyl-3H-imidazo[4,5-b]pyridine (hereinafter, referred to as Compound of Present Invention 11).

Compound of Present Invention 10

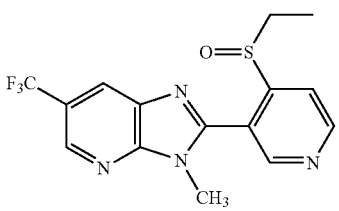 [SMILES: CCS(=O)c1ccncc1-c1nc2cc(C(F)(F)F)cnc2n1C]

$^1$H-NMR (CDCl$_3$) δ: 9.04 (1H, d), 8.93 (1H, d), 8.78 (1H, d), 8.34 (1H, d), 8.22 (1H, dd), 4.00 (3H, s), 3.57-3.48 (1H, m), 3.12-3.02 (1H, m), 1.37 (3H, t).

Compound of Present Invention 11

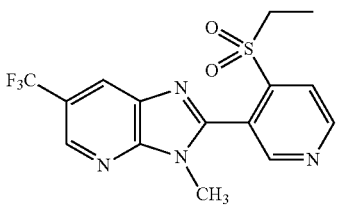 [SMILES: CCS(=O)(=O)c1ccncc1-c1nc2cc(C(F)(F)F)cnc2n1C]

$^1$H-NMR (CDCl$_3$) δ: 9.14 (1H, d), 8.89 (1H, d), 8.78 (1H, d), 8.31 (1H, d), 8.09 (1H, dd), 3.77 (3H, s), 3.47 (2H, q), 1.29 (3H, t).

Production Example 12 (1)

7.1 ml of n-butyl lithium (1.6 M hexane solution) was added dropwise to a mixture of 1.62 g of 2,2,6,6-tetrahydropiperidine and 15 ml of THF at −78° C., and the mixture was heated to 0° C., then stirred at 0° C. for 10 minutes. 7 ml of a THF solution of 1.0 g of 6-trifluoromethylnicotinic acid was added to the reaction mixture at −78° C., and the mixture was stirred at −78° C. for 1 hour. Next, 1.42 ml of diethyl disulfide was added to the reaction mixture at −78° C., and heated to room temperature, then stirred at room temperature for 30 minutes. 10 ml of 1 N hydrochloric acid was poured to the reaction mixture, and the reaction mixture was separated into the organic layer and the aqueous layer. 1 N hydrochloric acid was added to the aqueous layer, and the precipitated solid was filtered. The resulting solid was washed with 1 N hydrochloric acid and n-hexane to obtain 0.52 g of 4-ethylsulfanyl-6-trifluoromethylnicotinic acid. The separated organic layer was allowed to stand overnight, and the precipitated solid was filtered, then washed with n-hexane to further obtain 0.68 g of 4-ethylsulfanyl-6-trifluoromethylnicotinic acid. 4-Ethylsulfanyl-6-trifluoromethylnicotinic acid

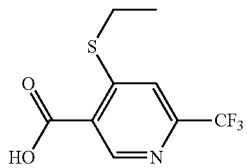

$^1$H-NMR (CDCl$_3$) δ: 9.24 (1H, s), 7.57 (1H, s), 3.05 (2H, q), 1.47 (3H, t).

Production Example 12 (2)

A mixture of 428 mg of N$^2$-methyl-5-trifluoromethylpyridine-2,3-diamine, 562 mg of 4-ethylsulfanyl-6-trifluoromethylnicotinic acid, 645 mg of EDCI hydrochloride, 30 mg of HOBt and 2.5 ml of pyridine was stirred at room temperature for 5 hours, then allowed to stand at room temperature overnight. Water was poured to the reaction mixture, and the precipitated solid was filtered. The resulting solid was washed with water and n-hexane and then dried to obtain 786 mg of 4-ethylsulfanyl-6-trifluoromethylpyridine-3-carboxylic acid (2-methylamino-5-trifluoromethylpyridin-3-yl)-amide. 4-Ethylsulfanyl-6-trifluoromethylpyridine-3-carboxylic acid (2-methylamino-5-trifluoromethylpyridin-3-yl)-amide

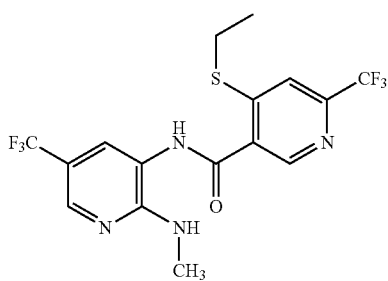 [SMILES: CCSc1cc(C(F)(F)F)ncc1C(=O)Nc1cc(C(F)(F)F)cnc1NC]

$^1$H-NMR (CDCl$_3$) δ: 8.84 (1H, s), 8.40 (1H, s), 7.75 (1H, s), 7.63 (1H, brs), 7.56 (1H, s), 5.15 (1H, brs), 3.14 (2H, q), 3.08 (3H, d), 1.48 (3H, t).

Production Example 12 (3)

A mixture of 786 mg of 4-ethylsulfanyl-6-trifluoromethylpyridine-3-carboxylic acid (2-methylamino-5-trifluoromethylpyridin-3-yl)-amide, 704 mg of p-toluenesolufonic acid-hydrate, 2.5 ml of DMF and 0.5 ml of toluene was heated and stirred at 150° C. for 2 hours. A saturated aqueous sodium bicarbonate solution was poured to the cooled reaction mixture, and the precipitated solid was filtered. The resulting solid was washed with water and n-hexane and then dried to obtain 716 mg of 2-(4-ethylsulfanyl-6-trifluoromethylpyridin-3-yl)-3-methyl-6-trifluoromethyl-3H-imidazo[4,5-b]pyridine (hereinafter, referred to as Compound of Present Invention 12).

Compound of Present Invention 12

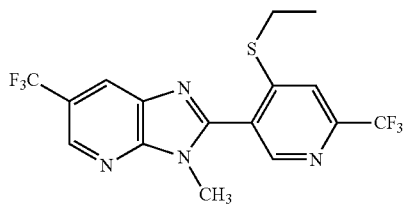 [SMILES: CCSc1cc(C(F)(F)F)ncc1-c1nc2cc(C(F)(F)F)cnc2n1C]

$^1$H-NMR (CDCl$_3$) δ: 8.77 (1H, d), 8.63 (1H, s), 8.39 (1H, d), 7.62 (1H, s), 3.85 (3H, s), 3.09 (2H, q), 1.40 (3H, t).

Production Example 13

423 mg of 3-chloroperoxybenzoic acid (purity of 65% or more) was added to a mixture of 340 mg of 2-(4-ethylsulfanyl-6-trifluoromethylpyridin-3-yl)-3-methyl-6-trifluoromethyl-3H-imidazo[4,5-b]pyridine and 6 ml of chloroform, then the mixture was stirred at room temperature for 4 hours. A 10% aqueous sodium thiosulfate solution was poured to the reaction mixture, and the mixture was extracted with chloroform. The organic layer was washed with a saturated aqueous sodium bicarbonate solution and dried over anhydrous magnesium sulfate, and then concentrated under reduced pressure to obtain 367 mg of 2-(4-ethylsulfanyl-6-trifluoromethylpyridin-3-yl)-3-methyl-6-trifluoromethyl-3H-imidazo[4,5-b]pyridine (hereinafter, referred to as Compound of Present Invention 13).

Compound of Present Invention 13

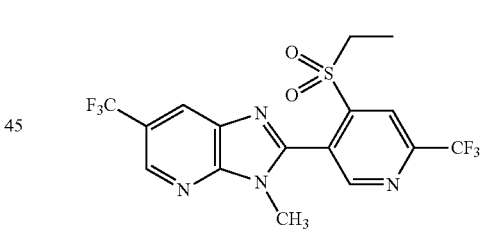

$^1$H-NMR (CDCl$_3$) δ: 9.00 (1H, s), 8.81 (1H, d), 8.45 (1H, s), 8.34 (1H, d), 3.80 (3H, s), 3.55 (2H, q), 1.33 (3H, t).

Production Example 14 (1)

2.77 g of ethyl mercaptan sodium salt (80%) was added to a mixture of 4.69 g of 4-chloropyrimidine-5-carboxylic acid ethyl ester, 8 ml of DMF and 7 ml of THF was added under ice cooling, then the mixture was heated to room temperature, and stirred for 1 hour. Water was poured to the reaction mixture, and the mixture was extracted with ethyl acetate. The organic layer was washed with water, then dried over anhydrous magnesium sulfate and concentrated under reduced pressure. The resulting residue was applied to a silica gel column chromatography to obtain 2.41 g of 4-ethylsulfanylpyrimidine-5-carboxylic acid ethyl ester. 4-Ethylsulfanylpyrimidine-5-carboxylic acid ethyl ester

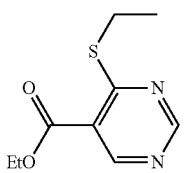

¹H-NMR (CDCl₃) δ: 9.01 (1H, s), 8.99 (1H, s), 4.42 (2H, q), 3.21 (2H, q), 1.45-1.34 (6H, m).

Production Example 14 (2)

A mixture of 2.40 g of 4-ethylsulfanylpyrimidine-5-carboxylic acid ethyl ester, 12 ml of a 2 M aqueous potassium hydroxide solution and 8 ml of THF was stirred at room temperature for 1 hour. Concentrated hydrochloric acid was poured to the reaction mixture and neutralized, then the mixture was concentrated under reduced pressure, and THF was distilled. Concentrated hydrochloric acid was further added to the reaction mixture to adjust pH of the reaction mixture at 5, and the precipitated crystal was filtered. The resulting solid was washed with water and n-hexane and dried to obtain 1.89 g of 4-ethylsulfanylpyrimidine-5-carboxylic acid.

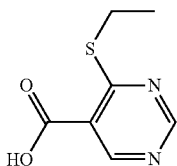

¹H-NMR (DMSO-D₆) δ: 9.06 (1H, s), 8.93 (1H, s), 3.12 (2H, q), 1.27 (3H, t).

Production Example 14 (3)

A mixture of 1.04 g of N²-methyl-5-trifluoromethylpyridine-2,3-diamine, 1.00 g of 4-ethylsulfanylpyrimidine-5-carboxylic acid, 1.57 g of EDCI hydrochloride, 73 mg of HOBt and 5 ml of pyridine was stirred at 60° C. for 4 hours. Water was poured to the cooled reaction mixture, and the mixture was extracted with ethyl acetate. The organic layer was washed with water, then dried over anhydrous magnesium sulfate and concentrated under reduced pressure to obtain 1.94 g of 4-ethylsulfanylpyrimidine-5-carboxylic acid (2-methylamino-5-trifluoromethylpyridin-3-yl)-amide.
4-Ethylsulfanylpyrimidine-5-carboxylic acid (2-methylamino-5-trifluoromethylpyridin-3-yl)-amide

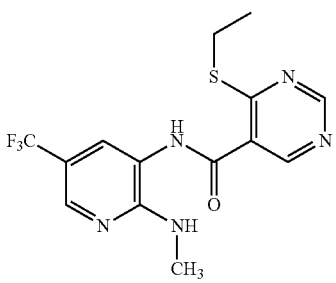 [SMILES: CCSc1ncncc1C(=O)Nc1cc(C(F)(F)F)cnc1NC]

¹H-NMR (CDCl₃) δ: 9.03 (1H, s), 8.85 (1H, s), 8.40 (1H, s), 7.73 (1H, s), 7.71 (1H, brs), 5.13 (1H, brs), 3.36 (2H, q), 3.09 (3H, d), 1.45 (3H, t).

Production Example 14 (4)

A mixture of 1.94 g of 4-ethylsulfanylpyrimidine-5-carboxylic acid (2-methylamino-5-trifluoromethylpyridin-3-yl)-amide, 2.07 g of p-toluenesolufonic acid-hydrate and 5 ml of NMP was heated and stirred at 150° C. for 2 hours. A saturated aqueous sodium bicarbonate solution was poured to the cooled reaction mixture, and the mixture was extracted with ethyl acetate. The organic layer was washed with water, then dried over anhydrous magnesium sulfate and concentrated under reduced pressure. The resulting residue was applied to a silica gel column chromatography to obtain 130 mg of 2-(4-ethylsulfanylpyrimidin-5-yl)-3-methyl-6-trifluoromethyl-3H-imidazo[4,5-b]pyridine (hereinafter, referred to as Compound of Present Invention 14).

Compound of Present Invention 14

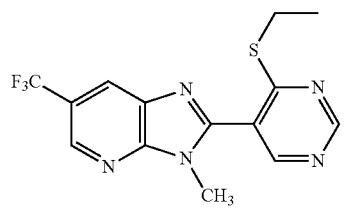

¹H-NMR (CDCl₃) δ: 9.10 (1H, s), 8.76 (1H, d), 8.55 (1H, s), 8.38 (1H, d), 3.87 (3H, s), 3.28 (2H, q), 1.38 (3H, t).

Production Example 15

189 mg of 3-chloroperoxybenzoic acid (purity of 65% or more) was added to a mixture of 130 mg of 2-(4-ethylsulfanylpyrimidin-5-yl)-3-methyl-6-trifluoromethyl-3H-imidazo[4,5-b]pyridine and 4 ml of chloroform, then the mixture was stirred at room temperature for 8 hours. A 10% aqueous sodium thiosulfate solution was poured to the reaction mixture, and the mixture was extracted with chloroform. The organic layer was washed with a saturated aqueous sodium bicarbonate solution and dried over anhydrous magnesium sulfate, and then concentrated under reduced pressure to obtain 130 mg of 2-(4-ethylsulfonylpyrimidin-5-yl)-3-methyl-6-trifluoromethyl-3H-imidazo[4,5-b]pyridine (hereinafter, referred to as Compound of Present Invention 15).

Compound of Present Invention 15

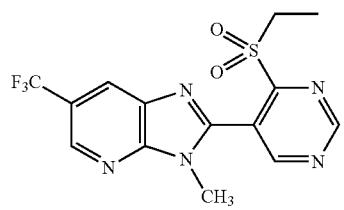

¹H-NMR (CDCl₃) δ: 9.59 (1H, s), 9.16 (1H, s), 8.78 (1H, d), 8.35 (1H, d), 3.85 (3H, s), 3.57 (2H, q), 1.35 (3H, t).

Production Example 16 (1)

A mixture of 693 mg of N²-methyl-5-trifluoromethylpyridine-2,3-diamine, 700 mg of 3,6-dichloropyridazine-carboxylic acid, 1.04 g of EDCI hydrochloride, 50 mg of HOBt and 2.5 ml of pyridine was stirred at room temperature for 4 hours and then allowed to stand at room temperature overnight. Water was poured to the reaction mixture, and the precipitated solid was filtered. The resulting solid was washed with water and n-hexane and then dried to obtain 1.19 g of 3,6-dichloropyridazine-4-carboxylic acid (2-methylamino-5-trifluoromethylpyridin-3-yl)-amide. 3,6-Dichloropyridazine-4-carboxylic acid (2-methylamino-5-trifluoromethylpyridin-3-yl)-amide

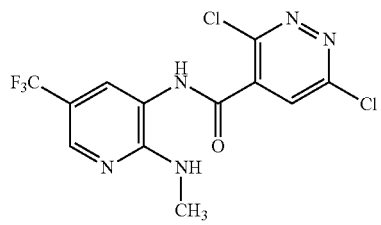 [SMILES: CNc1ncc(C(F)(F)F)cc1NC(=O)c1cc(Cl)nnc1Cl]

¹H-NMR (CDCl₃) δ: 8.44 (1H, s), 8.01 (1H, s), 7.78 (1H, s), 4.99 (1H, brs), 3.10 (3H, d).

Production Example 16 (2)

6 ml of a DMF solution of 342 mg of ethyl mercaptan sodium salt (80%) was added to a mixture of 1.19 g of 3,6-dichloropyridazine-4-carboxylic acid (2-methylamino-5-trifluoromethylpyridin-3-yl)-amide, 2 ml of DMF and 2 ml of THF under ice cooling, then the mixture was heated to room temperature, and stirred for 1 hour. The mixture was allowed to stand overnight, then water was poured to the reaction mixture, and the precipitated solid was filtered. The resulting solid was washed with water and n-hexane and then dried to obtain 1.04 g of 6-chloro-3-ethylsulfanylpyridazine-4-carboxylic acid (2-methylamino-5-trifluoromethylpyridin-3-yl)-amide. 6-chloro-3-ethylsulfanylpyridazine-4-carboxylic acid (2-methylamino-5-trifluoromethylpyridin-3-yl)-amide

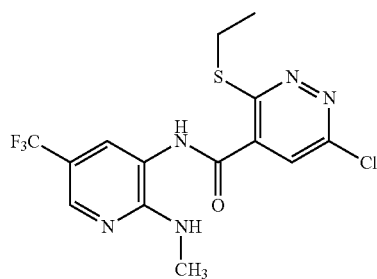 [SMILES: CCSc1nnc(Cl)cc1C(=O)Nc1cc(C(F)(F)F)cnc1NC]

¹H-NMR (CDCl₃) δ: 8.41 (1H, s), 7.95 (1H, brs), 7.79 (1H, s), 7.69 (1H, s), 5.27 (1H, brs), 3.48 (2H, q), 3.09 (3H, d), 1.49 (3H, t).

Production Example 16 (3)

A mixture of 900 mg of 6-chloro-3-ethylsulfanylpyridazine-4-carboxylic acid (2-methylamino-5-trifluoromethylpyridin-3-yl)-amide, 3.5 ml of phosphorus oxychloride, 592 mg of N,N-diisopropylethylamine and 15 ml of toluene was heated and stirred at 100° C. for 4 hours. Water was poured to the cooled reaction mixture, and the mixture was stirred at room temperature for 1 hour. The reaction mixture was neutralized with a saturated aqueous sodium bicarbonate solution, extracted with t-butyl methyl ether. The organic layer was washed with water, and then dried over anhydrous magnesium sulfate and concentrated under reduced pressure. The resulting residue was applied to a silica gel column chromatography to obtain 534 mg of 2-(6-chloro-3-ethylsulfanylpyridazin-4-yl)-3-methyl-6-trifluoromethyl-3H-imidazo[4,5-b]pyridine (hereinafter, referred to as Compound of Present Invention 16).

Compound of Present Invention 16

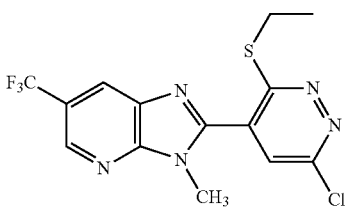

¹H-NMR (CDCl₃) δ: 8.79 (1H, s), 8.39 (1H, s), 7.49 (1H, s), 3.89 (3H, s), 3.41 (2H, q), 1.42 (3H, t).

Production Example 17

720 mg of 3-chloroperoxybenzoic acid (purity of 65% or more) was added to a mixture of 500 mg of 2-(6-chloro-3-ethylsulfanylpyridazin-4-yl)-3-methyl-6-trifluoromethyl-3H-imidazo[4,5-b]pyridine and 7 ml of chloroform, then the mixture was stirred at room temperature for 6 hours. A 10% aqueous sodium thiosulfate solution was poured to the reaction mixture, and the mixture was extracted with chloroform. The organic layer was washed with a saturated aqueous sodium bicarbonate solution and dried over anhydrous magnesium sulfate, and then concentrated under reduced pressure. The resulting residue was subjected to silica gel column chromatograpy to obtain 384 mg of 2-(6-chloro-3-ethylsulfanylpyridazin-4-yl)-3-methyl-6-trifluoromethyl-3H-imidazo[4,5-b]pyridine (hereinafter, referred to as Compound of Present Invention 17).

Compound of Present Invention 17

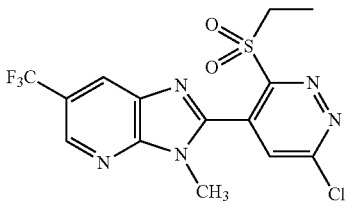 [SMILES: CCS(=O)(=O)c1nnc(Cl)cc1-c1nc2cc(C(F)(F)F)cnc2n1C]

¹H-NMR (CDCl₃) δ: 8.79 (1H, d), 8.36 (1H, d), 7.89 (1H, s), 3.88 (3H, s), 3.70 (2H, q), 1.39 (3H, t).

Production Example 18

A mixture of 384 mg of 2-(6-chloro-3-ethylsulfonylpyridazine-4-yl)-3-methyl-6-trifluoromethyl-3H-imidazo[4,5- b]pyridine, 30 mg of 10% palladium carbon, 1 ml of triethylamine and 10 ml of ethyl acetate was stirred at 30° C. for 3 hours. Water was poured to the reaction mixture, and the mixture was extracted with ethyl acetate. The organic layer was washed with water, then dried over anhydrous magnesium sulfate and concentrated under reduced pressure.

A mixture of the resulting residue, 150 mg of 2,3-dichloro-5,6-dicyano-p-benzoquinone, 25 ml of chloroform and 5 ml of water was stirred at room temperature for 1 hour, and allowed to stand overnight. A 10% aqueous sodium thiosulfate solution was poured to the reaction mixture, and the mixture was extracted with chloroform. The organic layer was sequentially washed with a saturated aqueous sodium bicarbonate solution, water and saturated sodium chloride and dried over anhydrous magnesium sulfate, then concentrated under reduced pressure. The resulting residue was applied to a silica gel column chromatography to obtain 59 mg of 2-(3-ethylsulfonylpyridazin-4-yl)-3-methyl-6-trifluoromethyl-3H-imidazo[4,5-b]pyridine (hereinafter, referred to as Compound of Present Invention 18).

Compound of Present Invention 18

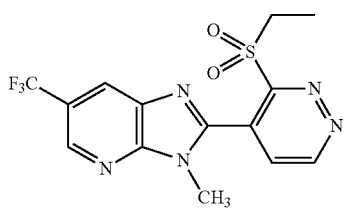 [SMILES: CCS(=O)(=O)c1nnccc1-c1nc2cc(C(F)(F)F)cnc2n1C]

$^1$H-NMR (CDCl$_3$) δ: 9.64 (1H, d), 8.78 (1H, d), 8.36 (1H, d), 7.86 (1H, d), 3.85 (3H, s), 3.73 (2H, q), 1.38 (3H, t).

Production Example 19 (1)

A mixture of 0.40 g of 2-ethylsulfanylpyridine-3-carbonyl acid chloride, 0.36 g of 2-hydroxy-3-amino-5-trifluoromethylpyridine and 8 ml of THF was stirred at room temperature for 1 hour. The reaction mixture was diluted with ethyl acetate and washed with a saturated aqueous sodium bicarbonate solution. The organic layer was washed with water and dried over anhydrous magnesium sulfate, then concentrated under reduced pressure to obtain 0.69 g of 2-ethylsulfanyl-N-(2-hydroxy-5-trifluoromethylpyridin-3-yl) nicotinamide. 2-Ethylsulfanyl-N-(2-hydroxy-5-trifluoromethylpyridin-3-yl) nicotinamide

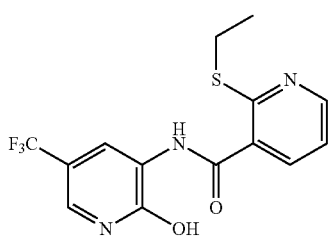 [SMILES: CCSc1ncccc1C(=O)Nc1cc(C(F)(F)F)cnc1O]

Production Example 19 (2)

A mixture of 0.69 g of 2-ethylsulfanyl-N-(2-hydroxy-5-trifluoromethylpyridin-3-yl) nicotinamide, 0.75 g of bis(2-methoxyethyl) azodicarboxylate (hereinafter referred to as DMEAD), 0.79 g of triphenylphosphine and 7 ml of THF was stirred at 50° C. for 4 hours. A saturated aqueous ammonium chloride solution was poured to the reaction mixture, and the mixture was extracted with ethyl acetate. The organic layer was washed with water, then dried over sodium sulfate, and concentrated under reduced pressure. The resulting residue was applied to a silica gel column chromatography to obtain 0.34 g of 2-(2-ethylsulfanylpyridin-3-yl)-6-(trifluoromethyl) oxazolo[5,4-b]pyridine (hereinafter, referred to as Compound of Present Invention 32).

Compound of Present Invention 32

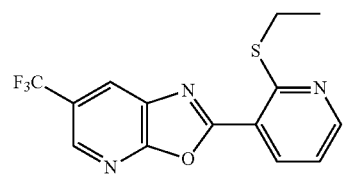 [SMILES: CCSc1ncccc1-c1nc2cc(C(F)(F)F)cnc2o1]

$^1$H-NMR (CDCl$_3$) δ: 8.69 (1H, d), 8.64 (1H, dd), 8.48 (1H, dd), 8.43 (1H, d), 7.21 (1H, dd), 3.32 (2H, q), 1.44 (3H, t).

Production Example 20

0.25 g of 3-chloroperoxybenzoic acid (purity of 65% or more) was added to a mixture of 0.34 g of 2-(2-ethylsulfanylpyridin-3-yl)-6-(trifluoromethyl)oxazolo[5,4-b]pyridine and 4 ml of chloroform under ice cooling, then the mixture was stirred for 30 minutes under ice cooling. 0.25 g of 3-chloroperoxybenzoic acid (purity of 65% or more) was added to the reaction mixture under ice cooling, then the mixture was stirred at room temperature for 1 hour. An aqueous sodium thiosulfate solution was poured to the reaction mixture, and the mixture was extracted with chloroform. The organic layer was washed with a saturated aqueous sodium bicarbonate solution and dried over anhydrous sodium sulfate, then concentrated under reduced pressure. The resulting residue was applied to a silica gel column chromatography to obtain 0.33 g of 2-(2-ethylsulfonylpyrimidin-3-yl)-6-(trifluoromethyl) oxazolo[5,4-b]pyridine (hereinafter, referred to as Compound of Present Invention 33).

Compound of Present Invention 33

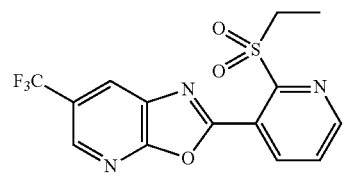 [SMILES: CCS(=O)(=O)c1ncccc1-c1nc2cc(C(F)(F)F)cnc2o1]

$^1$H-NMR (CDCl$_3$) δ: 8.94 (1H, dd), 8.77-8.73 (1H, m), 8.44-8.41 (1H, m), 8.38 (1H, dd), 7.77 (1H, dd), 3.70 (2H, q), 1.43 (3H, t).

Production Example 21 (1)

A mixture of 0.40 g of 2-ethylsulfanylpyridine-3-carbonyl acid chloride, 0.35 g of 2-amino-4-trifluoromethylphenol and 8 ml of THF was stirred at room temperature for 1 hour. The reaction mixture was diluted with ethyl acetate, and washed with a saturated aqueous sodium bicarbonate solution. The organic layer was washed with water and dried over anhydrous sodium sulfate, then concentrated under reduced pressure to obtain 0.71 g of 2-ethylsulfanyl-N-(2-hydroxy-5-trifluoromethylphenyl) nicotinamide. 2-Ethylsulfanyl-N-(2-hydroxy-5-trifluoromethylphenyl) nicotinamide

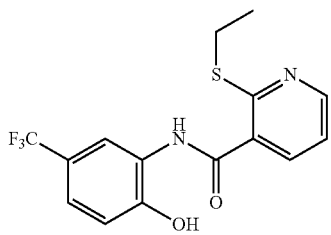 [SMILES: CCSc1ncccc1C(=O)Nc1cc(C(F)(F)F)ccc1O]

Production Example 21 (2)

A mixture of 0.69 g of 2-ethylsulfanyl-N-(2-hydroxy-5-trifluoromethylpyridin-3-yl) nicotinamide, 0.75 g of DMEAD, 0.79 g of triphenylphosphine and 7 ml of THF was stirred at 50° C. for 4 hours. A saturated aqueous ammonium chloride solution was poured to the reaction mixture, and the mixture was extracted with ethyl acetate. The organic layer was washed with water, then dried over anhydrous sodium sulfate and concentrated under reduced pressure. The resulting residue was applied to a silica gel column chromatography to obtain 0.45 g of 2-(2-ethylsulfanylpyridin-3-yl)-5-(trifluoromethyl)benzoxazole (hereinafter, referred to as Compound of Present Invention 34).

Compound of Present Invention 34

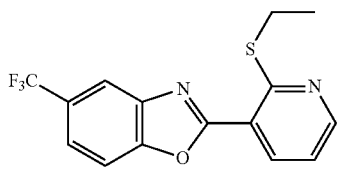

$^1$H-NMR (CDCl$_3$) δ: 8.60 (1H, dd), 8.41 (1H, dd), 8.19 (1H, s), 7.73-7.63 (2H, m), 7.17 (1H, dd), 3.31 (2H, q), 1.44 (3H, t).

Production Example 22

335 mg of 3-chloroperoxybenzoic acid (purity of 65% or more) was added to a mixture of 0.45 g of 2-(2-ethylsulfanylpyridin-3-yl)-5-(trifluoromethyl)benzoxazole and 5 ml of chloroform under ice cooling, then the mixture was stirred for 30 minutes under ice cooling. 335 mg of 3-chloroperoxybenzoic acid (purity of 65% or more) was added to the reacting mixture under ice cooling, then the mixture was stirred at room temperature for 1 hour. An aqueous sodium thiosulfate solution was poured to the reaction mixture, and the mixture was extracted with chloroform. The organic layer was washed with a saturated aqueous sodium bicarbonate solution and dried over anhydrous sodium sulfate, then concentrated under reduced pressure. The resulting residue was applied to a silica gel column chromatography to obtain 0.43 g of 2-(2-ethyl-sulfonylpyrimidin-3-yl)-5-(trifluoromethyl)benzoxazole (hereinafter, referred to as Compound of Present Invention 35).

Compound of Present Invention 35

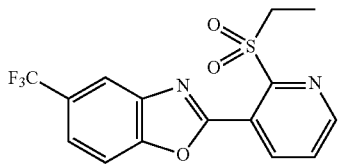

$^1$H-NMR (CDCl$_3$) δ: 8.89 (1H, dd), 8.39 (1H, dd), 8.14 (1H, s), 7.80-7.69 (3H, m), 3.70 (2H, q), 1.39 (3H, t).

Production Example 23 (1)

A mixture of 0.30 g of 2-ethylsulfanylpyridine-3-carbonyl acid chloride, 0.33 g of 2-amino-4-(pentafluoroethyl)phenol and 6 ml of THF was stirred at room temperature for 1 hour. The reaction mixture was diluted with ethyl acetate and washed with a saturated aqueous sodium bicarbonate solution. The organic layer was washed with water and dried over anhydrous sodium sulfate, then concentrated under reduced pressure to obtain 0.57 g of 2-ethylsulfanyl-N-[2-hydroxy-5-(pentafluoroethyl)phenyl]nicotinamide. 2-Ethylsulfanyl-N-[2-hydroxy-5-(pentafluoroethyl)phenyl]nicotinamide

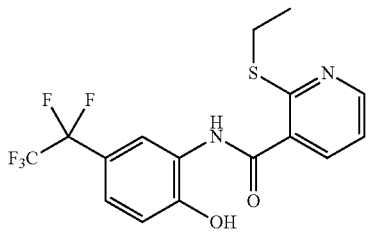 [SMILES: CCSc1ncccc1C(=O)Nc1cc(C(F)(F)C(F)(F)F)ccc1O]

Production Example 23 (2)

A mixture of 0.57 g of 2-ethylsulfanyl-N-[2-hydroxy-5-(pentafluoroethyl)phenyl]nicotinamide, 0.54 g of DMEAD, 0.57 g of triphenylphosphine and 6 ml of THF was stirred at 50° C. for 4 hours. A saturated aqueous ammonium chloride solution was poured to the reaction mixture, and the mixture was extracted with ethyl acetate. The organic layer was washed with water, then dried over anhydrous sodium sulfate and concentrated under reduced pressure. The resulting residue was applied to a silica gel column chromatography to obtain 0.35 g of 2-(2-ethylsulfanylpyridin-3-yl)-5-(pentafluoroethyl)benzoxazole (hereinafter, referred to as Compound of Present Invention 36).

Compound of Present Invention 36

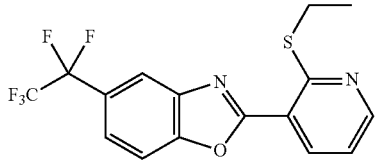 [SMILES: CCSc1ncccc1-c1nc2cc(C(F)(F)C(F)(F)F)ccc2o1]

$^1$H-NMR (CDCl$_3$) δ: 8.61 (1H, dd), 8.41 (1H, dd), 8.20-8.15 (1H, m), 7.72 (1H, dd), 7.66-7.61 (1H, m), 7.18 (1H, dd), 3.31 (2H, q), 1.44 (3H, t).

Production Example 24

220 mg of 3-chloroperoxybenzoic acid (purity of 65% or more) was added to a mixture of 0.35 g of 2-(2-ethylsulfanylpyridin-3-yl)-5-(pentafluoroethyl)benzoxazole and 5 ml of chloroform under ice cooling, then the mixture was stirred for 30 minutes under ice cooling. 220 mg of 3-chloroperoxybenzoic acid (purity of 65% or more) was added to the reacting mixture under ice cooling, then the mixture was stirred at room temperature for 1 hour. An aqueous sodium thiosulfate solution was poured to the reaction mixture, and the mixture was extracted with chloroform. The organic layer was washed with a saturated aqueous sodium bicarbonate solution and dried over anhydrous sodium sulfate, then concentrated under reduced pressure. The resulting residue was applied to a silica gel column chromatography to obtain 0.33 g of 2-(2-ethylsulfonylpyrimidin-3-yl)-5-(pentafluoroethyl)benzoxazole (hereinafter, referred to as Compound of Present Invention 37).

Compound of Present Invention 37

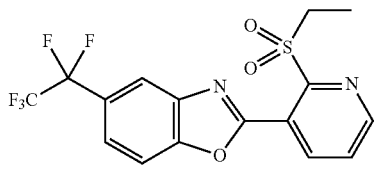 [SMILES: CCS(=O)(=O)c1ncccc1-c1nc2cc(C(F)(F)C(F)(F)F)ccc2o1]

$^1$H-NMR (CDCl$_3$) δ: 8.89 (1H, dd), 8.39 (1H, dd), 8.12 (1H, s), 7.79 (1H, d), 7.74 (1H, dd), 7.69 (1H, d), 3.70 (2H, q), 1.40 (3H, t).

Production Example 25 (1)

A mixture of 1.15 g of 2-ethylsulfanylpyridine-3-carbonyl acid chloride, 1.19 g of 2-amino-4-(trifluoromethylsulfanyl)phenol and 15 ml of THF was stirred at room temperature for 1 hour. The reaction mixture was diluted with ethyl acetate, and washed with a saturated aqueous sodium bicarbonate solution. The organic layer was washed with water and dried over anhydrous sodium sulfate, then concentrated under reduced pressure to obtain 2.26 g of 2-ethylsulfanyl-N-[2-hydroxy-5-(trifluoromethylsulfanyl)phenyl]nicotinamide.
2-ethylsulfanyl-N-[2-hydroxy-5-(trifluoromethylsulfanyl)phenyl]nicotinamide
[Chemical Formula 142]

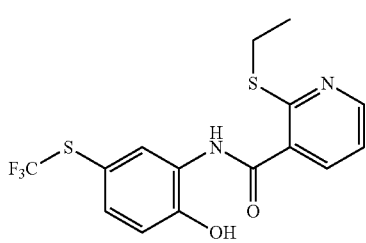 [SMILES: CCSc1ncccc1C(=O)Nc1cc(SC(F)(F)F)ccc1O]

Production Example 25 (2)

A mixture of 2.13 g of 2-ethylsulfanyl-N-[2-hydroxy-5-(trifluoromethylsulfanyl)phenyl]nicotinamide, 2.14 g of DMEAD, 2.24 g of triphenylphosphine and 20 ml of THF was stirred at 50° C. for 4 hours. A saturated aqueous ammonium chloride solution was poured to the reaction mixture, and the mixture was extracted with ethyl acetate. The organic layer was washed with water, then dried over anhydrous sodium sulfate and concentrated under reduced pressure. The resulting residue was applied to a silica gel column chromatography to obtain 1.52 g of 2-(2-ethylsulfanylpyridin-3-yl)-5-(trifluoromethylsulfanyl)benzoxazole (hereinafter, referred to as Compound of Present Invention 38).

Compound of Present Invention 38

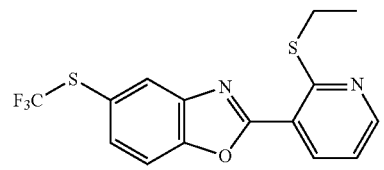 [SMILES: CCSc1ncccc1-c1nc2cc(SC(F)(F)F)ccc2o1]

$^1$H-NMR (CDCl$_3$) δ: 8.60 (1H, dd), 8.40 (1H, dd), 8.23 (1H, d), 7.69 (1H, dd), 7.66-7.62 (1H, m), 7.17 (1H, dd), 3.31 (2H, q), 1.44 (3H, t).

Production Example 26

0.88 g of 3-chloroperoxybenzoic acid (purity of 65% or more) was added to a mixture of 1.32 g of 2-(2-ethylsulfanylpyridin-3-yl)-5-(trifluoromethylsulfanyl)benzoxazole and 13 ml of chloroform under ice cooling, then the mixture was stirred for 30 minutes under ice cooling. 0.88 g of 3-chloroperoxybenzoic acid (purity of 65% or more) was added to the reacting mixture under ice cooling, then the mixture was stirred at room temperature for 1 hour. An aqueous sodium thiosulfate solution was poured to the reaction mixture, and the mixture was extracted with chloroform. The organic layer was washed with a saturated aqueous sodium bicarbonate solution and dried over anhydrous sodium sulfate, then concentrated under reduced pressure. The resulting residue was applied to a silica gel column chromatography to obtain 1.05 g of 2-(2-ethylsulfonylpyrimidin-3-yl)-5-(trifluoromethylsulfanyl)benzoxazole (hereinafter, referred to as Compound of Present Invention 39).

Compound of Present Invention 39

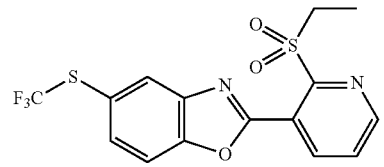 [SMILES: CCS(=O)(=O)c1ncccc1-c1nc2cc(SC(F)(F)F)ccc2o1]

$^1$H-NMR (CDCl$_3$) δ: 8.88 (1H, dd), 8.38 (1H, dd), 8.18 (1H, s), 7.78-7.69 (3H, m), 3.70 (2H, q), 1.40 (3H, t).

Production Example 27

0.43 g of 3-chloroperoxybenzoic acid (purity of 65% or more) was added to a mixture of 0.70 g of 2-(2-ethylsulfonylpyridin-3-yl)-5-(trifluoromethylsulfanyl)benzoxazole and 7 ml of chloroform under ice cooling, then the mixture was stirred at room temperature for 5 hours. An aqueous sodium thiosulfate solution was poured to the reaction mixture, and the mixture was extracted with chloroform. The organic layer was washed with a saturated aqueous sodium bicarbonate solution and dried over anhydrous sodium sulfate, then concentrated under reduced pressure. The resulting residue was applied to a silica gel column chromatography to obtain 0.35 g of 2-(2-ethylsulfonylpyrimidin-3-yl)-5-(trifluoromethylsulfinyl)benzoxazole (hereinafter, referred to as Compound of Present Invention 40).

Compound of Present Invention 40

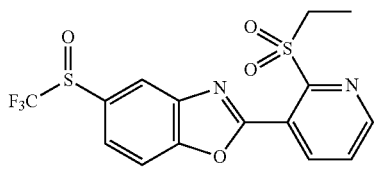 [SMILES: CCS(=O)(=O)c1ncccc1-c1nc2cc(S(=O)C(F)(F)F)ccc2o1]

$^1$H-NMR (CDCl$_3$) δ: 8.90 (1H, dd), 8.41 (1H, dd), 8.32 (1H, s), 7.94-7.85 (2H, m), 7.75 (1H, dd), 3.70 (2H, q), 1.40 (3H, t).

Production Example 28

A mixture of 0.38 g of 2-(2-ethylsulfonylpyridin-3-yl)-5-(trifluoromethylsulfanyl)benzoxazole, 40 mg of sodium tungstate dehydrate, 5 ml of aqueous hydrogen peroxide (30%) and 7 ml of acetonitrile was stirred at 80° C. for 5 hours. An aqueous sodium thiosulfate solution was poured to the reaction mixture cooled to room temperature, and the mixture was extracted with ethyl acetate. The organic layer was sequentially washed with an aqueous sodium thiosulfate solution and a saturated saline water and dried over anhydrous sodium sulfate, then concentrated under reduced pressure. The resulting residue was applied to a silica gel column chromatography to obtain 0.35 g of 2-(2-ethylsulfonylpyridin-3-yl)-5-(trifluoromethylsulfonyl)benzoxazole (hereinafter, referred to as Compound of Present Invention 41).

Compound of Present Invention 41

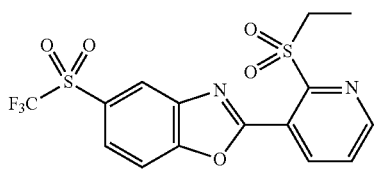 [SMILES: CCS(=O)(=O)c1ncccc1-c1nc2cc(S(=O)(=O)C(F)(F)F)ccc2o1]

$^1$H-NMR (CDCl$_3$) δ: 8.93 (1H, dd), 8.58 (1H, d), 8.40 (1H, dd), 8.15 (1H, dd), 7.95 (1H, d), 7.78 (1H, dd), 3.70 (2H, q), 1.39 (3H, t).

Production Example 29 (1)

1.72 g of sodium hydride (60% oil-based) was added to a mixture of 5.0 g of 4-chloronicotinonitrile, 3 ml of ethanethiol and 36 ml of THF under ice cooling, then the mixture was stirred at room temperature for 2 hours. A saturated aqueous sodium chloride solution was poured to the reaction mixture, and the mixture was extracted with ethyl acetate. The organic layer was dried over anhydrous sodium sulfate, and then concentrated under reduced pressure. The resulting residue was applied to a silica gel column chromatography to obtain 5.72 g of 4-ethylsulfanylnicotinonitrile. 4-ethylsulfanylnicotinonitrile

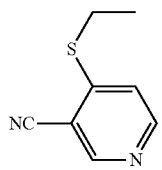

$^1$H-NMR (CDCl$_3$) δ: 8.66 (1H, s), 8.55 (1H, d), 7.18 (1H, d), 3.11 (2H, q), 1.45 (3H, t).

Production Example 29 (2)

A mixture of 4.0 g of 4-ethylsulfanylnicotinonitrile, 30 ml of sulfuric acid and 12 ml of water was stirred at 130° C. for 2 hours. An aqueous sodium hydroxide solution was added to the reaction mixture cooled to room temperature to adjust pH to 10, and the mixture was washed with chloroform. Hydrochloric acid was added to the aqueous layer to adjust pH to 4, and the mixture was concentrated under reduced pressure. 500 ml of ethanol was poured to the resulting residue, and the mixture was stirred at room temperature for 1 hour and then filtered. The resulting filtrate was concentrated under reduced pressure to obtain 5.87 g of 4-ethylsulfanylnicotinic acid hydrochloride. 4-ethylsulfanylnicotinic acid hydrochloride

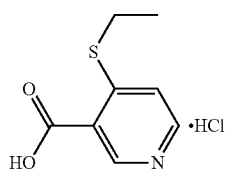

$^1$H-NMR (DMSO-D$_6$) δ: 8.93-8.82 (1H, m), 8.53-8.41 (1H, m), 7.65-7.02 (2H, m), 3.03-2.91 (2H, m), 1.30 (3H, t).

Production Example 29 (3)

A mixture of 450 mg of 3-amino-5-trifluoromethylpyridine-2-thiol, 637 mg of 4-ethylsulfanylnicotinic acid hydrochloride, 532 mg of EDCI hydrochloride, 31 mg of HOBt and 5 ml of pyridine was stirred at room temperature for 2 hours and then stirred at 60° C. for 30 minutes. Water was poured to the reaction mixture, and the precipitated solid was filtered. The resulting solid was washed with water and n-hexane and then dried to obtain 494 mg of 4-ethylsulfanyl-N-[2-mercapto-5-(trifluoromethyl)pyridin-3-yl]nicotinamide. 4-ethylsulfanyl-N-[2-mercapto-5-(trifluoromethyl)pyridin-3-yl]nicotinamide

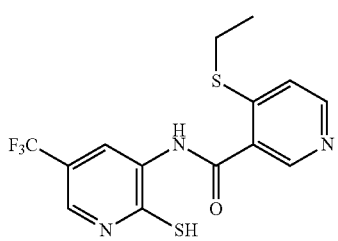 [SMILES: CCSc1ccncc1C(=O)Nc1cc(C(F)(F)F)cnc1S]

$^1$H-NMR (DMSO-D$_6$) δ: 10.15 (1H, brs), 8.77 (1H, s), 8.65 (1H, d), 8.57 (1H, d), 8.12-8.10 (1H, m), 7.52 (1H, d), 3.09 (2H, q), 1.29 (3H, t).

Production Example 29 (4)

A mixture of 494 mg of 4-ethylsulfanyl-N-[2-mercapto-5-(trifluoromethyl)pyridin-3-yl]nicotinamide, 1.05 g of p-toluenesolufonic acid-hydrate, 3 ml of DMF and 1 ml of toluene was heated and stirred at 150° C. for 10 hours. A saturated aqueous sodium bicarbonate solution was poured to the cooled reaction mixture, and the precipitated solid was filtered. The resulting solid was applied to a silica gel column chromatography to obtain 146 mg of 2-(4-ethylsulfanylpyridin-3-yl)-6-(trifluoromethyl)thiazolo[5,4-b]pyridine (hereinafter, referred to as Compound of Present Invention 42).

Compound of Present Invention 42

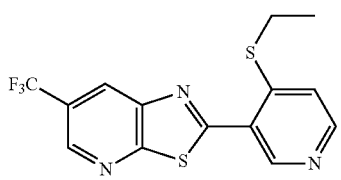 [SMILES: CCSc1ccncc1-c1nc2cc(C(F)(F)F)cnc2s1]

$^1$H-NMR (DMSO-D$_6$) δ: 9.11-9.08 (1H, m), 9.03-8.99 (2H, m), 8.59 (1H, d), 7.61 (1H, d), 3.18 (2H, q), 1.33 (3H, t).

Production Examples 30 and 31

217 mg of 3-chloroperoxybenzoic acid (purity of 65% or more) was added to a mixture of 146 mg of 2-(4-ethylsulfanylpyridin-3-yl)-6-(trifluoromethyl)thiazolo[5,4-b]pyridine and 5 ml of chloroform under ice cooling, then the mixture was stirred at room temperature for 8 hours. An aqueous sodium thiosulfate solution was poured to the reaction mixture, and the mixture was extracted with chloroform. The organic layer was washed with a saturated aqueous sodium bicarbonate solution and dried over anhydrous sodium sulfate, then concentrated under reduced pressure. The resulting residue was applied to a silica gel column chromatography to obtain 81 mg of 2-(4-ethylsulfonylpyridin-3-yl)-6-(trifluoromethyl)thiazolo[5,4-b]pyridine (hereinafter, referred to as Compound of Present Invention 43) and 29 mg of 2-(4-ethylsulfonyl-1-oxypyridin-3-yl)-6-(trifluoromethyl)thiazolo[5,4-b]pyridine (hereinafter, referred to as Compound of Present Invention 44).

Compound of Present Invention 43

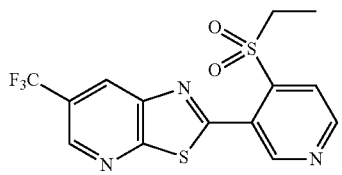 [SMILES: CCS(=O)(=O)c1ccncc1-c1nc2cc(C(F)(F)F)cnc2s1]

$^1$H-NMR (CDCl$_3$) δ: 9.10 (1H, d), 9.05 (1H, s), 8.96 (1H, s), 8.56 (1H, s), 8.11 (1H, d), 3.78 (2H, q), 1.40 (3H, t).

Compound of Present Invention 44

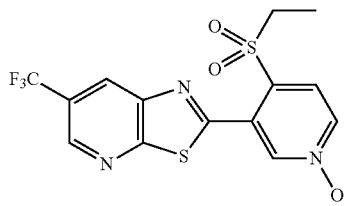

$^1$H-NMR (CDCl$_3$) δ: 8.99 (1H, d), 8.59 (1H, d), 8.44 (1H, d), 8.41 (1H, dd), 8.07 (1H, d), 3.75 (2H, q), 1.42 (3H, t).

Production Example 32

A mixture of 0.40 g of 2-ethylsulfanylpyridine-3-carbonyl acid chloride, 0.46 g of 2-amino-4-(trifluoromethyl)thiophenol hydrochloride and 6 ml of pyridine was stirred at 60° C. for 9 hours, then stirred at 80° C. for 5 hours. Diluted hydrochloric acid was added to the reaction mixture which was cooled to room temperature, and the mixture was extracted with ethyl acetate. The organic layer was washed with water and dried over anhydrous sodium sulfate, then concentrated under reduced pressure. The resulting obtained residue was applied to a silica gel column chromatography to obtain 0.38 g of 2-(2-ethylsulfanylpyridin-3-yl)-5-(trifluoromethyl)benzothiazole (hereinafter, referred to as Compound of Present Invention 45).

Compound of Present Invention 45

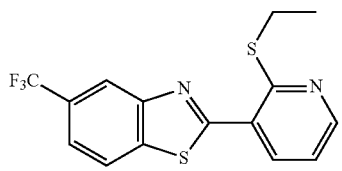 [SMILES: CCSc1ncccc1-c1nc2cc(C(F)(F)F)ccc2s1]

$^1$H-NMR (CDCl$_3$) δ: 8.57 (1H, dd), 8.43 (1H, s), 8.16 (1H, dd), 8.05 (1H, d), 7.66 (1H, d), 7.16 (1H, dd), 3.31 (2H, q), 1.41 (3H, t).

Production Example 33

265 mg of 3-chloroperoxybenzoic acid (purity of 65% or more) was added to a mixture of 0.38 g of 2-(2-ethylsulfanylpyridin-3-yl)-5-(trifluoromethyl)benzothiazole and 4 ml of chloroform under ice cooling, then the mixture was stirred for 30 minutes under ice cooling. 265 mg of 3-chloroperoxybenzoic acid (purity of 65% or more) was added to the reaction mixture under ice cooling, then the mixture was stirred at room temperature for 1 hour. An aqueous sodium thiosulfate solution was poured to the reaction mixture, and the mixture was extracted with chloroform. The organic layer was washed with a saturated aqueous sodium bicarbonate solution, dried over anhydrous sodium sulfate, and then concentrated under reduced pressure. The resulting residue was applied to a silica gel column chromatography to obtain 0.35 g of 2-(2-ethylsulfonylpyridin-3-yl)-5-(trifluoromethyl)benzothiazole (hereinafter, referred to as Compound of Present Invention 46).

Compound of Present Invention 46

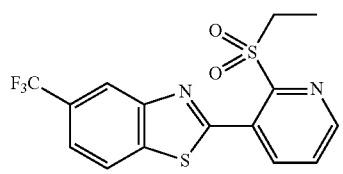 [SMILES: CCS(=O)(=O)c1ncccc1-c1nc2cc(C(F)(F)F)ccc2s1]

$^1$H-NMR (CDCl$_3$) δ: 8.86 (1H, dd), 8.41 (1H, s), 8.15 (1H, dd), 8.08 (1H, d), 7.73-7.66 (2H, m), 3.68 (2H, q), 1.40 (3H, t).

The compounds described in the production examples described above and the compounds manufactured by the manufacturing method according to the method described in the production examples described above are shown in the tables. Compound represented by formula (1)

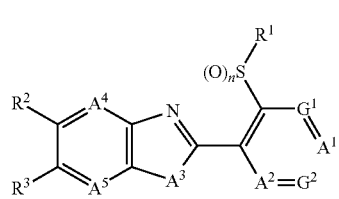

wherein $R^1$, $R^2$, $R^3$, $G^1$, $G^2$, $A^1$, $A^2$, $A^3$, $A^4$, $A^5$ and n represent the combinations shown in [Table 11] to [Table 13] shown below.

TABLE 11

| Compound of Present Invention | $R^1$ | $R^2$ | $R^3$ | $G^1$ | $G^2$ | $A^1$ | $A^2$ | $A^3$ | $A^4$ | $A^5$ | n |
|---|---|---|---|---|---|---|---|---|---|---|---|
| 1 | Et | CF$_3$ | H | N | CH | CH | CH | NMe | CH | N | 0 |
| 2 | Et | CF$_3$ | H | N | CH | CH | CH | NMe | CH | N | 1 |
| 3 | Et | CF$_3$ | H | N | CH | CH | CH | NMe | CH | N | 2 |
| 4 | Et | CF$_3$ | H | N | CH | CCF$_3$ | CH | NMe | CH | N | 0 |
| 5 | Et | CF$_3$ | H | N | CH | CCF$_3$ | CH | NMe | CH | N | 2 |

TABLE 11-continued

| Compound of Present Invention | $R^1$ | $R^2$ | $R^3$ | $G^1$ | $G^2$ | $A^1$ | $A^2$ | $A^3$ | $A^4$ | $A^5$ | n |
|---|---|---|---|---|---|---|---|---|---|---|---|
| 6 | Et | CF$_3$ | H | N | CH | CH | N | NMe | CH | N | 0 |
| 7 | Et | CF$_3$ | H | N | CH | CH | N | NMe | CH | N | 1 |
| 8 | Et | CF$_3$ | H | N | CH | CH | N | NMe | CH | N | 2 |
| 9 | Et | CF$_3$ | H | CH | N | CH | CH | NMe | CH | N | 0 |
| 10 | Et | CF$_3$ | H | CH | N | CH | CH | NMe | CH | N | 1 |
| 11 | Et | CF$_3$ | H | CH | N | CH | CH | NMe | CH | N | 2 |
| 12 | Et | CF$_3$ | H | H | N | CCF$_3$ | CH | NMe | CH | N | 0 |
| 13 | Et | CF$_3$ | H | H | N | CCF$_3$ | CH | NMe | CH | N | 2 |
| 14 | Et | CF$_3$ | H | N | N | CH | CH | NMe | CH | N | 0 |
| 15 | Et | CF$_3$ | H | N | N | CH | CH | NMe | CH | N | 2 |
| 16 | Et | CF$_3$ | H | N | CCl | N | CH | NMe | CH | N | 0 |
| 17 | Et | CF$_3$ | H | N | CCl | N | CH | NMe | CH | N | 2 |
| 18 | Et | CF$_3$ | H | N | CH | N | CH | NMe | CH | N | 2 |
| 19 | Et | CF$_3$ | H | CH | N | CCF$_3$ | N | NMe | CH | N | 0 |
| 20 | Et | CF$_3$ | H | CH | N | CCF$_3$ | N | NMe | CH | N | 2 |
| 21 | Et | CF$_3$ | H | N | N | CCF$_3$ | CH | NMe | CH | N | 0 |
| 22 | Et | CF$_3$ | H | N | N | CCF$_3$ | CH | NMe | CH | N | 2 |
| 23 | Et | CF$_2$CF$_3$ | H | N | CH | CCF$_3$ | CH | NMe | CH | N | 0 |
| 24 | Et | CF$_2$CF$_3$ | H | N | CH | CCF$_3$ | CH | NMe | CH | N | 2 |
| 25 | Et | SCF$_3$ | H | N | CH | CCF$_3$ | CH | NMe | CH | N | 0 |
| 26 | Et | SCF$_3$ | H | N | CH | CCF$_3$ | CH | NMe | CH | N | 2 |
| 27 | Et | S(O)$_2$CF$_3$ | H | N | CH | CCF$_3$ | CH | NMe | CH | N | 2 |
| 28 | Et | CF$_3$ | H | N | CH | CCF$_3$ | CH | O | CH | N | 0 |
| 29 | Et | CF$_3$ | H | N | CH | CCF$_3$ | CH | O | CH | N | 2 |
| 30 | Et | CF$_3$ | H | N | CH | CCF$_3$ | CH | S | CH | N | 0 |
| 31 | Et | CF$_3$ | H | N | CH | CCF$_3$ | CH | S | CH | N | 2 |

TABLE 12

| Compound of Present Invention | $R^1$ | $R^2$ | $R^3$ | $G^1$ | $G^2$ | $A^1$ | $A^2$ | $A^3$ | $A^4$ | $A^5$ | n |
|---|---|---|---|---|---|---|---|---|---|---|---|
| 32 | Et | CF$_3$ | H | N | CH | CH | CH | O | CH | N | 0 |
| 33 | Et | CF$_3$ | H | N | CH | CH | CH | O | CH | N | 2 |
| 34 | Et | CF$_3$ | H | N | CH | CH | CH | O | CH | CH | 0 |
| 35 | Et | CF$_3$ | H | N | CH | CH | CH | O | CH | CH | 2 |
| 36 | Et | CF$_2$CF$_3$ | H | N | CH | CH | CH | O | CH | CH | 0 |
| 37 | Et | CF$_2$CF$_3$ | H | N | CH | CH | CH | O | CH | CH | 2 |
| 38 | Et | SCF$_3$ | H | N | CH | CH | CH | O | CH | CH | 0 |
| 39 | Et | SCF$_3$ | H | N | CH | CH | CH | O | CH | CH | 2 |
| 40 | Et | S(O)CF$_3$ | H | N | CH | CH | CH | O | CH | CH | 2 |
| 41 | Et | S(O)$_2$CF$_3$ | H | N | CH | CH | CH | O | CH | CH | 2 |
| 42 | Et | CF$_3$ | H | CH | N | CH | CH | S | CH | N | 0 |
| 43 | Et | CF$_3$ | H | CH | N | CH | CH | S | CH | N | 2 |
| 44* | Et | CF$_3$ | H | CH | N | CH | CH | S | CH | N | 2 |
| 45 | Et | CF$_3$ | H | N | CH | CH | CH | S | CH | CH | 0 |
| 46 | Et | CF$_3$ | H | N | CH | CH | CH | S | CH | CH | 2 |
| 47 | Et | CF$_2$CF$_3$ | H | N | CH | CH | CH | NMe | CH | N | 0 |
| 48 | Et | CF$_2$CF$_3$ | H | N | CH | CH | CH | NMe | CH | N | 2 |
| 49 | Et | SCF$_3$ | H | N | CH | CH | CH | NMe | CH | N | 0 |
| 50 | Et | SCF$_3$ | H | N | CH | CH | CH | NMe | CH | N | 2 |
| 51 | Et | CF$_2$CF$_3$ | H | CH | N | CH | CH | NMe | CH | N | 0 |
| 52 | Et | CF$_2$CF$_3$ | H | CH | N | CH | CH | NMe | CH | N | 2 |
| 53 | Et | SCF$_3$ | H | CH | N | CH | CH | NMe | CH | N | 0 |
| 54 | Et | SCF$_3$ | H | CH | N | CH | CH | NMe | CH | N | 2 |
| 55 | Et | CF$_3$ | H | N | CH | CH | CH | S | CH | N | 0 |
| 56 | Et | CF$_3$ | H | N | CH | CH | CH | S | CH | N | 2 |

TABLE 13

| Compound of Present Invention | $R^1$ | $R^2$ | $R^3$ | $G^1$ | $G^2$ | $A^1$ | $A^2$ | $A^3$ | $A^4$ | $A^5$ | n |
|---|---|---|---|---|---|---|---|---|---|---|---|
| 57 | Et | CF$_3$ | H | CH | N | CH | CH | O | CH | N | 0 |
| 58 | Et | CF$_3$ | H | CH | N | CH | CH | O | CH | N | 2 |

TABLE 13-continued

| Compound of Present Invention | R¹ | R² | R³ | G¹ | G² | A¹ | A² | A³ | A⁴ | A⁵ | n |
|---|---|---|---|---|---|---|---|---|---|---|---|
| 59 | Et | CF$_3$ | H | CH | N | CH | CH | O | CH | CH | 0 |
| 60 | Et | CF$_3$ | H | CH | N | CH | CH | O | CH | CH | 2 |
| 61 | Et | CF$_2$CF$_3$ | H | CH | N | CH | CH | O | CH | CH | 0 |
| 62 | Et | CF$_2$CF$_3$ | H | CH | N | CH | CH | O | CH | CH | 2 |
| 63 | Et | SCF$_3$ | H | CH | N | CH | CH | O | CH | CH | 0 |
| 64 | Et | SCF$_3$ | H | CH | N | CH | CH | O | CH | CH | 2 |
| 65 | Et | S(O)CF$_3$ | H | CH | N | CH | CH | O | CH | CH | 2 |
| 66 | Et | S(O)$_2$CF$_3$ | H | CH | N | CH | CH | O | CH | CH | 2 |

Here, "*" in the compound of the present invention of the tables [Table 11] to [Table 13] shown above means that the compound is N-oxide, specifically, the following compound.

Compound of Present Invention 44

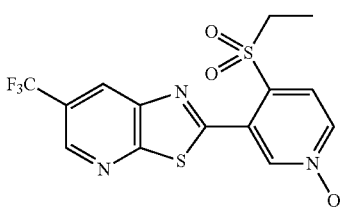

In [Table 11] to [Table 13] shown above, CH represents =CH—, CCl represents =CCl—, CCF$_3$ represents =C(CF$_3$)—, and NMe represents —NMe-.

¹H-NMR data of the compound of the present invention shown in [Table 11] to [Table 13] are shown below.

Compound of Present Invention 47

¹H-NMR (CDCl$_3$) δ: 8.68 (1H, d), 8.64 (1H, dd), 8.32 (1H, d), 7.66 (1H, dd), 7.19 (1H, dd), 3.83 (3H, s), 3.24 (2H, q), 1.35 (3H, t).

Compound of Present Invention 48

¹H-NMR (CDCl$_3$) δ: 8.99 (1H, dd), 8.69 (1H, s), 8.29 (1H, s), 8.02 (1H, dd), 7.78 (1H, dd), 3.81 (3H, s), 3.52 (2H, q), 1.32 (3H, t).

Compound of Present Invention 49

¹H-NMR (CDCl$_3$) δ: 8.67 (1H, d), 8.64 (1H, dd), 8.41 (1H, d), 7.66 (1H, dd), 7.18 (1H, dd), 3.81 (3H, s), 3.24 (2H, q), 1.35 (3H, t).

Compound of Present Invention 50

¹H-NMR (CDCl$_3$) δ: 8.98 (1H, dd), 8.69 (1H, d), 8.38 (1H, d), 8.02 (1H, dd), 7.77 (1H, dd), 3.79 (3H, s), 3.51 (2H, q), 1.31 (3H, t).

Compound of Present Invention 51

¹H-NMR (CDCl$_3$) δ: 8.69 (1H, d), 8.62 (1H, d), 8.54 (1H, s), 8.34 (1H, d), 7.30 (1H, d), 3.84 (3H, s), 3.03 (2H, q), 1.38 (3H, t).

Compound of Present Invention 52

¹H-NMR (CDCl$_3$) δ: 9.14 (1H, d), 8.88 (1H, s), 8.72 (1H, d), 8.29 (1H, d), 8.09 (1H, d), 3.77 (3H, s), 3.48 (2H, q), 1.29 (3H, t).

Compound of Present Invention 53

¹H-NMR (CDCl$_3$) δ: 8.68 (1H, d), 8.62 (1H, d), 8.54 (1H, s), 8.43 (1H, d), 7.30 (1H, d), 3.81 (3H, s), 3.03 (2H, q), 1.38 (3H, t).

Compound of Present Invention 54

¹H-NMR (CDCl$_3$) δ: 9.14 (1H, d), 8.88 (1H, s), 8.72 (1H, d), 8.38 (1H, d), 8.09 (1H, d), 3.75 (3H, s), 3.48 (2H, q), 1.29 (3H, t).

Compound of Present Invention 55

¹H-NMR (CDCl$_3$) δ: 8.89-8.86 (1H, m), 8.62-8.58 (2H, m), 8.17 (1H, dd), 7.18 (1H, dd), 3.31 (2H, q), 1.42 (3H, t).

Compound of Present Invention 56

¹H-NMR (CDCl$_3$) δ: 8.93 (1H, d), 8.88 (1H, dd), 8.61 (1H, d), 8.14 (1H, dd), 7.73 (1H, dd), 3.68 (2H, q), 1.40 (3H, t).

Compound of Present Invention 57

¹H-NMR (CDCl$_3$) δ: 9.36 (1H, s), 8.74-8.69 (1H, m), 8.57 (1H, d), 8.42 (1H, d), 7.32 (1H, d), 3.11 (2H, q), 1.50 (3H, t).

Compound of Present Invention 58

¹H-NMR (CDCl$_3$) δ: 9.36 (1H, s), 9.14 (1H, d), 8.78 (1H, d), 8.43 (1H, d), 8.14 (1H, d), 3.88 (2H, q), 1.45 (3H, t).

Compound of Present Invention 59

¹H-NMR (CDCl$_3$) δ: 9.29 (1H, s), 8.54 (1H, d), 8.20-8.16 (1H, m), 7.76-7.65 (2H, m), 7.30 (1H, d), 3.09 (2H, q), 1.50 (3H, t).

Compound of Present Invention 60

¹H-NMR (CDCl$_3$) δ: 9.32 (1H, s), 9.10 (1H, d), 8.17-8.09 (2H, m), 7.80-7.71 (2H, m), 3.93 (2H, q), 1.43 (3H, t).

Compound of Present Invention 61

¹H-NMR (CDCl$_3$) δ: 9.30 (1H, s), 8.54 (1H, d), 8.17 (1H, s), 7.75 (1H, d), 7.66 (1H, d), 7.31 (1H, d), 3.10 (2H, q), 1.50 (3H, t).

Compound of Present Invention 62

¹H-NMR (CDCl$_3$) δ: 9.33 (1H, s), 9.10 (1H, d), 8.16-8.09 (2H, m), 7.81-7.76 (1H, m), 7.74-7.69 (1H, m), 3.93 (2H, q), 1.43 (3H, t).

Compound of Present Invention 63

¹H-NMR (CDCl$_3$) δ: 9.28 (1H, s), 8.53 (1H, d), 8.22 (1H, d), 7.73-7.65 (2H, m), 7.30 (1H, d), 3.09 (2H, q), 1.50 (3H, t).

Compound of Present Invention 64

$^1$H-NMR (CDCl$_3$) δ: 9.32 (1H, s), 9.09 (1H, d), 8.18 (1H, d), 8.13 (1H, d), 7.77 (1H, dd), 7.71 (1H, d), 3.93 (2H, q), 1.43 (3H, t).

Compound of Present Invention 65

$^1$H-NMR (CDCl$_3$) δ: 9.33 (1H, s), 9.12 (1H, d), 8.33 (1H, s), 8.17-8.12 (1H, m), 7.94-7.87 (2H, m), 3.92 (2H, q), 1.44 (3H, t).

Compound of Present Invention 66

$^1$H-NMR (CDCl$_3$) δ: 8.71 (1H, d), 8.59 (1H, d), 8.43 (1H, dd), 8.20 (1H, dd), 8.11 (1H, d), 7.95 (1H, d), 3.89 (2H, q), 1.46 (3H, t).

Next, formulation examples of the compound of the present invention are shown. The part means part by weight.

Formulation Example 1

10 parts of any one of Compounds of Present Invention 1 to 66 is dissolved in a mixture of 35 parts of xylene and 35 parts of N,N-dimethylformamide, 14 parts of polyoxyethylenestyrylphenyl ether and 6 parts of calcium dodecylbenzenesulfonate are added thereto. The mixture is mixed to obtain each emulsifiable concentrate.

Formulation Example 2

4 parts of sodium lauryl sulfate, 2 parts of calcium lignosulfonate, 20 parts of synthetic hydrous silicon oxide fine powder and 54 parts of diatomaceous earth are mixed, and 20 parts of any one of Compounds of Present Invention 1 to 66 is further added thereto. The mixture is mixed to obtain each wettable powder.

Formulation Example 3

1 part of synthetic hydrous silicon oxide fine powder, 2 parts of calcium lignosulfonate, 30 parts of bentonite and 65 parts of kaolin clay are added to 2 parts of any one of Compounds of Present Invention 1 to 66. Subsequently, an appropriate amount of water is added to this mixture, and the mixture is further stirred, granulated with a granulator, and forced-air dried to obtain each granule.

Formulation Example 4

1 part of any one of Compounds of Present Invention 1 to 66 is dissolved in an appropriate amount of acetone, and 5 parts of synthetic hydrous silicon oxide fine powder, 0.3 parts of PAP and 93.7 parts of Fubasami clay are added thereto. The mixture is sufficiently stirred and mixed to evaporate and eliminate acetone to obtain each dust formulation.

Formulation Example 5

35 parts of a mixture of polyoxyethylene alkyl ether sulfate ammonium salt and white carbon (weight ratio 1:1), 10 parts of any one of Compounds of Present Invention 1 to 66 and 55 parts of water are mixed, and finely pulverized by wet grinding method to obtain each flowable.

Formulation Example 6

0.1 part of any one of Compounds of Present Invention 1 to 66 is dissolved in 5 parts of xylene and 5 parts of trichloroethane, and the mixture is mixed with 89.9 parts of deodorized kerosene to obtain each oil solution.

Formulation Example 7

10 mg of any one of Compounds of Present Invention 1 to 66 is dissolved in 0.5 ml of acetone, and this solution is applied to 5 g of solid feed powder for animal (solid feed powder for breeding CE-2, product of CLEA Japan, Inc.), and the mixture is uniformly mixed. Subsequently, acetone is evaporated to dryness to obtain each poisonous bait.

Formulation Example 8

0.1 part of any one of Compounds of Present Invention 1 to 66 and 49.9 parts of Neothiozol (Chuo Kasei Co., Ltd.) are filled into an aerosol can, and an aerosol valve is attached, then the container is filled with 25 parts of dimethyl ether and 25 parts of LPG and shaken, and an actuator is attached to obtain an oil-based aerosol.

Formulation Example 9

0.6 parts of any one of Compounds of Present Invention 1 to 66, 0.01 part of BHT (2,6-di-tert-butyl-4-methylphenol), 5 parts of xylene, 3.39 parts of deodorized kerosene and 1 part of emulsifier {RHEODOL MO60 (product name of Kao Corporation)} are mixed and dissolved, and the resulting solution and 50 parts of distilled water are filled into an aerosol container. A valve is attached to the container, then 40 parts of a propellant (LPG) is filled under pressure through the valve to obtain an aqueous aerosol.

Formulation Example 10

0.1 g of any one of Compounds of Present Invention 1 to 66 is dissolved in 2 ml of propylene glycol, and the solution is impregnated in a porous ceramic plate with a size of 4.0 cm×4.0 cm and 1.2 cm in thickness to obtain a heating type smoking agent.

Formulation Example 11

5 parts of any one of Compounds of Present Invention 1 to 66 and 95 parts of an ethylene-methyl methacrylate copolymer (a ratio of methyl methacrylate in the copolymer: 10% by weight, Acryft WD301, manufactured by SUMITOMO CHEMICAL Co., Ltd.) are melt-kneaded with a closed pressurizing kneader (manufactured by Moriyama Works), and the resulting kneaded matter is extruded from a molded matter through a molding die to obtain a rod-shaped molded body with a size of 15 cm in length and 3 mm in diameter.

Formulation Example 12

5 parts of any one of Compounds of Present Invention 1 to 66 and 95 parts of a soft vinyl chloride resin are melt-kneaded with a closed pressurizing kneader (manufactured by Moriyama Works), and the resulting kneaded matter is extruded from a molded matter through a molding die to obtain a rod-shaped molded body with a size of 15 cm in length and 3 mm in diameter.

Formulation Example 13

100 mg of any one of Compounds of Present Invention 1 to 66, 68.75 mg of lactose, 237.5 mg of corn starch, 43.75 mg of microcrystalline cellulose, 18.75 mg of polyvinylpyrrolidone, 28.75 mg of sodium carboxymethyl starch and 2.5 mg of magnesium stearate are mixed, and the resulting mixture was compressed to an appropriate size to obtain a tablet.

Formulation Example 14

25 mg of any one of Compounds of Present Invention 1 to 66, 60 mg of lactose, 25 mg of corn starch, 6 mg of carmellose calcium and an appropriate amount of 5% hydroxypropyl methylcellulose, and the resulting mixture is filled into a hard shell gelatin capsule or a hydroxypropyl methylcellulose capsule to obtain an encapsulated formulation.

Formulation Example 15

Distilled water is added to 1000 mg of any one of Compounds of Present Invention 1 to 66, 500 mg of fumaric acid, 2000 mg of sodium chloride, 150 mg of methylparaben, 50 mg of propylparaben, 25000 mg of granulated sugar, 13000 mg of sorbitol (70% solution), 100 mg of Veegum K (Vanderbilt Co.), 35 mg of flavor and 500 mg of colorant, such that a final volume is 100 ml, and the mixture is mixed to obtain a suspension for oral administration.

Formulation Example 16

5 parts of any one of Compounds of Present Invention 1 to 66, 5 parts of polysorbate 85 and 3 parts of benzyl alcohol are dissolved in 30 parts of propylene glycol, and a phosphate buffer is added to this solution so as to have a pH of 6.0 to 6.5, then water is added until a total amount is 100 parts to obtain a liquid formulation for oral administration.

Formulation Example 17

5 parts of aluminum distearate is dispersed in 57 parts of fractionated palm oil and 3 parts of polysorbate 85 by heating. 25 parts of saccharin is dispersed in an oily vehicle obtained by cooling this dispersion to room temperature. Further, 10 parts of any one of Compounds of Present Invention 1 to 66 is added thereto to obtain a paste formulation for oral administration.

Formulation Example 18

5% by weight of any one of Compounds of Present Invention 1 to 66 and 95% by weight of limestone filler are mixed, and a granule for oral administration is obtained using wet granulation method.

Formulation Example 19

5 parts of any one of Compounds of Present Invention 1 to 66 is dissolved in 80 parts of diethylene glycol monoethyl ether, and 15 parts of propylene carbonate is mixed therewith to obtain a spot-on solution.

Formulation Example 20

10 parts of any one of Compounds of Present Invention 1 to 66 is dissolved in 70 parts of diethylene glycol monoethyl ether, and 20 parts of 2-octyl dodecanol is mixed therewith to obtain a pour-on solution.

Formulation Example 21

60 parts of NIKKOL TEALS-42 (Nikko Chemicals Co., Ltd., 42% aqueous solution of triethanolamine lauryl sulfate) and 20 parts of propylene glycol are added to 0.5 parts of any one of Compounds of Present Invention 1 to 66, and the mixture is sufficiently stirred and mixed until it becomes a uniform solution, then 19.5 parts of water is added and further sufficiently stirred and mixed to obtain a shampoo agent as a uniform solution.

Formulation Example 22

0.15 parts of any one of Compounds of Present Invention 1 to 66, 95 parts of an animal feed and 4.85 parts of a mixture of secondary calcium phosphate, diatomaceous earth, Aerosil and carbonate (or chalk) are sufficiently stirred and mixed to obtain a feed premix for animal.

Formulation Example 23

7.2 g of any one of Compounds of Present Invention 1 to 66 and 92.8 g of VOSCO S-55 (manufactured by Maruishi Pharmaceutical Co., Ltd.) are dissolved and mixed at 100° C., poured into a suppository mold, and cooled and solidified to obtain a suppository.

Next, the pest control effect of the compound of the present invention is shown as test examples.

Test Example 1

The formulations of Compounds of Present Invention 1 to 3, 5 to 11, 13, 18, 47, 48 and 50 to 54 obtained in Formulation Example 5 were diluted with water so as to have a concentration of the active ingredient of 500 ppm to prepare a test drug solution.

On the other hand, on a cucumber seedling (the first true leaf stage) planted in a plastic cup was inoculated with about 30 *Aphis gossypii*, and leaving it for a day. 20 ml of the test drug solution was sprayed on the seedling.

Six days after spraying, the number of the surviving *Aphis gossypii* parasitized on the leaves of the cucumber was examined, and the control value was calculated according to the following equation:

$$\text{Controlling value (\%)} = \{1 - (Cb \times Tai)/(Cai \times Tb)\} \times 100$$

wherein the symbols represent as follows:
Cb: the number of the insects in a non-treated section before treatment
Cai: the number of the insects in a non-treated section on observation
Tb: the number of the insects in a treated-section before treatment
Tai: the number of the insects in a treated section on observation
wherein the non-treated section refers to a section where the test drug solution prepared by diluting the formulation not containing the compound of the present invention as in Formulation Example 5 with the same amount of water as in the treated-section was sprayed.

As a result, in the treated-section using each test drug solution containing each of Compounds of Present Invention 1 to 3, 5 to 11, 13, 18, 47, 48 and 50 to 54, the control value was 90% or more.

Test Example 2

The formulations of Compounds of Present Invention 2, 3, 5, 11, 18, 48, 50, 52 and 54 as obtained in Formulation Example 5 were diluted with water, so as to have a concentration of the active ingredient of 500 ppm, to prepare a test drug solution.

On the other hand, a cucumber seedling (the second true leaf stage) planted in a plastic cup was drenched at its foot with 5 ml of the test drug solution, and kept in a greenhouse at 25° C. for 7 days. On the cucumber leaf surface was inoculated about 30 *Aphis gossypii* (whole stage), and further kept in the greenhouse for 6 days, then the number of the surviving *Aphis gossypii* parasitized on the leaves of the cucumber was examined, and the control value was calculated according to the following equation:

Controlling value (%)=$\{1-(Cb \times Tai)/(Cai \times Tb)\} \times 100$ wherein the symbols represent as follows:
Cb: the number of the insects in a non-treated section before treatment
Cai: the number of the insects in a non-treated section on observation
Tb: the number of the insects in a treated-section before treatment
Tai: the number of the insects in a treated section on observation
wherein the non-treated section refers to a section where the test drug solution prepared by diluting the formulation not containing the compound of the present invention as in Formulation Example 5 with the same amount of water as in the treated-section was sprayed.

As a result, in the treated-section using each test drug solution containing each of Compounds of Present Invention 2, 3, 5, 11, 18, 48, 50, 52 and 54, the control value was 90% or more.

Test Example 3

The formulations of Compounds of Present Invention 1 to 5, 47, 48 and 50 to 52 as obtained in Formulation Example 5 were diluted with water, so as to have a concentration of the active ingredient of 500 ppm, to prepare a test drug solution.

On a rice seedling in the second leaf stage planted in a polyethylene cup was sprayed 10 ml of each test drug solution. After air-drying, 20 third-fourth instar larvae of *Nilaparvata lugens* were released, and kept in the greenhouse at 25° C. After 6 days, the number of *Nilaparvata lugens* parasitized on the rice was examined, and the control value was calculated according to the following equation:

Controlling value (%)=$\{1-(Cb \times Tai)/(Cai \times Tb)\} \times 100$ wherein the symbols represent as follows:
Cb: the number of the insects in a non-treated section before treatment
Cai: the number of the insects in a non-treated section on observation
Tb: the number of the insects in a treated-section before treatment
Tai: the number of the insects in a treated section on observation
wherein the non-treated section refers to a section where the test drug solution prepared by diluting the formulation not containing the compound of the present invention as in Formulation Example 5 with the same amount of water as in the treated-section was sprayed.

As a result, in the treated-section using each test drug solution containing each of Compounds of Present Invention 1 to 5, 47, 48 and 50 to 52, the control value was 90% or more.

Test Example 4

The formulations of Compounds of Present Invention 3, 5, 11, 18, 47, 48, 50, 52 and 54 as obtained in Formulation Example 5 were diluted with water, so as to have a concentration of the active ingredient of 500 ppm, to prepare a test drug solution.

On the other hand, a rice seedling (2 weeks after sowing, the second leaf stage) planted in a plastic cup was drenched at its foot with 5 ml of each test drug solution, and kept in a greenhouse of 25° C. for 7 days. Twenty third-fourth instar larvae of *Nilaparvata lugens* were released, and further kept in the greenhouse for 6 days, then the number of surviving *Nilaparvata lugens* parasitized on the rice was examined, and the control value was calculated according to the following equation:

Controlling value (%)=$\{1-(Cb \times Tai)/(Cai \times Tb)\} \times 100$ wherein the symbols represent as follows:
Cb: the number of the insects in a non-treated section before treatment
Cai: the number of the insects in a non-treated section on observation
Tb: the number of the insects in a treated-section before treatment
Tai: the number of the insects in a treated section on observation
wherein the non-treated section refers to a section where the test drug solution prepared by diluting the formulation not containing the compound of the present invention as in Formulation Example 5 with the same amount of water as in the treated-section was sprayed.

As a result, in the treated-section using each test drug solution containing each of Compounds of Present Invention 3, 5, 11, 18, 47, 48, 50, 52 and 54, the control value was 90% or more.

Test Example 5

The formulations of Compounds of Present Invention 2, 3, 18, 47, 48, 50 and 52 as obtained in Formulation Example 5 were diluted with water, so as to have a concentration of the active ingredient of 500 ppm, to prepare a test drug solution.

On the other hand, *Bemisia tabaci* adult was released on a tomato seedling (the third true leaf stage) planted in a polyethylene cup, and made to lay eggs for about 72 hours. The tomato seedling was kept in a greenhouse for 8 days, and when instar larvae hatched from the eggs, the above test drug solution was sprayed in the amount of 20 ml/cup, and the cup was kept in a greenhouse at 25° C. After 7 days, the number of surviving instar larvae on the tomato leaves was examined, and the control value was calculated according to the following equation:

Controlling value (%)=$\{1-(Cb \times Tai)/(Cai \times Tb)\} \times 100$ wherein the symbols represent as follows:
Cb: the number of the insects in a non-treated section before treatment
Cai: the number of the insects in a non-treated section on observation
Tb: the number of the insects in a treated-section before treatment
Tai: the number of the insects in a treated section on observation
wherein the non-treated section refers to a section where the test drug solution prepared by diluting the formulation not containing the compound of the present invention as in Formulation Example 5 with the same amount of water as in the treated-section was sprayed.

As a result, in the treated-section using each test drug solution containing each of Compounds of Present Invention 2, 3, 18, 47, 48, 50 and 52, the control value was 90% or more.

Test Example 6

The formulations of Compounds of Present Invention 3 to 5, 7, 8, 10 to 12, 47, 48, 51 to 54 and 56 as obtained in Formulation Example 5 were diluted with water, so as to have a concentration of the active ingredient of 500 ppm, to prepare a test drug solution.

On the other hand, on cabbage at the third leaf stage planted in a polyethylene cup was sprayed 20 mL/cup of the test drug solution. After the drug solution was dried, the foliage part was cut off, and then placed in a 50 mL volume cup. Five second instar larvae of *Plutella xylostella* were released into the cup, and the cup was sealed with a lid. After the cup was kept at 25° C. for 5 days, the number of surviving insects was counted. The death rate was calculated according to the following equation:

Death rate (%)=(Number of dead insects/Number of tested insects)×100

As a result, in the treated-section using each test drug solution of Compounds of Present Invention 3 to 5, 7, 8, 10 to 12, 47, 48, 51 to 54 and 56, the death rate was 80% or more.

Test Example 7

The formulations of Compounds of Present Invention 5, 11, 13, 44, 47, 48, 51, 52, 54 and 56 as obtained in Formulation Example 5 were diluted with water, so as to have a concentration of the active ingredient of 500 ppm, to prepare a test spray solution.

On the other hand, an apple tree was planted in a plastic cup, and grown until the seventh-eighth true leaf was spread. To the apple tree was sprayed 20 mL/cup of the test drug solution. After the drug solution was dried, 60 first-instar *Adoxophyes orana fasciata* were released, and the plastic cup the bottom of which was cut off and on which a filter paper was put was upside-down and covered. After 7 days, the number of surviving insects was counted, and the death rate was calculated according to the following equation:

Death rate (%)=(Number of dead insects/Number of tested insects)×100

As a result, in the treated-section using each test drug solution of Compounds of Present Invention 5, 11, 13, 44, 47, 48, 51, 52, 54 and 56, the death rate was 90% or more.

Test Example 8

The formulations of Compounds of Present Invention 52 and 54 as obtained in Formulation Example 5 were diluted with water, so as to have a concentration of the active ingredient of 500 ppm, to prepare a test drug solution.

A filter paper having a diameter of 5.5 cm was spread on the bottom of a polyethylene cup having the same diameter and 0.7 ml of the test drug solution was added dropwise onto the filter paper, and 30 mg of sucrose was uniformly placed as bait. Into the polyethylene cup, 10 female imagoes of *Musca domestica* were released, and the cup was sealed with a lid. After 24 hours, the life and death of *Musca domestica* was examined, and the death rate was calculated according to the following equation.

Death rate (%)=(Number of dead insects/Number of tested insects)×100

As a result, in the treatment with Compounds of Present Invention 52 and 54, the death rate was 100% or more.

Test Example 9

The formulation of Compound of Present Invention as obtained in Formulation Example 5 was diluted with water, so as to have a concentration of the active ingredient of 500 ppm, to prepare a test drug solution.

A filter paper having a diameter of 5.5 cm was spread on the bottom of a polyethylene cup having the same diameter and 0.7 ml of the test drug solution was added dropwise onto the filter paper, and 30 mg of sucrose was uniformly placed as bait. Into the polyethylene cup, 2 male imagoes of *Blattalla germanica* were released, and the cup was sealed with a lid. After 6 days, the life and death of *Blattalla germanica* was examined, and the death rate was calculated according to the following equation.

Death rate (%)=(Number of dead insects/Number of tested insects)×100

Test Example 10

The formulations of Compounds of Present Invention 1, 4, 5, 47 and 50 as obtained in Formulation Example 5 were diluted with water, so as to have a concentration of the active ingredient of 500 ppm, to prepare a test drug solution.

0.7 ml of the test drug solution was added to 100 ml of ion-exchanged water (active ingredient concentration: 3.5 ppm). Twenty last-instar larvae of *Culex pipiens pallens* were released into the solution. One day later, the life and death of the *Culex pipiens pallens* was examined, and the death rate of the pest was calculated.

As a result, in the treatment with Compounds of Present Invention 1, 4, 5, 47 and 50, the death rate was 91% or more.

Test Example 11

2 mg of Compound of Present Invention 15 was weighed in a screw tube (Maruemu No. 5; 27×55 mm), and 0.2 mL of acetone was added thereto and sealed with a cap to dissolve the compound. The screw tube was rotated and inverted to uniformity coat the drug solution onto the whole inner wall of the tube. After removing the cap, the solution was air-dried for about 2 hours, then non-blood-sucking nymphal ticks, *Haemaphysalis longicornis* (5 ticks/group) were released, and the tube was sealed with the cap. After 2 days, the number of dead ticks was examined, and the death rate was calculated according to the following equation:

Death rate (%)=(Number of dead ticks/Number of tested ticks)×100

As a result, in the treatment with Compound of Present Invention 15, the death rate was 100%.

INDUSTRIAL APPLICABILITY

The compound of the present invention has a controlling effect on pests and is useful as an active ingredient of a pest control agent.

The invention claimed is:

1. A method for controlling pests comprising applying an effective amount of a fused heterocyclic compound represented by formula (A-1) or an N-oxide thereof,

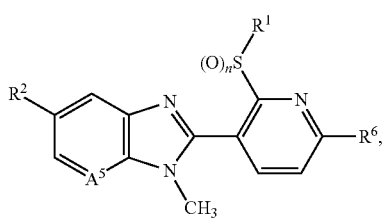

(A-1)

wherein
$A^5$ represents a nitrogen atom or $=CR^{10}-$;
$R^1$ represents a C1 to C6 chain hydrocarbon group optionally having one or more atoms or groups selected from group X or a C3 to C6 alicyclic hydrocarbon group optionally having one or more atoms or groups selected from group Y;
$R^2$ is a C1 to C6 haloalkyl group, $-OR^{11}$, or $-S(O)_mR^{11}$;
$R^{11}$ is a C1 to C6 haloalkyl group;
$R^6$ is a C1 to C6 alkyl group optionally having one or more halogen atoms, $-OR^{13}$, $-S(O)_mR^{13}$, a halogen atom, or a hydrogen atom;
$R^{13}$ is a C1 to C6 alkyl group optionally having one or more halogen atoms;
$R^{10}$ represents a C1 to C6 chain hydrocarbon group optionally having one or more halogen atoms, $-OR^{16}$, $-S(O)_mR^{16}$, $-NR^{16}N^{17}$, $-CO_2R^{16}$, $-C(O)R^{16}$, a cyano group, a nitro group, a halogen atom, or a hydrogen atom;
$R^{16}$ and $R^{17}$ are the same or different and represent a C1 to C6 chain hydrocarbon group optionally having one or more atoms or groups selected from group X, or a hydrogen atom;
each m independently represents 0, 1, or 2;
n represents 0, 1, or 2;
when m is 1 or 2 in $-S(O)_mR^{16}$, $R^{16}$ does not represent a hydrogen atom;
group X is selected from the group consisting of C1 to C6 alkoxy groups optionally having one or more halogen atoms, C2 to C6 alkenyloxy groups optionally having one or more halogen atoms, C2 to C6 alkynyloxy groups optionally having one or more halogen atoms, C1 to C6 alkylsulfanyl groups optionally having one or more halogen atoms, C1 to C6 alkylsulfinyl groups optionally having one or more halogen atoms, C1 to C6 alkylsulfonyl groups optionally having one or more halogen atoms, C2 to C6 alkylcarbonyl groups optionally having one or more halogen atoms, C2 to C6 alkoxycarbonyl groups optionally having one or more halogen atoms, C3 to C6 cycloalkyl groups optionally having one or more halogen atoms or one or more C1 to C3 alkyl groups, cyano groups, hydroxy groups, and halogen atoms; and
group Y is selected from the group consisting of C1 to C6 chain hydrocarbon groups optionally having one or more halogen atoms, C1 to C6 alkoxy groups optionally having one or more halogen atoms, C2 to C6 alkenyloxy groups optionally having one or more halogen atoms, C2 to C6 alkynyloxy groups optionally having one or more halogen atoms, and halogen atoms.

2. The method for controlling pests according to claim 1, wherein $A^5$ is a nitrogen atom.

3. The method for controlling pests according to claim 1, wherein $A^5$ is $=CR^{10}$, and $R^{10}$ is a halogen atom or a hydrogen atom.

* * * * *